(12) United States Patent
Chibon et al.

(10) Patent No.: US 9,708,666 B2
(45) Date of Patent: Jul. 18, 2017

(54) PROGNOSTIC MOLECULAR SIGNATURE OF SARCOMAS, AND USES THEREOF

(75) Inventors: Frédéric Chibon, Isle-Saint-Georges (FR); Jean-Michel Coindre, Bordeaux (FR); Alain Aurias, Bures-sur-Yvette (FR)

(73) Assignees: Université Bordeaux Segalen, Bordeaux (FR); Institut Bergonié, Bordeaux (FR); Institut curie, Paris (FR)

( * ) Notice: Subject to any disclaimer, the term of this patent is extended or adjusted under 35 U.S.C. 154(b) by 1652 days.

(21) Appl. No.: 13/265,764

(22) PCT Filed: Apr. 21, 2010

(86) PCT No.: PCT/FR2010/000323
§ 371 (c)(1),
(2), (4) Date: Oct. 4, 2012

(87) PCT Pub. No.: WO2010/122243
PCT Pub. Date: Oct. 28, 2010

(65) Prior Publication Data
US 2013/0065772 A1    Mar. 14, 2013

Related U.S. Application Data

(60) Provisional application No. 61/171,495, filed on Apr. 22, 2009.

(30) Foreign Application Priority Data

Apr. 22, 2009  (FR) ...................................... 09 01936

(51) Int. Cl.
*C12Q 1/68*    (2006.01)

(52) U.S. Cl.
CPC ...... *C12Q 1/6886* (2013.01); *C12Q 2600/118* (2013.01); *C12Q 2600/136* (2013.01); *C12Q 2600/158* (2013.01)

(58) Field of Classification Search
None
See application file for complete search history.

(56) References Cited

FOREIGN PATENT DOCUMENTS

WO    WO 2004/048938 A2    6/2004
WO    WO 2005/117943 A2    12/2005

OTHER PUBLICATIONS

"Affymetrix GeneChip Human Genome U133 Array Set HG-U133A", GEO, Mar. 11, 2002.
Elai Davicioni et al., "Identification of a PAX-FKHR Gene Expression Signature that Defines Molecular Classes and Determines the Prognosis of Alveolar Rhabdomyosarcomas" Cancer Research, Jul. 15, 2006, vol. 66(14) pp. 6936-6946.
Princy Francis et al., "Diagnostic and Prognostic Gene Expression Signatures in 177 Soft Tissue Sarcomas: Hypoxia-Induced Transcription Profile Signifies Metastatic Potential", BMC Genomics, Mar. 14, 2007, vol. 8(1), pp. 1-16.
H. Taubert et al., "Stem-Cell-Associated Genes are Extremely Poor Prognostic Factors for Soft-Tissue Sarcoma Patients", Oncogene, Nov. 2007, vol. 26(50), pp. 7170-7174.
K.M. Linton et al., "Acquisition of Biologically Relevant Gene Expression Data by Affymetrix Microarray Analysis of Archival Formalin-Fixed Paraffin-Embedded Tumours", British Journal of Cancer, Apr. 22, 2008, vol. 98(8), pp. 1403-1414.

*Primary Examiner* — Addison D Ault
(74) *Attorney, Agent, or Firm* — Arent Fox LLP

(57) ABSTRACT

Described herein are methods and compositions that can be used for diagnosis and treatment of soft tissue sarcoma cancer phenotypes and soft tissue sarcoma cancer-associated diseases. Also described herein are methods that can be used to identify modulators of soft tissue sarcoma cancer.

7 Claims, 4 Drawing Sheets

78 breast cancers
Survival without progression
(Van't Veer et al., 2002)

295 breast cancers
Survival without progression
(Van de Vijver et al., 2002)

29 GISTs [gastrointestinal stromal tumors]
Survival without metastases
(Yamaguchi et al., 2008)

SEQUENCE LISTING

<160> NUMBER OF SEQ ID NOS: 67

<210> SEQ ID NO 1
<211> LENGTH: 10906

```
<212> TYPE: DNA
<213> ORGANISM: Homo sapiens

<400> SEQUENCE: 1
attggtggag gcggcaagtt taaacagagt caaaacgcca tacttgtttg gctcctcttt      60
ttaatttgcg agtttattgg gcttgttttc tgttttctag ggagtaggtt agtggaaaag     120
aaaaagggcc gaattcactc ccacgacctc tacagccgcc cctgagggga agcggtcagc     180
gtaagtcccg gatccccgct ccggagccgc ctcgtgggag cggggcaagg agatccagga     240
ggggtctcga atctgccatg gcgaaccggc gagtggggcg aggctgctgg gaagtgagcc     300
cgaccgagcg gaggccgccc gcggggctgc ggggccccgc ggccgaggag gaggcgtctt     360
ccccgccggt cctgtctctc agccacttct gcaggtctcc tttcctttgc ttcggggacg     420
ttctcctggg agcctcacgg acgctgtctc tggccctaga caaccctaac gaggaggtgg     480
cagaagtgaa gatctcccac ttcccggccg cggacctggg cttcagtgtg tcgcagcgct     540
gtttcgtgtt gcagcctaaa gagaaaattg ttatttctgt taactggaca ccactcaaag     600
aaggccgagt aagagagatt atgacatttc ttgtaaatga tgttctgaaa caccaagcta     660
tattactagg aaatgcagaa gagcagaaaa agaaaaagag gagtctttgg gataccatta     720 aaagaagaa aatttcagcc tctacaagtc acaacagaag ggtttcaaat attcagaatg     780
ttaataaaac atttagtgtt tcccaaaaag ttgacagagt taggagccca ctacaagctt     840
gtgaaaactt ggctatgaat gaaggcggtc ccccaacaga aaacaattct ttaatacttg     900
aagaaaataa atacccata tcacctatta gccctgcttt caatgaatgc catggtgcaa     960
cttgcttgcc actctctgta cgtcgatcta ctacctactc atctcttcat gcatcagaaa    1020 ataggaact attaaatgta cacagtgcca acgtttcaaa agtttctttt aatgagaaag    1080
ctgtaactga aacttccttt aattccgtaa atgttaatgg ccaaagagga gagaatagta    1140
aacttagtct taccccccaac tgttcttcaa ctttgaacat tacacaaagc caaatacatt    1200
ttctaagtcc agattctttt gtaaataata gtcatggagc taataatgaa ctagaattag    1260
taacatgtct ttcatcagat atgtttatga aagataattc acagcctgtg catttggaat    1320
caacaattgc acatgaaatt tatcagaaaa ttttaagtcc agattctttc ataaaagata    1380
attatggact aaatcaggat ctagaatcag agtcagttaa tcctatttta tcccctaatc    1440
aatttttaaa agataacatg gcatatatgt gtacatctca gcaaacatgt aaagtaccat    1500
tatcaaatga aaattctcaa gtcccacagt ctcctgaaga ttggagaaaa agtgaagttt    1560
cgccacgtat tcctgaatgt cagggttcaa aatctcccaa agctattttt gaagaactag    1620
tagaaatgaa gtcaaattac tacagtttta taaaacaaaa taatcctaaa ttttctgcag    1680
ttcaggatat ttctagtcat agccacaata acaacctaa gagacgtcca atactttctg    1740
ccactgttac taaaggaag gccacctgta ccagagaaaa ccaaactgag attaataaac    1800
caaaagcaaa aagatgtctc aacagtgcag tgggtgaaca tgaaaaagta ataaataatc    1860
aaaaggaaaa agaagatttt cattcttatc ttccaattat agatccaata ttaagtaaat    1920
ctaagagtta taaaacgag gtaacaccct cttcgacaac agcttcagtt gctcggaaaa    1980
gaaagagcga tggaagcatg gaagatgcaa atgtgagagt tgcaattaca gaacatacag    2040
aagtgcgaga atcaaaaga atccattttt ctccctcaga gcctaaaaca tcagctgtta    2100
agaaaacaaa aatgtgtaca cacccatct caaaacgtat tagcaacaga gagaaattaa    2160
acctgaagaa gaaaactgat ttatcaatat tcagaactcc aatttctaaa acaaacaaaa    2220
```

```
ggacaaaacc cattatcgct gtggcacagt ccagtttgac cttcataaaa ccattaaaaa    2280
cagatattcc cagacacccg atgccatttg ctgcaaaaaa catgttttat gatgaacgct    2340
ggaaggaaaa gcaggaacag ggcttcactt ggtggttaaa ttttatatta acccctgatg    2400
acttcactgt aaaacaaat atttctgaag taaatgctgc tactcttctt ttgggaatag     2460
agaatcaaca taaaataagt gttcctagag cacctacaaa agaggaaatg tctctcagag    2520
cttatactgc tcggtgtagg ttaaacagac tacgtcgtgc agcatgccgt ttgtttactt    2580
ctgaaaaaat ggttaaagct attaaaaagc ttgaaattga aattgaagct aggcggttaa    2640
ttgttcgaaa agatagacac ctatggaaag atgtgggaga acgtcagaaa gtcctgaatt    2700
ggctgttgtc ctacaatcct ttgtggcttc gaattggtct agagacaact tatggagaac    2760
tcatatcttt ggaagataac agtgatgtca cagggttggc tatgtttatt ctgaatcgcc    2820
tactttggaa tcctgatata gcagctgagt atagacaccc cactgttcct cacctgtata    2880
gagatggtca tgaagaagct ttgtccaagt ttacattgaa aaagttattg ttgttggtct    2940
gttttcttga ttatgctaaa atttccagac tcattgatca tgatccttgt ctcttctgta    3000
aagatgccga attcaaggct agtaaagaaa tccttttggc tttttcacga gatttcctaa    3060
gtggtgaagg tgacctttcc cgtcaccttg gcttattggg attacctgtt aaccatgttc    3120
agacaccatt tgatgaattt gattttgccg ttacaaatct tgccgtagac ttgcaatgtg    3180
gagtgcgcct tgtgcgaacc atggaacttc tcacacagaa ctgggacctc tcaaagaaac    3240
tcaggattcc ggcaataagt cgtcttcaaa agatgcacaa tgttgacatt gttcttcaag    3300
ttcttaaatc acgaggaatt gaattaagtg atgagcatgg aaatacaatt ctatctaagg    3360
atattgtgga taggcacaga gaaaaaactc tcaggttgct ttggaaaata gcgtttgctt    3420
ttcaggtgga tatttccctt aacttagatc aattaaagga agaaattgcc tttctaaaac    3480
acacaaagag tataaagaaa acaatatctc tactatcatg ccattctgat gatcttatta    3540
ataagaaaaa aggcaaaagg gatagtggtt cctttgaaca atatagtgaa aacataaagt    3600
tattgatgga ttgggtaaat gctgtttgtg ccttctataa taaaaaggtg gagaattta     3660 cagtgtcttt ctcagacggc cgtgtgttat gttacctgat ccaccattac catccttgct    3720
atgtgccatt tgacgctata tgtcagcgta ctactcaaac tgtggaatgt acgcaaactg    3780
gttcagtggt attaaattca tcatctgaat ctgatgacag ttctctggat atgtctctta    3840
aagcatttga tcatgaaaat acttcagagc tatacaaaga gctcctagaa aatgaaaaga    3900
aaaattttca cttggttagg tctgcagtta gagaccttgg tggaatacct gctatgatta    3960
atcattcaga tatgtcaaat acaattccag atgaaaaggt ggttattacc tatttgtcat    4020
ttctttgtgc aaggcttttg gatcttcgta aagaaataag agctgctcga ctcatacaaa    4080
caacatggag aaaatataaa ctaaaaacag atctcaaacg ccatcaggag agagagaaag    4140
ctgcaagaat tattcaattg gctgtaatca attttctagc aaaacaaaga ttgagaaaaa    4200
gagttaatgc agcactcgtc attcagaaat attggcgaag agtcttagca cagagaaaat    4260
tattaatgtt aaaaaaggaa aagctggaaa aagttcaaaa taaagcagca tcacttattc    4320
agggatattg gagaagatat tccactagac aaagatttct gaaattgaaa tattattcaa    4380
tcatcctgca atctaggata agaatgataa ttgctgttac atcttataaa cgatatcttt    4440
gggctacagt tacaattcag aggcattggc gtgcttattt aagaagaaaa caagatcaac    4500
aaagatatga aatgctaaaa tcatcaactc ttataatcca atctatgttc agaaaatgga    4560
agcaacgtaa aatgcaatca caagtaaaag ctacagtaat attgcaaaga gcttttagag    4620
```

```
aatggcattt aagaaaacaa gctaaagaag aaaattctgc tattatcata caatcatggt    4680
atagaatgca taaagaatta cggaaatata tttatattag atcttgtgtt gttatcattc    4740
agaaaagatt tcggtgcttt caagcccaaa agttatataa aagaagaaaa gagtccatac    4800
taaccatcca gaagtactac aaagcatatc tgaaaggaaa gattgagcgc accaactatt    4860
tgcagaaacg agctgcagcc attcaattac aagctgcttt taggagactg aaagctcata    4920
atttatgtag acaaattaga gctgcttgtg ttattcagtc atactggaga atgagacaag    4980
acagagttcg attttttaaac cttaagaaga ctattatcaa atttcaggca catgtaagaa    5040
aacatcaaca acgacagaaa tataagaaga tgaagaaagc agctgttata attcagactc    5100
atttccgagc ttatattttt gccatgaaag ttctagcatc ttaccagaaa acacgctctg    5160
ctgtcattgt gctgcagtct gcatatagag ggatgcaagc caggaaaatg tatattcaca    5220
tcctcacatc tgttataaag attcaatcat attatcgtgc ttatgtttct aaaaaggaat    5280
ttttgagcct aaaaaatgct acaataaaat tgcagtcaac tgttaagatg aaacaaacac    5340
gtaaacaata tttgcatttta agagcagctg cactatttat ccagcaatgt taccgttcca    5400
aaaaaatagc tgcacaaaag agagaagagt atatgcagat gcgggaatct tgtatcaaac    5460
tgcaagcatt tgttagagga taccttgtcc gaaagcagat gaggttacaa agaaaagctg    5520
ttatttcact acagtcttat ttcagaatga gaaaggctcg gcagtattat ctgaaaatgt    5580
ataaagcaat tattgtcatt cagaattact atcatgcata caaagcacag gtcaatcaga    5640
ggaagaactt cttgcaagtc aaaaaagcag ctacttgctt gcaagcagct tacagaggtt    5700
ataaagtacg ccagctaatc aaacaacaat ctatagctgc tcttaaaatt cagtctgctt    5760
ttagaggcta aataaaaagg gtaaaatatc aatctgtgct tcaatctata ataaagattc    5820
agagatggta cagggcgtac aagactcttc atgatacaag aacacatttt tgaagacaa    5880 aggcagctgt gatttccctc cagtctgctt atcgtggctg gaaggttcgg aaacagatta    5940
gaagggaaca tcaagctgcc ttgaagattc agtctgcttt tagaatggcc aaggcccaga    6000
aacagtttag attgtttaaa acagcagcat tagtcatcca gcaaaatttc agagcatgga    6060
ctgcaggaag gaagcaatgt atggagtata ttgaactccg tcatgcggta ctggtgcttc    6120
aatctatgtg gaagggaaaa acactgagaa gacagcttca aaggcaacat aaatgtgcta    6180
tcatcataca gtcatactat agaatgcatg tgcaacaaaa gaagtggaaa atcatgaaaa    6240
aagctgctct tctgattcaa aagtattata gggcttacag tattggaaga gaacagaatc    6300
atttatattt gaaaacaaaa gcagctgtag taactttaca gtcagcttat cgtggtatga    6360
aagtgagaaa aagaataaag gattgcaaca aagcagcagt cactatacag tctaaataca    6420
gagcttacaa aaccaaaaag aaatatgcaa cctatagagc ttcagctatt ataattcaga    6480
gatggtatcg aggtattaaa attacaaacc atcagcataa ggagtatctt aatttgaaga    6540
agacagcaat taaatccaa tctgtttata gaggtattag agttagaaga catattcaac    6600
acatgcacag ggcagccact tttattaaag ccatgtttaa aatgcatcag tcaagaataa    6660
gttaccatac aatgagaaaa gcagctattg ttattcaagt aagatgtaga gcatattatc    6720
aagtaaaaat gcagcgtgaa aagtacctga caatttttgaa agctgttaaa gtccttcagg    6780
caagttttag aggagtaaga gttagacgga ctcttagaaa gatgcagact gcagcaacac    6840
tcattcagtc aaactacaga agatacagac agcaaacata ctttaataag ttaaagaaaa    6900
taacaaaaac agtacagcaa agatactggg caatgaaaga aagaaacata caatttcaaa    6960
```

```
ggtataacaa actgaggcat tctgtaatat acattcaggc tattttagg ggaaagaaag      7020 ctagaagaca tttaaaaatg atgcatatag ccgcaactct cattcagagg agatttagaa      7080
ctctaatgat gagaagaaga ttcctctctc tcaagaaaac tgctattttg attcagagaa      7140
aatatcgggc acatctttgt acaaagcatc acttacagtt ccttcaggta caaaatgcag      7200
ttattaaaat ccagtcatca tacagaagat ggatgataag gaaaaggatg cgagagatgc      7260
acagggctgc tactttcatc cagtctactt tcagaatgca cagattacat atgagatatc      7320
aggctttgaa acaggcctcc gttgtgatcc aacagcaata ccaagcaaat agagctgcaa      7380
aactgcagag gcagcattat ctcagacaaa gacactctgc tgtgatcctt caggctgcat      7440 tcagggtat gaaaactaga agacatttga agagtatgca ttcctctgca acccttattc      7500
agagtaggtt tagatcatta ctggtgagga gaagattcat ttccctcaaa aaagctacta      7560
tttttgttca gaggaaatat cgagccacca tttgtgccaa acataaattg taccaattct      7620
tgcacttaag aaaggcagcc attacaatac agtcatctta cagaagactg atggtaaaga      7680
agaagttaca agaaatgcaa agggctgcag ttctcattca ggctactttc aggatgtaca      7740
gaacatatat tacatttcag acttggaaac atgcttcaat tctaattcag caacattatc      7800
gaacatatag agctgcaaaa ttacaaagag aaaattatat cagacaatgg cattctgctg      7860
tggttattca ggctgcatat aaaggaatga agcaagaca acttttaagg gaaaaacaca      7920
aagcttctat cgtaatacaa agcacctaca gaatgtatag gcagtattgt ttctaccaaa      7980
agcttcagtg ggctacaaaa atcatacaag aaaatatag agcaaataaa aagaaacaga      8040
aagtatttca acacaatgaa cttaagaaag agacttgtgt tcaggcaggt tttcaggaca      8100
tgaacataaa aaacagatt caggaacagc accaggctgc cattattatt cagaagcatt      8160
gtaaagcctt taaataagg aagcattatc tccaccttag agcaacagta gtttctattc      8220
aaagaagata cagaaaacta actgcagtgc gtacccaagc agttatttgt atacagtctt      8280
attacagagg ctttaaagta cgaaaggata ttcaaaatat gcaccgggct gccacactaa      8340
ttcagtcatt ctatcgaatg cacagggcca agttgatta tgaaacaaag aaaactgcaa      8400
ttgtggttat acagaattat tataggttgt atgttagagt aaaaacagaa agaaaaaact      8460
ttttagcagt tcagaaatct gtacgaacta ttcaggctgc ttttagaggc atgaaagtta      8520
gacaaaaatt gaaaaatgta tcagaggaaa agatggcagc cattgttaac caatctgcac      8580
tctgctgtta cagaagtaaa actcagtatg aagctgttca aagtgaaggt gttatgattc      8640
aagagtggta taaagcttct ggccttgctt gttcacagga agcagagtat cattctcaaa      8700
gtagggctgc agtaacaatt caaaaagctt tttgtagaat ggtcacaaga aaactggaaa      8760
cacagaaatg tgctgcccta cggattcagt tcttccttca gatggctgtg tatcggagaa      8820
gatttgttca gcagaaaaga gctgctatca ctttacagca ttattttagg acgtggcaaa      8880
ccagaaaaca gttttactat atagaaaag cagcagtggt tttacaaaat cactacagag      8940
catttctgtc tgcaaaacat caaagacaag tctatttaca gatcagaagc agtgttatca      9000
ttattcaagc tagaagtaaa ggatttatac agaaacggaa gtttcaggaa attaaaaata      9060
gcaccataaa aattcaggct atgtggagga gatatagagc caagaaatat ttatgtaaag      9120
tgaaagctgc ctgcaagatt caagcctggt atagatgttg gagagcacac aaagaatatc      9180
tagctatatt aaaagctgtt aaaattattc aaggttgctt ctataccaaa ctagagaaaa      9240
cacggttttt gaatgtgaga gcatcagcaa ttatcattca gagaaatgg agagctatac      9300 ttcctgcaaa gatagctcat gaacacttct taatgataaa aagacatcga gctgcttgtt      9360
```

```
tgatccaagc acattataga ggatataaag gaaggcaggt ctttcttcgg cagaaatctg      9420
ctgctttgat catacaaaaa tatatacgag ccagggaggc tggaaagcat gaaaggataa      9480
aatatattga atttaaaaaa tctacagtta tcctacaagc actggtgcgt ggttggctag      9540
tacgaaaaag attttagaa cagagagcca aaattcgact tcttcacttc actgcagctg       9600
catattatca cctgaatgct gttagaattc aaagagccta taaactttac ctggctgtga      9660
agaatgctaa caagcaggtt aattcagtca tctgtattca gagatggttt cgagcaagat      9720
tacaagaaaa gagatttatt cagaaatatc atagcatcaa aaagattgag catgaaggtc      9780
aagaatgtct gagccagcga aatagggctg catcagtaat acagaaagca gtgcgccatt      9840
ttctcctccg taaaaagcag gaaaaattca ctagtggaat cattaaaatt caggcattat      9900
ggagaggcta ttcttggagg aagaaaaatg attgtacaaa aattaaagct atacgactaa      9960
gtcttcaagt tgttaatagg gagattcgag aagaaaacaa actctacaaa agaactgcac     10020
ttgcacttca ttacctttg acatataagc acctttctgc cattcttgag gccttaaaac       10080
acctagaggt agttactaga ttgtctccac tttgttgtga aacatggcc cagagtggag       10140 caatttctaa aatatttgtt ttgatccgaa gttgtaatcg cagtattcct tgtatggaag     10200
tcatcagata tgctgtgcaa gtcttgctta atgtatctaa gtatgagaaa actacttcag     10260
cagtttatga tgtagaaaat tgtatagata tactattgga gcttttgcag atataccgag     10320
aaaagcctgg taataaagtt gcagacaaag gcggaagcat ttttacaaaa acttgttgtt     10380
tgttggctat tttactgaag acaacaaata gagcctctga tgtacgaagt aggtccaaag     10440
ttgttgaccg tatttacagt ctctacaaac ttacagctca taaacataaa atgaatactg     10500
aaagaatact ttacaagcaa aagaagaatt cttctataag cattccttt atcccagaaa      10560 cacctgtaag gaccagaata gtttcaagac ttaagccaga ttgggttttg agaagagata     10620
acatggaaga aatcacaaat cccctgcaag ctattcaaat ggtgatggat acgcttggca     10680
ttccttatta gtaaatgtaa acattttcag tatgtatagt gtaaagaaat attaaagcca     10740
atcatgagta cgtaaagtga tttttgctct ccgtgtacaa cttttaaaat ctgactttgt     10800
tttaaaaaaa cataaactgt tcattacatt cttcattttt atcatttata gttttatgca     10860
tgtaataaac taatatgtca taagatgaaa aaaaaaaaaa aaaaaa                    10906
```

<210> SEQ ID NO 2
<211> LENGTH: 3527
<212> TYPE: DNA
<213> ORGANISM: Homo sapiens

<400> SEQUENCE: 2

```
actgaaagct ccggtgccag accccacccc cggccccggc ccgggacccc ctcccctccc        60
gggatccccc ggggttccca ccccgcccgc accgccgggg accggccgg tccggcgcga        120 gccccgtcc gggccctgg ctcggccccc aggttggagg agcccggagc ccgccttcgg         180
agctacggcc taacggcggc ggcgactgca gtctggaggg tccacacttg tgattctcaa       240
tggagagtga aaacgcagat tcataatgaa aactagcccc cgtcggccac tgattctcaa       300
aagacggagg ctgccccttc ctgttcaaaa tgccccaagt gaaacatcag aggaggaacc       360
taagagatcc cctgcccaac aggagtctaa tcaagcagag gcctccaagg aagtggcaga       420
gtccaactct tgcaagtttc cagctgggat caagattatt aaccaccca ccatgcccaa        480 cacgcaagta gtggccatcc ccaacaatgc taatattcac agcatcatca cagcactgac       540
```

-continued

```
tgccaaggga aaagagagtg gcagtagtgg gcccaacaaa ttcatcctca tcagctgtgg    600
gggagcccca actcagcctc caggactccg gcctcaaacc caaaccagct atgatgccaa    660
aaggacagaa gtgaccctgg agaccttggg accaaaacct gcagctaggg atgtgaatct    720
tcctagacca cctggagccc tttgcgagca gaaacgggag acctgtgcag atggtgaggc    780
agcaggctgc actatcaaca atagcctatc aacatccag tggcttcgaa agatgagttc     840
tgatggactg ggctcccgca gcatcaagca agagatggag gaaaaggaga attgtcacct    900
ggagcagcga caggttaagg ttgaggagcc ttcgagacca tcagcgtcct ggcagaactc    960
tgtgtctgag cggccaccct actcttacat ggccatgata caattcgcca tcaacagcac   1020
tgagaggaag cgcatgactt tgaaagacat ctatacgtgg attgaggacc actttcccta   1080
ctttaagcac attgccaagc caggctggaa gaactccatc cgccacaacc tttccctgca   1140
cgacatgttt gtccgggaga cgtctgccaa tggcaaggtc tccttctgga ccattcaccc   1200
cagtgccaac cgctacttga cattggacca ggtgtttaag ccactggacc cagggtctcc   1260
acaattgccc gagcacttgg aatcacagca gaaacgaccg aatccagagc tccgccggaa   1320
catgaccatc aaaaccgaac tcccctgggg cgcacggcgg aagatgaagc cactgctacc   1380
acgggtcagc tcatacctgg tacctatcca gttcccggtg aaccagtcac tggtgttgca   1440
gccctcggtg aaggtgccat tgcccctggc ggcttccctc atgagctcag agcttgcccg   1500
ccatagcaag cgagtccgca ttgccccaa ggtgctgcta gctgaggagg ggatagctcc    1560
tctttcttct gcaggaccag ggaaagagga gaaactcctg tttggagaag gttttctcc    1620 tttgcttcca gttcagacta tcaaggagga agaaatccag cctggggagg aaatgccaca   1680
cttagcgaga cccatcaaag tggagagccc tcccttggaa gagtggccct cccggcccc    1740 atctttcaaa gaggaatcat ctcactcctg ggaggattcg tcccaatctc caccccaag    1800 acccaagaag tcctacagtg ggcttaggtc cccaacccgg tgtgtctcgg aaatgcttgt    1860
gattcaacac agggagagga gggagaggag ccggtctcgg aggaaacagc atctactgcc   1920
tccctgtgtg gatgagccgg agctgctctt ctcagagggg cccagtactt cccgctgggc   1980
cgcagagctc ccgttcccag cagactcctc tgacccctgcc tccagctca gctactccca   2040 ggaagtggga ggaccttta agacacccat taaggaaacg ctgcccatct cctccacccc    2100
gagcaaatct gtcctcccca gaaccctga atcctggagg ctcacgcccc cagccaaagt    2160
agggggactg gatttcagcc cagtacaaac ctcccagggt gcctctgacc ccttgcctga   2220 cccctgggg ctgatggatc tcagcaccac tcccttgcaa agtgctcccc ccttgaatc     2280 accgcaaagg ctcctcagtt cagaacctt agacctcatc tccgtcccct ttggcaactc    2340
ttctccctca gatatagacg tccccaagcc aggctcccg gagccacagg tttctggcct    2400
tgcagccaat cgttctctga cagaaggcct ggtcctggac acaatgaatg acagcctcag   2460
caagatcctg ctggacatca gctttcctgg cctggacgag gacccactgg gccctgacaa   2520
catcaactgg tcccagttta ttcctgagct acagtagagc cctgcccttg ccctgtgct    2580 caagctgtcc accatcccgg gcactccaag gctcagtgca ccccaagcct ctgagtgagg   2640
acagcaggca gggactgttc tgctcctcat agctccctgc tgcctgatta tgcaaaagta   2700
gcagtcacac cctagccact gctgggacct tgtgttcccc aagagtatct gattcctctg   2760
ctgtccctgc caggagctga agggtgggaa caacaaaggc aatggtgaaa agagattagg   2820
aaccccccag cctgtttcca ttctctgccc agcagtctct taccttccct gatctttgca   2880
gggtggtccg tgtaaatagt ataaattctc caaattatcc tctaattata aatgtaagct   2940
```

```
tatttcctta gatcattatc cagagactgc cagaaggtgg gtaggatgac ctggggtttc    3000
aattgacttc tgttccttgc ttttagtttt gatagaaggg aagacctgca gtgcacggtt    3060
tcttccaggc tgaggtacct ggatcttggg ttcttcactg cagggaccca gacaagtgga    3120
tctgcttgcc agagtccttt ttgcccctcc ctgccacctc cccgtgtttc caagtcagct    3180
ttcctgcaag aagaaatcct ggttaaaaaa gtcttttgta ttgggtcagg agttgaattt    3240
ggggtgggag gatggatgca actgaagcag agtgtgggtg cccagatgtg cgctattaga    3300
tgtttctctg ataatgtccc caatcatacc agggagactg cattgacga gaactcaggt     3360 ggaggcttga gaaggccgaa agggcccctg acctgcctgg cttccttagc ttgcccctca    3420
gctttgcaaa gagccaccct aggccccagc tgaccgcatg ggtgtgagcc agcttgagaa    3480
cactaactac tcaataaaag cgaaggtgga caaaaaaaaa aaaaaaa                  3527

<210> SEQ ID NO 3
<211> LENGTH: 823
<212> TYPE: DNA
<213> ORGANISM: Homo sapiens

<400> SEQUENCE: 3
aaacgcgggc gggcgggccc gcagtcctgc agttgcagtc gtgttctccg agttcctgtc      60
tctctgccaa cgccgcccgg atggcttccc aaaaccgcga cccagccgcc actagcgtcg     120
ccgccgcccg taaaggagct gagccgagcg ggggcgccgc ccggggtccg gtgggcaaaa     180
ggctacagca ggagctgatg accctcatga tgtctggcga taagggatt tctgccttcc     240 ctgaatcaga caaccttttc aaatgggtag ggaccatcca tggagcagct ggaacagtat     300
atgaagacct gaggtataag ctctcgctag agttccccag tggctaccct tacaatgcgc     360
ccacagtgaa gttcctcacg ccctgctatc accccaacgt ggacacccag ggtaacatat     420
gcctggacat cctgaaggaa aagtggtctg ccctgtatga tgtcaggacc attctgctct     480
ccatccagag ccttctagga gaacccaaca ttgatagtcc cttgaacaca catgctgccg     540
agctctggaa aaaccccaca gcttttaaga agtacctgca agaaacctac tcaaagcagg     600
tcaccagcca ggagccctga cccaggctgc ccagcctgtc cttgtgtcgt ctttttaatt     660
tttccttaga tggtctgtcc ttttgtgat ttctgtatag gactctttat cttgagctgt      720 ggtattttg ttttgttttt gtcttttaaa ttaagcctcg gttgagccct tgtatattaa      780
ataaatgcat ttttgtcctt tttagacaa aaaaaaaaa aaa                          823

<210> SEQ ID NO 4
<211> LENGTH: 3222
<212> TYPE: DNA
<213> ORGANISM: Homo sapiens

<400> SEQUENCE: 4
aagtgttgcg caggcgcatc cgatcgactc ggtaggtggg gatctcttgg agacggcgac       60
ccaggcatct ggggagccac agaagtcgta ctcccttaaa ccctgctttg ctcccctgt       120 ggatgtaacc ccttagctgg cattttgcat ctcaattggc ttgtgatgga ggcgtctttg      180
gggattcaga tggatgagcc aatggctttt tctccccagc gtgaccggtt tcaggctgaa      240
ggctctttaa aaaaaaacga gcagaatttt aaacttgcag gtgttaaaaa agatattgag      300
aagctttatg aagctgtacc acagcttagt aatgtgttta agattgagga caaaattgga      360
gaaggcactt tcagctctgt ttatttggcc acagcacagt tacaagtagg acctgaagag      420
```

```
aaaattgctc taaaacactt gattccaaca agtcatccta taagaattgc agctgaactt    480
cagtgcctaa cagtggctgg ggggcaagat aatgtcatgg gagttaaata ctgctttagg    540
aagaatgatc atgtagttat tgctatgcca tatctggagc atgagtcgtt tttggacatt    600
ctgaattctc tttcctttca agaagtacgg gaatatatgc ttaatctgtt caaagctttg    660
aaacgcattc atcagtttgg tattgttcac cgtgatgtta agcccagcaa ttttttatat    720
aataggcgcc tgaaaagta tgccttggta gactttggtt tggcccaagg aacccatgat     780
acgaaaatag agcttcttaa atttgtccag tctgaagctc agcaggaaag gtgttcacaa    840
aacaaatccc acataatcac aggaaacaag attccactga gtgcccagt acctaaggag     900 ctggatcagc agtccaccac aaaagcttct gttaaaagac cctacacaaa tgcacaaatt    960
cagattaaac aaggaaaaga cggaaaggag ggatctgtag gcctttctgt ccagcgctct    1020 gttttttggag aaagaaattt caatatacac agctccattt cacatgagag ccctgcagtg    1080
aaactcatga agcagtcaaa gactgtggat gtactgtcta aaagttagc aacaaaaaag      1140 aaggctattt ctacaaaagt tatgaatagt gctgtgatga ggaaaactgc cagttcttgc    1200
ccagctagcc tgacctgtga ctgctatgca acagataaag tttgtagtat ttgccttca     1260 aggcgtcagc aggttgcccc tagggcaggt acaccaggat tcagagcacc agaggtcttg    1320
acaaagtgcc ccaatcaaac tacagcaatt gacatgtggt ctgcaggtgt catatttctt    1380
tctttgctta gtggacgata tccatttat aaagcaagtg atgatttaac tgctttggcc      1440
caaattatga caattagggg atccagagaa actatccaag ctgctaaaac ttttgggaaa    1500
tcaatattat gtagcaaaga agttccagca caagacttga aaaactctg tgagagactc     1560 aggggtatgg attctagcac tcccaagtta acaagtgata taaagggca tgcttctcat      1620 caaccagcta tttcagagaa gactgaccat aaagcttctt gcctcgttca aacacctcca    1680
ggacaatact cagggaattc atttaaaaag ggggatagta atagctgtga gcattgtttt    1740
gatgagtata ataccaattt agaaggctgg aatgaggtac ctgatgaagc ttatgacctg    1800
cttgataaac ttctagatct aaatccagct tcaagaataa cagcagaaga agctttgttg    1860
catccatttt ttaaagatat gagccttgtga taatggatct tcatttaatg tttactgtta    1920
tgaggtagaa taaaaagaa tactttgtaa tagccacaag ttcttgttta gagaccagag    1980
caggattaat aatttatttt aacattttag tgtttggtgg cacattctaa aatatagatt    2040
aagaatactt aaaatgcctg ggatagttct tgggactaac aacatgatct tctttgagtt    2100
aaacctacct aagtagattt taggtgggtt cctattaggt cagattttta gcttccctaa    2160 ttaccttttca ctgacatata cagaaaaagg agcagtttta gttttaatta attaaaatta    2220
acagatgtga tgaggattaa atgaatcaaa agacttaatt tgtagattct tttagagtta    2280
tgagctaggt atagtttggg gaaactcaac ctggtgctgg tgctcttaac aattttgtaa    2340
ataaagaaga taatttcctt ttctagaggt acatattagg cctttatga acactaaaac    2400 aatgaggaaa tgttggtcat ggggcaaagt atcacttaaa attgaattca tccattttta    2460 aaaacactt catgaaagca ttctggtgtg aattgccatt tttttcttac tggcttctca     2520
attttcttcc ttctctgccc ctacctaaaa cattctcctc ggaaattaca tggtgctgac    2580
cacaaagttt ctggatgttt tattaaatat tgtacgtgtt tacagttggg aatttaaaat    2640
aatacataca ctggttgata aagggaagct gcaggaccaa ggtgaagatt gatagtccaa    2700 atgctttct ttttgagtt gtatattttt tcacaccatc ttagatataa ttaggtagct      2760
gctgaaagga aaagtgaata cagaattgac ggtattattg gagattttc ctctgcgtag     2820
```

```
agccatccag atctctgtat cctgttttga ctaagtctta ggtgggttgg gaagacagat   2880
aatgaagtag gcaaagagaa aaggacccaa gatagaggtt tatattcaga aatggtatat   2940
atcaatgaca gcatatcaaa cttcctatgg gaaaaagtct ggtgggtggt cagctgacag   3000
atttcccatt tagtagtcat agaatacaga aatagtttag gacatgtat tcattttgtt    3060 attttgagca ttgataggtc agtatatcta cctaatctgt ttggtaagta taggatatat   3120
aaaccattac cattgatctg tcttatgcca taatcttaaa aaaaatttga atgctcttga   3180
atttgtatat tcaataaagt tatccttta tatttttaa aa                        3222

<210> SEQ ID NO 5
<211> LENGTH: 1697
<212> TYPE: DNA
<213> ORGANISM: Homo sapiens

<400> SEQUENCE: 5
gaggcgtaag ccaggcgtgt taaagccggt cggaactgct ccggagggca cgggctccgt     60
aggcaccaac tgcaaggacc cctcccctg cgggcgctcc catggcacag ttcgcgttcg    120
agagtgacct gcactcgctg cttcagctgg atgcacccat ccccaatgca cccctgcgc    180 gctggcagcg caaagccaag gaagccgcag gcccggcccc ctcacccatg cgggccgcca    240
accgatccca cagcgccggc aggactccgg gccgaactcc tggcaaatcc agttccaagg    300
ttcagaccac tcctagcaaa cctggcggtg accgctatat cccccatcgc agtgctgccc    360
agatggaggt ggccagcttc ctcctgagca aggagaacca gcctgaaaac agccagacgc    420
ccaccaagaa ggaacatcag aaagcctggg cttttgaacct gaacggtttt gatgtagagg    480
aagccaagat ccttcggctc agtggaaaac cacaaaatgc gccagagggt tatcagaaca    540
gactgaaagt actctacagc caaaaggcca ctcctggctc cagccggaag acctgccgtt    600
acattccttc cctgccagac cgtatcctgg atgcgcctga atccgaaat gactattacc    660 tgaaccttgt ggattggagt tctgggaatg tactggccgt ggcactggac aacagtgtgt    720
acctgtggag tgcaagctct ggtgacatcc tgcagctttt gcaaatggag cagcctgggg    780
aatatatatc ctctgtggcc tggatcaaag agggcaacta cttggctgtg gcaccagca    840 gtgctgaggt gcagctatgg gatgtgcagc agcagaaacg gcttcgaaat atgaccagtc    900
actctgcccg agtgggctcc ctaagctgga acagctatat cctgtccagt ggttcacgtt    960
ctggccacat ccaccaccat gatgttcggg tagcagaaca ccatgtggcc acactgagtg   1020
gccacagcca ggaagtgtgt gggctgcgct gggcccaga tggacgacat ttggccagtg   1080
gtggtaatga taacttggtc aatgtgtggc ctagtgctcc tggagagggt ggctgggttc   1140
ctctgcagac attcacccag catcaagggg ctgtcaaggc cgtagcatgg tgtccctggc   1200
agtccaatgt cctggcaaca ggaggggggca ccagtgatcg acacattcgc atctggaatg   1260
tgtgctctgg ggcctgtctg agtgccgtgg atgcccattc ccaggtgtgc tccatcctct   1320
ggtctcccca ttacaaggag ctcatctcag gccatggctt tgcacagaac cagctagtta   1380
tttggaagta cccaaccatg gccaaggtgg ctgaactcaa aggtcacaca tcccgggtcc   1440
tgagtctgac catgagccca gatggggcca cagtggcatc cgcagcagca gatgagaccc   1500
tgaggctatg gcgctgtttt gagttggacc ctgcgcggcg gcgggagcgg gagaaggcca   1560
gtgcagccaa aagcagcctc atccaccaag gcatccgctg aagaccaacc catcacctca   1620
gttgtttttt attttctaa taaagtcatg tctcccttca tgtttttttt ttaaaaaaaa    1680
```
aaaaaaaaaa aaaaaaa                                                        1697

<210> SEQ ID NO 6
<211> LENGTH: 1938
<212> TYPE: DNA
<213> ORGANISM: Homo sapiens

<400> SEQUENCE: 6
gatttggcgg gagtcttgac cgccgccggg ctcttggtac ctcagcgcga gcgccaggcg    60
tccggccgcc gtggctatgt tcgtgtccga tttccgcaaa gagttctacg aggtggtcca   120
gagccagagg gtccttctct tcgtggcctc ggacgtggat gctctgtgtg cgtgcaagat   180
ccttcaggcc ttgttccagt gtgaccacgt gcaatatacg ctggttccag tttctgggtg   240
gcaagaactt gaaactgcat tcttgagca taaagaacag tttcattatt ttattctcat   300
aaactgtgga gctaatgtag acctattgga tattcttcaa cctgatgaag acactatatt   360
ctttgtgtgt gacacccata ggccagtcaa tgtcgtcaat gtatacaacg atacccagat   420
caaattactc attaaacaag atgatgacct tgaagttccc gcctatgaag acatcttcag   480
ggatgaagag gaggatgaag agcattcagg aaatgacagt gatgggtcag agccttctga   540
gaagcgcaca cggttagaag aggagatagt ggagcaaacc atgcggagga ggcagcggcg   600
agagtgggag gcccggagaa gagacatcct ctttgactac gagcagtatg aatatcatgg   660
gacatcgtca gccatggtga tgtttgagct ggcttggatg ctgtccaagg acctgaatga   720
catgctgtgg tgggccatcg ttggactaac agaccagtgg gtgcaagaca gatcactca   780
aatgaaatac gtgactgatg ttggtgtcct gcagcgccac gtttcccgcc acaaccaccg   840
gaacgaggat gaggagaaca cactctccgt ggactgcaca cggatctcct tgagtatga   900
cctccgcctg gtgctctacc agcactggtc cctccatgac agcctgtgca acaccagcta   960
taccgcagcc aggttcaagc tgtggtctgt gcatggacag aagcggctcc aggagttcct  1020
tgcagacatg ggtcttcccc tgaagcaggt gaagcagaag ttccaggcca tggacatctc  1080
cttgaaggag aatttgcggg aaatgattga agtctgca aataaatttg ggatgaagga  1140
catgcgcgtg cagactttca gcattcattt tgggttcaag cacaagtttc tggccagcga  1200
cgtggtcttt gccaccatgt ctttgatgga gagccccgag aaggatggct cagggacaga  1260
tcacttcatc caggctctgg acagcctctc caggagtaac ctggacaagc tgtaccatgg  1320
cctggaactc gccaagaagc agctgcgagc cacccagcag accattgcca gctgcctttg  1380
caccaacctc gtcatctccc aggggccttt cctgtactgc tctctcatgg agggcactcc  1440
agatgtcatg ctgttctcta ggccggcatc cctaagcctg ctcagcaaac acctgctcaa  1500
gtccttttgtg tgttcgacaa agaaccggcg ctgcaaactg ctgcccctgg tgatggctgc  1560
ccccctgagc atggagcatg gcacagtgac cgtggtgggc atccccccag agaccgacag  1620
ctcggacagg aagaactttt tggggagggc gtttgagaag gcagcggaaa gcaccagctc  1680
ccggatgctg cacaaccatt ttgacctctc agtaattgag ctgaaagctg aggatcggag  1740
caagtttctg gacgcactta tttccctcct gtcctaggaa tttgattctt ccagaatgac  1800
cttcttattt atgtaactgg ctttcattta gattgtaagt tatggacatg atttgagatg  1860
tagaagccat tttttattaa ataaaatgct tattttaggc tccgtcccca aaaaaaaaa   1920
aaaaaaaaaa aaaaaaa                                                 1938

<210> SEQ ID NO 7
<211> LENGTH: 2811

<212> TYPE: DNA
<213> ORGANISM: Homo sapiens

<400> SEQUENCE: 7

```
ccatttcaat agtcgcggga tacttgaact gcaagaacag ccgccgctcc ggcgggctgc      60
tcgctgcatc tctgggcgtc tttggctcgc cacgctgggc agtgcctgcc tgcgcctttc     120
gcaacctcct cggccctgcg tggtctcgag ctgggtgagc gagcgggcgg gctggtaggc     180
tggcctgggc tgcgaccggc ggctacgact attctttggc cgggtcggtg cgagtggtcg     240
gctgggcaga gtgcacgctg cttggcgccg caggctgatc ccgccgtcca ctcccgggag     300
cagtgatgtt gggcaactct cgccggggc ctgcgacccg cgaggcgggc tcggcgctgc     360
tagcattgca gcagacggcg ctccaagagg accaggagaa tatcaacccg gaaaaggcag     420
cgcccgtcca acaaccgcgg acccgggccg cgctggcgt actgaagtcc gggaaccccgc     480
ggggtctagc gcagcagcag aggccgaaga cgagacgggt tgcacccctt aaggatcttc     540
ctgtaaatga tgagcatgtc accgttcctc cttggaaagc aaacagtaaa cagcctgcgt     600
tcaccattca tgtggatgaa gcagaaaaag aagctcagaa gaagccagct gaatctcaaa     660
aaatagagcg tgaagatgcc ctggctttta attcagccat tagtttacct ggacccagaa     720
aaccattggt ccctcttgat tatccaatgg atggtagttt tgagtcacca catactatgg     780
acatgtcaat tgtattagaa gatgaaaagc cagtgagtgt taatgaagta ccagactacc     840
atgaggatat tcacacatac cttagggaaa tggaggttaa atgtaaacct aaagtgggtt     900
acatgaagaa acagccagac atcactaaca gtatgagagc tatcctcgtg gactggttag     960
ttgaagtagg agaagaatat aaactacaga atgagaccct gcatttggct gtgaactaca    1020
ttgataggtt cctgtcttcc atgtcagtgc tgagaggaaa acttcagctt gtgggcactg    1080
ctgctatgct gttagcctca aagtttgaag aaatatacc cccagaagta gcagagtttg    1140
tgtacattac agatgatacc tacaccaaga acaagttct gagaatggag catctagttt    1200
tgaaagtcct tacttttgac ttagctgctc caacagtaaa tcagtttctt acccaatact    1260
ttctgcatca gcagcctgca aactgcaaag ttgaaagttt agcaatgttt ttgggagaat    1320
taagtttgat agatgctgac ccataccctca agtatttgcc atcagttatt gctggagctg    1380
cctttcattt agcactctac acagtcacgg gacaaagctg gcctgaatca ttaatacgaa    1440
agactggata taccctggaa agtcttaagc cttgtctcat ggaccttcac cagacctacc    1500
tcaaagcacc acagcatgca caacagtcaa taagagaaaa gtacaaaaat tcaaagtatc    1560
atggtgtttc tctcctcaac ccaccagaga cactaaatct gtaacaatga aagactgcct    1620
ttgtttccta agatgtaaat cactcaaagt atatggtgta cagttttaa cttaggtttt    1680
aattttacaa tcatttctga atacagaagt tgtggccaag tacaaattat ggtatctatt    1740
actttttaaa tggttttaat ttgtatatct tttgtatatg tatctgtctt agatatttgg    1800
ctaattttaa gtggttttgt taagtatta atgatgccag ctgtcaggat aataaattga    1860
tttggaaaac tttgcaagtc aaatttaact tcttcaggat tttgcttagt aaagaagttt    1920
acttggttta ctatataatg ggaagtgaaa agccttcctc taaaattaaa gtaggtttag    1980
gaaaacagac cctcaaattc tgacattcat tttcctaagc aactggatca atttgctgac    2040
ttgggcataa tctaatctaa gcatatctga atacagtatt cagagataga tacagtagag    2100
attccccaga cttttttcgct cttttgtaaaa cctgtttgtt taggttttgc gaggtaaact    2160
caacagaggt tgggagtgga agagggtggg aagcttatat gcaaattaac agacgagaaa    2220
```

```
tgctccagaa ggtttattat tttaaagcac attaaaaaca aaaaactatt tttaaaatcc      2280
tgctagattt tataatggat ttgtgaataa aaaatacccca gggttctcag aatggaataa      2340 atatccctttt taatagttat atatacagat atacaactgt tagctttaat tggcagctct      2400
cttctttttt cttcttttca ctggcttttt acttggtgct ttttcttgtt ttgcactggt      2460
ggtctgtgtt ctgtgaataa agcaaagtaa gaatttacta agagtatgtt aagttttgga      2520
ttattgaaat aagaggcatt tcttagtttt ccagtaggat ctaaaatgtg tcagctatga      2580
gtaagactgg catccaagaa gtttatatta tagatttagg tcctaatttt tataaatcac      2640
aaggtaaaaa aatcacagaa cagatggatc tctaatgaaa aagggatgtc tttttgttta      2700
tagtcatgtg gcaagatgag agtaaaacca gagagcaaac ctctataagt gttgagtata      2760
tgtatacatt tgaaataaac cagaaatttg ttaccttaaa aaaaaaaaa a               2811
```

<210> SEQ ID NO 8
<211> LENGTH: 2101
<212> TYPE: DNA
<213> ORGANISM: Homo sapiens

<400> SEQUENCE: 8

```
acgaacaggc caataaggag ggagcagtgc ggggtttaaa tctgaggcta ggctggctct       60
tctcggcgtg ctgcggcgga acggctgttg gtttctgctg ggtgtaggtc cttggctggt      120
cgggcctccg tgttctgct tctccccgct gagctgctgc ctggtgaaga ggaagccatg       180
gcgctccgag tcaccaggaa ctcgaaaatt aatgctgaaa ataaggcgaa gatcaacatg      240
gcaggcgcaa agcgcgttcc tacggcccct gctgcaacct ccaagcccgg actgaggcca      300
agaacagctc ttggggacat tggtaacaaa gtcagtgaac aactgcaggc caaaatgcct      360
atgaagaagg aagcaaaacc ttcagctact ggaaaagtca ttgataaaaa actaccaaaa      420
cctcttgaaa aggtacctat gctggtgcca gtgccagtgt ctgagccagt gccagagcca      480
gaacctgagc cagaacctga gcctgttaaa gaagaaaaac tttcgcctga gcctattttg      540
gttgatactg cctctccaag cccaatggaa acatctggat gtgcccctgc agaagaagac      600
ctgtgtcagg ctttctctga tgtaattctt gcagtaaatg atgtggatgc agaagatgga      660
gctgatccaa accttttgtag tgaatatgtg aaagatattt atgcttatct gagacaactt      720
gaggaagagc aagcagtcag accaaaatac ctactgggtc gggaagtcac tggaaacatg      780
agagccatcc taattgactg gctagtacag gttcaaatga aattcaggtt gttgcaggag      840
accatgtaca tgactgtctc cattattgat cggttcatgc agaataattg tgtgcccaag      900
aagatgctgc agctggttgg tgtcactgcc atgtttattg caagcaaata tgaagaaatg      960
taccctccag aaattggtga ctttgctttt gtgactgaca cacttatac taagcaccaa      1020 atcagacaga tggaaatgaa gattctaaga gctttaaact ttggtctggg tcggcctcta      1080
cctttgcact tccttcggag agcatctaag attggagagg ttgatgtcga gcaacatact      1140
ttggccaaat acctgatgga actaactatg ttggactatg acatggtgca ctttcctcct      1200
tctcaaattg cagcaggagc tttttgctta gcactgaaaa ttctggataa tggtgaatgg      1260
acaccaactc tacaacatta cctgtcatat actgaagaat ctcttcttcc agttatgcag      1320
cacctggcta agaatgtagt catggtaaat caaggactta caaagcacat gactgtcaag      1380
aacaagtatg ccacatcgaa gcatgctaag atcagcactc taccacagct gaattctgca      1440
ctagttcaag atttagccaa ggctgtggca aaggtgtaac ttgtaaactt gagttggagt      1500 actatatttta caaataaaat tggcaccatg tgccatctgt acatattact gttgcattta      1560
```

-continued

| | |
|---|---|
| cttttaataa agcttgtggc cccttttact tttttatagc ttaactaatt tgaatgtggt | 1620 |
| tacttcctac tgtagggtag cggaaaagtt gtcttaaaag gtatggtggg gatatttta | 1680 |
| aaaactcctt ttggtttacc tggggatcca attgatgtat atgtttatat actgggttct | 1740 |
| tgttttatat acctggcttt tactttatta atatgagtta ctgaaggtga tggaggtatt | 1800 |
| tgaaaatttt acttccatag gacatactgc atgtaagcca agtcatggag aatctgctgc | 1860 |
| atagctctat tttaaagtaa aagtctacca ccgaatccct agtcccctg ttttctgttt | 1920 |
| cttcttgtga ttgctgccat aattctaagt tatttacttt taccactatt taagttatca | 1980 |
| actttagcta gtatcttcaa actttcactt tgaaaaatga gaattttata ttctaagcca | 2040 |
| gttttcattt tggttttgtg ttttggttaa taaaacaata ctcaaataca aaaaaaaaa | 2100 |
| a | 2101 |

<210> SEQ ID NO 9
<211> LENGTH: 1530
<212> TYPE: DNA
<213> ORGANISM: Homo sapiens

<400> SEQUENCE: 9

| | |
|---|---|
| aatcctggaa caaggctaca gcgtcgaaga tccccagcgc tgcgggctcg gagagcagtc | 60 |
| ctaacggcgc ctcgtacgct agtgtcctcc cttttcagtc cgcgtccctc cctgggccgg | 120 |
| gctggcactc ttgccttccc cgtccctcat ggcgctgctc cgacgcccga cggtgtccag | 180 |
| tgatttggag aatattgaca caggagttaa ttctaaagtt aagagtcatg tgactattag | 240 |
| gcgaactgtt ttagaagaaa ttggaaatag agttacaacc agagcagcac aagtagctaa | 300 |
| gaaagctcag aacaccaaag ttccagttca acccaccaaa acaacaaatg tcaacaaaca | 360 |
| actgaaaccct actgcttctg tcaaaccagt acagatggaa aagttggctc caaagggtcc | 420 |
| ttctcccaca cctgaggatg tctccatgaa ggaagagaat ctctgccaag cttttttctga | 480 |
| tgccttgctc tgcaaaatcg aggacattga taacgaagat tgggagaacc ctcagctctg | 540 |
| cagtgactac gttaaggata tctatcagta tctcaggcag ctggaggttt tgcagtccat | 600 |
| aaacccacat ttcttagatg gaagagatat aaatggacgc atgcgtgcca tcctagtgga | 660 |
| ttggctggta caagtccact ccaagtttag gcttctgcag gagactctgt acatgtgcgt | 720 |
| tggcattatg gatcgatttt tacaggttca gccagtttcc cggaagaagc ttcaattagt | 780 |
| tgggattact gctctgctct tggcttccaa gtatgaggag atgttttctc caaatattga | 840 |
| agactttgtt tacatcacag acaatgctta taccagttcc caaatccgag aaatggaaac | 900 |
| tctaattttg aaagaattga aatttgagtt gggtcgaccc ttgccactac acttcttaag | 960 |
| gcgagcatca aaagccgggg aggttgatgt tgaacagcac actttagcca agtatttgat | 1020 |
| ggagctgact ctcatcgact atgatatggt gcattatcat ccttctaagg tagcagcagc | 1080 |
| tgcttcctgc ttgtctcaga aggttctagg acaaggaaaa tggaacttaa agcagcagta | 1140 |
| ttacacagga tacacagaga atgaagtatt ggaagtcatg cagcacatgg ccaagaatgt | 1200 |
| ggtgaaagta aatgaaaact taactaaatt catcgccatc aagaataagt atgcaagcag | 1260 |
| caaactcctg aagatcagca tgatccctca gctgaactca aaagccgtca agaccttgc | 1320 |
| ctccccactg ataggaaggt cctaggctgc cgtgggccct ggggatgtgt gcttcattgt | 1380 |
| gcccttttc ttattggttt agaactcttg attttgtaca tagtcctctg gtctatctca | 1440 |
| tgaaacctct tctcagacca gttttctaaa catatattga ggaaaaataa agcgattggt | 1500 |

```
ttttcttaag gtaaaaaaaa aaaaaaaaa                                    1530
```

<210> SEQ ID NO 10
<211> LENGTH: 627
<212> TYPE: DNA
<213> ORGANISM: Homo sapiens

<400> SEQUENCE: 10

```
agtctccggc gagttgttgc ctgggctgga cgtggttttg tctgctgcgc ccgctcttcg     60
cgctctcgtt tcattttctg cagcgcgcca cgaggatggc ccacaagcag atctactact    120
cggacaagta cttcgacgaa cactacgagt accggcatgt tatgttaccc agagaacttt    180
ccaaacaagt acctaaaact catctgatgt ctgaagagga gtggaggaga cttggtgtcc    240
aacagagtct aggctgggtt cattacatga ttcatgagcc agaaccacat attcttctct    300
ttagacgacc tcttccaaaa gatcaacaaa atgaagtttt atctggggat cgtcaaatct    360
ttttcaaatt taatgtatat gtgtatataa ggtagtattc agtgaatact tgagaaatgt    420
acaaatcttt catccatacc tgtgcatgag ctgtattctt cacagcaaca gagctcagtt    480
aaatgcaact gcaagtaggt tactgtaaga tgtttaagat aaaagttctt ccagtcagtt    540
tttctcttaa gtgcctgttt gagtttactg aaacagttta cttttgttca ataaagtttg    600
tatgttgcat ttaaaaaaaa aaaaaaa                                        627
```

<210> SEQ ID NO 11
<211> LENGTH: 2501
<212> TYPE: DNA
<213> ORGANISM: Homo sapiens

<400> SEQUENCE: 11

```
cgaaaagatt cttaggaacg ccgtaccagc cgcgtctctc aggacagcag gcccctgtcc     60
ttctgtcggg cgccgctcag ccgtgccctc cgcccctcag gttcttttc taattccaaa    120
taaacttgca agaggactat gaaagattat gatgaacttc tcaaatatta tgaattacat    180
gaaactattg ggacaggtgg ctttgcaaag gtcaaacttg cctgccatat ccttactgga    240
gagatggtag ctataaaaat catggataaa acacactag ggagtgattt gccccggatc    300
aaaacggaga ttgaggcctt gaagaacctg agacatcagc atatatgtca actctaccat    360
gtgctagaga cagccaacaa atattcatg gttcttgagt actgccctgg aggagagctg    420
tttgactata taatttccca ggatcgcctg tcagaagagg agacccgggt tgtcttccgt    480
cagatagtat ctgctgttgc ttatgtgcac agccagggct atgctcacag ggacctcaag    540
ccagaaaatt tgctgtttga tgaatatcat aaattaaagc tgattgactt tggtctctgt    600
gcaaaaccca gggtaacaa ggattaccat ctacagacat gctgtgggag tctggcttat    660
gcagcacctg agttaataca aggcaaatca tatcttggat cagaggcaga tgtttggagc    720
atgggcatac tgttatatgt tcttatgtgt ggatttctac catttgatga tgataatgta    780
atggcttat acaagaagat tatgagagga aaatatgatg ttcccaagtg gctctctccc    840
agtagcattc tgcttcttca acaaatgctg caggtggacc caaagaaacg gatttctatg    900
aaaaatctat tgaaccatcc ctggatcatg caagattaca actatcctgt tgagtggcaa    960
agcaagaatc cttttattca cctcgatgat gattgcgtaa cagaactttc tgtacatcac   1020
agaaacaaca gcaaacaat ggaggattta atttcactgt ggcagtatga tcacctcacg   1080
gctacctatc ttctgcttct agccaagaag gctcggggaa aaccagttcg tttaaggctt   1140
tcttctttct cctgtggaca agccagtgct acccccattca cagacatcaa gtcaaataat   1200
```

```
tggagtctgg aagatgtgac cgcaagtgat aaaaattatg tggcgggatt aatagactat    1260
gattggtgtg aagatgattt atcaacaggt gctgctactc cccgaacatc acagtttacc    1320
aagtactgga cagaatcaaa tggggtggaa tctaaatcat taactccagc cttatgcaga    1380
acacctgcaa ataaattaaa gaacaaagaa atgtatata ctcctaagtc tgctgtaaag     1440
aatgaagagt actttatgtt tcctgagcca agactccag ttaataagaa ccagcataag     1500
agagaaatac tcactacgcc aaatcgttac actacaccct caaaagctag aaaccagtgc    1560
ctgaaagaaa ctccaattaa ataccagta aattcaacag gaacagacaa gttaatgaca    1620
ggtgtcatta gccctgagag gcggtgccgc tcagtggaat tggatctcaa ccaagcacat    1680
atggaggaga ctccaaaaag aaagggagcc aaagtgtttg ggagccttga aggggggttg    1740
gataaggtta tcactgtgct caccaggagc aaaaggaagg gttctgccag agacgggccc    1800
agaagactaa agcttcacta taatgtgact acaactagat tagtgaatcc agatcaactg    1860
ttgaatgaaa taatgtctat tcttccaaag aagcatgttg actttgtaca aaagggttat    1920
acactgaagt gtcaaacaca gtcagatttt gggaaagtga caatgcaatt tgaattagaa    1980
gtgtgccagc ttcaaaaacc cgatgtggtg ggtatcagga ggcagcggct taagggcgat    2040
gcctgggttt acaaaagatt agtggaagac atcctatcta gctgcaaggt ataattgatg    2100
gattcttcca tcctgccgga tgagtgtggg tgtgatacag cctacataaa gactgttatg    2160
atcgctttga ttttaaagtt cattggaact accaacttgt ttctaaagag ctatcttaag    2220
accaatatct ctttgttttt aaacaaaaga tattattttg tgtatgaatc taaatcaagc    2280
ccatctgtca ttatgttact gtctttttta atcatgtggt tttgtatatt aataattgtt    2340
gactttctta gattcacttc catatgtgaa tgtaagctct taactatgtc tctttgtaat    2400
gtgtaatttc tttctgaaat aaaaccattt gtgaatataa aaaaaaaaa aaaaaaaaa     2460 aaaaaaaaa aaaaaaaaa aaaaaaaaa aaaaaaaaa a                           2501
```

<210> SEQ ID NO 12
<211> LENGTH: 1170
<212> TYPE: DNA
<213> ORGANISM: Homo sapiens

<400> SEQUENCE: 12

```
aagtttgaaa ctggtaactt cgggagttga gccacgagct gttgtgcatc cagaggtgga      60
attggggccc ggcattccct cctcgtcccg ggctggccct tgcccccacc ctgcaactcc     120
tggttgagat gggctcagcc aagagcgtcc cagtcacacc agcgcggcct ccgccgcaca     180
acaagcatct ggctcgagtg gcggaccccc gttcacctag tgctggcatc ctgcgcactc     240
ccatccaggt ggagagctct ccacagccag gcctaccagc aggggagcaa ctggagggtc     300
ttaaacatgc ccaggactca gatccccgct ctcctactct tggtattgca cggacaccta     360
tgaagaccag cagtggagac cccccaagcc cactggtgaa acagctgagt gaagtatttg     420
aaactgaaga ctctaaatca aatcttcccc cagagcctgt tctgcccca gaggcacctt      480 tatcttctga attggacttg cctctgggta cccagttatc tgttgaggaa cagatgccac     540
cttggaacca gactgagttc ccctccaaac aggtgttttc caaggaggaa gcaagacagc     600
ccacagaaac ccctgtggcc agccagagct ccgacaagcc ctcaagggac cctgagactc     660
ccagatcttc aggttctatg cgcaatagat ggaaaccaaa cagcagcaag gtactaggga     720 gatccccct caccatcctg caggatgaca actcccctgg caccctgaca ctacgacagg     780
```

-continued

```
gtaagcggcc ttcaccccta agtgaaaatg ttagtgaact aaaggaagga gccattcttg    840
gaactggacg acttctgaaa actggaggac gagcatggga gcaaggccag gaccatgaca    900
aggaaaatca gcactttccc ttggtggaga gctaggccct gcatggcccc agcaatgcag    960
tcacccaggg cctggtgata tctgtgtcct ctcacccctt ctttcccagg gatactgagg   1020
aatggcttgt tttcttagac tcctcctcag ctaccaaact gggactcaca gctttattgg   1080
gctttctttg tgtcttgtgt gtttcttttta tattaaagga agtaattttta aatgttactt   1140
taaaaaggta tatgtaaacc ttgcaccgag                                    1170
```

<210> SEQ ID NO 13
<211> LENGTH: 4495
<212> TYPE: DNA
<213> ORGANISM: Homo sapiens

<400> SEQUENCE: 13

```
gccggcgacg tcacgcggcc gttacggcgc tcaggcgtct cgacgcgcgc gatttaaaac     60
cagctcagga gacgccaagg aaagatggga cctcccggcc cagcactgcc agccacaatg    120
aataactctt cttcagagac gcgaggacac ccccacagtg cctcctctcc ttcagagcgt    180
gtgttcccga tgcccctgcc caggaaggcg cctctcaata ttcctggcac cccagtcctc    240
gaagactttc ctcagaatga cgatgagaag gagcggctgc agcggaggcg ctcgagggtc    300
tttgatctgc agttcagcac tgactcacct cgcttattgg cctcccccctc cagcaggagt    360
attgacattt cagctactat ccccaagttt acaaacacgc agattacgga acattactcc    420
acctgtatca aactgtccac tgaaaataaa atcactacca agaatgcttt ggtttgcac     480
ttgattgatt ttatgtcaga gattcttaaa cagaaagaca ccgaaccaac caactttaaa    540
gtggctgcgg gtactctgga tgccagcacc aagatctatg ctgtgcgcgt ggatgccgtc    600
catgccgatg tatacagagt ccttgggggg ctgggcaaag atgcaccgtc tttggaagaa    660
gtagaaggcc atgttgctga tggaagtgct actgaaatgg gaacaaccaa aaaggctgta    720
aagccaaaga agaagcactt acacagaact attgagcaga acataaacaa cctcaatgtc    780
tccgaagcag atcggaagtg tgagattgat cccatgtttc agaagacagc agcctcattt    840
gatgagtgca gcacagcagg ggtgtttctg tccactctcc actgccagga ctacagaagt    900
gaactgctgt ttccctctga tgtccagact ctctccacgg gagaacctct cgagttgcca    960
gagttaggtt gtgtagaaat gacagattta aaagcgccct gcagcagtg tgcagaagat   1020
cgccagatct gccctttccct ggccgggttc cagtttacac agtgggacag tgaaacacat   1080
aatgagtctg tgtcggccct ggtagacaag tttaagaaga tgaccaggt atttgacatc   1140
aatgctgaag ttgacgagag tgactgtgga gacttccccg atgggtccct ggggatgac    1200
tttgatgcca acgatgaacc tgaccacacc gcagttgggg atcatgaaga gttcaggagc   1260
tggaaggagc cctgccaggt tcagagctgc caggaagaaa tgatttccct tggggatgga   1320
gacatcagga ccatgtgccc ccttctgtct atgaaacctg gagaatattc ttatttcagt   1380
cctcggacca tgtcgatgtg ggctggcccg gatcactggc gctttaggcc tcgacgcaaa   1440
caagatgctc cttcccaatc agaaaacaaa aagaagagta caaaaaaaga ttttgaaatt   1500
gactttgaag atgatattga ctttgatgta tattttagaa aaacaaaggc tgctactatt   1560
ctgaccaagt ccactttgga gaaccagaat tggagagcta ccaccttcc tacagatttc   1620
aactacaatg ttgacactct ggtccagctt cacctcaaac caggcaccag gttacttaag   1680
atggcccagg ccatagggt agagactgag cattatgaag aaattgaaga ctatgattac   1740
```

```
aacaacccta acgacacctc caacttttgc cctggattac aggctgctga cagtgatgat    1800
gaagatttgg atgacttatt tgtgggacct gttgggaact ctgacctctc accttatcct    1860
tgccatccac ctaagacagc acaacagaat ggtgacactc cagaagccca aggattagac    1920
atcacaacat atggggagtc aaacttggta gctgagcctc agaaggtaaa taaaattgaa    1980
attcactatg ccaagactgc caaaaagatg gacatgaaga aactgaagca gagcatgtgg    2040
agtctgctga cagcgctctc cggaaaggag gcagatgcag aggcaaacca cagggaagct    2100
ggaaaagaag cggccctggc agaagtggct gacgagaaga tgcttagcgg gctcacgaag    2160
gacctgcaga ggagcctgcc ccctgtcatg gctcagaacc tctccatacc tctggctttt    2220
gcctgtctcc tacatttagc caatgaaaag aatctaaaac tggaaggaac agaggacctc    2280
tctgatgttc ttgtgaggca aggagattga gttcactatg gagaagtcag cagcaggagg    2340
cccatccctt actcagttgc cgggacatcc ccagtctcgg gggaagaaga tgccatgggc    2400
ttatacccag gctgtagcca actaccaacg tgcctgtttg tttgttgctc tttccttctc    2460
tccatcatag tctgggtgcc agcgccctga agctccgtgc tcaactgatt aaactttact    2520
gccctatggt gaccatctag gagaggggag ggcagagggg gtgagggtac tattctggat    2580
tgagaaaacc tatatccatt ctttatatca atgtatagtt ttagtctcct aaattgatct    2640
gttattttcc aaactattct cttgtagaaa attttccagt gggcacttaa tggtgccctt    2700
gaagaacttc ctaatccatg tacataaaat acatcatatg tacacttata aatgtatata    2760
gaatgctcaa aaataaaatt cttaataata gaactggcaa atatttgag tgtccactag     2820 atgagtatca gacctagtcc ttacccttag ggggatgcag tcctggttgt tatccaggat    2880
acacacctgt cagtataagg cagaagatgc ctaagggcca agatggtttg cctcggagga    2940
gaatggaaga gagagattgc tgactggaca ttcagatgca agactgggtc ctgcttaaat    3000
cccaggattc tgctggaggg agctgatagt gatacttgtc ccttctgtac attgcttcat    3060
gtagccttct cagcatccct aggagaaact tactattgtg actctcatgt tggaggagga    3120
aacggacacc caaggtagag gaacttgcaa aagggcagcc ggcaaactgt cagggggtggc   3180 ctgagcctgg caatctgcct ccagagtctg ctctcggcca ttgtgctatg tgctacctgg    3240
ataggtcata caggctcagc agtgggtgga gagcagtgct cagatttgtc catctccaca    3300
gaatgcagca cacacacaaa tgtacaagtt cttcccctaa cctcagagga ataggggaat    3360
taactttgct tgcaatttgg aacaatatta tagatgttga tccaagtagt tctgttactg    3420
gctggtcctg gatctctgcc agaacacccg tcatcattga ctggctaaat agagatcttg    3480
gatataggcc agaagcagtg aagtatataa ttggaaattg ctcctgataa taacttcctt    3540
cttagccaaa aaccacacaa aacaaaaata atccctccc cacaggaata tgctttccaa     3600
attgtgtcca aaacattacc tgctctgtta tattgagaag gttagagact tcagagcatg    3660
cttagaaaaa gcagtggtgc cacaggtgag actccacact ctgtcttgct ggggctgaag    3720
cctccatcac tttcccaggc caggttagtg ctgggcttct tgctttcctt ctattcctga    3780
gagtagaact ggctaagccc attccttccc tcagtcagcc ccacttctct atagtgggtt    3840
ctggggtgtg ggggctgaat taccagtaaa actagaaaga ttgggaccaa gtgcagtggc    3900
ccacacctgt aaatcctagc gctttgaaag gaagaggcag gaggattgct tgaagtcagg    3960
agttcaagac cagcctgggc aaaatagaac cccatctttta aaaaaaagt ttaaaaatta    4020 gccaggtacg gaggtgtgtg cctgtaatcc cagctactca gaaggctgag gtgggataat    4080
```

```
cacttgagcc caggagtttg aggctgcagt gagctgtgat cacactactg cattccagcc    4140
aggacaacag agtgagatcc tatctcttaa acaaaaaaaa aaactggcga gttcaatacc    4200
aacttctaca atgaaatccc cttcccccca aaccctgct tctcctaagt ttccctcatt     4260
acatggttgc tgtgggctat gtgtgctgtg gtctgaatgt ttgtgtctaa aattcacatg    4320
ttggtattaa gagatagggc ctttgggagg tgattaggtt atgagggcag atccctcgtg    4380
aatgggatta gtgctcttat aaaagaggcc tgaggaagct tgttcgttcc tcttgccctt    4440
ctgccatgta aggatgcaat gagaaggcac catctgtgag caaggagccc ctcac        4495

<210> SEQ ID NO 14
<211> LENGTH: 3938
<212> TYPE: DNA
<213> ORGANISM: Homo sapiens

<400> SEQUENCE: 14
gttctccgcc cccgccgccg ccattacgga gctcccagtg gttgattctt caccacactg      60
aaaccattag gaaaaatcct tgtggttaac agcagaggct tcagagtgta acctgtactc     120
gggcctagaa attatttaaa atggcgactg atacgtctca aggtgaactc gtccatccta     180
aggcactccc acttatagta ggagctcagc tgatccacgc ggacaagtta ggtgagaagg     240
tagaagatag caccatgccg attcgtcgaa ctgtgaattc tacccgggaa actcctccca     300
aaagcaagct tgctgaaggg gaggaagaaa agccagaacc agacataagt tcagaggaat     360
ctgtctccac tgtagaagaa caagagaatg aaactccacc tgctacttcg agtgaggcag     420
agcagccaaa gggggaacct gagaatgaag agaaggaaga aaataagtct ctgaggaaaa     480
ccaaaaagga tgagaaagat cagtctaaag aaaaggagaa gaaagtgaaa aaaacaattc     540
cttcctgggc tacccttcct gccagccagc tagccagggc ccagaaacaa acaccgatgg     600
cttcttcccc acgtcccaag atggatgcaa tcttaactga ggccattaag gcatgcttcc     660
agaagagtgg tgcatcagtg gttgctattc gaaaatacat catccataag tatccttctc     720
tggagctgga gagaagggggt tatctcctta acaagcact gaaaagagaa ttaaatagag     780
gagtcatcaa acaggttaaa ggaaaaggtg cttctggaag ttttgttgtg gttcagaaat     840
caagaaaaac acctcagaaa tccagaaaca gaaagaatag gagctctgca gtggatccag     900
aaccacaagt aaaattggag gatgtcctcc cactggcctt tactcgcctt tgtgaaccta     960
aagaagcttc ctacagtctc atcaggaaat atgtgtctca gtattatcct aagcttagag    1020
tggacatcag gcctcagctg ttgaagaacg ctctgcagag agcagtagag aggggccagt    1080
tagaacagat aactggcaaa ggtgcttcgg ggacattcca gctgaagaaa tcaggggaga    1140
aacccctgct tggtggaagc ctgatggaat atgcaatctt gtctgccatt gctgccatga    1200
atgagccgaa gacctgctct accactgctc tgaagaagta tgtcctagag aatcacccag    1260
gaaccaattc taactatcaa atgcatttgc tgaaaaaaac cctgcagaaa tgcgaaaaga    1320
atgggtggat ggaacagatc tctgggaaag ggttcagtgg caccttccag ctctgttttc    1380
cctattatcc cagcccagga gttctgtttc gaagaaaga gccagatgat tctagagatg     1440
aggatgaaga tgaagatgag tcatcagaag aagactctga ggatgaagag ccgccaccta    1500
agagaaggtt gcagaagaaa accccagcca agtcccagg gaaggccgca tctgtgaagc      1560
agagagggtc caaacctgca cctaaagtct cagctgccca gcggggaaa gctaggccct      1620 tgcctaagaa agcacctcct aaggccaaaa cgcctgccaa gagaccaga ccctcatcca     1680 cagtcatcaa gaaacctagt ggtggctcct caaagaagcc tgcaaccagt gcaagaaagg    1740
```

```
aagtaaaatt gccgggcaag ggcaaatcca ccatgaagaa gtctttcaga gtgaaaaagt    1800
aaattttata ggaaaaaagg gtatcatgat gaaattcaaa atcttatttt ctaaggtcag    1860
tgtgcatttg tttagttttg atgcttttca aattacatta ttttcctccc ctatgaacat    1920
tgtggggagg gactctaaat aaaccagttt aggcatttgc tagctttagg tgcttttatt    1980
ggtgcctgcc cttttccttg ttcattttaa tttctgcaat aatcctggac tttcctaaac    2040
tatgtaatgt atacttgtcc ttttttctctg cctcccccaa ccccctgttg tttttatggt    2100
cagctttgcc ttttttttt cttccaattt tatctaaaca gttgcagaga tttttatatt    2160
tgtagaaagc atcaagaacg gtatgccagt caggtcctgg aagtaaaatg gaggcacaat    2220
atagcactga ctgagttgta aagcctcctg cctggagact tcagttatag ctgtaataat    2280
taatcttatt tataaaagcc actccactaa ccttttctct ccaactgtaa acacagagac    2340
agctttggga ataagccaaa acagggtga tctcattaga ttttgaagat atatgactcc    2400
tttgggctac atttcatatt gatcaatttc taggtatttt tcactggccc aaagtattgc    2460
attcccttaa cagcaagcac aagttctcta tatcacttgt tttttgttgt tgttgttgtt    2520
gtcgtcgttg ttttgagacg gagtcttgct caggtgcccc ggagtgcagt ggtgcaatct    2580
cagctcactg caacctccac ctcctgggtt caagcaattc tcctgcttca gcctcccgag    2640
tagctgggat tacaggtgtg taccaccacg cctggcaatt ttttttgtatt tttagtagag    2700 atggggtttc gccgtgttgg tcaggctggt ctcgaactcc tgacctcagg tgatccgcct    2760
gcctcggcct cccaaagtgc tgggattaca ggagtgagcc actgtgcctg cctatccca    2820 cttggttttt gactgaaggg gaagtgtaga aatatattga tttgtgattt ctggtgtcac    2880
ctgtgttacc aaaaatcaaa acaaatcttt tttattttttt attattatta ttattttga    2940 gacagagtct cgctctgtcg cccagtgtgg agtgcagtgg tgtgatcttg gctcactgca    3000
aactccgcct cccaggttca agcgattctc ccacctcagc ctcctgagtt gggtcctaca    3060
ggcgcacacg accacgccca gctaattttt tgtatttta gtagagttgg ggtttcacca    3120
tgttagccag gatggtctcg atctcctgac ctcgtgatcc actcacctca gcctcccaaa    3180 atcctgggt tacagatgtg agctaccact cacggcccaa atcttcttga tcatatgttt    3240
aaatatattt tttaatattt ggagcatgag ttgtcacttc ttgtttgcct tttttataag    3300
gaaatgttgg agagttacat cattgctaat gtagaaatgt taagtggaaa atatacagt    3360 ttggtaaaat aaactagatt ctacatttat ttgtgggttt ttttcccctc ctttctttcc    3420
acagcacttt tgatatcaag caagtggctt ccttttgag atattaaaaa aaaaagaaa    3480 aggaaaaaag taaatgaagc ccaactacct aacccttttct tatttgtatt tgttttagta    3540
ttgtgaagtt gtgttaaata gtactagcta gaaatacaaa tttctggtta tcatttctct    3600
tccctgtggc acttgacatt ttaattgtct taaagttttt gaagtacatc ttctggcccc    3660
ttgagtactg ccagaggcaa aagatgtttg tttcttattc attccacttt tgtctcctgg    3720
gatcccttct gtagcctaaa gtatggctgg gaaatggact tgagaagatt ggcttgaatt    3780
agatcataat catgtgtgat cccatcatga attcattgga atttgtgttg catgtaaggc    3840
aatctttcct gttgtaaatc ttccttttt aatgtacata tattttgaaa aatatgaata    3900
aacatgaaat tttaaaagct gaaaaaaaaa aaaaaaa    3938
```

<210> SEQ ID NO 15
<211> LENGTH: 1352
<212> TYPE: DNA

<213> ORGANISM: Homo sapiens

<400> SEQUENCE: 15

| | | | | | |
|---|---|---|---|---|---|
| cgtgaagtgg | gcggagcgag | cgatttgaac | gcgagcggcg | cggacttctg | ccaagcaccg | 60 |
| gctcatgtga | ggctcgcggc | acagcgttct | ctgggctccc | cagaagccag | cctttcgctc | 120 |
| ccggacccgg | cagcccgagc | aggagccgtg | ggaccgggcg | ccagcaccct | ctgcggcgtg | 180 |
| tcatgggccc | gcgccgccgg | agccgaaagc | ccgaggcccc | gaggaggcgc | agcccgagcc | 240 |
| cgaccccgac | ccccggcccc | tcccggcggg | gcccctcctt | aggcgcttcc | tcccatcaac | 300 |
| acagtcggcg | gagacaaggt | tggctaaagg | agatccgaaa | gcttcagaag | agcacacacc | 360 |
| tcttgataag | gaagctgccc | ttcagccgcc | tggcagcaga | agcatttcta | gttcatctct | 420 |
| ttgaggacgc | ctatctcctc | accttacatg | caggccgagt | tactctcttc | ccaaaggatg | 480 |
| tgcaactggc | ccggaggatc | cggggccttg | aggagggact | cggctgagct | cctgcaccca | 540 |
| gtgtttctgt | cagtctttcc | tgctcagcca | gggggatga | taccggggac | tctccagagc | 600 |
| catgactaga | tccaatggat | tctgcgatgc | tgtctgact | ttgctgtctc | tgaacagtat | 660 |
| gtgtgtgttg | ctttaaatat | tttctttt | tttgagaagg | agaagactgc | atgactttcc | 720 |
| tctgtaacag | aggtaatata | tgagacaatc | aacaccgttc | caaaggcctg | aaaataattt | 780 |
| tcagataaag | agactccaag | gttgacttta | gtttgtgagt | tactcatgtg | actatttgag | 840 |
| gattttgaaa | acatcagatt | tgctgtggta | tgggagaaaa | ggctatgtac | ttattatttt | 900 |
| agctctttct | gtaatattta | cattttttac | catatgtaca | tttgtacttt | tatttacac | 960 |
| ataagggaaa | aaataagacc | actttgagca | gttgcctgga | aggctgggca | tttccatcat | 1020 |
| atagacctct | gcccttcaga | gtagcctcac | cattagtggc | agcatcatgt | aactgagtgg | 1080 |
| actgtgcttg | tcaacggatg | tgtagctttt | cagaaactta | attggggatg | aatagaaaac | 1140 |
| ctgtaagctt | tgatgttctg | gttacttcta | gtaaattcct | gtcaaaatca | attcagaaat | 1200 |
| tctaacttgg | agaatttaac | attttactct | tgtaaatcat | agaagatgta | tcataacagt | 1260 |
| tcagaatttt | aaagtacatt | ttcgatgctt | ttatgggtat | ttttgtagtt | tctttgtaga | 1320 |
| gagataataa | aaatcaaaat | atttaatgaa | aa | | | 1352 |

<210> SEQ ID NO 16
<211> LENGTH: 4569
<212> TYPE: DNA
<213> ORGANISM: Homo sapiens

<400> SEQUENCE: 16

| | | | | | |
|---|---|---|---|---|---|
| tcttgttgtt | acgggtaacg | gaagtgtggc | ggcgttgggt | tgagcgggct | ttttggaagt | 60 |
| ttgtggcgga | gttctgtgat | atgagcaaca | atggaccaga | agattttatc | tctagcagca | 120 |
| gaaaaaacag | cagacaaact | gcaagaattt | cttcaaaccc | tgagagaagg | tgatttgact | 180 |
| aatctccttc | agaatcaagc | agtgaaagga | aagttgctg | gagcactcct | gagagccatc | 240 |
| ttcaaaggtt | ccccctgctc | tgaggaagct | ggaacactta | ggagacgtaa | gatatacact | 300 |
| tgttgtatcc | agttggtgga | atcggggat | ttgcagaaag | aaatagcgtc | tgagatcata | 360 |
| ggattactga | tgctggaggc | tcaccatttt | ccaggaccat | tattggttga | attagccaat | 420 |
| gagtttatta | gtgctgtcag | agaaggcagc | ctagtgaatg | gaaaatcttt | ggagttacta | 480 |
| cctatcattc | tcactgccct | ggctacgaaa | aaggaaaatc | tggcttatgg | aaaaggtgta | 540 |
| ctgagtgggg | aagaatgtaa | gaaacagttg | attaacaccc | tgtgttctgg | caggtgggat | 600 |
| cagcaatatg | taatccaact | cacctccatg | ttcaaggatg | tccctctgac | tgcagaagag | 660 |

```
gtggaatttg tggtggaaaa agcattgagc atgttctcca agatgaatct tcaagaaata      720 ccaccttttgg tctatcagct tctggttctc tcctccaagg gaagcagaaa gagtgttttg     780
gaaggaatca tagccttctt cagtgcacta gataagcagc acaatgagga acagagtggt     840
gacgagctat tggatgttgt cactgtgcca tcaggtgaac ttcgtcatgt ggaaggcacc     900
attattctac acattgtgtt tgccatcaaa ttggactatg aactaggcag agaactcgtg     960
aaacacttaa aggtaggaca gcaaggagat tccaataata acttaagtcc cttcagcatt    1020
gctcttcttc tgtctgtaac aagaatacaa agatttcagg accaggtgct tgatcttta     1080 aagacttcgg ttgtaaagag ctttaaggat cttcaactcc tccaaggctc aaaatttctt    1140
cagaatctag ttcctcatag atcttatgtt tcaaccatga tcttggaagt agtgaagaat    1200
agcgttcata gctgggacca tgttactcag ggcctcgtag aacttggttt cattttgatg    1260
gattcatatg gccaaagaa ggttcttgat ggaaaaacta ttgaaaccag cccaagtctt     1320
tctagaatgc caaccagca tgcatgtaag ctcggagcta atatcctgtt ggaaactttt      1380
aagatccatg agatgatcag acaagaaatt ttggagcagg tcctcaacag ggttgttacc    1440
agagcatctt ctcccatcag tcatttctta gacctgcttt caaatatcgt catgtatgca    1500
cccttagttc ttcaaagttg ttcttctaaa gtcacagaag cttttgacta tttgtccttt    1560
ctgccccttc agactgtaca aaggctgctt aaggcagtgc agccccttct caaagtcagc    1620
atgtcaatga gagactgctt gatacttgtc cttcggaaag ctatgtttgc caaccagctt    1680
gatgcccgaa atctgcagt tgctgggttt tgctgctcc tgaagaactt taaagttta       1740 ggcagcctgt catcctctca gtgcagtcag tctctcagtg tcagtcaggt tcatgtggat    1800
gttcacagcc attacaattc tgtcgccaat gaaacttttt gccttgagat catggatagt    1860
ttgaggagat gcttaagcca gcaagctgat gttcgactca tgctttatga ggggttttat    1920
gatgttcttc gaaggaactc tcagctggct aattcagtca tgcaaactct gctctcacag    1980
ttaaaacagt tctatgagcc aaaacctgat ctgctgcctc ctctgaaatt agaagcttgt    2040
attctgaccc aaggagataa gatctctcta caagaaccac tggattatct gctgtgttgt    2100
attcagcatt gtttggcctg gtataagaat acagtcatac ccttacagca gggagaggag    2160
gaagaggagg aggaagaggc attctacgaa gacctagatg atatattgga gtccattact    2220
aatagaatga ttaagagtga gctggaagac tttgaactgg ataaatcagc agatttttct    2280
cagagcacca gtattggcat aaaaaataat atctgtgctt ttcttgtgat gggagtttgt    2340 gaggtttta tagaatacaa tttctccata agtagtttca gtaagaatag gtttgaggac     2400
attctgagct tatttatgtg ttacaaaaaa ctctctgaca ttcttaatga aaaagcgggt    2460
aaagccaaaa ctaaaatggc caacaagaca agtgatagtc ttttgtccat gaaatttgtg    2520
tccagtcttc tcactgctct tttcagagtc ttgctatgga gatacacttc aattcctact    2580
tcagtggaag agtcgggaaa gaagagaaa ggaaagagca tctcactgct gtgcttggag    2640
ggtttacaga aaatattcag tgctgtgcaa cagttctatc agcccaagat tcagcagttt    2700
ctcagagctc tggatgtcac agataaggaa ggagaagaga gagaagatgc agatgtcagt    2760
gtcactcaga gaacagcatt ccagatccgg caatttcaga ggtccttgtt gaatttactt    2820
agcagtcaag aggaagattt taatagcaaa gaagccctcc tgctagtcac ggttcttacc    2880
agtttgtcca agttactgga gccctcctct cctcagtttg tgcagatgtt atcctggaca    2940
tcaaagattt gcaaggaaaa cagccgggag gatgccttgt tttgcaagag cttgatgaac    3000
```

```
ttgctcttca gcctgcatgt ttcgtataag agtcctgtca ttctgctgcg tgacttgtcc      3060
caggatatcc acgggcatct gggagatata gaccaggatg tagaggtgga gaaaacaaac      3120
cactttgcaa tagtgaattt gagaacggct gcccccactg tctgtttact tgttctgagt      3180
caggccgaga aggttctaga agaagtggac tggctaatca ccaagcttaa gggacaagtg      3240
agccaagaaa ccttatcaga gaggcctct  tctcaggcaa ccctaccaaa tcagcctgtt      3300
gagaaagcta tcatcatgca actgggaact ctgcttacat ttttccacga gctggtgcag      3360
acagctctgc catcaggcag ctgtgtggac accttgttaa aggacttgtg caaaatgtac      3420
accacactta cagcccttgt cagatattat ctccaggtgt gtcagagctc cggaggaatt      3480
ccaaaaaata tggaaaagct ggtgaagctg tctggttctc atctgacccc cctgtgttat      3540
tctttcattt cttacgtaca gaataagagt aagagcctga actatacggg agagaaaaag      3600
gagaaacctg ctgccgttgc cacagccatg gccagagttc ttcgggaaac caagccaatc      3660
cctaacctca tctttgccat agaacagtat gaaaaatttc tcatccacct ttctaagaag      3720
tccaaggtga acctgatgca gcacatgaag ctcagcacct cacgagactt caagatcaaa      3780
ggaaacatcc tagacatggt tcttcgagag gatggtgaag atgaaaatga agagggcact      3840
gcatcagagc atgggggaca gaacaaagaa ccagccaaga agaaaaggaa aaaataaatg      3900
aaatgcctga gttaatgtga actttggggc ttctgcttca tttttaccca acaagcaaca      3960
atgccccttg tcctgtagtc cacaccgatg ttggcatctt ggttctgaac ccactgaatt      4020
caactgcacc ttcagttaga aggaatcttc ttggcaggtc ctgctactga aaaatggctg      4080
gccttaggca agccctttg  caaaaagcac agctgaaagc ctgagtttgg gagcctgcac      4140
caccccgatg aagctccacg ggagcaaata cagagcctcc aggcagtgct atggtccagg      4200
ctggcttcgt ttttccaagg agcctttggt gagttcaatt atctggtaaa tatccagcgc      4260
ttcacctgaa agatagtgca aattggttag gatgccacct caagaactgt aactgagagc      4320
tcagaagtga gcaaaggagc ttaatgctaa ggtcaaaagg agagtgaaag gttgagaaca      4380
attgccacga acggtaatgt tacatgttag gagggtctgt tttcttttta tataagtgtg      4440
tcttagatat attttaaata gaaataagc tttctgattt acttgtttgg tatttaaagc       4500
acagtttgtt tttctgtcac ctatagagtg caagaatgca ctctatagaa taaattatct      4560
ttaaacatt                                                              4569

<210> SEQ ID NO 17
<211> LENGTH: 6054
<212> TYPE: DNA
<213> ORGANISM: Homo sapiens

<400> SEQUENCE: 17
ggggcgcggg gcgcggggc tgtagggagg gggaccagtg gcagagggac cttaggtgat        60
ccttagaaat aaaggctagc ttctgttcga ccttggagta gggcgaagag gtgtagacag      120
gcctggagaa gcgaggtaaa agcctgagta aaagcaagaa gttggagaat atgagataca      180
tctcatctct agtaaatact taaatgactt cccctcctcc cggagtcaag cacaattcgg      240
ggatgcaatg acggacgtag gtgaagacac tgcgggaact tacagacaaa actggtttgt      300
ggcctgtttg attcctgtca gaggtttgct gacccaagac agtatcgaaa atgcatatta      360
agtcaattat tctagaggga ttcaagtcct atgctcagag gaccgaagtc aatggttttg      420
accccctctt caatgctatc actggcttaa atggtagtgg gaaatccaac atattggact      480
ccatctgctt tttgctgggc atctccaacc tgtctcaggt tcgggcttct aatttacaag      540
```

```
atttagttta caaaaatggg caggctggta ttaccaaagc tctgtgtca atcactttg      600 ataattctga caaaaagcaa agtcctttag gatttgaggt tcatgatgaa atcacagtaa     660
caaggcaggt ggttattggt ggtagaaata aatatttaat caatggagtc aatgccaaca     720
acaccagagt acaggatctc ttctgttctg ttggccttaa tgttaacaac cctcactttc     780
tcatcatgca gggccgaatt acaaaagtat tgaatatgaa acctccagag attttatcca     840
tgatagaaga agcagctgga accaggatgt atgaatacaa aaaatagct gcacagaaaa       900 ctatagaaaa aaaggaggct aagctgaaag aaattaagac gatacttgaa gaagagatta     960
ctccaaccat tcaaaaatta aaagaggaaa gatcgtccta cttggagtac caaaaagtaa    1020
tgagagaaat agaacatttg agtcgtttat atattgctta tcagtttttg ctggctgaag    1080
ataccaaagt acgctcagct gaggaattaa agaaatgca agataaagtt ataaagcttc      1140
aggaagaatt gtctgagaat gataaaaaaa taaaagcact taatcatgaa atagaagaat    1200
tggaaaaaag aaaagataag gaaactggag gtatacttcg atctttagaa gatgctcttg    1260
cagaggctca gcgagttaat actaaatctc aaagcgcatt tgatctcaag aagaaaaatc    1320
tggcatgtga ggaaagcaaa cgcaaagagc tggaaaaaaa tatggttgag gactcaaaaa    1380
ctttagcagc aaaggaaaaa gaggttaaaa agataacaga tggactgcat gcccttcaag    1440
aagcaagtaa taaagatgct gaagctctgg cagctgcaca gcagcacttc aatgctgttt    1500
ccgctggcct gtccagtaat gaagatggag cagaagcaac tcttgctggt caaatgatgg    1560
cctgtaaaaa tgatataagt aaagctcaga cagaagccaa acaggctcag atgaagttga    1620
agcatgctca acaggaatta aagaataaac aagctgaagt taagaagatg gatagtggct    1680
acaggaagga tcaagaagct ctagaagctg taaaaagact taagaaaaaa cttgaagctg    1740
aaatgaaaaa gctaaattat gaagaaaata aagaggaaag ccttttggaa aagcgcaggc    1800
agctgtctcg tgatattggt agattgaaag aaacatatga agctctatta gccagatttc    1860
ccaatcttcg atttgcatac aaggatccag agaagaactg gaatagaaat tgtgtgaaag    1920
gacttgtggc ttctctgatt agtgtgaaag acacttctgc aaccacagct ttagaattag    1980
tggctggaga acgactctac aatgttgtag tagacacaga agttactggt aaaaagctac    2040
tagaaagggg ggaactgaaa cgtcgataca ctataattcc actcaataaa atttcagcca    2100
gatgtattgc accagaaact ctgagagttg ctcagaatct tgttggccct gacaacgttc    2160
atgtggctct ttccttggtt gaatataaac cagaacttca gaaagcaatg gagtttgtct    2220
ttggaacaac atttgtttgt gacaatatgg ataatgccaa aaaagtggcc tttgataaga    2280
ggataatgac tagaactgta actctcggag gtgatgtgtt tgatcctcat gggacattga    2340
gtggaggtgc tcgatcccag gcagcttcca ttttaaccaa gtttcaagaa ctcaaagatg    2400
ttcaggatga actgagaatc aaagagaatg agctgcgggc tctagaagag gaattagcag    2460
gtcttaaaaa cactgctgaa aagtatcgcc aactaaaaca gcagtgggag atgaaaactg    2520
aagaggcaga tttattacaa accaagctcc agcaaagctc atatcacaag caacaagaag    2580
aattagatgc ccttaaaaaa accattgagg aaagtgagga gactttgaaa aacactaaag    2640
aaatccaaag aaaagcagaa gaaaaatatg aagtattgga aaataaaatg aaaaatgcag    2700
aagctgaaag agagcgagaa ctgaaagatg ctcagaaaaa actggattgt gccaaaacaa    2760
aggcagatgc atctagcaag aagatgaaag aaaaacaaca ggaagttgaa gctatcactc    2820
tggaactgga agagctcaag agagagcata catcttacaa acaacagctt gaagctgtaa    2880
```

```
atgaagctat caaatcctat gaaagtcaga ttgaagtaat ggcagctgag gtggctaaaa    2940
ataaggagtc agtaaataaa gctcaagaag aggtgaccaa gcaaaaagag gtgataacag    3000
cccaagacac tgtaattaaa gctaaatatg cagaagtggc aaaacacaag gagcaaaaca    3060
atgattctca gcttaaaatt aaggaattag accacaacat cagcaaacat aaacgggagg    3120
ctgaagatgg tgctgcaaag gtatccaaaa tgttgaaaga ttatgactgg attaatgcag    3180
agagacacct ctttggccaa cccaatagtg cctatgattt caaaactaac aaccctaaag    3240
aagctggtca gagacttcag aagttgcaag aaatgaagga gaaactagga agaaatgtca    3300
atatgagagc tatgaatgta ttgacagaag ctgaagagcg atacaatgac ttgatgaaga    3360
agaagagaat tgtagaaaat gacaaatcca aaattcttac aactatagaa gaccttgacc    3420
agaagaaaaa ccaagcccta atattgcat ggcaaaaggt gaacaaggac tttgggtcta    3480
ttttttctac tcttttgcct ggtgctaatg ctatgcttgc accaccagag ggtcaaactg    3540
ttttggatgg tctggagttc aaggttgcct gggaaatac ctggaaagaa acctaactg    3600
aacttagtgg tggtcagagg tctttagtgg ccttgtcatt aatactgtcc atgcttctct    3660
tcaaacctgc tccaatttat atccttgatg aggtagatgc agccttggat ctttctcata    3720
cccaaaacat tggacagatg ctgcgtactc atttcacaca ttctcagttc attgtggtgt    3780
cactaaaaga aggtatgttc aacaatgcaa acgttctttt caaaaccaag tttgtggatg    3840
gtgtttctac agtagccaga tttactcaat gtcaaaatgg aaagatttca aaggaagcaa    3900
aatccaaggc aaaaccaccc aaaggagcac atgtggaagt ttaaactaca agttatttc    3960
ttcatcttga cctgtttttt taaatgtaaa cttttaagga cttgagataa ctaatttgtt    4020
tatatacaaa aattaatgtt actgtgttac ttaacccatg ttttctcttt atataatcac    4080
ttatcgctta caaatgagca tatattcctc atctcttaac tagtctaatt atggtccaat    4140
tattgtggtt gtgattttat gcatatcatc aaatgttttt ttcttatgcg ggtctttat    4200
atattaggga tcctgagata cccgattcta tatgtaaaag ctaatataca aaaaagcaga    4260
ttaaattaca tgataaatgt agctgatcat cagtgtttaa ttgatttaat tcctaaggca    4320
atattaatgt gttttctaaa gtcattcagg taaggaagaa ttataaatca ggtaactgga    4380
ccaacaaagg gaacacatat aaagctatta tgcatgcatg gagccgtttg aggctagttt    4440
tttaaggcca caactccaga cccctgattt agactgagat aggaaacaga tcttgaaaga    4500
atccttattt taatgataca tgaatatcat gttcctatac gcttaataat tggtctctac    4560
gttttaatga tacatgaata tcatgttcct atacgcttaa taattggtct ctacgacttt    4620
aatgttttg tttttttaag ctgtgtaagt attttaaat caaagcttag gaggtgtgtt    4680
gcgtggtact atctgctgca aatttatctg aagtttgtta atattttcca agatttttgt    4740
cagccttttc ataatccagt cattaacaac ctattggtaa acaagaatgt aggtgccagt    4800
agactaaacc aaatttattt ttccctgagt ctgatatata tatgtataaa tataaataac    4860
tcaatccatc tgttccacca aaataactca aaagttggat gattatttgt cttccgcttt    4920
ccagttcaaa gggatgaaat tcctttagaa cttgaaagat gacactagcg aacaccatga    4980
gaatactgtc tacagttttt ggtacgtcat cactagaaca gtgaccccaa actgaatcat    5040
gaaaggtctg acatgatgta atctgatctt ccatgtgtta ttttggcccc acatctcttc    5100
ttgatttttt agtcttattt ccttagtgtt attatcatac ttcccctgat atatggccgt    5160
acttcctggc cctgggcttg acatttccca cccttcattc tccatacata tgagatgtca    5220
gaaaacatgc agtaattgat attatgggac acattggaaa ggattgaatc tggaattagt    5280
```

-continued

```
tctgtccact gtggagggga gaggaaataa tgctgtaaat gttgagttac agaaagtcca    5340
atgtcaaata tagtttttt gtttcctttc aaatgtatta cagactgtgc caaaacagtt     5400
accaattcac actgtcaata ttaaagtata ccatagtata caaattagtc agtacttgct    5460
gttaatttta atatttctga tttaacagtt agttattaag tggtacttca ttgctgtttt    5520
agccaacgtt ttaaaaataa tttgggagtt tgactatttt ggcttacgta ctcatttcct    5580
tttctctgct aaaaatgttt tgcttgtgtg cgttcctgat ttttgtcttg tataatcttg    5640
atctttgaaa accctcaaac atgtattaaa ttgttgtaac ttttttttcat tagagggaag   5700
acattaaggg gattgggggac atttgtttca cacatctgca gtaatatgag ttaactaata   5760
tttaacaagc tctttcttta cattagctgc tgttctcatt tgtatgtatt gtcatattta    5820
atcctcagag taacctagtg aggtaaatac tgttgttgtc agcatggtgt aatcgaggaa    5880
ttgagtgagt tgagcagaaa agttaggaaa cttgctcagg gtgataatac agttaggagt    5940
gtcagggccc atggacaaat cttgtcagtc tccagaacct aagatatact acgtcactga    6000
cagcttgaac atttgtattt attgtacaga ataaatttaa gaaaaataaa aaaa          6054
```

<210> SEQ ID NO 18
<211> LENGTH: 2035
<212> TYPE: DNA
<213> ORGANISM: Homo sapiens

<400> SEQUENCE: 18

```
accccccacct ctccctcctc cttccccagt cgttcgccgg aaagcatttg tctcccacct     60
cttcataaca acaattaatt tcctctgggg cctgaggagg gcagaatttc aaccttcggt    120
gtgcttggga gtggcgattg tgatttacac gacaaaatgc cgaggtgctc ggtggagtca    180
tggcagtgcc ctttgtggaa gactgggact tggtgcaaac cctgggagaa ggtgcctatg    240
gagaagttca acttgctgtg aatagagtaa ctgaagaagc agtcgcagtg aagattgtag    300
atatgaagcg tgccgtagac tgtccagaaa atattaagaa agagatctgt atcaataaaa    360
tgctaaatca tgaaaatgta gtaaaattct atggtcacag gagagaaggc aatatccaat    420
atttatttct ggagtactgt agtggaggag agcttttga cagaatagag ccagacatag     480
gcatgcctga accagatgct cagagattct ccatcaact catggcaggg gtggtttatc     540
tgcatggtat tggaataact cacagggata ttaaaccaga aaatcttctg ttggatgaaa    600
gggataaccct caaatctca gactttggct tggcaacagt atttcggtat aataatcgtg     660
agcgtttgtt gaacaagatg tgtggtactt taccatatgt tgctccagaa cttctgaaga    720
gaagagaatt tcatgcagaa ccagttgatg tttggtcctg tggaatagta cttactgcaa    780
tgctcgctgg agaattgcca tgggaccaac ccagtgacag ctgtcaggag tattctgact    840
ggaaagaaaa aaaaacatac ctcaacccctt ggaaaaaaat cgattctgct cctctagctc    900
tgctgcataa atcttagtt gagaatccat cagcaagaat taccattcca gacatcaaaa     960
aagatagatg gtacaacaaa cccctcaaga aaggggcaaa aaggccccga gtcacttcag   1020
gtggtgtgtc agagtctccc agtggatttt ctaagcacat tcaatccaat ttggacttct   1080
ctccagtaaa cagtgcttct agtgaagaaa atgtgaagta ctccagttct cagccagaac   1140
cccgcacagg tctttcctta tgggatacca gcccctcata cattgataaa ttggtacaag   1200
ggatcagctt tccccagccc acatgtcctg atcatatgct tttgaatagt cagttacttg   1260
gcaccccagg atcctcacag aacccctggc agcggttggt caaaagaatg acacgattct   1320
```

-continued

| | |
|---|---|
| ttaccaaatt ggatgcagac aaatcttatc aatgcctgaa agagacttgt gagaagttgg | 1380 |
| gctatcaatg gaagaaaagt tgtatgaatc aggttactat atcaacaact gataggagaa | 1440 |
| acaataaact cattttcaaa gtgaatttgt tagaaatgga tgataaaata ttggttgact | 1500 |
| tccggctttc taagggtgat ggattggagt tcaagagaca cttcctgaag attaaaggga | 1560 |
| agctgattga tattgtgagc agccagaaga tttggcttcc tgccacatga tcggaccatc | 1620 |
| ggctctgggg aatcctggtg aatatagtgc tgctatgttg acattattct tcctagagaa | 1680 |
| gattatcctg tcctgcaaac tgcaaatagt agttcctgaa gtgttcactt ccctgtttat | 1740 |
| ccaaacatct tccaatttat tttgtttgtt cggcatacaa ataataccta tatcttaatt | 1800 |
| gtaagcaaaa ctttggggaa aggatgaata gaattcattt gattatttct tcatgtgtgt | 1860 |
| ttagtatctg aatttgaaac tcatctggtg gaaaccaagt ttcagggdac atgagttttc | 1920 |
| cagcttttat acacacgtat ctcattttta tcaaaacatt ttgtttaatt caaaaagtac | 1980 |
| atattccatg ttgatttaat tctaagatga accaataaag acataattct tgtga | 2035 |

<210> SEQ ID NO 19
<211> LENGTH: 1651
<212> TYPE: DNA
<213> ORGANISM: Homo sapiens

<400> SEQUENCE: 19

| | |
|---|---|
| acagcagtta cactgcggcg ggcgtctgtt ctagtgtttg agccgtcgtg cttcaccggt | 60 |
| ctacctcgct agcatgtcgg gccgcggcaa gactggcggc aaggcccgcg ccaaggccaa | 120 |
| gtcgcgctcg tcgcgcgccg gcctccagtt cccagtgggc cgtgtacacc ggctgctgcg | 180 |
| gaagggccac tacgccgagc gcgttggcgc cggcgcgcca gtgtacctgg cggcagtgct | 240 |
| ggagtacctc accgctgaga tcctggagct ggcgggcaat gcggcccgcg acaacaagaa | 300 |
| gacgcgaatc atcccccgcc acctgcagct ggccatccgc aacgacgagg agctcaacaa | 360 |
| gctgctgggc ggcgtgacga tcgcccaggg aggcgtcctg cccaacatcc aggccgtgct | 420 |
| gctgcccaag aagaccagcg ccaccgtggg gccgaaggcg ccctcgggcg caagaaggc | 480 |
| cacccaggcc tcccaggagt actaagaggg ccgcgccgc ggccggccgc caggcctccc | 540 |
| catgccacca caaaggccct tttaagggcc accaccgccc tcatggaaag agctgagccg | 600 |
| cttcagactg cggggcaagc gggcgcggc tcccttcccc tcccctcccc tcgcccgcct | 660 |
| tcgccgcccg gcctcgagtc cccgcccgcc cccgctcccg tcccgcaccg cctgccgcgt | 720 |
| cggcctcggg ccctgccctg tccgccgtcc gccctccggt agggttcggg ccttccggat | 780 |
| gcggcttggg cgctcttcgg ggacctccgt ggcgcggaag acccgagcct gccgggggga | 840 |
| ggccggcggc gccgcacctg cccgcctcgg cgttcgtgac tcagccgccc catcccgagt | 900 |
| cgctaagggg ctgcggggag gccgcagcac cttctggaag acttggcctt ccgctctgac | 960 |
| gcagggccga ggtgggcagt ccaggccgag aggccggcgg ccctgaaggt gagtgaggcc | 1020 |
| ctcggcagct gcagccgggg tgtctggtac ccccccggcg tggtgcttag cccaggactt | 1080 |
| tcagacgcgg ccgctggccg ggaggctttg tgggagaga cgcgatcgcc gatttcggtc | 1140 |
| tggcgccct tctgcggccg gacccaggcc ctttcacatc agctctccct ccatcttcat | 1200 |
| tcataggtct gcgctggggc cgggacgaag cacttggtaa caggcacatc ttcctcccga | 1260 |
| gtgactgcct cctaggagga catttagggg agggcagagg cctgcagttt ggcttcacgg | 1320 |
| ctggctatgt ggacagcaag agtcgttttc gcggaagccg actggcagcc aggcctgtcg | 1380 |
| ggccccccga cgccgcccca tttcccttcc agcaaactca actcggcaat ccaagcacct | 1440 |

| | |
|---|---:|
| agataccagc acaagtcggt taatccctgt ctggactgag cctccgttgg cttctgaact | 1500 |
| ggaattctgc agctaaccct tccacgacta gaaccttagg cattgggag ttttagatgg | 1560 |
| actaatttta ttaaaggatt gttttttttt taaaaaaaaa aaaaaaaaaa aaaaaaaaaa | 1620 |
| aaaaaaaaaa aaaaaaaaaa aaaaaaaaaa a | 1651 |

<210> SEQ ID NO 20
<211> LENGTH: 1249
<212> TYPE: DNA
<213> ORGANISM: Homo sapiens

<400> SEQUENCE: 20

| | |
|---|---:|
| gagctgtgct tggggcgggg cctggcgtgt attcgaaagg aaggcgccgg ctgcgggaag | 60 |
| atggcggctc agccgctgcg gcatcgctca cgttgtgcaa cgccgccccg ggggacttt | 120 |
| tgtggtggca ctgagagggc gattgaccaa gcttctttta cgacctccat ggagtgggat | 180 |
| acgcaggtgg tgaaggggtc ctcgccgctc ggccccgcag ggctggggc tgaggagcca | 240 |
| gccgccggcc cgcagctgcc gtcttggctg cagcctgaga ggtgcgctgt gttccagtgc | 300 |
| gcacagtgtc acgcagtgct cgccgactcg gtgcacctcg cctgggacct gtcgcggtcc | 360 |
| ctcggggccg tggtcttctc cagagttaca ataacgtcg ttttggaagc gcccttccta | 420 |
| gttggcattg aaggttcact caaaggcagt acttacaacc ttttattctg tggttcttgt | 480 |
| gggattcccg ttggtttcca tctgtattct acccatgctg ccctggctgc cttgagaggt | 540 |
| cacttctgcc tttccagtga caaaatggtg tgctatctct taaaaacaaa agccatagta | 600 |
| aatgcatcag agatggatat tcaaaatgtt cctctatcag aaaagattgc agagctgaaa | 660 |
| gagaagatag tgctaacgca caatcgctta aaatcactaa tgaagattct gagtgaagtg | 720 |
| actcctgacc agtccaagcc agaaaactga tcctgtacca aagcttgagt gtcaggttca | 780 |
| ggctttattg ctgtcttcaa caacaggtgc tgcttagtca tttcttgaaa agattggct | 840 |
| tcaagaatgg agggaaatg cagtttctat ttacctttag gctgattttc caaattattt | 900 |
| gtgaagctgt ttttagaaga tgagagacta aggattcttc tcttttatag ctatttgcct | 960 |
| taagaaccтta ctttagattc ttattgaatt cataatactt atctctgaaa atgtctttga | 1020 |
| ctgtaaattt aggaattaag atgcagagtc ccatgtgtcc tctgatctaa agttgcatgg | 1080 |
| ttggtctgaa aaтagaгттg gcttaatgt tgacttctat tactcctgca tggagcagtt | 1140 |
| gttatgaata ctaatacatc acttttaac ttctgtaaaa tacagatcat aatattctat | 1200 |
| aggtaatgtt taataaattg cctgaataat atacaaaaaa aaaaaaaa | 1249 |

<210> SEQ ID NO 21
<211> LENGTH: 3453
<212> TYPE: DNA
<213> ORGANISM: Homo sapiens

<400> SEQUENCE: 21

| | |
|---|---:|
| acttttcgcg cgaaacctgg ttgttgctgt agtggcggag aggatcgtgg tactgctatg | 60 |
| gcggaatcat cggaatcctt caccatggca tccagcccgg cccagcgtcg gcgaggcaat | 120 |
| gatcctctca cctccagccc tggccgaagc tcccggcgta ctgatgccct cacctccagc | 180 |
| cctggccgtg accttccacc аттттgaggaт gagtccgagg ggctcctagg cacagagggg | 240 |
| cccстggagaa agaagagga tggagaggag ctcattggga atggcatgga aagggactac | 300 |
| cgcgccatcc cagagctgga cgcctatgag gccgagggac tggctctgga tgatgaggac | 360 |

```
gtagaggagc tgacggccag tcagagggag gcagcagagc gggccatgcg gcagcgtgac    420
cgggaggctg gccggggcct gggccgcatg cgccgtgggc tcctgtatga cagcgatgag    480
gaggacgagg agcgccctgc ccgcaagcgc cgccaggtgg agcgggccac ggaggacggc    540
gaggaggacg aggagatgat cgagagcatc gagaacctgg aggatctcaa aggccactct    600
gtgcgcgagt gggtgagcat ggcgggcccc cggctggaga tccaccaccg cttcaagaac    660
ttcctgcgca ctcacgtcga cagccacggc acaacgtct tcaaggagcg catcagcgac    720
atgtgcaaag agaaccgtga gagcctggtg gtgaactatg aggacttggc agccagggag    780
cacgtgctgg cctacttcct gcctgaggca ccggcggagc tgctgcagat ctttgatgag    840
gctgccctgg aggtggtact ggccatgtac cccaagtacg accgcatcac caaccacatc    900
catgtccgca tctcccacct gcctctggtg gaggagctgc gctcgctgag gcagctgcat    960
ctgaaccagc tgatccgcac cagtgggtg gtgaccagct gcactggcgt cctgccccag   1020
ctcagcatgg tcaagtacaa ctgcaacaag tgcaatttcg tcctgggtcc tttctgccag   1080
tcccagaacc aggaggtgaa accaggctcc tgtcctgagt gccagtcggc cggcccctt    1140 gaggtcaaca tggaggagac catctatcag aactaccagc gtatccgaat ccaggagagt   1200
ccaggcaaag tggcggctgg ccggctgccc cgctccaagg acgccattct cctcgcagat   1260
ctggtggaca gctgcaagcc aggagacgag atagagctga ctggcatcta tcacaacaac   1320
tatgatggct ccctcaacac tgccaatggc ttccctgtct tgccactgt catcctagcc   1380 aaccacgtgg ccaagaagga caacaaggtt gctgtagggg aactgaccga tgaagatgtg   1440
aagatgatca ctagcctctc caaggatcag cagatcggag agaagatctt tgccagcatt   1500
gctccttcca tctatggtca tgaagacatc aagagaggcc tggctctggc cctgttcgga   1560
ggggagccca aaaacccagg tggcaagcac aaggtacgtg tgatatcaa cgtgctcttg   1620 tgcggagacc ctggcacagc gaagtcgcag tttctcaagt atattgagaa agtgtccagc   1680
cgagccatct tcaccactgg ccaggggggcg tcggctgtgg gcctcacggc gtatgtccag   1740
cggcaccctg tcagcaggga gtggaccttg gaggctgggg ccctggttct ggctgaccga   1800
ggagtgtgtc tcattgatga atttgacaag atgaatgacc aggacagaac cagcatccat   1860
gaggccatgg agcaacagag catctccatc tcgaaggctg gcatcgtcac ctccctgcag   1920
gctcgctgca cggtcattgc tgccgccaac cccataggag ggcgctacga cccctcgctg   1980
actttctctg agaacgtgga cctcacagag cccatcatct cacgctttga catcctgtgt   2040
gtggtgaggg acaccgtgga cccagtccag gacgagatgc tggcccgctt cgtggtgggc   2100
agccacgtca gacaccaccc cagcaacaag gaggaggagg ggctggccaa tggcagcgct   2160
gctgagcccg ccatgcccaa cacgtatggc gtggagcccc tgcccccagga ggtcctgaag   2220 aagtacatca tctacgccaa ggagagggtc cacccgaagc tcaaccagat ggaccaggac   2280
aaggtggcca agatgtacag tgacctgagg aaagaatcta tggcgacagg cagcatcccc   2340
attacggtgc ggcacatcga gtccatgatc cgcatggcgg aggcccacgc gcgcatccat   2400
ctgcgggact atgtgatcga agacgacgtc aacatggcca tccgcgtgat gctggagagc   2460
ttcatagaca cacagaagtt cagcgtcatg cgcagcatgc gcaagacttt tgcccgctac   2520 cttttcattcc ggcgtgacaa caatgagctg ttgctcttca tactgaagca gttagtggca   2580
gagcaggtga catatcagcg caaccgcttt ggggcccagc aggacactat tgaggtccct   2640
gagaaggact tggtggataa ggctcgtcag atcaacatcc acaacctctc tgcattttat   2700
gacagtgagc tcttcaggat gaacaagttc agccacgacc tgaaaaggaa aatgatcctg   2760
```

| | |
|---|---|
| cagcagttct gaggccctat gccatccata aggattcctt gggattctgg tttggggtgg | 2820 |
| tcagtgccct ctgtgcttta tggacacaaa accagagcac ttgatgaact cggggtacta | 2880 |
| gggtcagggc ttatagcagg atgtctggct gcacctggca tgactgtttg tttctccaag | 2940 |
| cctgctttgt gcttctcacc tttgggtggg atgccttgcc agtgtgtctt acttggttgc | 3000 |
| tgaacatctt gccacctccg agtgctttgt ctccactcag taccttggat cagagctgct | 3060 |
| gagttcagga tgcctgcgtg tggtttaggt gttagccttc ttacatggat gtcaggagag | 3120 |
| ctgctgccct cttggcgtga gttgcgtatt caggctgctt ttgctgcctt tggccagaga | 3180 |
| gctggttgaa gatgtttgta atcgttttca gtctcctgca ggtttctgtg ccctgtggt | 3240 |
| ggaagagggc acgacagtgc cagcgcagcg ttctgggctc ctcagtcgca ggggtgggat | 3300 |
| gtgagtcatg cggattatcc actgccaca gttatcagct gccattgctc cctgtctgtt | 3360 |
| tccccactct cttatttgtg cattcggttt ggtttctgta gttttaattt ttaataaagt | 3420 |
| tgaataaaat ataaaaaaaa aaaaaaaaaa aaa | 3453 |

<210> SEQ ID NO 22
<211> LENGTH: 2821
<212> TYPE: DNA
<213> ORGANISM: Homo sapiens

<400> SEQUENCE: 22

| | |
|---|---|
| cgccccttcc cagccccaag ggtctaggat acagtctttg tagatgagcg ggtccccctt | 60 |
| ggaggacaga atgaagaatt gggaaatcat ggccgttctg gagagtagac aagaagacgg | 120 |
| cgaaagtcgg gcctgccccg ccctgcggcc ccggaacaaa agaacgcgtg tgcgctggcc | 180 |
| ctttaagagc gattctcctc cgcccgcgcc agctcggacc gcgggaaacc cggcgcctgc | 240 |
| actacccccgc ccggagattc ccttccgacg cccgcaccgc ctccccgtca ctcattctag | 300 |
| gcccgcacgg tgattggctt gcggctagcg ggaggtgaag aaggccgcct tgtccgattg | 360 |
| gcccgcacgc agtggcgccg gtcacgtggg gggcgacgtt tcgcgccaat ttcggttggc | 420 |
| cggccacagt ccaccgcgcg gagattctca gcttccccag gagcaagacc tctgagcccg | 480 |
| ccaagcgcgg ccgcacggcc ctcggcagcg atggcactga aggactacgc gctagagaag | 540 |
| gaaaaggtta agaagttctt acaagagttc taccaggatg atgaactcgg gaagaagcag | 600 |
| ttcaagtatg gaaccagtt ggttcggctg gctcatcggg aacaggtggc tctgtatgtg | 660 |
| gacctggacg acgtagccga ggatgacccc gagttggtgg actcaatttg tgagaatgcc | 720 |
| aggcgctacg cgaagctctt tgctgatgcc gtacaagagc tgctgcctca gtacaaggag | 780 |
| agggaagtgg taaataaaga tgtcctggac gtttacattg agcatcggct aatgatggag | 840 |
| cagcggagtc gggaccctgg gatggtccga agccccagaa accagtaccc tgctgaactc | 900 |
| atgcgcagat ttgagctgta ttttcaaggc cctagcagca caagcctcg tgtgatccgg | 960 |
| gaagtgcggg ctgactctgt ggggaagttg gtaactgtgc gtggaatcgt cactcgtgtc | 1020 |
| tctgaagtca aacccaagat ggtggtggcc acttacactt gtgaccagtg tggggcagag | 1080 |
| acctaccagc cgatccagtc tcccactttc atgcctctga tcatgtgccc aagccaggag | 1140 |
| tgccaaacca accgctcagg agggcggctg tatctgcaga cacggggctc cagattcatc | 1200 |
| aaattccagg agatgaagat gcaagaacat agtgatcagg tgcctgtggg aaatatccct | 1260 |
| cgtagtatca cggtgctggt agaaggagag aacacaagga ttgcccagcc tggagaccac | 1320 |
| gtcagcgtca ctggtatttt cttgccaatc ctgcgcactg ggttccgaca ggtggtacag | 1380 |

```
ggtttactct cagaaaccta cctggaagcc catcggattg tgaagatgaa caagagtgag   1440
gatgatgagt ctggggctgg agagctcacc agggaggagc tgaggcaaat tgcagaggag   1500
gatttctacg aaaagctggc agcttcaatc gccccagaaa tatacgggca tgaagatgtg   1560
aagaaggcac tgctgctcct gctagtcggg ggtgtggacc agtctcctcg aggcatgaaa   1620
atccggggca acatcaacat ctgtctgatg ggggatcctg gtgtggccaa gtctcagctc   1680
ctgtcataca ttgatcgact ggcgcctcgc agccagtaca caacaggccg ggctcctca    1740 ggagtggggc ttacggcagc tgtgctgaga actccgtga gtggagaact gaccttagag    1800
ggtggggccc tggtgctggc tgaccagggt gtgtgctgca ttgatgagtt cgacaagatg   1860
gctgaggccg accgcacagc catccacgag gtcatggagc agcagaccat ctccattgcc   1920
aaggccggca ttctcaccac actcaatgcc cgctgctcca tcctggctgc cgccaaccct   1980
gcctacgggc gctacaaccc tcgccgcagc ctggagcaga acatacagct acctgctgca   2040
ctgctctccc ggtttgacct cctctggctg attcaggacc ggcccgaccg agacaatgac   2100
ctacggttgg cccagcacat cacctatgtg caccagcaca gccggcagcc ccctcccag    2160 tttgaacctc tggacatgaa gctcatgagg cgttacatag ccatgtgccg cgagaagcag   2220
cccatggtgc cagagtctct ggctgactac atcacagcag catacgtgga gatgaggcga   2280
gaggcttggg ctagtaagga tgccacctat acttctgccc ggaccctgct ggctatcctg   2340
cgcctttcca ctgctctggc acgtctgaga atggtggatg tggtggagaa agaagatgtg   2400
aatgaagcca tcaggctaat ggagatgtca aaggactctc ttctaggaga caaggggcag   2460
acagctagga ctcagagacc agcagatgtg atatttgcca ccgtccgtga actggtctca   2520
gggggccgaa gtgtccggtt ctctgaggca gagcagcgct gtgtatctcg tggcttcaca   2580
cccgcccagt tccaggcggc tctggatgaa tatgaggagc tcaatgtctg gcaggtcaat   2640
gcttcccgga cacggatcac ttttgtctga ttccagcctg cttgcaaccc tggggtcctc   2700
ttgttccctg ctggcctgcc ccttgggaag gggcagtgat gcctttgagg ggaaggagga   2760
gccctctttt ctcccatgct gcacttactc cttttgctaa taaaagtgtt tgtagattgt   2820
c                                                                   2821
```

<210> SEQ ID NO 23
<211> LENGTH: 2537
<212> TYPE: DNA
<213> ORGANISM: Homo sapiens

<400> SEQUENCE: 23

```
cccagaaggc cgcgggggt ggaccgccta agagggcgtg cgctcccgac atgccccgcg      60
gcgcgccatt aaccgccaga tttgaatcgc gggacccgtt ggcagaggtg gcggcggcgg    120
catgggtgcc ccgacgttgc cccctgcctg gcagcccttt ctcaaggacc accgcatctc    180
tacattcaag aactgcccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc atgcaaagga aaccaacaat    360
aagaagaaag aatttgagga aactgcggag aaagtgcgcc gtgccatcga gcagctggct    420
gccatggatt gaggcctctg gccggagctg cctggtccca gagtggctgc accacttcca    480
gggtttattc cctggtgcca ccagccttcc tgtgggcccc ttagcaatgt cttaggaaag    540
gagatcaaca ttttcaaatt agatgtttca actgtgctct tgttttgtct tgaaagtggc    600
accagaggtg cttctgcctg tgcagcgggt gctgctggta acagtggctg cttctctctc    660
```

```
tctctctctt ttttgggggc tcattttttgc tgttttgatt cccgggctta ccaggtgaga    720
agtgagggag gaagaaggca gtgtcccttt tgctagagct gacagctttg ttcgcgtggg    780
cagagccttc cacagtgaat gtgtctggac ctcatgttgt tgaggctgtc acagtcctga    840
gtgtggactt ggcaggtgcc tgttgaatct gagctgcagg ttccttatct gtcacacctg    900
tgcctcctca gaggacagtt ttttttgttgt tgtgttttttt tgttttttttt ttttttggtag    960 atgcatgact tgtgtgtgat gagagaatgg agacagagtc cctggctcct ctactgttta   1020
acaacatggc tttcttattt tgtttgaatt gttaattcac agaatagcac aaactacaat   1080
taaaactaag cacaaagcca ttctaagtca ttggggaaac ggggtgaact tcaggtggat   1140
gaggagacag aatagagtga taggaagcgt ctggcagata ctccttttgc cactgctgtg   1200
tgattagaca ggcccagtga gccgcggggc acatgctggc cgctcctccc tcagaaaaag   1260
gcagtggcct aaatcctttt taaatgactt ggctcgatgc tgtgggggac tggctgggct   1320
gctgcaggcc gtgtgtctgt cagcccaacc ttcacatctg tcacgttctc cacacggggg   1380
agagacgcag tccgcccagg tccccgcttt ctttggaggc agcagctccc gcagggctga   1440 agtctgbgcgt aagatgatgg atttgattcg ccctcctccc tgtcatagag ctgcagggtg   1500
gattgttaca gcttcgctgg aaacctctgg aggtcatctc ggctgttcct gagaaataaa   1560
aagcctgtca tttcaaacac tgctgtggac cctactgggt tttttaaaata ttgtcagttt   1620 ttcatcgtcg tccctagcct gccaacagcc atctgcccag acagccgcag tgaggatgag   1680
cgtcctggca gagacgcagt tgtctctggg cgcttgccag agccacgaac cccagacctg   1740
tttgtatcat ccgggctcct tccgggcaga aacaactgaa aatgcacttc agacccactt   1800
atttctgcca catctgagtc ggcctgagat agacttttcc ctctaaactg ggagaatatc   1860
acagtggttt ttgttagcag aaaatgcact ccagcctctg tactcatcta agctgcttat   1920
ttttgatatt tgtgtcagtc tgtaaatgga tacttcactt taataactgt tgcttagtaa   1980
ttggctttgt agagaagctg gaaaaaaatg gttttgtctt caactccttt gcatgccagg   2040
cggtgatgtg gatctcggct tctgtgagcc tgtgctgtgg gcagggctga gctggagccg   2100 ccctctcag cccgcctgcc acggcctttc cttaaaggcc atccttaaaa ccagaccctc   2160
atggctacca gcacctgaaa gcttcctcga catctgttaa taaagccgta ggcccttgtc   2220
taagtgcaac cgcctagact ttctttcaga tacatgtcca catgtccatt tttcaggttc   2280
tctaagttgg agtggagtct gggaagggtt gtgaatgagg cttctgggct atgggtgagg   2340
ttccaatggc aggttagagc ccctcgggcc aactgccatc ctggaaagta gagacagcag   2400
tgcccgctgc ccagaagaga ccagcaagcc aaactggagc ccccattgca ggctgtcgcc   2460
atgtggaaag agtaactcac aattgccaat aaagtctcat gtggtttttat ctaaaaaaaa   2520 aaaaaaaaaa aaaaaaa                                                   2537
```

<210> SEQ ID NO 24
<211> LENGTH: 2346
<212> TYPE: DNA
<213> ORGANISM: Homo sapiens

<400> SEQUENCE: 24

```
acaaggcagc ctcgctcgag cgcaggccaa tcggctttct agctagaggg tttaactcct     60
atttaaaaag aagaaccttt gaattctaac ggctgagctc ttggaagact tgggtccttg    120
ggtcgcaggt gggagccgac gggtgggtag accgtggggg atatctcagt ggcggacgag    180
```

```
gacggcgggg acaaggggcg gctggtcgga gtggcggagc gtcaagtccc ctgtcggttc    240
ctccgtccct gagtgtcctt ggcgctgcct tgtgcccgcc cagcgccttt gcatccgctc    300
ctgggcaccg aggcgccctg taggatactg cttgttactt attacagcta gaggcatcat    360
ggaccgatct aaagaaaact gcatttcagg acctgttaag gctacagctc cagttggagg    420
tccaaaacgt gttctcgtga ctcagcaatt tccttgtcag aatccattac ctgtaaatag    480
tggccaggct cagcgggtct tgtgtccttc aaattcttcc cagcgcattc ctttgcaagc    540
acaaaagctt gtctccagtc acaagccggt tcagaatcag aagcagaagc aattgcaggc    600
aaccagtgta cctcatcctg tctccaggcc actgaataac acccaaaaga gcaagcagcc    660
cctgccatcg gcacctgaaa ataatcctga ggaggaactg gcatcaaaac agaaaaatga    720
agaatcaaaa aagaggcagt gggctttgga agactttgaa attggtcgcc ctctgggtaa    780
aggaaagttt ggtaatgttt atttggcaag agaaaagcaa agcaagttta ttctggctct    840
taaagtgtta tttaaagctc agctggagaa agccggagtg gagcatcagc tcagaagaga    900
agtagaaata cagtcccacc ttcggcatcc taatattctt agactgtatg gttatttcca    960
tgatgctacc agagtctacc taattctgga atatgcacca cttggaacag tttatagaga   1020
acttcagaaa ctttcaaagt ttgatgagca gagaactgct acttatataa cagaattggc   1080
aaatgccctg tcttactgtc attcgaagag agttattcat agagacatta gccagagaa   1140 cttacttctt ggatcagctg gagagcttaa aattgcagat tttgggtggt cagtacatgc   1200
tccatcttcc aggaggacca ctctctgtgg caccctggac tacctgcccc ctgaaatgat   1260
tgaaggtcgg atgcatgatg agaaggtgga tctctggagc cttggagttc tttgctatga   1320
atttttagtt gggaagcctc cttttgaggc aaacacatac caagagacct acaaagaat   1380 atcacggggtt gaattcacat tccctgactt tgtaacagag ggagccaggg acctcatttc   1440
aagactgttg aagcataatc ccagccagag gccaatgctc agagaagtac ttgaacaccc   1500
ctggatcaca gcaaattcat caaaaccatc aaattgccaa acaaagaat cagctagcaa   1560 acagtcttag gaatcgtgca gggggagaaa tccttgagcc agggctgcca tataacctga   1620
caggaacatg ctactgaagt ttattttacc attgactgct gccctcaatc tagaacgcta   1680
cacaagaaat atttgttta ctcagcaggt gtgccttaac ctccctattc agaaagctcc   1740
acatcaataa acatgacact ctgaagtgaa agtagccacg agaattgtgc tacttatact   1800
ggttcataat ctggaggcaa ggttcgactg cagccgcccc gtcagcctgt gctaggcatg   1860
gtgtcttcac aggaggcaaa tccagagcct ggctgtgggg aaagtgacca ctctgccctg   1920
accccgatca gttaaggagc tgtgcaataa ccttcctagt acctgagtga gtgtgtaact   1980
tattgggttg gcgaagcctg gtaaagctgt tggaatgagt atgtgattct ttttaagtat   2040
gaaaataaag atatatgtac agacttgtat tttttctctg gtggcattcc tttaggaatg   2100
ctgtgtgtct gtccggcacc ccggtaggcc tgattgggtt tctagtcctc cttaaccact   2160
tatctcccat atgagagtgt gaaaaatagg aacacgtgct ctacctccat ttagggattt   2220
gcttgggata cagaagaggc catgtgtctc agagctgtta agggcttatt ttttaaaac    2280 attggagtca tagcatgtgt gtaaactta aatatgcaaa taataagta tctatgtcta    2340 aaaaaa                                                              2346
```

<210> SEQ ID NO 25
<211> LENGTH: 1453
<212> TYPE: DNA
<213> ORGANISM: Homo sapiens

<400> SEQUENCE: 25

```
cgcaaaggac ctgacgacgt gctgcgtcgt tactttttgaa acgcttggcg gggaagtgct      60
gttggagccg ctgtggttgc tgtccgcgga gtggaagcgc gtgcttttgt ttgtgtccct     120
ggccatggcg ctgcagctct cccgggagca gggaatcacc ctgcgcggga cgccgaaat     180
cgtggccgag ttcttctcat tcggcatcaa cagcatttta tatcagcgtg catatatcc     240
atctgaaacc tttactcgag tgcagaaata cggactcacc ttgcttgtaa ctactgatct     300
tgagctcata aaatacctaa ataatgtggt ggaacaactg aaagattggt tatacaagtg     360
ttcagttcag aaactggttg tagttatctc aaatattgaa agtggtgagg tcctggaaag     420
atggcagttt gatattgagt gtgacaagac tgcaaaagat gacagtgcac ccagagaaaa     480
gtctcagaaa gctatccagg atgaaatccg ttcagtgatc agacagatca cagctacggt     540
gacatttctg ccactgttgg aagtttcttg ttcatttgat ctgctgattt atacagacaa     600
agatttggtt gtacctgaaa atgggaaga gtcgggacca cagttattta ccaattctga     660
ggaagtccgc cttcgttcat ttactactac aatccacaaa gtaaatagca tggtggccta     720
caaaattcct gtcaatgact gaggatgaca tgaggaaaat aatgtaattg taattttgaa     780
atgtggtttt cctgaaatca agtcatctat agttgatatg ttttatttca ttggttaatt     840
tttacatgga gaaaccaaa atgatactta ctgaactgtg tgtaattgtt cctttattt     900
ttttggtacc tatttgactt accatggagt taacatcatg aatttattgc acattgttca     960
aaaggaacca ggaggttttt ttgtcaacat tgtgatgtat attcctttga agatagtaac    1020
tgtagatgga aaacttgtg ctataaagct agatgctttc ctaaatcaga tgttttggtc    1080
aagtagtttg actcagtata ggtagggaga tatttaagta taaatacaa caaggaagt    1140
ctaaatattc agaatctttg ttaaggtcct gaaagtaact cataatctat aaacaatgaa    1200
atattgctgt atagctcctt ttgaccttca tttttcatgtat agttttccct attgaatcag    1260
tttccaatta tttgacttta atttatgtaa cttgaaccta tgaagcaatg gatatttgta    1320
ctgtttaatg ttctgtgata cagaactctt aaaaatgttt tttcatgtgt tttataaaat    1380
caagttttaa gtgaaagtga ggaaataaag ttaagtttgt tttaaatttg tcttaaaaaa    1440
aaaaaaaaaa aaa                                                        1453
```

<210> SEQ ID NO 26
<211> LENGTH: 3509
<212> TYPE: DNA
<213> ORGANISM: Homo sapiens

<400> SEQUENCE: 26

```
ggcgccctga acgttcggc gagccgactg cggctgcgcg gggtattcga atcggcggcg       60
gcttctagtt tgcggttcag gtttggccgc tgccggccag cgtcctctgg ccatggacac     120
cccgaaaat gtccttcaga tgcttgaagc ccacatgcag agctacaagg gcaatgaccc     180
tcttggtgaa tgggaaagat acatacagtg ggtagaagag aattttcctg agaataaaga     240
atacttgata actttactag aacatttaat gaaggaattt ttagataaga agaaatacca     300
caatgaccca agattcatca gttattgttt aaaatttgct gagtacaaca gtgacctcca     360
tcaatttttt gagtttctgt acaaccatgg gattggaacc ctgtcatccc ctctgtacat     420
tgcctgggcg gggcatctgg aagcccaagg agagctgcag catgccagtg ctgtccttca     480
gagaggaatt caaaaccagg ctgaacccag agagttcctg caacaacaat acaggttatt     540
```

```
tcagacacgc ctcactgaaa cccatttgcc agctcaagct agaacctcag aacctctgca    600
taatgttcag gttttaaatc aaatgataac atcaaaatca aatccaggaa ataacatggc    660
ctgcatttct aagaatcagg gttcagagct ttctggagtg atatcttcag cttgtgataa    720
agagtcaaat atggaacgaa gagtgatcac gatttctaaa tcagaatatt ctgtgcactc    780
atctttggca tccaaagttg atgttgagca ggttgttatg tattgcaagg agaagcttat    840
tcgtggggaa tcagaatttt cctttgaaga attgagagcc cagaaataca atcaacggag    900
aaagcatgag caatgggtaa atgaagacag acattatatg aaaaggaaag aagcaaatgc    960
ttttgaagaa cagctattaa acagaaaat ggatgaactt cataagaagt tgcatcaggt    1020
ggtggagaca tcccatgagg atctgcccgc ttcccaggaa aggtccgagg ttaatccagc    1080
acgtatgggg ccaagtgtag gctcccagca ggaactgaga cgccatgtc ttccagtaac    1140
ctatcagcag acaccagtga acatggaaaa gaacccaaga gaggcacctc ctgttgttcc    1200
tcctttggca aatgctattt ctgcagcttt ggtgtcccca gccaccagcc agagcattgc    1260
tcctcctgtt cctttgaaag cccagacagt aacagactcc atgtttgcag tggccagcaa    1320
agatgctgga tgtgtgaata agagtactca tgaattcaag ccacagagtg gagcagagat    1380
caaagaaggg tgtgaaacac ataaggttgc caacacaagt tcttttcaca caactccaaa    1440
cacatcactg ggaatggttc aggcaacgcc atccaaagtg cagccatcac ccaccgtgca    1500
cacaaaagaa gcattaggtt tcatcatgaa tatgtttcag gctcctacac ttcctgatat    1560
ttctgatgac aaagatgaat ggcaatctct agatcaaaat gaagatgcat tgaagcccaa    1620
gtttcaaaaa aatgtaaggt catctggggc ttggggagtc aataagatca tctcttcttt    1680
gtcatctgct tttcatgtgt ttgaagatgg aaacaaagaa aattatggat taccacagcc    1740
taaaaataaa cccacaggag ccaggacctt tggagaacgc tctgtcagca gacttccttc    1800
aaaaccaaag gaggaagtgc ctcatgctga agagttttg gatgactcaa ctgtatgggg    1860
tattcgctgc aacaaaaccc tggcacccag tcctaagagc ccaggagact tcacatctgc    1920
tgcacaactt gcgtctacac cattccacaa gcttccagtg gagtcagtgc acattttaga    1980
agataaagaa aatgtggtag caaaacagtg tacccaggcg actttggatt cttgtgagga    2040
aaacatggtg gtgccttcaa gggatggaaa attcagtcca attcaagaga aaagcccaaa    2100
acaggccttg tcgtctcaca tgtattcagc atccttactt cgtctgagcc agcctgctgc    2160
aggtggggta cttacctgtg aggcagagtt gggcgttgag gcttgcagac tcacagacac    2220
tgacgctgcc attgcagaag atccaccaga tgctattgct gggctccaag cagaatggat    2280
gcagatgagt tcacttggga ctgttgatgc tccaaacttc attgttggga acccatggga    2340
tgataagctg attttcaaac ttttatctgg gcttttctaaa ccagtgagtt cctatccaaa    2400
tacttttgaa tggcaatgta acttccagc catcaagccc aagactgaat ttcaattggg    2460
ttctaagctg gtctatgtcc atcaccttct tggagaagga gcctttgccc aggtgtacga    2520
agctacccag ggagatctga atgatgctaa aaataaacag aaatttgttt taaggtcca    2580
aaagcctgcc aaccctggg aattctacat tgggacccag ttgatggaaa gactaaagcc    2640
atctatgcag cacatgttta tgaagttcta ttctgcccac ttattccaga atggcagtgt    2700
attagtagga gagctctaca gctatggaac attattaaat gccattaacc tctataaaaa    2760
taccctgaa aaagtgatgc ctcaaggtct tgtcatctct tttgctatga gaatgcttta    2820
catgattgag caagtgcatg actgtgaaat cattcatgga gacattaaac cagacaattt    2880
catacttgga aacggatttt tggaacagga tgatgaagat gatttatctg ctggcttggc    2940
```

```
actgattgac ctgggtcaga gtatagatat gaaacttttt ccaaaaggaa ctatattcac    3000
agcaaagtgt gaaacatctg gttttcagtg tgttgagatg ctcagcaaca aaccatggaa    3060
ctaccagatc gattactttg gggttgctgc aacagtatat tgcatgctct ttggcactta    3120
catgaaagtg aaaaatgaag gaggagagtg taagcctgaa ggtcttttta gaaggcttcc    3180
tcatttggat atgtggaatg aattttttca tgttatgttg aatattccag attgtcatca    3240
tcttccatct ttggatttgt taaggcaaaa gctgaagaaa gtatttcaac aacactatac    3300
taacaagatt agggccctac gtaataggct aattgtactg ctcttagaat gtaagcgttc    3360
acgaaaataa aatttggata tagacagtcc ttaaaaatca cactgtaaat atgaatctgc    3420
tcactttaaa cctgtttttt tttcatttat tgtttatgta aatgtttgtt aaaaataaat    3480
cccatggaat atttccatgt aaaaaaaaa                                     3509
```

<210> SEQ ID NO 27
<211> LENGTH: 1253
<212> TYPE: DNA
<213> ORGANISM: Homo sapiens

<400> SEQUENCE: 27

```
gggcggccgg gagagtagca gtgccttgga ccccagctct cctcccccctt tctctctaag    60 gatggcccag aaggagaact cctacccctg gccctacggc cgacagacgg ctccatctgg   120
cctgagcacc ctgccccagc gagtcctccg gaaagagcct gtcaccccat ctgcacttgt   180
cctcatgagc cgctccaatg tccagcccac agctgcccct ggccagaagg tgatggagaa   240
tagcagtggg acacccgaca tcttaacgcg gcacttcaca attgatgact tgagattgg    300 gcgtcctctg gcaaaggca agtttggaaa cgtgtacttg gctcgggaga gaaaagcca    360 tttcatcgtg gcgctcaagg tcctcttcaa gtcccagata gagaaggagg gcgtggagca   420
tcagctgcgc agagagatcg aaatccaggc ccacctgcac catcccaaca tcctgcgtct   480
ctacaactat ttttatgacc ggaggaggat ctacttgatt ctagagtatg cccccgcgg    540 ggagctctac aaggagctgc agaagagctg cacatttgac gagcagcgaa cagccacgat   600
catggaggag ttggcagatg ctctaatgta ctgccatggg aagaaggtga ttcacagaga   660
cataaagcca gaaaatctgc tcttagggct caagggagag ctgaagattg ctgacttcgg   720
ctggtctgtg catgcgccct ccctgaggag gaagacaatg tgtggcaccc tggactacct   780
gcccccagag atgattgagg ggcgcatgca caatgagaag gtggatctgt ggtgcattgg   840
agtgctttgc tatgagctgc tggtggggaa cccacccttt gagagtgcat cacacaacga   900
gacctatcgc cgcatcgtca aggtggacct aaagttcccc gcttccgtgc ccatgggagc   960 ccaggaccte atctccaaac tgctcaggca taaccctcg gaacggctgc ccctggccca   1020
ggtctcagcc caccccttggg tccgggccaa ctctcggagg gtgctgcctc cctctgccct   1080
tcaatctgtc gcctgatggt ccctgtcatt cactcgggtg cgtgtgttg tatgtctgtg   1140 tatgtatagg ggaaagaagg gatccctaac tgttcccttat tctgtttcct acctcctcct   1200
ttgtttaata aaggctgaag ctttttgtac tcatgaaaaa aaaaaaaaaa aaa          1253
```

<210> SEQ ID NO 28
<211> LENGTH: 3749
<212> TYPE: DNA
<213> ORGANISM: Homo sapiens

<400> SEQUENCE: 28

```
aggggcgtgg ccacgtcgac cgcgcgggac cgttaaattt gaaacttggc ggctaggggt        60
gtgggcttga ggtggccggt ttgttaggga gtcgtgtacg tgccttggtc gcttctgtag       120
ctccgagggc aggttgcgga agaaagccca ggcggtctgt ggcccagagg aaaggcctgc       180
agcaggacga ggacctgagc caggaatgca ggatggcggc ggtgaagaag aaggggggtg       240
ctctgagtga agccatgtcc ctggagggag atgaatggga actgagtaaa gaaaatgtac       300
aacctttaag gcaagggcgg atcatgtcca cgcttcaggg agcactggca caagaatctg       360
cctgtaacaa tactcttcag cagcagaaac gggcatttga atatgaaatt cgattttaca       420
ctggaaatga ccctctggat gtttgggata ggtatatcag ctggacagag cagaactatc       480
ctcaaggtgg aaggagagt aatatgtcaa cgttattaga aagagctgta gaagcactac        540
aaggagaaaa acgatattat agtgatcctc gatttctcaa tctctggctt aaattagggc       600
gtttatgcaa tgagcctttg gatatgtaca gttacttgca caaccaaggg attggtgttt       660
cacttgctca gttctatatc tcatgggcag aagaatatga agctagagaa actttagga        720 aagcagatgc gatatttcag gaagggattc aacagaaggc tgaaccacta gaaagactac       780
agtcccagca ccgacaattc caagctcgag tgtctcggca aactctgttg gcacttgaga       840
aagaagaaga ggaggaagtt tttgagtctt ctgtaccaca acgaagcaca ctagctgaac       900
taaagagcaa agggaaaaag acagcaagag ctccaatcat ccgtgtagga ggtgctctca       960
aggctccaag ccagaacaga ggactccaaa atccatttcc tcaacagatg caaaataata      1020
gtagaattac tgttttgat gaaaatgctg atgaggcttc tacagcagag ttgtctaagc       1080
ctacagtcca gccatggata gcaccccca tgcccagggc caaagagaat gagctgcaag       1140
caggcccttg gaacacaggc aggtccttgg aacacaggcc tcgtggcaat acagcttcac      1200
tgatagctgt acccgctgtg cttcccagtt tcactccata tgtggaagag actgcacaac      1260
agccagttat gacaccatgt aaaattgaac ctagtataaa ccacatccta agcaccagaa      1320
agcctggaaa ggaagaagga gatcctctac aaagggttca gagccatcag caagcgtctg      1380
aggagaagaa agagaagatg atgtattgta aggagaagat ttatgcagga gtaggggaat      1440
tctcctttga agaaattcgg gctgaagttt tccggaagaa attaaaagag caaagggaag      1500
ccgagctatt gaccagtgca gagaagagag cagaaatgca gaaacagatt gaagagatgg      1560
agaagaagct aaaagaaatc caaactactc agcaagaaag aacaggtgat cagcaagaag      1620
agacgatgcc tacaaaggag acaactaaac tgcaaattgc ttccgagtct cagaaaatac      1680
caggaatgac tctatccagt tctgtttgtc aagtaaactg ttgtgccaga gaaacttcac      1740
ttgcggagaa catttggcag gaacaacctc attctaaagg tcccagtgta cctttctcca      1800 ttttttgatga gtttcttctt tcagaaaaga agaataaaag tcctcctgca gatcccccac      1860
gagttttagc tcaacgaaga ccccttgcag ttctcaaaac ctcagaaagc atcacctcaa      1920
atgaagatgt gtctccagat gtttgtgatg aatttacagg aattgaaccc ttgagcgagg      1980
atgccattat cacaggcttc agaaatgtaa caatttgtcc taacccagaa gacacttgtg      2040
actttgccag agcagctcgt tttgtatcca ctccttttca tgagataatg tccttgaagg      2100
atctcccttc tgatcctgag agactgttac cggaagaaga tctagatgta aagacctctg      2160
aggaccagca gacagcttgt ggcactatct acagtcagac tctcagcatc aagaagctga      2220
gcccaattat tgaagacagt cgtgaagcca cacactcctc tggcttctct ggttcttctg      2280
cctcggttgc aagcacctcc tccatcaaat gtcttcaaat tcctgagaaa ctagaactta      2340
ctaatgagac ttcagaaaac cctactcagt caccatggtg ttcacagtat cgcagacagc      2400
```

```
tactgaagtc cctaccagag ttaagtgcct ctgcagagtt gtgtatagaa gacagaccaa    2460
tgcctaagtt ggaaattgag aaggaaattg aattaggtaa tgaggattac tgcattaaac    2520
gagaatacct aatatgtgaa gattacaagt tattctgggt ggcgccaaga aactctgcag    2580
aattaacagt aataaaggta tcttctcaac ctgtcccatg ggactttat atcaacctca     2640 agttaaagga acgtttaaat gaagattttg atcattttg cagctgttat caatatcaag     2700
atggctgtat tgtttggcac caatatataa actgcttcac ccttcaggat cttctccaac    2760
acagtgaata tattacccat gaaataacag tgttgattat ttataacctt ttgacaatag    2820
tggagatgct acacaaagca gaaatagtcc atggtgactt gagtccaagg tgtctgattc    2880
tcagaaacag aatccacgat ccctatgatt gtaacaagaa caatcaagct ttgaagatag    2940
tggacttttc ctacagtgtt gaccttaggg tgcagctgga tgttttacc ctcagcggct     3000 ttcggactgt acagatcctg gaaggacaaa agatcctggc taactgttct tctccctacc    3060
aggtagacct gtttggtata gcagatttag cacatttact attgttcaag gaacacctac    3120
aggtcttctg ggatgggtcc ttctggaaac ttagccaaaa tatttctgag ctaaaagatg    3180
gtgaattgtg gaataaattc tttgtgcgga ttctgaatgc caatgatgag gccacagtgt    3240
ctgttcttgg ggagcttgca gcagaaatga atggggtttt tgacactaca ttccaaagtc    3300
acctgaacaa agcctatgg aaggtaggga agttaactag tcctgggggct ttgctctttc    3360 agtgagctag gcaatcaagt ctcacagatt gctgcctcag agcaatggtt gtattgtgga    3420
acactgaaac tgtatgtgct gtaatttaat ttaggacaca tttagatgca ctaccattgc    3480
tgttctactt tttggtacag gtatattttg acgtcactga tatttttat acagtgatat     3540 acttactcat ggccttgtct aacttttgtg aagaactatt ttattctaaa cagactcatt    3600
acaaatggtt accttgttat ttaacccatt tgtctctact tttccctgta cttttcccat    3660
ttgtaatttg taaaatgttc tcttatgatc accatgtatt ttgtaaataa taaaatagta    3720
tctgttaaat ttgtgcttct aaaaaaaaa                                       3749

<210> SEQ ID NO 29
<211> LENGTH: 4212
<212> TYPE: DNA
<213> ORGANISM: Homo sapiens

<400> SEQUENCE: 29
gagctgggtg ggggtgcccc acgctgaaag agagtgatgg agtgcccagt gatggaaact      60
gactcacttt ttacctcagg aattaagaga catttgaaag acaaaagaat ttcaaagact     120
actaagttga atgtttctct tgcttcaaaa ataaaaacaa aaatactaaa taattcttct     180
attttcaaaa tatctttaaa gcacaacaac agggcattag ctcaggctct tagtagagaa     240
aaagagaatt ctcgaagaat tacaactgaa aagatgctat tgcaaaaaga agtagagaaa     300
ctgaattttg agaacacatt tcttcgccta agctaaaata acttgaataa gaagcttata     360
gacatagaag ctctcatgaa caataacttg ataactgcaa ttgaaatgag cagtctttct     420
gagttccatc agagttcctt tctactgtca gctagcaaga agaaacgaat tagtaaacag     480
tgcaagttga tgcgtcttcc atttgcaagg gttccattaa cttcaaatga tgatgaagat     540
gaagataaag agaaaatgca gtgtgacaac aatattaaat caaagacatt acctgatatt     600
ccctcttcag gatcaacaac acaacccttta tcaactcagg ataattcgga agtgttattt    660
cttaaagaaa ataatcaaaa tgtatatggt ttagatgatt cagaacatat ttcttctata    720
```

```
gttgatgtac ctcccagaga aagccattcc cactcagacc aaagttctaa gacttctcta    780
atgagtgaga tgagaaacgc ccagtctatt ggccgcagat gggagaaacc atctcctagt    840
aatgtgactg aaaggaagaa gcgtgggtca tcttgggaat caaataatct ttctgcagac    900
actccctgtg caacagtttt agataaacaa cacatttcaa gtccagaatt aaattgcaat    960
aatgagataa atggtcatac taatgaaaca aatactgaaa tgcaaagaaa taaacaggat   1020
cttcctggct tatcttctga gtctgccaga gaacctaatg cagagtgcat gaatcaaatt   1080
gaggataatg atgactttca attgcagaaa actgtgtatg atgctgacat ggatttaact   1140
gctagtgaag tcagcaaaat tgtcacagtc tcaacaggca ttaaaaagaa aagtaataaa   1200
aaaacaaatg aacatggaat gaaaactttc agaaagtga aagattccag ctctgaaaaa    1260
aagagagaaa gatcaaagag acagttaaa aatagttcag atgtcgatat tggggaaaag    1320
attgaaaaca ggacagaaag atctgatgtc ctggatggca aaggggtgc agaagatccc     1380 ggttttattt tcaataatga acagctggct cagatgaatg aacagctggc tcaggtgaat   1440
gaactaaaga aaatgaccct tcaaactggc tttgaacaag gtgacagaga aaatgtactg   1500
tgtaataaaa aggagaaaag aataacaaat gagcaagagg aaacatactc tttatcccaa   1560
agttcaggta aatttcacca ggagagtaaa tttgataagg gtcagaattc cctaacttgt   1620
aataaaagta aagcttctag acagacattt gtgattcaca aattagaaaa agataactta   1680
ctcccaaacc aaaaggataa agtaaccatt tatgaaaacc tagacgtcac aaatgaattt   1740
cacacagcca atctttccac caaagataat ggaaatttat gtgattatgg gacccacaat   1800
atattggatt tgaaaaagta tgtcactgat attcaaccct cagagcaaaa tgaatcaaac   1860
attaataagc ttagaaagaa agtaaaccgg aagacagaaa taatttctgg aatgaaccac   1920
atgtatgagg ataatgataa agatgtggtg catggcctaa aaaaggtaa ttttttttc     1980 aaacccaag aggataaaga acctatctct gaaaacatag aagtttccaa agagcttcaa    2040
atcccagctc tttctactag agataatgaa atcaatgtg actataggac ccagaatgtg    2100
ttgggtttgc aaaagcagat caccaatatg taccccgttc agcaaaatga atcaaaagtt   2160
aataagaagc ttaggcagaa agtaaatcgg aagacagaaa taatttctga agtgaatcat   2220
ttagataatg acaaaagtat agaatacaca gttaaaagtc actcactctt tttaacgcaa   2280
aaagataagg aaatcatccc tggaaaccta aagacccaa gtgagtttga aacacctgct    2340 cttttctacca aagatagtgg aaacctgtat gattctgaga ttcaaaatgt ttgggggtg   2400 aaacatggcc atgatatgca acctgcttgt caaaatgatt caaaaatagg taagaagcct   2460
agactaaatg tatgtcaaaa gtcagaaata attcctgaaa ccaaccaaat atatgagaat   2520
gataacaaag gtgtacatga cctagaaaaa gataacttct tctctctaac cccaaaggat   2580
aaagaaacaa tttctgaaaa tctacaagtc acaaatgaat tcaaacagt tgatcttctc    2640 atcaaagata tggaaatttt atgtgattat gacacccaga atattggga gttgaaaaag    2700 tatgttactg ataggaaatc tgctgagcaa atgaatcaa aataaataa gctcaggaat    2760 aaagtgaatt ggaagacaga ataatttct gaaatgaacc agatatatga ggataatgat    2820
aaagatgcac atgtccaaga aagctataca aaagatcttg attttaaagt aaataaatct   2880
aaacaaaaac ttgaatgcca agacattatc aataaacact atatggaagt caacagtaat   2940
gaaaaggaaa gttgtgatca aatttttagat tcctacaaag tagttaaaaa acgtaagaaa   3000
gaatcatcat gcaaggcaaa gaacattttg acaaaagcta agaacaaact tgcttcacag   3060
ttaacagaat cttcacagac atctatctcc ttagaatctg attaaaaaca tattactagt   3120
```

```
gaagcagatt ctgatccagg aaacccagtt gaactatgta agactcagaa gcaaagcact    3180
accactttga ataaaaaaga tctcccttt gtggaagaaa taaaagaagg agagtgtcag     3240
gttaaaaagg taaataaaat gacatctaag tcaagaaaaa ggaagacctc catagatcct    3300
tctccagaga gccatgaagt aatggaaaga atacttgaca gcgttcaggg aaagtctact    3360
gtatctgaac aagctgataa ggaaaacaat ttggagaatg agaaaatggt caaaaataag    3420
ccagactttt acacaaaggc atttagatct ttgtctgaga tacattcacc taacatacaa    3480
gattcttcct ttgacagtgt tcgtgaaggt ttagtacctt tgagcgtttc ttctggtaaa    3540
aatgtgataa taaagaaaaa ttttgccttg gagtgctccc cagcctttca agtaagtgat    3600
gatgagcatg agaagatgaa caagatgaaa tttaaagtca accggagaac ccaaaaatca    3660
ggaataggtg atagaccatt acaggacttg tcaaatacca gttttgtttc aaataacact    3720
gctgaatctg aaaataagtc agaagatcta tcttcagaac ggacaagcag aagaagaagg    3780
tgtactcctt tctattttaa agagccaagc ctcagagaca agatgagaag atgaagtgaa    3840
tttatggatt ctggttttc tgaattttca aagcataagg aatcaaaaca gaaatatagt     3900
atcaagaaga tgaaatgctt aatgaaaagg ttttttttt gtttctttgg cctttcatgg    3960
agtgttgatt tgtccattct taatgtttat taataggtat atgtgcataa aatagctatt    4020
ttgtaacatt aaaccttttg agtcattttg gtcatcatat aacttacctt cctgtttatt    4080
taagcttctt tttacctagt agcctttaac caaacaataa ccttttaacc aaataaaatg    4140
tgttaataaa taaaaaaaaa aaaaaaaaaa aaaaaaaaa aaaaaaaaaa aaaaaaaaaa     4200
aaaaaaaaaa aa                                                        4212

<210> SEQ ID NO 30
<211> LENGTH: 728
<212> TYPE: DNA
<213> ORGANISM: Homo sapiens

<400> SEQUENCE: 30
gcggcctcag atgaatgcgg ctgttaagac ctgcaataat ccagaatggc tactctgatc      60
tatgttgata aggaaaatgg agaaccaggc acccgtgtgg ttgctaagga tgggctgaag    120
ctggggtctg gaccttcaat caaagcctta gatgggagat ctcaagtttc aacaccacgt    180
tttggcaaaa cgttcgatgc cccaccagcc ttacctaaag ctactagaaa ggctttggga    240
actgtcaaca gagctacaga aaagtctgta aagaccaagg gaccccctcaa acaaaaacag   300 ccaagctttt ctgccaaaaa gatgactgag aagactgtta agcaaaaaag ctctgttcct    360
gcctcagatg atgcctatcc agaaatagaa aaattctttc ccttcaatcc tctagacttt    420
gagagttttg acctgcctga agagcaccag attgcgcacc tccccttgag tggagtgcct    480
ctcatgatcc ttgacgagga gagagagctt gaaaagctgt tcagctgggc cccccttca    540 cctgtgaaga tgccctctcc accatgggaa tccaatctgt tgcagtctcc ttcaagcatt    600
ctgtcgaccc tggatgttga attgccacct gtttgctgtg acatagatat ttaaatttct    660
tagtgcttca gagtttgtgt gtatttgtat taataaagca ttcttcaaca gaaaaaaaaa    720
aaaaaaaa                                                             728

<210> SEQ ID NO 31
<211> LENGTH: 8630
<212> TYPE: DNA
<213> ORGANISM: Homo sapiens
```

```
<400> SEQUENCE: 31
taaatttaaa ggcggggcgg cctgtgagcc ctgaagtgcc ggccgcggag ggtcctggcc      60
attttcctgg gaccagttca gcctgatagg atggcggagg aaggagccgt ggccgtctgc     120
gtgcgagtgc ggccgctgaa cagcagagaa gaatcacttg gagaaactgc ccaagtttac     180
tggaaaactg acaataatgt catttatcaa gttgatggaa gtaaatcctt caattttgat     240
cgtgtctttc atggtaatga aactaccaaa aatgtgtatg aagaaatagc agcaccaatc     300
atcgattctg ccatacaagg ctacaatggt actatatttg cctatggaca gactgcttca     360
ggaaaaacat ataccatgat gggttcagaa gatcatttgg gagttatacc cagggcaatt     420
catgacattt tccaaaaaat taagaagttt cctgataggg aatttctctt acgtgtatct     480
tacatggaaa tatacaatga aaccattaca gatttactct gtggcactca aaaaatgaaa     540
cctttaatta ttcgagaaga tgtcaatagg aatgtgtatg ttgctgatct cacagaagaa     600
gttgtatata catcagaaat ggctttgaaa tggattacaa agggagaaaa gagcaggcat     660
tatgagaaaa caaaaatgaa tcaaagaagc agtcgttctc ataccatctt taggatgatt     720
ttggaaagca gagagaaggg tgaaccttct aattgtgaag gatctgttaa ggtatcccat     780
ttgaatttgg ttgatcttgc aggcagtgaa agagctgctc aaacaggcgc tgcaggtgtg     840
cggctcaagg aaggctgtaa tataaatcga agcttattta ttttgggaca agtgatcaag     900
aaacttagtg atggacaagt tggtggtttc ataaattatc gagatagcaa gttaacacga     960
attctccaga attccttggg aggaaatgca agacacgta ttatctgcac aattactcca    1020
gtatcttttg atgaaacact tactgctctc cagtttgcca gtactgctaa atatatgaag    1080
aatactcctt atgttaatga ggtatcaact gatgaagctc tcctgaaaag gtatagaaaa    1140
gaaataatgg atcttaaaaa acaattagag gaggtttctt tagagacgcg ggctcaggca    1200
atggaaaaag accaattggc ccaacttttg gaagaaaaag atttgcttca gaaagtacag    1260
aatgagaaaa ttgaaaactt aacacggatg ctggtgacct cttcttccct cacgttgcaa    1320
caggaattaa aggctaaaag aaaacgaaga gttacttggt gccttggcaa aattaacaaa    1380
atgaagaact caaactatgc agatcaattt aatataccaa caaatataac aacaaaaaca    1440
cataagcttt ctataaattt attacgagaa attgatgaat ctgtctgttc agagtctgat    1500
gttttcagta acactcttga tacattaagt gagatagaat ggaatccagc aacaaagcta    1560
ctaaatcagg agaatataga aagtgagttg aactcacttc gtgctgacta tgataatctg    1620
gtattagact atgaacaact acgaacagaa aaagaagaaa tggaattgaa attaaaagaa    1680
aagaatgatt tggatgaatt tgaggctcta gaaagaaaaa ctaaaaaaga tcaagagatg    1740
caactaattc atgaaatttc gaacttaaag aatttagtta agcatgcaga agtatataat    1800
caagatcttg agaatgaact cagttcaaaa gtagagctgc ttagagaaaa ggaagaccag    1860
attaagaagc tacaggaata catagactct caaaagctag aaaatataaa aatggacttg    1920
tcatactcat tggaaagcat tgaagaccca aaacaaatga agcagactct gtttgatgct    1980
gaaactgtag cccttgatgc caagagagaa tcagcctttc ttagaagtga aaatctggag    2040
ctgaaggaga aaatgaaaga acttgcaact acatacaagc aaatggaaaa tgatattcag    2100
ttatatcaaa gccagttgga ggcaaaaaag aaaatgcaag ttgatctgga gaagaatta     2160 caatctgctt ttaatgagat aacaaaactc acctccctta tagatggcaa agttccaaaa    2220
gatttgctct gtaatttgga attggaagga aagattactg atcttcagaa agaactaaat    2280
aaagaagttg aagaaatga agctttgcgg gaagaagtca ttttgctttc agaattgaaa    2340
```

-continued

```
tctttacctt ctgaagtaga aaggctgagg aaagagatac aagacaaatc tgaagagctc    2400
catataataa catcagaaaa agataaattg ttttctgaag tagttcataa ggagagtaga    2460
gttcaaggtt tacttgaaga aattgggaaa acaaaagatg acctagcaac tacacagtcg    2520
aattataaaa gcactgatca agaattccaa aatttcaaaa cccttcatat ggactttgag    2580
caaaagtata agatggtcct tgaggagaat gagagaatga atcaggaaat agttaatctc    2640
tctaaagaag cccaaaaatt tgattcgagt ttgggtgctt tgaagaccga gctttcttac    2700
aagacccaag aacttcagga gaaaacacgt gaggttcaag aaagactaaa tgagatggaa    2760
cagctgaagg aacaattaga aaatagagat tctacgctgc aaactgtaga aagggagaaa    2820
acactgatta ctgagaaact gcagcaaact ttagaagaag taaaaacttt aactcaagaa    2880
aaagatgatc taaacaact ccaagaaagc ttgcaaattg agagggacca actcaaaagt    2940
gatattcacg atactgttaa catgaatata gatactcaag aacaattacg aaatgctctt    3000
gagtctctga acaacatca agaaacaatt aatacactaa aatcgaaaat ttctgaggaa    3060
gtttccagga atttgcatat ggaggaaaat acaggagaaa ctaaagatga atttcagcaa    3120
aagatggttg gcatagataa aaaacaggat ttggaagcta aaaataccca aacactaact    3180
gcagatgtta aggataatga gataattgag caacaaagga agatattttc tttaatacag    3240
gagaaaaatg aactccaaca aatgttagag agtgttatag cagaaaagga acaattgaag    3300
actgacctaa aggaaaatat tgaaatgacc attgaaaacc aggaagaatt aagacttctt    3360
ggggatgaac ttaaaaagca acaagagata gttgcacaag aaaagaacca tgccataaag    3420
aaagaaggag agctttctag gacctgtgac agactggcag aagttgaaga aaaactaaag    3480
gaaaagagcc agcaactcca agaaaaacag caacaacttc ttaatgtaca agaagagatg    3540
agtgagatgc agaaaaagat taatgaaata gagaatttaa agaatgaatt aagaacaaa    3600 gaattgacat tggaacatat ggaaacagag aggcttgagt tggctcagaa acttaatgaa    3660
aattatgagg aagtgaaatc tataaccaaa gaaagaaaag ttctaaagga attacagaag    3720
tcatttgaaa cagagagaga ccaccttaga ggatatataa gagaaattga agctacaggc    3780
ctacaaacca aagaagaact aaaaattgct catattcacc taaaagaaca ccaagaaact    3840
attgatgaac taagaagaag cgtatctgag aagacagctc aaataataaa tactcaggac    3900
ttagaaaaat cccataccaa attacaagaa gagatcccag tgcttcatga ggaacaagag    3960
ttactgccta atgtgaaaga agtcagtgag actcaggaaa caatgaatga actggagtta    4020
ttaacagaac agtccacaac caaggactca acaacactgg caagaataga aatggaaagg    4080
ctcaggttga atgaaaaatt tcaagaaagt caggaagaga taaaatctct aaccaaggaa    4140
agagacaacc ttaaaacgat aaaagaagcc cttgaagtta acatgaccaa gctgaaagaa    4200
catattagag aaactttggc taaaatccag gagtctcaaa gcaaacaaga acagtcctta    4260
aatatgaaag aaaaagacaa tgaaactacc aaaatcgtga gtgagatgga gcaattcaaa    4320
cccaaagatt cagcactact aaggatagaa atagaaatgc tcggattgtc caaaagactt    4380
caagaaagtc atgatgaaat gaaatctgta gctaaggaga aagatgacct acagaggctg    4440
caagaagttc ttcaatctga aagtgaccag ctcaaagaaa acataaaaga aattgtagct    4500
aaacacctgg aaactgaaga ggaacttaaa gttgctcatt gttgcctgaa agaacaagag    4560
gaaactatta atgagttaag agtgaatctt tcagagaagg aaactgaaat atcaaccatt    4620
caaaagcagt tagaagcaat caatgataaa ttacagaaca agatccaaga gatttatgag    4680
```

-continued

```
aaagaggaac aatttaatat aaaacaaatt agtgaggttc aggaaaaagt gaatgaactg    4740
aaacaattca aggagcatcg caaagccaag gattcagcac tacaaagtat agaaagtaag    4800
atgctcgagt tgaccaacag acttcaagaa agtcaagaag aaatacaaat tatgattaag    4860 gaaaagagg aaatgaaaag agtacaggag gcccttcaga tagagagaga ccaactgaaa    4920
gaaaacacta agaaattgt agctaaaatg aaagaatctc aagaaaaaga atatcagttt    4980
cttaagatga cagctgtcaa tgagactcag gagaaaatgt gtgaaataga acacttgaag    5040
gagcaatttg agacccagaa gttaaacctg gaaaacatag aaacggagaa tataaggttg    5100
actcagatac tacatgaaaa ccttgaagaa atgagatctg taacaaaaga aagagatgac    5160
cttaggagtg tggaggagac tctcaaagta gagagagacc agctcaagga aaaccttaga    5220
gaaactataa ctagagacct agaaaaacaa gaggagctaa aaattgttca catgcatctg    5280
aaggagcacc aagaaactat tgataaacta agagggattg tttcagagaa aacaaatgaa    5340
atatcaaata tgcaaaagga cttagaacac tcaaatgatg ccttaaaagc acaggatctg    5400
aaaatacaag aggaactaag aattgctcac atgcatctga aagagcagca ggaaactatt    5460
gacaaactca gaggaattgt ttctgagaag acagataaac tatcaaatat gcaaaaagat    5520
ttagaaaatt caaatgctaa attacaagaa aagattcaag aacttaaggc aaatgaacat    5580
caacttatta cgttaaaaaa agatgtcaat gagacacaga aaaagtgtc tgaaatggag    5640 caactaaaga aacaaataaa agaccaaagc ttaactctga gtaaattaga aatagagaat    5700
ttaaatttgg ctcagaaact tcatgaaaac cttgaagaaa tgaaatctgt aatgaaagaa    5760
agagataatc taagaagagt agaggagaca ctcaaactgg agagagacca actcaaggaa    5820
agcctgcaag aaaccaaagc tagagatctg gaaatacaac aggaactaaa aactgctcgt    5880
atgctatcaa agaacacaa agaaactgtt gataaactta gagaaaaaat ttcagaaaag    5940
acaattcaaa tttcagacat tcaaaaggat ttagataaat caaagatga attacagaaa    6000 aagatccaag aacttcagaa aaaagaactt caactgctta gagtgaaaga agatgtcaat    6060
atgagtcata aaaaattaa tgaaatggaa cagttgaaga agcaatttga ggcccaaaac    6120
ttatctatgc aaagtgtgag aatggataac ttccagttga ctaagaaact tcatgaaagc    6180
cttgaagaaa taagaattgt agctaaagaa agagatgagc taaggaggat aaaagaatct    6240
ctcaaaatgg aaagggacca attcatagca accttaaggg aaatgatagc tagagaccga    6300
cagaaccacc aagtaaaacc tgaaaaaagg ttactaagtg atggacaaca gcaccttacg    6360
gaaagcctga gagaaaagtg ctctagaata aaagagcttt tgaagagata ctcagagatg    6420
gatgatcatt atgagtgctt gaatagattg tctcttgact tggagaagga aattgaattc    6480
caaaaagagc tttcaatgag agttaaagca aacctctcac ttccctattt acaaaccaaa    6540
cacattgaaa aacttttac tgcaaaccag agatgctcca tggaattcca cagaatcatg    6600
aagaaactga gtatgtgtt aagctatgtt acaaaaataa aagaagaaca acatgaatcc    6660
atcaataaat ttgaaatgga ttttattgat gaagtggaaa agcaaaagga attgctaatt    6720
aaaatacagc accttcaaca agattgtgat gtaccatcca gagaattaag ggatctcaaa    6780
ttgaaccaga atatggatct acatattgag gaaattctca aagatttctc agaaagtgag    6840
ttccctagca taaagactga atttcaacaa gtactaagta ataggaaaga aatgacacag    6900
tttttggaag agtggttaaa tactcgttt gatatagaaa agcttaaaaa tggcatccag    6960
aaagaaaatg ataggatttg tcaagtgaat aacttcttta ataacagaat aattgccata    7020
atgaatgaat caacagagtt tgaggaaaga agtgctacca tatccaaaga gtgggaacag    7080
```

| | |
|---|---|
| gacctgaaat cactgaaaga gaaaaatgaa aaactatttta aaaactacca aacattgaag | 7140 |
| acttccttgg catctggtgc ccaggttaat cctaccacac aagacaataa gaatcctcat | 7200 |
| gttacatcaa gagctacaca gttaaccaca gagaaaattc gagagctgga aaattcactg | 7260 |
| catgaagcta aagaaagtgc tatgcataag gaaagcaaga ttataaagat gcagaaagaa | 7320 |
| cttgaggtga ctaatgacat aatagcaaaa cttcaagcca agttcatga atcaaataaa | 7380 |
| tgccttgaaa aaacaaaaga gacaattcaa gtacttcagg acaaagttgc tttaggagct | 7440 |
| aagccatata agaagaaat tgaagatctc aaaatgaagc ttgtgaaaat agacctagag | 7500 |
| aaaatgaaaa atgccaaaga atttgaaaag gaaatcagtg ctacaaaagc cactgtagaa | 7560 |
| tatcaaaagg aagttataag gctattgaga gaaaatctca gaagaagtca acaggcccaa | 7620 |
| gatacctcag tgatatcaga acatactgat cctcagcctt caaataaacc cttaacttgt | 7680 |
| ggaggtggca gcggcattgt acaaaacaca aaagctctta ttttgaaaag tgaacatata | 7740 |
| aggctagaaa aagaaatttc taagttaaag cagcaaaatg aacagctaat aaaacaaaag | 7800 |
| aatgaattgt taagcaataa tcagcatctt tccaatgagg tcaaaacttg aaggaaaga | 7860 |
| acccttaaaa gagaggctca caaacaagta acttgtgaga attctccaaa gtctcctaaa | 7920 |
| gtgactggaa cagcttctaa aaagaaacaa attacaccct ctcaatgcaa ggaacggaat | 7980 |
| ttacaagatc ctgtgccaaa ggaatcacca aaatcttgtt tttttgatag ccgatcaaag | 8040 |
| tctttaccat cacctcatcc agttcgctat tttgataact caagtttagg cctttgtcca | 8100 |
| gaggtgcaaa atgcaggagc agagagtgtg gattctcagc caggtccttg gcacgcctcc | 8160 |
| tcaggcaagg atgtgcctga gtgcaaaact cagtagactc ctctttgtca cttctctgga | 8220 |
| gatccagcat tccttatttg gaaatgactt tgtttatgtg tctatccctg gtaatgatgt | 8280 |
| tgtagtgcag cttaatttca attcagtctt tactttgcca ctagagttga aagataaggg | 8340 |
| aacaggaaat gaatgcattg tggtaattta gaatggtgat agcaatacct tcttcttgca | 8400 |
| tatggtaata cttttaaaag ttgaattgtt ttatttattt gtatattttg taaagaataa | 8460 |
| agttattgaa agaaatgtaa agttatctac atgacttagc atattccaaa gcataataca | 8520 |
| tacattaata taaaacatca ttttattaac aaaattgtaa atgttttaa taccttacac | 8580 |
| attcaataaa tgtttagtag ttctgaatca ccaaaaaaaa aaaaaaaaa | 8630 |

<210> SEQ ID NO 32
<211> LENGTH: 1843
<212> TYPE: DNA
<213> ORGANISM: Homo sapiens

<400> SEQUENCE: 32

| | |
|---|---|
| gcggaatggg gcgggacttc cagtaggagg cggcaagttt gaaaagtgat gacggttgac | 60 |
| gtttgctgat tttttgacttt gcttgtagct gctccccgaa ctcgccgtct tcctgtcggc | 120 |
| ggccggcact gtagattaac aggaaacttc caagatggaa actttgtctt tccccagata | 180 |
| taatgtagct gagattgtga ttcatattcg caataagatc ttaacaggag ctgatggtaa | 240 |
| aaacctcacc aagaatgatc tttatccaaa tccaaagcct gaagtcttgc acatgatcta | 300 |
| catgagagcc ttacaaatag tatatggaat tcgactggaa cattttttaca tgatgccagt | 360 |
| gaactctgaa gtcatgtatc cacatttaat ggaaggcttc ttaccattca gcaatttagt | 420 |
| tactcatctg gactcatttt tgcctatctg ccgggtgaat gactttgaga ctgctgatat | 480 |
| tctatgtcca aaagcaaaac ggacaagtcg gttttaagt ggcattatca actttattca | 540 |

```
cttcagagaa gcatgccgtg aaacgtatat ggaatttctt tggcaatata atcctctgc      600 ggacaaaatg caacagttaa acgccgcaca ccaggaggca ttaatgaaac tggagagact     660
tgattctgtt ccagttgaag agcaagaaga gttcaagcag ctttcagatg gaattcagga     720
gctacaacaa tcactaaatc aggattttca tcaaaaaacg atagtgctgc aagagggaaa     780
ttcccaaaag aagtcaaata tttcagagaa aaccaagcgt ttgaatgaac taaaattgtc     840
ggtggtttct ttgaaagaaa tacaagagag tttgaaaaca aaaattgtgg attctccaga     900
gaagttaaag aattataaag aaaaaatgaa agatacggtc cagaagctta aaaatgccag     960
acaagaagtg gtggagaaat atgaaatcta tggagactca gttgactgcc tgccttcatg    1020
tcagttggaa gtgcagttat atcaaagaa atacaggac ctttcagata atagggaaaa     1080
attagccagt atcttaaagg agagcctgaa cttggaggac caaattgaga gtgatgagtc    1140
agaactgaag aaattgaaga ctgaagaaaa ttcgttcaaa agactgatga ttgtgaagaa    1200
ggaaaaactt gccacagcac aattcaaaat aaataagaag catgaagatg ttaagcaata    1260
caaacgcaca gtaattgagg attgcaataa agttcaagaa aaaagaggtg ctgtctatga    1320
acgagtaacc acaattaatc aagaaatcca aaaattaaa cttggaattc aacaactaaa     1380
agatgctgct gaaagggaga aactgaagtc ccaggaaata tttctaaact tgaaaactgc    1440
tttggagaaa taccacgacg gtattgaaaa ggcagcagag gactcctatg ctaagataga    1500
tgagaagaca gctgaactga agaggaagat gttcaaaatg tcaacctgat taacaaaatt    1560
acatgtcttt ttgtaaatgg cttgccatct tttaatttc tatttagaaa gaaaagttga    1620
agcgaatgga agtatcagaa gtaccaaata atgttggctt catcagtttt tatacactct    1680
cataagtagt taataagatg aatttaatgt aggcttttat taatttataa ttaaaataac    1740
ttgtgcagct attcatgtct ctactctgcc ccttgttgta aatagtttga gtaaaacaaa    1800
actagttacc tttgaaatat atatatttt ttctgttact atc                       1843

<210> SEQ ID NO 33
<211> LENGTH: 2319
<212> TYPE: DNA
<213> ORGANISM: Homo sapiens

<400> SEQUENCE: 33
gtggagtttg aattgggtgg cggttgactg tagagccgct ctctctcact ggcacagcga      60
ggttttgctc agcccttgtc tcgggaccgc agcctccgcc gagcgccatg gctcctagga     120
agggcagtag tcgggtggcc aagaccaact ccttacggag gcggaagctc gcctcctttc     180
tgaaagactt cgaccgtgaa gtggaaatac gaatcaagca aattgagtca gacaggcaga     240
acctcctcaa ggaggtggat aacctctaca acatcgagat cctgcggctc cccaaggctc     300
tgcgcgagat gaactggctt gactacttcg cccttggagg aaacaaacag gccctggaag     360
aggcggcaac agctgacctg gatatcaccg aaataaacaa actaacagca gaagctattc     420
agacacccct gaaatctgcc aaaacacgaa aggtaataca ggtagatgaa atgatagtgg     480
aagaggaaga agaagaagaa aatgaacgta agaatcttca aactgcaaga gtcaaaaggt     540
gtcctccatc caagaagaga actcagtcca tacaaggaaa aggaaaaggg aaaaggtcaa     600
gccgtgctaa cactgttacc ccagccgtgg gccgattgga ggtgtccatg gtcaaaccaa     660
ctccaggcct gacacccagg tttgactcaa gggtcttcaa gacccctggc ctgcgtactc     720
cagcagcagg agagcggatt tacaaacatc tcagggaatgg cagccctctt gctgacagca    780
aagagatctt cctcactgtg ccagtgggcg gcggagagag cctgcgatta ttggccagtg     840
```

```
acttgcagag gcacagtatt gcccagctgg atccagaggc cttgggaaac attaagaagc    900
tctccaaccg tctcgcccaa atctgcagca gcatacggac ccacaaatga dacaccaaag    960
ttgacaggat ggacttttaa tgggcacttc tgggaccctg aagagacttc ttcccttcag   1020
gcttattgtt tgagtgtgaa gttccagagc aaggagccat gttcctctaa gggaattcag   1080
gaattcagac gtgctagtcc cacaccagtt aggtagagct gtctgttcac cctcccatcc   1140
cagctgatcc cagtcactgc ttgctggggc catgccatgg aagcttccca tcagtctccc   1200
agctgaatcc tccctgctct ctgagctgct gccttttgcc tcctgcaact caacatcctc   1260
ttcaccctgc cctgcctgca gttgaggggg cgaagaagaa ccctgtgttc tcaggaagac   1320
tgcctccacc accgctaccc agagaacctc tgcatctggc atttctgctc tctatgcttg   1380
agaccgggag gttaggctc agataagtga gctctgggcc atgagagggt aggtccagaa   1440
ggtgggggga actgtacaga tcagcagagc aggacagttg gcagcagtga cctcagtagg   1500
gaacatgtcc gtctaccctc tcgcactcat gacacctccc cctaccagcc ctcctcttcc   1560
tcctcctcct cctcctgtgg gaggtggtca gtgggactta gggatctttc acctgctgtg   1620
cccagtagtt ctgaagtctg cttgtggagc agtgttttat gtttatccct gtttactgaa   1680
gaccaaatac tggtttggag acaacttcca tgtcttgctc ttctacctcc ctagttagtg   1740
gaaatttgga taagggaact gtagggccca gattctggag gttttatgtc attggccaca   1800
gaataactgt ctctaagcta tccatggtcc agtggtccct gccaagtctg tagacttcag   1860
agagcacttc tctcttatgg ggttcatggg aacaggggtg ggtgtgactt gcttggtggc   1920
ctcattccat gtgtgcctgt gcctggggca tggactttgt taagcagagt cagcagtgag   1980
gtcctcattc tccagccagc ctctctgccc tggagaatca tgtgctatgt tctaagaatt   2040
tgagaactag agtcctcatc cccaggcttg aaggcacatg gctttctcat gtagggctct   2100
ctgtggtatt tgttattatt ttgcaacaag accatttag taaaacagtc ctgttcaagt    2160
tgtattcttt taagttcttt tattctcctt tccctgagat ttttgtatat attgttctga   2220
gtaatggtat ctttgagctg attgttctaa tcagagctgg tacctacttt caataaattc   2280
tggttttgtg ttttcttttg taaaaaaaaa aaaaaaaaa                          2319
```

<210> SEQ ID NO 34
<211> LENGTH: 2509
<212> TYPE: DNA
<213> ORGANISM: Homo sapiens

<400> SEQUENCE: 34

```
gaggcggtca caaggtatac gcccttctcc tctttccacg cttctcgaga ggctcccgcg     60
gccagaaccg gaaacaagg agtaacagtc gcgtttcaaa tctcgcagac ctgctggccg    120
atttcgagtc ttctgaaaga ggaaggcgag caaagccaaa attctcccag agcgcgaacc    180
caaacacaga tcgccgctgg ggtccaagcg cccttcaact ccgcccgcta gtgcccaaga    240
ttaccgggaa ggaattcaac gaatcagtgg tgaggtgccg ccgccatgcc tactacgggc    300
ggaaatttga gagaaagctt cgcaccggta ggaaaactga ggagcaaccg agcacgattg    360
gaaaggttga cgatagtggt taagtggctc ggccttgccc tcagttaaaa tggcaatttt    420
agttgcttca ctgatacgga atcggcgagg cgccaaggag gcttcctgcg tggggccgca    480
gagcgagtcg ggaaacgatt ttaaactgaa gaggcggcgg agggccgaat tcccttttct    540
caacggcttg atttcagagc tgggctggtc tctgacaggc tcagctggag agggacgggt    600
```

```
tgggacgcac tgtcctttttg cccttccccc tccgcgagca gaagctgact ccgcaggagc      660
gagggtcgca gagctgggtg agcggaaatg tccctcccag agtgaagtcg cagggcccgc      720
cccgcgtctg agggagcgga ggtcttcctg ggggatttca gtctccacat agttttggag      780
ccggactttt gaagaatgat tcgtgaatcc ggaatgggtg acagcgtcat cacggcattt      840
tattgacaga ccatggattc ttacagtgca ccagagtcaa ctcctagtgc atcctcaaga      900
cctgaagatt actttatagg tgccactcct ctgcagaaac gattagaatc ggtcaggaag      960
cagagttcat ttatcctgac tccacctcga aggaaaattc cccagtgttc gcagttgcag     1020
gaagatgttg accctcaaaa ggttgcattc cttctgcata aacagtggac tttatatagt     1080
ttaactccct tatataaatt ctcctatagt aatctcaaag agtattctag acttctcaat     1140
gcttttattg ttgctgaaaa gcaaaaagga cttgctgtgg aagtgggaga agacttcaac     1200
atcaaagtga tttttttctac tctcctagga atgaaaggaa cacaaaggga cccggaagca     1260
tttcttgtcc agattgtgtc aaaatctcaa ttgccatctg agaatagaga aggtaaagtg     1320
ctgtggactg gctggttctg ctgtgtattt ggagacagtc ttctggagac tgtttcagaa     1380
gatttcacct gtctgccctt attccttgca aatggagcag agtctaacac agcaataatt     1440
ggaacttggt ttcagaaaac ctttgactgt tatttcagtc ctttagcaat caatgcattt     1500
aatctttcct ggatggctgc catgtggact gcatgcaaaa tggaccatta tgtggctact     1560
actgaatttc tttggtctgt acctgtagc cctcaaagtc tggacatttc tttcgcaata     1620
catccagagg atgcaaaagc tctatgggac agtgtccaca aaacacctgg ggaggttacc     1680
caggaagaag ttgacctatt catggattgc ctttattcac atttccatag acatttcaaa     1740
attcatttat cagccacaag attagttcgt gtttcaacat ctgtagcttc agcacatact     1800
gatgaaaaaa taaagattct gtgtcataaa taccttattg gagtgttagc atatttgaca     1860
gaactggcaa ttttttcaaat tgagtgaagc cttatgtgga ctataagtta tagattatat     1920
actcttattg ataacttgcc taattgctat gctgaaagag actgcaggag aaataggcat     1980
ctatctctgc atctgttttc cccaccatgc ctttggagtt gccaagatgg aagccaagaa     2040
ggatctagaa gaacaaagaa tatggtagta gatgagccac agccaggtgc ccatgtacta     2100
atcatgataa cctgacatgc cattctcaaa atgctgagtt gttaatttct tgtcatcttt     2160
aaatatatat atataggctg gcttggtggg ctcacacctg taattccagc actttgggag     2220
gctgaggtgg gtggatcatt tgaggccagg aattcaagac cagcctggcc aacatggtga     2280
aaccccttct ctactgaaaa tacaataatt agctgggcgt ggtggcacat gcctatgatc     2340
ccagctactg gggaggctga ggcaggagaa tcgttttaac ccagaagaca ggctgcagtg     2400
agccaagact gcaccactgc actccagcct gggcaacaaa gtgagactct gcctcaaaaa     2460 ataaaaaga aataaaacga aaaaaaaaaa aaaaaaaaa aaaaaaaa                    2509
```

<210> SEQ ID NO 35
<211> LENGTH: 1546
<212> TYPE: DNA
<213> ORGANISM: Homo sapiens

<400> SEQUENCE: 35

```
gattgtggga aggcagctga actcggcgcc tggaaagatg gaggcagcgg agacagaggc       60
ggaagctgca gccctagagg tcctggctga ggtggcaggc atcttggaac ctgtaggcct      120
gcaggaggag gcagaactgc cagccaagat cctggttgag tttgtggtgg actctcagaa      180
gaaagacaag ctgctctgca gccagcttca ggtagcggat ttcctgcaga acatcctggc      240
```

```
tcaggaggac actgctaagg gtctcgaccc cttggcttct gaagacacga gccgacagaa      300
ggcaattgca gctaaggaac aatggaaaga gctgaaggcc acctacaggg agcacgtaga      360
ggccatcaaa attggcctca ccaaggccct gactcagatg gaggaagccc agaggaaacg      420
gacacaactc cgggaagcct tgagcagctc caggccaag aaacaaatgg ccatggagaa       480
acgcagagca gtccagaacc agtggcagct acaacaggag aagcatctgc agcatctggc      540
ggaggtttct gcagagggta agctgttgtt ccctgaggct gaggctgagg cagagaatct      600
tccagatgat aaaccccagc agccgactcg accccaggag cagagtacag gagacaccat      660
ggggagagac cctggtgtgt ccttcaaggc tgttggtcta caacctgctg gagatgtaaa      720
tttgccatga cttcctggag gacagcagca tggagaaaga tcctagaaaa ggcctctgac      780
ttccctcacc tcccaaccat cattacagga aagactgtga actcctgagt tcagcttgat      840
ttctgactac atcccagcaa gctctggcat ctgtggatta aaatccctgg atctctctca      900
gttgtgtatt tgttcatctt catatgctgg caggaacaac tattaataca gatactcaga      960
agccaataac atgacaggag ctgggactgg tttgaacaca gggtgtgcag atggggaggg     1020
ggtactggcc ttgggcctcc tatgatgcag acatggtgaa tttaattcaa ggaggaggag     1080
aatgttttag gcaggtggtt atatgtggga agataatttt attcatggat ccaaatgttt     1140
gttgagtcct ttctttgtgc taaggttctt gcggtgaacc agaattataa cagtgagctc     1200
atctgactgt tttaggatgt acagcctagt gttaacattc ttggtatctt tttgtgcctt     1260
atctaaaaca tttctcgatc actggtttca gatgttcatt tattatattc ttttcaaaga     1320
ttcagagatt ggcttttgtc atccactatt gtatgttttg tttcattgac ctctagtgat     1380 acctttgatct ttcccacttt ctgttttcgg attggagaag atgtaccttt tttgtcaact    1440
cttactttta tcagatgatc aactcacgta tttggatctt tatttgtttt ctcaaataaa     1500
tatttaaggt tatacatttta aaaaaaaaaa aaaaaaaaaa aaaaaa                    1546

<210> SEQ ID NO 36
<211> LENGTH: 1375
<212> TYPE: DNA
<213> ORGANISM: Homo sapiens

<400> SEQUENCE: 36
gtttgaaatc ggaaagttgg cggggctgcg ggagctgagc ctagagtccg gctgttggct       60
agagtgggcg cggatctggt gtggggaagg cggcgggact caggcctgcc tgcgaagcat      120
tgtcctacat aatggtagag gacgaactgg cacttttcga taaaagcata aatgaatttt      180
ggaataaatt caaaagtacg gacacctcct gtcagatggc gggactaaga gatacctaca      240
aggattccat caaagcattt gcagaaaagc tgtctgtgaa attaaaggaa gaagaacgaa      300
tggttgagat gtttctggaa tatcaaaatc agatcagcag gcaaaataag ctcattcaag      360
aaaaaaagga taacttgtta aaattgattg ctgaagtaaa aggcaaaaag caggaattgg      420
aagtactgac tgcaaatatc caggatctta aggaagaata ttctaggaag aaggaaacta      480
tttctactgc taataaagcg aatgcagaga ggttgaaaag gctgcagaaa tctgcagact      540
tgtataaaga tcgacttgga ctagaaattc gaaaatttta tggtgagaaa ttgcagttta      600
ttttcactaa tattgaccct aagaatcctg agagcccatt tatgtttttcc ttacatctca     660 atgaagcaag ggactatgaa gtgtcagata tgcccctca tcttgagggc ctagcagaat       720
ttcaagagaa tgtaaggaag accaacaatt tttcagcttt tcttgccaat gttcggaaag      780
```

| | |
|---|---|
| cttttactgc cacggtttat aattaacata caaatagtgt atataaaaac ggtttatttt | 840 |
| tcttctctat tacatatctc ttttttttctt gttttttatta ttattatact ttaagtttta | 900 |
| gggtacatgt gcacaatgtg caggtttgtt acatatgtat acatgtgcca tattggtgtg | 960 |
| ctgcacccat taactcgtca tttcattagg tatatctcct aatgctatcc ctcccccctc | 1020 |
| ccccaaccca caacagtccc cgttgtgtga tgttcccctt cctgtgtcca tgtgttctca | 1080 |
| ttgttcaatt cccacctagg agtgagaata tgtggtgttt ggttttttgt cctttcgata | 1140 |
| gtttgctgag aatgatggtt tccagcttca tccatgttcc tacaaaggac atgaactcat | 1200 |
| ccttttttat ggctgcatag tattccatgg tgtatatgtg ccacattttc ttaatccagt | 1260 |
| ctatcattgt tggacatttg ggttggttcc aagtctttgc tattgtgaat agtgccgaaa | 1320 |
| taaacatacg tgtgcatgtg tctttaaaaa aaaaaaaaa aaaaaaaaaa aaaaa | 1375 |

<210> SEQ ID NO 37
<211> LENGTH: 5698
<212> TYPE: DNA
<213> ORGANISM: Homo sapiens

<400> SEQUENCE: 37

| | |
|---|---|
| aggttcaagt ggagctctcc taaccgacgc gcgtctgtgg agaagcggct tggtcggggg | 60 |
| tggtctcgtg gggtcctgcc tgtttagtcg cttttcagggt tcttgagccc cttcacgacc | 120 |
| gtcaccatgg aagtgtcacc attgcagcct gtaaatgaaa atatgcaagt caacaaaata | 180 |
| aagaaaaatg aagatgctaa gaaaagactg tctgttgaaa gaatctatca aaagaaaaca | 240 |
| caattggaac atatttttgct ccgcccagac acctacattg ttctgtggga attagtgacc | 300 |
| cagcaaatgt gggtttacga tgaagatgtt ggcattaact atagggaagt cacttttgtt | 360 |
| cctggttttgt acaaaatctt tgatgagatt ctagttaatg ctgcggacaa caaacaaagg | 420 |
| gacccaaaaa tgtcttgtat tagagtcaca attgatccgg aaaacaattt aattagtata | 480 |
| tggaataatg gaaaaggtat tcctgttgtt gaacacaaag ttgaaaagat gtatgtccca | 540 |
| gctctcatat ttggacagct cctaacttct agtaactatg atgatgatga aagaaagtg | 600 |
| acaggtggtc gaaatggcta tggagccaaa ttgtgtaaca tattcagtac caaatttact | 660 |
| gtggaaacag ccagtagaga atacaagaaa atgttcaaac agacatggat ggataatatg | 720 |
| ggaagagctg gtgagatgga actcaagccc ttcaatggag aagattatac atgtatcacc | 780 |
| tttcagcctg atttgtctaa gtttaaaatg caaagcctgg acaaagatat tgttgcacta | 840 |
| atggtcagaa gagcatatga tattgctgga tccaccaaag atgtcaaagt ctttcttaat | 900 |
| ggaaataaac tgccagtaaa aggatttcgt agttatgtgg acatgtattt gaaggacaag | 960 |
| ttggatgaaa ctggtaactc cttgaaagta atacatgaac aagtaaaacca caggtgggaa | 1020 |
| gtgtgtttaa ctatgagtga aaaaggcttt cagcaaatta gctttgtcaa cagcattgct | 1080 |
| acatccaagg gtggcagaca tgttgattat gtagctgatc agattgtgac taaacttgtt | 1140 |
| gatgttgtga agaagaagaa caagggtggt gttgcagtaa agcacatca ggtgaaaaat | 1200 |
| cacatgtgga tttttgtaaa tgccttaatt gaaaacccaa cctttgactc tcagacaaaa | 1260 |
| gaaaacatga ctttacaacc caagagcttt ggatcaacat gccaattgag tgaaaaattt | 1320 |
| atcaaagctg ccattggctg tggtattgta gaaagcatac taaactgggt gaagtttaag | 1380 |
| gcccaagtcc agtaaacaa gaagtgttca gctgtaaaac ataatagaat caagggaatt | 1440 |
| cccaaactcg atgatgccaa tgatgcaggg ggccgaaact ccactgagtg tacgcttatc | 1500 |
| ctgactgagg gagattcagc caaaactttg gctgtttcag gccttggtgt ggttgggaga | 1560 |

```
gacaaatatg gggttttccc tcttagagga aaaatactca atgttcgaga agcttctcat     1620
aagcagatca tggaaaatgc tgagattaac aatatcatca agattgtggg tcttcagtac     1680
aagaaaaact atgaagatga agattcattg aagacgcttc gttatgggaa gataatgatt     1740
atgacagatc aggaccaaga tggttcccac atcaaaggct tgctgattaa ttttatccat     1800
cacaactggc cctctcttct gcgacatcgt tttctggagg aatttatcac tcccattgta     1860
aaggtatcta aaaacaagca agaaatggca ttttacagcc ttcctgaatt tgaagagtgg     1920
aagagttcta ctccaaatca taaaaaatgg aaagtcaaat attacaaagg tttgggcacc     1980
agcacatcaa aggaagctaa agaatacttt gcagatatga aaagacatcg tatccagttc     2040
aaatattctg gtcctgaaga tgatgctgct atcagcctgg cctttagcaa aaaacagata     2100
gatgatcgaa aggaatggtt aactaatttc atggaggata aagacaacg aaagttactt     2160 gggcttcctg aggattactt gtatggacaa actaccacat atctgacata taatgacttc     2220
atcaacaagg aacttatctt gttctcaaat tctgataacg agagatctat cccttctatg     2280
gtggatggtt tgaaaccagg tcagagaaag gttttgttta cttgcttcaa acggaatgac     2340
aagcgagaag taaaggttgc ccaattagct ggatcagtgg ctgaaatgtc ttcttatcat     2400
catggtgaga tgtcactaat gatgaccatt atcaatttgg ctcagaattt tgtgggtagc     2460
aataatctaa acctcttgca gcccattggt cagtttggta ccaggctaca tggtggcaag     2520
gattctgcta gtccacgata catctttaca atgctcagct ctttggctcg attgttattt     2580
ccaccaaaag atgatcacac gttgaagttt ttatatgatg acaaccagcg tgttgagcct     2640
gaatggtaca ttcctattat tcccatggtg ctgataaatg gtgctgaagg aatcggtact     2700
gggtggtcct gcaaaatccc caactttgat gtgcgtgaaa ttgtaaataa catcaggcgt     2760
ttgatggatg agaagaaacc tttgccaatg cttccaagtt acaagaactt caagggtact     2820
attgaagaac tggctccaaa tcaatatgtg attagtggtg aagtagctat tcttaattct     2880
acaaccattg aaatctcaga gcttcccgtc agaacatgga cccagacata caagaacaa     2940 gttctagaac ccatgttgaa tggcaccgag aagacacctc ctctcataac agactatagg     3000
gaataccata cagataccac tgtgaaattt gttgtgaaga tgactgaaga aaaactggca     3060
gaggcagaga gagttggact acacaaagtc ttcaaactcc aaactagtct cacatgcaac     3120
tctatggtgc ttttgacca cgtaggctgt ttaaagaaat atgacacggt gttggatatt     3180
ctaagagact tttttgaact cagacttaaa tattatggat taagaaaaga atggctccta     3240
ggaatgcttg gtgctgaatc tgctaaactg aataatcagg ctcgctttat cttagagaaa     3300
atagatggca aaataatcat tgaaaataag cctaagaaag aattaattaa agttctgatt     3360 cagagggat atgattcgga tcctgtgaag gcctggaaaa aagcccagca aaaggttcca     3420
gatgaagaag aaaatgaaga gagtgacaac gaaaaggaaa ctgaaaagag tgactccgta     3480
acagattctg gaccaacctt caactatctt cttgatatgc ccctttggta tttaaccaag     3540
gaaaagaaag atgaactctg caggctaaga aatgaaaaag aacaagagct ggacacatta     3600
aaaagaaaga gtccatcaga tttgtggaaa gaagacttgg ctacatttat tgaagaattg     3660
gaggctgttg aagccaagga aaaacaagat gaacaagtcg gacttcctgg aaagggggg     3720 aaggccaagg ggaaaaaaac acaaatggct gaagttttgc cttctccgcg tggtcaaaga     3780
gtcattccac gaataaccat agaaatgaaa gcagaggcag aaaagaaaaa taaaagaaa     3840 attaagaatg aaaaatactga aggaagccct caagaagatg gtgtggaact agaaggccta     3900
```

| | |
|---|---|
| aaacaaagat tagaaaagaa acagaaaaga gaaccaggta caaagacaaa gaaacaaact | 3960 |
| acattggcat ttaagccaat caaaaaagga aagaagagaa atccctggtc tgattcagaa | 4020 |
| tcagatagga gcagtgacga aagtaatttt gatgtccctc cacgagaaac agagccacgg | 4080 |
| agagcagcaa caaaaacaaa attcacaatg gatttggatt cagatgaaga tttctcagat | 4140 |
| tttgatgaaa aaactgatga tgaagatttt gtcccatcag atgctagtcc acctaagacc | 4200 |
| aaaacttccc caaaacttag taacaaagaa ctgaaaccac agaaaagtgt cgtgtcagac | 4260 |
| cttgaagctg atgatgttaa gggcagtgta ccactgtctt caagccctcc tgctacacat | 4320 |
| ttcccagatg aaactgaaat tacaaaccca gttcctaaaa agaatgtgac agtgaagaag | 4380 |
| acagcagcaa aaagtcagtc ttccacctcc actaccggtg ccaaaaaaag ggctgcccca | 4440 |
| aaaggaacta aaagggatcc agctttgaat tctggtgtct ctcaaaagcc tgatcctgcc | 4500 |
| aaaaccaaga atcgccgcaa aaggaagcca tccacttctg atgattctga ctctaatttt | 4560 |
| gagaaaattg tttcgaaagc agtcacaagc aagaaatcca aggggagag tgatgacttc | 4620 |
| catatggact ttgactcagc tgtggctcct cgggcaaaat ctgtacgggc aaagaaacct | 4680 |
| ataaagtacc tggaagagtc agatgaagat gatctgtttt aaaatgtgag gcgattattt | 4740 |
| taagtaatta tcttaccaag cccaagactg gttttaaagt tacctgaagc tcttaacttc | 4800 |
| ctcccctctg aatttagttt ggggaaggtg ttttttagtac aagacatcaa agtgaagtaa | 4860 |
| agcccaagtg ttctttagct ttttataata ctgtctaaat agtgaccatc tcatgggcat | 4920 |
| tgttttcttc tctgctttgt ctgtgttttg agtctgcttt cttttgtctt taaaacctga | 4980 |
| tttttaagtt cttctgaact gtagaaatag ctatctgatc acttcagcgt aaagcagtgt | 5040 |
| gtttattaac catccactaa gctaaaacta gagcagtttg atttaaaagt gtcactcttc | 5100 |
| ctcctttct actttcagta gatatgagat agagcataat tatctgtttt atcttagttt | 5160 |
| tatacataat ttaccatcag atagaacttt atggttctag tacagatact ctactacact | 5220 |
| cagcctctta tgtgccaagt ttttctttaa gcaatgagaa attgctcatg ttcttcatct | 5280 |
| tctcaaatca tcagaggcca agaaaaaca ctttggctgt gtctataact tgacacagtc | 5340 |
| aatagaatga agaaaattag agtagttatg tgattatttc agctcttgac ctgtcccctc | 5400 |
| tggctgcctc tgagtctgaa tctcccaaag agagaaacca atttctaaga ggactggatt | 5460 |
| gcagaagact cggggacaac attttgatcca agatcttaaa tgttatattg ataaccatgc | 5520 |
| tcagcaatga gctattagat tcattttggg aaatctccat aatttcaatt tgtaaacttt | 5580 |
| gttaagacct gtctacattg ttatatgtgt gtgacttgag taatgttatc aacgttttg | 5640 |
| taaatattta ctatgttttt ctattagcta aattccaaca attttgtact ttaataaa | 5698 |

<210> SEQ ID NO 38
<211> LENGTH: 6641
<212> TYPE: DNA
<213> ORGANISM: Homo sapiens

<400> SEQUENCE: 38

| | |
|---|---|
| ggttacattt tggatcctcg cggagtactg gtcaggcggt taagtcctgt acctaggaaa | 60 |
| gagggcgagc tctggggcgc tctccggtgt catgaggagc ttcaaaagag tcaactttgg | 120 |
| gactctgcta agcagccaga aggaggctga agagttgctg cccgccttga aggagttcct | 180 |
| gtccaaccct ccagctggtt ttcccagcag ccgatctgat gctgagagga gacaagcttg | 240 |
| tgatgccatc tgagggcctt gcaaccagca gctgactgct aagctagctt gcccctaggca | 300 |
| tctggggagc ctgctggagc tggcagagct ggcctgtgat ggctacttag tgtctacccc | 360 |

```
acagcgtcct cccctctacc tggaacgaat tctctttgtc ttactgcgga atgctgctgc    420
acaaggaagc ccagaggcca cactccgcct tgctcagccc ctccatgcct gcttggtgca    480
gtgctctcgc gaggctgctc cccaggacta tgaggccgtg gctcggggca gcttttctct    540
gctttggaag ggggcagaag ccctgttgga acggcgagct gcatttgcag ctcggctgaa    600
ggccttgagc ttcctagtac tcttggagga tgaaagtacc ccttgtgagg ttcctcactt    660
tgcttctcca acagcctgtc gagcggtagc tgcccatcag ctatttgatg ccagtggcca    720
tggtctaaat gaagcagatg ctgatttcct agatgacctg ctctccaggc acgtgatcag    780
agccttggtg ggtgagagag ggagctcttc tgggcttctt tctccccaga gggccctctg    840
cctcttggag ctcaccttgg aacactgccg tcgcttttgc tggagccgcc accatgacaa    900
agccatcagc gcagtggaga aggctcacag ttacctaagg aacaccaatc tagcccctag    960
ccttcagcta tgtcagctgg gggttaagct gctgcaggtt ggggaggaag gacctcaggc   1020
agtggccaag cttctgatca aggcatcagc tgtcctgagc aagagtatgg aggcaccatc   1080 accccccactt cgggcattgt atgagagctg ccagttcttc ctttcaggcc tggaacgagg   1140
caccaagagg cgctatagac ttgatgccat tctgagcctc tttgcttttc ttggagggta   1200
ctgctctctt ctgcagcagc tgcgggatga tggtgtgtat gggggctcct ccaagcaaca   1260
gcagtctttt cttcagatgt actttcaggg acttcacctc tacactgtgg ggtttatga   1320 ctttgcccaa ggctgtcaga tagttgattt ggctgacctg acccaactag tggacagttg   1380
taaatctacc gttgtctgga tgctggaggc cttagagggc ctgtcgggcc aagagctgac   1440
ggaccacatg gggatgaccg cttcttacac cagtaatttg gcctacagct tctatagtca   1500
caagctctat gccgaggcct gtgccatctc tgagccgctc tgtcagcacc tgggtttggt   1560
gaagccaggc acttatcccg aggtgcctcc tgagaagttg cacaggtgct ccggctaca   1620 agtagagagt ttgaagaaac tgggtaaaca ggcccagggc tgcaagatgg tgattttgtg   1680
gctggcagcc ctgcaaccct gtagccctga acacatggct gagccagtca ctttctgggt   1740
tcgggtcaag atggatgcgg ccagggctgg agacaaggag ctacagctaa agactctgcg   1800
agacagcctc agtggctggg acccggagac cctggccctc ctgctgaggg aggagctgca   1860
ggcctacaag gcggtgcggg ccgacactgg acaggaacgc ttcaacatca tctgtgacct   1920
cctggagctg agccccgagg agacaccagc cggggcctgg gcacgagcca cccacctggt   1980
agaactggct caggtgctct gctaccacga ctttacgcag cagaccaact gctctgctct   2040
ggatgctatc cgggaagccc tgcagcttct ggactctgtg aggcctgagg cccaggccag   2100
agatcagctt ctggacgata aagcacaggc cttgctgtgg cttacatct gtactctgga   2160 agccaaaatg caggaaggta tcgagcggga tcggagagcc caggccctg gtaacttgga   2220 ggaatttgaa gtcaatgacc tgaactatga agataaactc caggaagatc gtttcctata   2280
cagtaacatt gccttcaacc tggctgcaga tgctgctcag tccaaaatgcc tggaccaagc   2340 cctggccctg tggaaggagc tgcttacaaa ggggcaggcc ccagctgtac ggtgtctcca   2400
gcagacagca gcctcactgc agatcctagc agccctctac cagctggtgg caaagcccat   2460
gcaggctctg gaggtcctcc tgctgctacg gattgtctct gagagactga aggaccactc   2520
gaaggcagct ggctcctcct gccacatcac ccagctcctc ctgaccctcg gctgtcccag   2580
ctatgcccag ttacacctgg aagaggcagc atcgagcctg aagcatctcg atcagactac   2640
tgacacatac ctgctccttt ccctgacctg tgatctgctt cgaagtcaac tctactggac   2700
```

```
tcaccagaag gtgaccaagg gtgtctctct gctgctgtct gtgcttcggg atcctgccct   2760
ccagaagtcc tccaaggctt ggtacttgct gcgtgtccag gtcctgcagc tggtggcagc   2820
ttaccttagc ctcccgtcaa caacctctc acactccctg tgggagcagc tctgtgccca    2880
aggctggcag acacctgaga tagctctcat agactcccat aagctcctcc gaagcatcat   2940
cctcctgctg atgggcagtg acattctctc aactcagaaa gcagctgtgg agacatcgtt   3000
tttggactat ggtgaaaatc tggtacaaaa atggcaggtt ctttcagagg tgctgagctg   3060
ctcagagaag ctggtctgcc acctgggccg cctgggtagt gtgagtgaag ccaaggcctt   3120
ttgcttggag ccctaaaaac ttacaacaaa gctgcagata ccacgccagt gtgccctgtt   3180
cctggtgctg aagggcgagc tggagctggc ccgcaatgac attgatctct gtcagtcgga   3240
cctgcagcag gttctgttct tgcttgagtc ttgcacagag tttggtgggg tgactcagca   3300
cctggactct gtgaagaagg tccacctgca gaaggggaag cagcaggccc aggtcccctg   3360
tcctccacag ctcccagagg aggagctctt cctaagaggc cctgctctag agctggtggc   3420
cactgtggcc aaggagcctg gccccatagc accttctaca aactcctccc cagtcttgaa   3480
aaccaagccc cagcccatac ccaacttcct gtcccattca cccacctgtg actgctcgct   3540
ctgcgccagc cctgtcctca cagcagtctg tctgcgctgg gtattggtca cggcaggggt   3600
gaggctggcc atgggccacc aagcccaggg tctggatctg ctgcaggtcg tgctgaaggg   3660
ctgtcctgaa gccgctgagc gcctcaccca agctctccaa gcttccctga atcataaaac   3720 accccctcc ttggttccaa gcctcttgga tgagatcttg gctcaagcat acacactgtt    3780
ggcactggag ggcctgaacc agccatcaaa cgagagcctg cagaaggttc tacagtcagg   3840
gctgaagttt gtagcagcac ggatacccca cctagagccc tggcgagcca gcctgctctt   3900
gatttggccc ctcacaaaac taggtggcct cagctgctgt actacccaac tttttgcaag   3960 ctcctgggc tggcagccac cattaataaa agtgtccct ggctcagagc cctctaagac     4020
tcagggccaa aaacgttctg gacgagggcg ccaaaagtta gcctctgctc ccctgcgcct   4080
caataatacc tctcagaaag gtctggaagg tagaggactg ccctgcacac ctaaaccccc   4140
agaccggatc aggcaagctg gccctcatgt cccctteacg gtgtttgagg aagtctgccc   4200
tacagagagc aagcctgaag taccccaggc ccccagggta caacagagag tccagacgcg   4260
cctcaaggtg aacttcagtg atgacagtga cttggaagac cctgtctcag ctgaggcctg   4320
gctggcagag gagcctaaga cgcggggcac tgcttcccgg ggccgggggc gagcaaggaa   4380
gggcctgagc ctaaagacgg atgccgtggt tgccccaggt agtgccctg ggaaccctgg    4440 cctgaatggc aggagccgga gggccaagaa ggtggcatca agacattgtg aggagcggcg   4500
tccccagagg gccagtgacc aggccaggcc tggccctgag atcatgagga ccatccctga   4560
ggaagaactg actgacaact ggagaaaaat gagctttgag atcctcaggg gctctgacgg   4620
ggaagactca gcctcaggtg ggaagactcc agctccgggc cctgaggcag cttctggaga   4680
atgggagctg ctgaggctgg attccagcaa gaagaagctg cccagcccat gcccagacaa   4740
ggagagtgac aaggaccttg gtcctcggct ccggctcccc tcagcccccg tagccactgg   4800
tctttctacc ctggactcca tctgtgactc cctgagtgtt gctttccggg gcattagtca   4860
ctgtcctcct agtgggctct atgcccacct ctgccgcttc ctggccttgt gcctgggcca   4920
ccgggatcct tatgccactg ctttccttgt caccgagtct gtctccatca cctgtcgcca   4980
ccagctgctc acccacctcc acagacagct cagcaaggcc cagaagcacc gaggatcact   5040
tgaaatagca gaccagctgc aggggctgag ccttcaggag atgcctggag atgtcccccct  5100
```

-continued

```
ggcccgcatc cagcgcctct tttccttcag ggctttggaa tctggccact tcccccagcc   5160
tgaaaaggag agtttccagg agcgcctggc tctgatcccc agtggggtga ctgtgtgtgt   5220
gttggccctg gccaccctcc agcccggaac cgtgggcaac accctcctgc tgacccggct   5280
ggaaaaggac agtcccccag tcagtgtgca gattccccact ggccagaaca agcttcatct   5340
```

```
ggcccgcatc cagcgcctct tttccttcag ggctttggaa tctggccact tcccccagcc   5160
tgaaaaggag agtttccagg agcgcctggc tctgatcccc agtggggtga ctgtgtgtgt   5220
gttggccctg gccaccctcc agcccggaac cgtgggcaac accctcctgc tgacccggct   5280
ggaaaaggac agtcccccag tcagtgtgca gattccccact ggccagaaca agcttcatct   5340
gcgttcagtc ctgaatgagt ttgatgccat ccagaaggca cagaaagaga cagcagctg    5400
tactgacaag cgagaatggt ggacagggcg gctggcactg gacccacagga tggaggttct   5460
catcgcttcc ctagagaagt ctgtgctggg ctgctggaag gggctgctgc tgccgtccag   5520
tgaggagccc ggccctgccc aggaggcctc ccgcctacag gagctgctac aggactgtgg   5580
ctggaaatat cctgaccgca ctctgctgaa aatcatgctc agtggtgccg gtgccctcac   5640
ccctcaggac attcaggccc tggcctacgg gctgtgccca acccagccag agcgagccca   5700
ggagctcctg aatgaggcag taggacgtct acagggcctg acagtaccaa gcaatagcca   5760
ccttgtcttg gtcctagaca aggacttgca gaagctgccg tgggaaagca tgcccagcct   5820
ccaagcactg cctgtcaccc ggctgccctc cttccgcttc ctactcagct actccatcat   5880
caaagagtat ggggcctcgc cagtgctgag tcaaggggtg gatccacgaa gtaccttcta   5940
tgtcctgaac cctcacaata acctgtcaag cacagaggag caatttcgag ccaatttcag   6000
cagtgaagct ggctggagag gagtggttgg ggaggtgcca agacctgaac aggtgcagga   6060
agccctgaca aagcatgatt tgtatatcta tgcagggcat ggggctggtg cccgcttcct   6120
tgatgggcag gctgtcctgc ggctgagctg tcgggcagtg gccctgctgt ttggctgtag   6180
cagtgcggcc ctggctgtgc gtggaaacct ggaggggggct ggcatcgtgc tcaagtacat   6240
catggctggt tgcccccttgt ttctgggtaa tctctgggat gtgactgacc gcgacattga   6300
ccgctacacg gaagctctgc tgcaaggctg gcttggagca ggcccagggg cccccccttct   6360
ctactatgta aaccaggccc gccaagctcc ccgactcaag tatcttattg gggctgcacc   6420
tatagcctat ggcttgcctg tctctctgcg gtaaccccat ggagctgtct tattgatgct   6480
agaagcctca taactgttct acctccaagg ttagatttaa tccttaggat aactctttta   6540
aagtgatttt ccccagtgtt ttatatgaaa catttccttt tgatttaacc tcagtataat   6600
aaagatacat catttaaacc ctgaaaaaaa aaaaaaaaa a                         6641
```

<210> SEQ ID NO 39
<211> LENGTH: 1916
<212> TYPE: DNA
<213> ORGANISM: Homo sapiens

<400> SEQUENCE: 39

```
gagtttgaaa ctgctcgcac ttggcttcaa agctggctct tggaaattga gcggagagcg     60
acgcggttgt tgtagctgcc gctgcggccg ccgcggaata ataagccggg atctaccata    120
cccattgact aactatggaa gattatacca aaatagagaa aattggagaa ggtacctatg    180
gagttgtgta aagggtagac acaaaacta caggtcaagt ggtagccatg aaaaaaatca     240
gactagaaag tgaagaggaa ggggttccta gtactgcaat tcgggaaatt tctctattaa    300
aggaacttcg tcatccaaat atagtcagtc ttcaggatgt gcttatgcag gattccaggt    360
tatatctcat ctttgagttt cttttccatgg atctgaagaa atacttggat tctatccctc    420
ctggtcagta catggattct tcacttgtta agagttattt ataccaaatc ctacagggga    480
ttgtgttttg tcactctaga agagttcttc acagagactt aaaacctcaa aatctcttga    540
```

```
ttgatgacaa aggaacaatt aaactggctg attttggcct tgccagagct tttggaatac    600
ctatcagagt atatacacat gaggtagtaa cactctggta cagatctcca gaagtattgc    660
tggggtcagc tcgttactca actccagttg acatttggag tataggcacc atatttgctg    720
aactagcaac taagaaacca cttttccatg gggattcaga aattgatcaa ctcttcagga    780
ttttcagagc tttgggcact cccaataatg aagtgtggcc agaagtggaa tctttacagg    840
actataagaa tacatttccc aaatggaaac caggaagcct agcatcccat gtcaaaaact    900
tggatgaaaa tggcttggat tgctctcga aaatgttaat ctatgatcca gccaaacgaa     960
tttctggcaa aatggcactg aatcatccat attttaatga tttggacaat cagattaaga   1020
agatgtagct ttctgacaaa aagtttccat atgttatatc aacagatagt tgtgttttta   1080
ttgttaactc ttgtctattt ttgtcttata tatatttctt tgttatcaaa cttcagctgt   1140
acttcgtctt ctaatttcaa aaatataact taaaaatgta aatattctat atgaatttaa   1200
atataattct gtaaatgtgt gtaggtctca ctgtaacaac tatttgttac tataataaaa   1260
ctataatatt gatgtcagga atcaggaaaa aatttgagtt ggcttaaatc atctcagtcc   1320
ttatggcagt tttattttcc tgtagttgga actactaaaa tttaggaaaa tgctaagttc   1380
aagtttcgta atgctttgaa gtattttat gctctgaatg tttaaatgtt ctcatcagtt    1440
tcttgccatg ttgttaacta tacaacctgg ctaaagatga atatttttct actggtattt   1500 taattttga cctaaatgtt taagcattcg gaatgagaaa actatacaga tttgagaaat   1560
gatgctaaat ttataggagt tttcagtaac ttaaaaagct aacatgagag catgccaaaa   1620
tttgctaagt cttacaaaga tcaagggctg tccgcaacag ggaagaacag ttttgaaaat   1680
ttatgaacta tcttattttt aggtaggttt tgaaagcttt ttgtctaagt gaattcttat   1740
gccttggtca gagtaataac tgaaggagtt gcttatcttg gctttcgagt ctgagtttaa   1800
aactacacat tttgacatag tgtttattag cagccatcta aaaaggctct aatgtatatt   1860
taactaaaat tactagcttt gggaattaaa ctgtttaaca aataaaaaaa aaaaaa       1916
```

<210> SEQ ID NO 40
<211> LENGTH: 2984
<212> TYPE: DNA
<213> ORGANISM: Homo sapiens

<400> SEQUENCE: 40

```
ggaaattcaa acgtgtttgc ggaaaggagt ttgggttcca tcttttcatt tccccagcgc     60
agctttctgt agaaatggaa tccgaggatt taagtggcag agaattgaca attgattcca    120
taatgaacaa agtgagagac attaaaaata gtttaaaaa tgaagacctt actgatgaac    180
taagcttgaa taaatttct gctgatacta cagataactc gggaactgtt aaccaaatta    240
tgatgatggc aaacaaccca gaggactggt tgagtttgtt gctcaaacta gagaaaaaca    300
gtgttccgct aagtgatgct cttttaaata aattgattgg tcgttacagt caagcaattg    360
aagcgcttcc cccagataaa tatggccaaa atgagagttt tgctagaatt caagtgagat    420
ttgctgaatt aaaagctatt caagagccag atgatgcacg tgactacttt caaatggcca    480
gagcaaactg caagaaattt gcttttgttc atatatcttt tgcacaattt gaactgtcac    540
aaggtaatgt caaaaaagt aaacaacttc ttcaaaaagc tgtagaacgt ggagcagtac    600
cactagaaat gctggaaatt gccctgcgga atttaaacct ccaaaaaaag cagctgcttt    660
cagaggagga aaagaagaat ttatcagcat ctacggtatt aactgcccaa gaatcatttt    720
ccggttcact tggcatttta cagaatagga acaacagttg tgattccaga ggacagacta    780
```

-continued

```
ctaaagccag gtttttatat ggagagaaca tgccaccaca agatgcagaa ataggttacc      840
ggaattcatt gagacaaact aacaaaacta aacagtcatg cccatttgga agagtcccag      900
ttaaccttct aaatagccca gattgtgatg tgaagacaga tgattcagtt gtaccttgtt      960
ttatgaaaag acaaacctct agatcagaat gccgagattt ggttgtgcct ggatctaaac     1020
caagtggaaa tgattcctgt gaattaagaa atttaaagtc tgttcaaaat agtcatttca     1080
aggaacctct ggtgtcagat gaaaagagtt ctgaacttat tattactgat tcaataaccc     1140
tgaagaataa aacggaatca agtcttctag ctaaattaga agaaactaaa gagtatcaag     1200
aaccagaggt tccagagagt aaccagaaac agtggcaatc aagagaaag tcagagtgta      1260
ttaaccagaa tcctgctgca tcttcaaatc actggcagat tccggagtta gcccgaaaag     1320
ttaatacaga gcagaaacat accacttttg agcaacctgt cttttcagtt tcaaaacagt     1380
caccaccaat atcaacatct aaatggtttg acccaaaatc tatttgtaag acaccaagca     1440
gcaatacctt ggatgattac atgagctgtt ttagaactcc agttgtaaag aatgactttc     1500
cacctgcttg tcagttgtca acaccttatg gccaacctgc ctgtttccag cagcaacagc     1560
atcaaatact tgccactcca cttcaaaatt tacaggtttt agcatcttct tcagcaaatg     1620
aatgcatttc ggttaaagga agaatttatt ccattttaaa gcagatagga agtggaggtt     1680
caagcaaggt atttcaggtg ttaaatgaaa agaaacagat atatgctata aaatatgtga     1740
acttagaaga agcagataac caaactcttg atagttaccg gaacgaaata gcttatttga     1800
ataaactaca acaacacagt gataagatca tccgacttta tgattatgaa atcacggacc     1860
agtacatcta catggtaatg gagtgtggaa atattgatct taatagttgg cttaaaaaga     1920
aaaaatccat tgatccatgg gaacgcaaga gttactggaa aaatatgtta gaggcagttc     1980
acacaatcca tcaacatggc attgttcaca gtgatcttaa accagctaac tttctgatag     2040
ttgatggaat gctaaagcta attgattttg ggattgcaaa ccaaatgcaa ccagatacaa     2100
caagtgttgt taaagattct caggttggca cagttaatta tatgccacca gaagcaatca     2160
aagatatgtc ttcctccaga gagaatggga atctaagtc aaagataagc cccaaaagtg      2220
atgtttggtc cttaggatgt atttttgtact atatgactta cgggaaaaca ccatttcagc     2280
agataattaa tcagattct aaattacatg ccataattga tcctaatcat gaaattgaat       2340
ttcccgatat tccagagaaa gatcttcaag atgtgttaaa gtgttgttta aaagggacc       2400
caaaacagag gatatccatt cctgagctcc tggctcatcc ctatgttcaa attcaaactc      2460
atccagttaa ccaaatggcc aagggaacca ctgaagaaat gaatatgtt ctgggccaac      2520
ttgttggtct gaattctcct aactccattt tgaaagctgc taaaactta tatgaacact       2580
atagtggtgg tgaaagtcat aattcttcat cctccaagac ttttgaaaaa aaagggggaa     2640
aaaaatgatt tgcagttatt cgtaatgtca aataccacct ataaaatata ttggactgtt     2700
atactcttga atccctgtgg aaatctacat ttgaagacaa catcactctg aagtgttatc     2760
agcaaaaaaa attcagtaga ttatctttaa aagaaaactg taaaaatagc aaccacttat     2820
ggtactgtat atattgtaga cttgtttttct ctgttttatg ctcttgtgta atctacttga    2880
catcatttta ctcttggaat agtgggtgga tagcaagtat attctaaaaa actttgtaaa     2940
taaagttttg tggctaaaat gacactaaaa aaaaaaaaa aaaa                        2984
```

<210> SEQ ID NO 41
<211> LENGTH: 3412
<212> TYPE: DNA

<213> ORGANISM: Homo sapiens

<400> SEQUENCE: 41

| | | | | | |
|---|---|---|---|---|---|
| aggcgcagcc | aatgggaagg | gtcggaggca | tggcacagcc | aatgggaagg | gccggggcac | 60 |
| caaagccaat | gggaagggcc | gggagcgcgc | ggcgcgggag | atttaaaggc | tgctggagtg | 120 |
| aggggtcgcc | cgtgcaccct | gtcccagccg | tcctgtcctg | gctgctcgct | ctgcttcgct | 180 |
| gcgcctccac | tatgctctcc | ctccgtgtcc | cgctcgcgcc | catcacggac | ccgcagcagc | 240 |
| tgcagctctc | gccgctgaag | gggctcagct | tggtcgacaa | ggagaacacg | ccgccggccc | 300 |
| tgagcgggac | ccgcgtcctg | gccagcaaga | ccgcgaggag | gatcttccag | gagcccacgg | 360 |
| agccgaaaac | taaagcagct | gccccggcg | tggaggatga | gccgctgctg | agagaaaacc | 420 |
| cccgccgctt | tgtcatcttc | cccatcgagt | accatgatat | ctggcagatg | tataagaagg | 480 |
| cagaggcttc | cttttggacc | gccgaggagg | tggacctctc | caaggacatt | cagcactggg | 540 |
| aatccctgaa | acccgaggag | agatatttta | tatcccatgt | tctggctttc | tttgcagcaa | 600 |
| gcgatggcat | agtaaatgaa | aacttggtgg | agcgatttag | ccaagaagtt | cagattacag | 660 |
| aagcccgctg | tttctatggc | ttccaaattg | ccatggaaaa | catacattct | gaaatgtata | 720 |
| gtcttcttat | tgacacttac | ataaaagatc | ccaaagaaag | ggaatttctc | ttcaatgcca | 780 |
| ttgaaacgat | gccttgtgtc | aagaagaagg | cagactgggc | cttgcgctgg | attggggaca | 840 |
| aagaggctac | ctatggtgaa | cgtgttgtag | cctttgctgc | agtggaaggc | attttctttt | 900 |
| ccggttcttt | tgcgtcgata | ttctggctca | agaaacgagg | actgatgcct | ggcctcacat | 960 |
| tttctaatga | acttattagc | agagatgagg | gtttacactg | tgattttgct | tgcctgatgt | 1020 |
| tcaaacacct | ggtacacaaa | ccatcggagg | agagagtaag | agaataatt | atcaatgctg | 1080 |
| ttcggataga | acaggagttc | ctcactgagg | ccttgcctgt | gaagctcatt | gggatgaatt | 1140 |
| gcactctaat | gaagcaatac | attgagtttg | tggcagacag | acttatgctg | gaactgggtt | 1200 |
| ttagcaaggt | tttcagagta | gagaacccat | ttgactttat | ggagaatatt | tcactggaag | 1260 |
| gaaagactaa | cttctttgag | aagagagtag | gcgagtatca | gaggatggga | gtgatgtcaa | 1320 |
| gtccaacaga | gaattctttt | accttggatg | ctgacttcta | aatgaactga | agatgtgccc | 1380 |
| ttacttggct | gatttttttt | ttccatctca | taagaaaaat | cagctgaagt | gttaccaact | 1440 |
| agccacacca | tgaattgtcc | gtaatgttca | ttaacagcat | cttaaaact | gtgtagctac | 1500 |
| ctcacaacca | gtcctgtctg | tttatagtgc | tggtagtatc | accttttgcc | agaaggcctg | 1560 |
| gctggctgtg | acttaccata | gcagtgacaa | tggcagtctt | ggctttaaag | tgaggggtga | 1620 |
| cccctttagtg | agcttagcac | agcgggatta | aacagtcctt | taaccagcac | agccagttaa | 1680 |
| aagatgcagc | ctcactgctt | caacgcagat | tttaatgttt | acttaaatat | aaacctggca | 1740 |
| ctttacaaac | aaataaacat | tgtttgtact | cacaaggcga | taatagcttg | atttatttgg | 1800 |
| tttctacacc | aaatacattc | tcctgaccac | taatgggagc | caattcacaa | ttcactaagt | 1860 |
| gactaaagta | agttaaactt | gtgtagacta | agcatgtaat | ttttaagttt | tatttttaatg | 1920 |
| aattaaaata | tttgttaacc | aactttaaag | tcagtcctgt | gtatacctag | atattagtca | 1980 |
| gttggtgcca | gatagaagac | aggttgtgtt | tttatcctgt | ggcttgtgta | gtgtcctggg | 2040 |
| attctctgcc | ccctctgagt | agagtgttgt | gggataaagg | aatctctcag | ggcaaggagc | 2100 |
| ttcttaagtt | aaatcactag | aaatttaggg | gtgatctggg | ccttcatatg | tgtgagaagc | 2160 |
| cgtttcattt | tatttctcac | tgtattttcc | tcaacgtctg | gttgatgaga | aaaaattctt | 2220 |
| gaagagtttt | catatgtggg | agctaaggta | gtattgtaaa | atttcaagtc | atccttaaac | 2280 |

-continued

```
aaaatgatcc acctaagatc ttgcccctgt taagtggtga aatcaactag aggtggttcc    2340
tacaagttgt tcattctagt tttgtttggt gtaagtaggg tgtgtgagtt aattcattta    2400
tatttactat gtctgttaaa tcagaaattt tttattatct atgttcttct agattttacc    2460
tgtagttcat acttcagtca cccagtgtct tattctggca ttgtctaaat ctgagcattg    2520
tctaggggga tcttaaactt tagtaggaaa ccatgagctg ttaatacagt ttccattcaa    2580
atattaattt cagaatgaaa cataattttt tttttttttt ttgagatgga gtctcgctct    2640
gttgcccagg ctggagtgca gtggcgcgat tttggctcac tgtaacctcc atctcctggg    2700
ttcaagcaat tctcctgtct cagcctccct agtagctggg actgcaggta tgtgctacca    2760
cacctggcta attttgtat ttttagtaga gatggagttt caccatattg gtcaggctgg    2820
tcttgaactc ctgacctcag gtgatccacc cacctcggcc tcccaaagtg ctgggattgc    2880
aggcgtgata aacaaatatt cttaataggg ctactttgaa ttaatctgcc tttatgtttg    2940
ggagaagaaa gctgagacat tgcatgaaag atgatgagag ataaatgttg atcttttggc    3000
cccatttgtt aattgtattc agtatttgaa cgtcgtcctg tttattgtta gttttcttca    3060
tcatttattg tatagacaat ttttaaatct ctgtaatatg atacattttc ctatctttta    3120
agttattgtt acctaaagtt aatccagatt atatggtcct tatatgtgta caacattaaa    3180
atgaaaggct ttgtcttgca ttgtgaggta caggcggaag ttggaatcag gttttaggat    3240
tctgtctctc attagctgaa taatgtgagg attaacttct gccagctcag accatttcct    3300
aatcagttga aagggaaaca agtatttcag tctcaaaatt gaataatgca caagtcttaa    3360
gtgattaaaa taaaactgtt cttatgtcag tttcaaaaaa aaaaaaaaaa aa            3412
```

<210> SEQ ID NO 42
<211> LENGTH: 3824
<212> TYPE: DNA
<213> ORGANISM: Homo sapiens

<400> SEQUENCE: 42

```
ggaagcgcag agcaggttca aacacagacg gcgggtgaac atggcgtcct cgacttggtc     60
tgagacgtga taggcctgcc ttctggttga agatgtggcg agtgaaaaaa ctgagcctca    120
gcctgtcgcc ttcgccccag acgggaaaac catctatgag aactcctctc cgtgaactta    180
ccctgcagcc cggtgccctc accaactctg gaaaaagatc ccccgcttgc tcctcgctga    240
ccccatcact gtgcaagctg gggctgcagg aaggcagcaa caactcatct ccagtggatt    300
ttgtaaataa caagaggaca gacttatctt cagaacattt cagtcattcc tcaaagtggc    360
tagaaacttg tcagcatgaa tcagatgagc agcctctaga tccaattccc caaattagct    420
ctactcctaa aacgtctgag gaagcagtag acccactggg caattatatg gttaaaacca    480
tcgtccttgt accatctcca ctggggcagc aacaagacat gatatttgag gcccgtttag    540
ataccatggc agagacaaac agcatatctt taaatggacc tttgagaaca gacgatctgg    600
tgagagagga ggtggcaccc tgcatgggag acaggttttc agaagttgct gctgtatctg    660
agaaacctat ctttcaggaa tctccgtccc atctcttaga ggagtctcca ccaaatccct    720
gttctgaaca actacattgc tccaaggaaa gcctgagcag tagaactgag gctgtgcgtg    780
aggacttagt accttctgaa agtaacgcct tcttgccttc ctctgttctc tggctttccc    840
cttcaactgc cttggcagca gatttccgtg tcaatcatgt ggacccagag gaggaaattg    900
tagagcatgg agctatggag gaaagagaaa tgaggtttcc cacacatcct aaggagtctg    960
```

| | |
|---|---|
| aaacagaaga tcaagcactt gtctcaagtg tggaagatat tctgtccaca tgcctgacac | 1020 |
| caaatctagt agaaatggaa tcccaagaag ctccaggccc agcagtagaa gatgttggta | 1080 |
| ggattcttgg ctctgataca gagtcttgga tgtccccact ggcctggctg aaaaaggtg | 1140 |
| taaataccte cgtcatgctg gaaaatctcc gccaaagctt atcccttccc tcgatgcttc | 1200 |
| gggatgctgc aattggcact accccttct ctacttgctc ggtggggact tggtttactc | 1260 |
| cttcagcacc acaggaaaag agtcaaaaca catcccagac aggcctggtt ggcaccaagc | 1320 |
| acagtacttc tgagacagag cagctcctgt gtggccggcc tccagatctg actgccttgt | 1380 |
| ctcgacatga cttggaagat aacctgctga gctctcttgt cattctggag gttctctccc | 1440 |
| gccagcttcg ggactggaag agccagctgg ctgtccctca cccagaaacc caggacagta | 1500 |
| gcacacagac tgacacatct cacagtggga taactaataa acttcagcat cttaaggaga | 1560 |
| gccatgagat gggacaggcc ctacagcagg ccagaaatgt catgcaatca tgggtgctta | 1620 |
| tctctaaaga gctgatatcc ttgcttcacc tatccctgtt gcatttagaa gaagataaga | 1680 |
| ctactgtgag tcaggagtct cggcgtgcag aaacattggt ctgttgctgt tttgatttgc | 1740 |
| tgaagaaatt gagggcaaag ctccagagcc tcaaagcaga agggaggag gcaaggcaca | 1800 |
| gagaggaaat ggctctcaga ggcaaggatg cggcagagat agtgttggag gctttctgtg | 1860 |
| cacacgccag ccagcgcatc agccagctgg aacaggacct agcatccatg cgggaattca | 1920 |
| gaggccttct gaaggatgcc cagacccaac tggtagggct tcatgccaag caagaagagc | 1980 |
| tggttcagca gacagtgagt cttacttcta ccttgcaaca agactggagg tccatgcaac | 2040 |
| tggattatac aacatggaca gctttgctga gtcggtcccg acaactcaca gagaaactca | 2100 |
| cagtcaagag ccagcaagcc ctgcaggaac gtgatgtggc aattgaggaa aagcaggagg | 2160 |
| tttctagggt gctggaacaa gtctctgccc agttagagga gtgcaaaggc caaacagaac | 2220 |
| aactggagtt ggaaaacagt cgtctagcaa cagatctccg ggctcagttg cagattctgg | 2280 |
| ccaacatgga cagccagcta aaagagctac agagtcagca tacccattgt gcccaggacc | 2340 |
| tggctatgaa ggatgagtta ctctgccagc ttacccagag caatgaggag caggctgctc | 2400 |
| aatggcaaaa ggaagagatg gcactaaaac acatgcaggc agaactgcag cagcaacaag | 2460 |
| ctgtcctggc caaagaggtg cgggacctga agagaccttt ggagtttgca gaccaggaga | 2520 |
| atcaggttgc tcacctggag ctgggtcagg ttgagtgtca attgaaaacc acactggaag | 2580 |
| tgctccggga gcgcagcttg cagtgtgaga acctcaagga cactgtagag aacctaacgg | 2640 |
| ctaaactggc cagcaccata gcagataacc aggagcaaga tctggagaaa acacggcagt | 2700 |
| actctcaaaa gctagggctg ctgactgagc aactacagag cctgactctc tttctacaga | 2760 |
| caaaactaaa ggagaagact gaacaagaga cccttctgct gagtacagcc tgtcctccca | 2820 |
| cccaggaaca ccctctgcct aatgacagga ccttcctggg aagcatcttg acagcagtgg | 2880 |
| cagatgaaga gccagaatca actcctgtgc ccttgcttgg aagtgacaag agtgctttca | 2940 |
| cccgagtagc atcaatggtt tcccttcagc ccgcagagac cccaggcatg gaggagagcc | 3000 |
| tggcagaaat gagtattatg actactgagc ttcagagtct tgttccctg ctacaagagt | 3060 |
| ctaaagaaga agccatcagg actctgcagc gaaaaatttg tgagctgcaa gctaggctgc | 3120 |
| aggcccagga agaacagcat caggaagtcc agaaggcaaa agaagcagac atagagaagc | 3180 |
| tgaaccagcc cttgtgcttg cgctacaaga atgaaaagga gctccaggaa gtgatacagc | 3240 |
| agcagaatga gaagatccta gaacagatag acaagagtgg cgagctcata agccttagag | 3300 |
| aggaggtgac ccaccttacc cgctcacttc ggcgtgcgga gacagagacc aaagtgctcc | 3360 |

| | |
|---|---:|
| aggaggccct ggcaggccag ctggactcca actgccagcc tatggccacc aattggatcc | 3420 |
| aggagaaagt gtggctctct caggaggtgg acaaactgag agtgatgttc ctggagatga | 3480 |
| aaaatgagaa ggaaaaactc atgatcaagt tccagagcca tagaaatatc ctagaggaga | 3540 |
| accttcggcg ctctgacaag gagttagaaa aactagatga cattgttcag catatttata | 3600 |
| agaccctgct ctctattcca gaggtggtga ggggatgcaa agaactacag ggattgctgg | 3660 |
| aatttctgag ctaagaaact gaaagccaga atctgcttca cctcttttta cctgcaatac | 3720 |
| ccccttaccc caataccaag accaactggc atagagccaa ctgagataaa tgctatttaa | 3780 |
| ataaagtgta tttaatgaat ttctccaaaa aaaaaaaaaa aaaa | 3824 |

<210> SEQ ID NO 43
<211> LENGTH: 2109
<212> TYPE: DNA
<213> ORGANISM: Homo sapiens

<400> SEQUENCE: 43

| | |
|---|---:|
| aaagtaccag ctggcgcctt ttaagagata caggtctgtg aagcaggcag gttgctcagc | 60 |
| tgccccgga gcggttcctc cacctgaggc agactccacg tcggctggca tgagccggcg | 120 |
| cccctgcagc tgcgccctac ggccaccccg ctgctcctgc agcgccagcc ccagcgcagt | 180 |
| gacagccgcc gggcgccctc gaccctcgga tagttgtaaa gaagaaagtt ctacccttc | 240 |
| tgtcaaaatg aagtgtgatt ttaattgtaa ccatgttcat tccggactta aactggtaaa | 300 |
| acctgatgac attggaagac tagtttccta caccccctgca tatttggaag gttcctgtaa | 360 |
| agactgcatt aaagactatg aaaggctgtc atgtattggg tcaccgattg tgagccctag | 420 |
| gattgtacaa cttgaaactg aaagcaagcg cttgcataac aaggaaaatc aacatgtgca | 480 |
| acagacactt aatagtacaa atgaaataga agcactagag accagtagac tttatgaaga | 540 |
| cagtggctat tcctcatttt ctctacaaag tggcctcagt gaacatgaag aaggtagcct | 600 |
| cctggaggag aatttcggtg acagtctaca atcctgcctg ctacaaatac aaagcccaga | 660 |
| ccaatatccc aacaaaaact tgctgccagt tcttcatttt gaaaaagtgg tttgttcaac | 720 |
| attaaaaaag aatgcaaaac gaaatcctaa agtagatcgg gagatgctga aggaaattat | 780 |
| agccagagga aattttagac tgcagaatat aattggcaga aaaatgggcc tagaatgtgt | 840 |
| agatattctc agcgaactct ttcgaagggg actcagacat gtcttagcaa ctattttagc | 900 |
| acaactcagt gacatggact taatcaatgt gtctaaagtg agcacaactt ggaagaagat | 960 |
| cctagaagat gataagggg cattccagtt gtacagtaaa gcaatacaaa gagttaccga | 1020 |
| aaacaacaat aaatttttcac ctcatgcttc aaccagagaa tatgttatgt tcagaacccc | 1080 |
| actggcttct gttcagaaat cagcagccca gacttctctc aaaaagatg ctcaaaccaa | 1140 |
| gttatccaat caaggtgatc agaaaggttc tacttatagt cgacacaatg aattctctga | 1200 |
| ggttgccaag acattgaaaa agaacgaaag cctcaaagcc tgtattcgct gtaattcacc | 1260 |
| tgcaaaatat gattgctatt tacaacgggc aacctgcaaa cgagaaggct gtggatttga | 1320 |
| ttattgtacg aagtgtctct gtaattatca tactactaaa gactgttcag atggcaagct | 1380 |
| cctcaaagcc agttgtaaaa taggtcccct gcctggtaca agaaaagca aaagaatttt | 1440 |
| acgaagattg tgatctctta ttaaatcaat tgttactgat catgaatgtt agttagaaaa | 1500 |
| tgttaggttt taacttaaaa aaaattgtat tgtgattttc aatttatgt tgaaatcggt | 1560 |
| gtagtatcct gaggttttt tcccccaga agataaagag gatagacaac ctcttaaaat | 1620 |

```
attttttacaa tttaatgaga aaaagtttaa aattctcaat acaaatcaaa caatttaaat    1680
attttaagaa aaaaggaaaa gtagatagtg atactgaggg taaaaaaaaa ttgattcaat    1740
tttatggtaa aggaaaccca tgcaattta cctagacagt cttaaatatg tctggttttc    1800
catctgttag catttcagac attttatgtt cctcttactc aattgatacc aacagaaata    1860
tcaacttctg gagtctatta aatgtgttgt caccttttcta aagctttttt tcattgtgtg    1920
tatttcccaa gaaagtatcc tttgtaaaaa cttgcttgtt ttccttattt ctgaaatctg    1980
ttttaatatt tttgtataca tgtaaatatt tctgtatttt ttatatgtca aagaatatgt    2040
ctcttgtatg tacatataaa aataaatttt gctcaataaa attgtaagct taaaaaaaaa    2100
aaaaaaaaa                                                            2109
```

<210> SEQ ID NO 44
<211> LENGTH: 3222
<212> TYPE: DNA
<213> ORGANISM: Homo sapiens

<400> SEQUENCE: 44

```
cggggccgca ccgccttcg cagccgcctc tgccgccgcc gccgcgttgg cctcgccgcc      60
cctgctcgga caccatgcca caaggagagt gatctcttcc cctgttttca caatggagga    120
ctccggaaag actttcagct ccgaggagga agaagctaac tattggaaag atctggcgat    180
gacctacaaa cagagggcag aaaatacgca agaggaactc cgagaattcc aggagggaag    240
ccgagaatat gaagctgaat tggagacgca gctgcaacaa attgaaacca ggaacagaga    300
cctcctgtcc gaaaataacc gccttcgcat ggagctggaa accatcaagg agaagtttga    360
agtgcagcac tctgaaggct accggcagat ctcagccttg gaggatgacc tcgcgcagac    420
caaagccatt aaagaccaat gcagaaaata catcagagag ctggagcaag caaatgacga    480
cctggaaaga gccaagcgcg ccacgatcat gtctctcgaa gactttgagc agcgcttgaa    540
tcaggccatc gaaagaaatg ccttcctgga aagtgaactt gatgaaaaag agaatctcct    600
ggaatctgtt cagagactga aggatgaagc cagagatttg cggcaggaac tggccgtgca    660
gcagaagcag gagaaaccca ggacccccat gcccagctca gtggaagctg agaggacaga    720
cacagctgtg caggccacgg gctccgtgcc gtccacgccc attgctcacc gaggacccag    780
ctcaagttta aacacacctg ggagcttcag acgtggcctg gacgactcca ccggggggac    840
ccccctcaca cctgcggccc ggatatcagc cctcaacatt gtgggagacc tactgcggaa    900
agtcggggca ctggagtcca aactcgcttc ctgccggaac ctcgtgtacg atcagtcccc    960
aaaccgaaca ggtggcccag cctctgggcg gagcagcaag aacagagatg gcggggagag   1020
acggccaagc agcaccagcg tgcctttggg tgataagggg ttggacacga gttgccgctg   1080
gttgtccaaa tcaacaacca gtcgtccag ctcctgctga agcctgttct tggtcttttc    1140
cagtttatca taagcggccg ccttctcctc gtactgctgg gtgaggttct cgatctcctt   1200
ctggaacctc ttcttcccct cttccagagc ttccacggtg ctgcaaagt cctgcagctt    1260 cttcttcgag tcggagagct acaaggacag cgtccagggt agggtgagag ggggaccatg   1320
agtggcccct gtcctggcc ccacagactc tgagaagcga agaccatgtc tcctcgttgg    1380
agaaacccaa tagcagggga agctgggggg tcaagcacca tcgcaccaac actccaccgc   1440
gatctgcctg cgggggatct cagcgcagag aagttgagag gacccatgaa ggaagcaagg   1500
acacggggca ggcacctgga tgttgagagt ggagatgtgg cgctccaggt tctgcttggc   1560
ctccatctcc tcgtccagct ggtcttgcag gctgttccgc tcctcctcca gctggcgcag   1620
```

-continued

```
cttcgtagac acgttgagct tctgccgggt ttcttcttga agcagctcct gcaaaaggga      1680
tgcaaagagg tcccagggac ctgccccgag gaaggccacc ccccaggtcc cctggatgat      1740
gtggcaggac actcacctgg gtgtcctgga gctgggaact gagggacgcc acgtccttgg      1800
ccagcttaat ggccttcccc tcggcctcgt taagcatccc tgtgacgctc tcaacttcat      1860
tctaagggtg ccaagagact ggttagtcaa agcctctaga aggggatcct cgttgaaagg      1920
agcccttttt actcaaaaca catgggctag tacttgaggt gttcactgat tgagaaaata      1980
cccgtgaggt atgggactct gataaaaaaa aaaaaaaaca cacacacaca caaaaaaaac      2040
agaatctgtg gcttgaaggg aactccgtca cctatgagtt gggaccctgg ccctagactc      2100
tgtggttcta agaacttatt tgagccccaa tggtattgac tgggacctga tcccactaaa      2160
tggatcctag atccctgcca aggttggtag agacaaagca gcaggtctga gagtccagac      2220
gaggtgctct ggctggtcca ctctctaagg ctggagaagg gagaccagga tggtacttga      2280
acgtcccagg gatgctgtcc catcccttcc ttcctcactc ctactctttg accctgatgg      2340
ccaaagccag agacgcaggc cctaaaggta aaaacgtcct ctctgtattc tctggctttt      2400 actcccctagt gtctctgcat aagtccctt gaggctgtta gcctacccct ccatctcttc      2460
cattgacaag gaggatatga atgatcttga cactgcttat atgagggcgg caaaagccct      2520
gctctcaact gcatgtgaga aaaaaacatc tcacttaatt cttccctcgc cccttggtcc      2580
ctggctgtgg acatgttaaa catttgtgaa actttggcc acgtccccat gagtggcaag      2640
gcagggtaaa tggctatgcc aagtgaaaga agaccaaaga caaaaagacc atgtcattca      2700
gcagcttaaa accctcaac agcttcacat gcccagagt aaggatcaac atacatgtaa      2760
taggttctca aaagccctac atcatctggg tacaagctcc ccctccaacc ccactctgta      2820
ctatctcccc ctaccccaa ccccagctgg gcactccagc tctactggct gtatgtctct      2880
ctcctaattt ttctacttac cacagggcct ttgcacacgc tgttccctct gcctggtaga      2940
cttatccatg ctccttaggg aagcctttcg tggctcctcc tcccccaggt taggccccct      3000
ggttatttac acttgggcat catgtgcctt ccctttgctg catcatttga cattcatttg      3060
tgtgattatt catgtctttc ccttcccttc ccttcccctt actcggctgg agtcctactg      3120
gggcagcgac agtgtctctt cttccttgct gttggatctc aggattaagc acagtgcctg      3180
gcatacagca ggtgctcaat aaatacttat caaattggaa aa                        3222
```

<210> SEQ ID NO 45
<211> LENGTH: 3053
<212> TYPE: DNA
<213> ORGANISM: Homo sapiens

<400> SEQUENCE: 45

```
gagcgcggct ggagtttgct gctgccgctg tgcagtttgt tcaggggctt gtggtggtga       60
gtccgagagg ctgcgtgtga gagacgtgag aaggatcctg cactgaggag gtggaaagaa      120
gaggattgct cgaggaggcc tggggtctgt gaggcagcgg agctgggtga aggctgcggg      180
ttccggcgag gcctgagctg tgctgtcgtc atgcctcaaa cccgatccca ggcacaggct      240
acaatcagtt ttcaaaaaag gaagctgtct cgggcattga acaaagctaa aaactccagt      300
gatgccaaac tagaaccaac aaatgtccaa accgtaacct gttctcctcg tgtaaaagcc      360
ctgcctctca gccccaggaa acgtctgggc gatgacaacc tatgcaacac tcccatttta      420
cctccttgtt ctccaccaaa gcaaggcaag aaagagaatg gtcccctca ctcacataca      480
```

| | |
|---|---|
| cttaagggac gaagattggt atttgacaat cagctgacaa ttaagtctcc tagcaaaaga | 540 |
| gaactagcca aagttcacca aaacaaaata ctttcttcag ttagaaaaag tcaagagatc | 600 |
| acaacaaatt ctgagcagag atgtccactg aagaaagaat ctgcatgtgt gagactattc | 660 |
| aagcaagaag gcacttgcta ccagcaagca aagctggtcc tgaacacagc tgtcccagat | 720 |
| cggctgcctg ccagggaaag ggagatggat gtcatcagga atttcttgag ggaacacatc | 780 |
| tgtgggaaaa aagctggaag cctttacctt tctggtgctc ctggaactgg aaaaactgcc | 840 |
| tgcttaagcc ggattctgca agacctcaag aaggaactga aaggctttaa aactatcatg | 900 |
| ctgaattgca tgtccttgag gactgcccag gctgtattcc cagctattgc tcaggagatt | 960 |
| tgtcaggaag aggtatccag gccagctggg aaggacatga tgaggaaatt ggaaaaacat | 1020 |
| atgactgcag agaagggccc catgattgtg ttggtattgg acgagatgga tcaactggac | 1080 |
| agcaaaggcc aggatgtatt gtacacgcta tttgaatggc catggctaag caattctcac | 1140 |
| ttggtgctga ttggtattgc taatacccctg gatctcacag atagaattct acctaggctt | 1200 |
| caagctagag aaaaatgtaa gccacagctg ttgaacttcc caccttatac cagaaatcag | 1260 |
| atagtcacta ttttgcaaga tcgacttaat caggtatcta gagatcaggt tctggacaat | 1320 |
| gctgcagttc aattctgtgc ccgcaaagtc tctgctgttt caggagatgt tcgcaaagca | 1380 |
| ctggatgttt gcaggagagc tattgaaatt gtagagtcag atgtcaaaag ccagactatt | 1440 |
| ctcaaaccac tgtctgaatg taaatcacct tctgagcctc tgattcccaa gagggttggt | 1500 |
| cttattcaca tatcccaagt catctcagaa gttgatggta acaggatgac cttgagccaa | 1560 |
| gaaggagcac aagattcctt ccctcttcag cagaagatct tggtttgctc tttgatgctc | 1620 |
| ttgatcaggc agttgaaaat caaagaggtc actctgggga agttatatga agcctacagt | 1680 |
| aaagtctgtc gcaaacagca ggtggcggct gtggaccagt cagagtgttt gtcactttca | 1740 |
| gggctcttgg aagccagggg catttttagga ttaaagagaa acaaggaaac ccgtttgaca | 1800 |
| aaggtgtttt tcaagattga agagaaagaa atagaacatg ctctgaaaga taagctttta | 1860 |
| attggaaata tcttagctac tggattgcct taaattcttc tcttacaccc caccgaaag | 1920 |
| tattcagctg gcatttagag agctacagtc ttcattttag tgctttacac attcgggcct | 1980 |
| gaaaacaaat atgaccttttt ttacttgaag ccaatgaatt ttaatctata gattctttaa | 2040 |
| tattagcaca gaataatatc tttgggtctt actatttta cccataaaag tgaccaggta | 2100 |
| gaccctttt aattacattc actacttcta ccacttgtgt atctctagcc aatgtgcttg | 2160 |
| caagtgtaca gatctgtgta gaggaatgtg tgtatattta cctcttcgtt tgctcaaaca | 2220 |
| tgagtgggta tttttttgtt tgttttttt gttgttgttg ttttgaggc gcgtctcacc | 2280 |
| ctgttgccca ggctggagtg caatggcgcg ttctctgctc actacagcac ccgcttccca | 2340 |
| ggttgaagtg attctcttgc ctcagcctcc cgagtagctg ggattacagg tgcccaccac | 2400 |
| cgcgcccagc taatttttta atttttagta gagacagggt tttaccatgt tggccaggct | 2460 |
| ggtcttgaac tcctgaccct caagtgatct gcccaccttg gcctccctaa gtgctgggat | 2520 |
| tataggcgtg agccaccatg ctcagccatt aaggtatttt gttaagaact ttaagtttag | 2580 |
| ggtaagaaga atgaaaatga tccagaaaaa tgcaagcaag tccacatgga gatttggagg | 2640 |
| acactggtta aagaatttat ttctttgtat agtatactat gttcatggtg cagatactac | 2700 |
| aacattgtgg cattttagac tcgttgagtt tcttgggcac tcccaagggc gttgggtca | 2760 |
| taaggagact ataactctac agattgtgaa tatatttatt ttcaagttgc attctttgtc | 2820 |
| tttttaagca atcagatttc aagagagctc aagctttcag aagtcaatgt gaaaattcct | 2880 |

| | |
|---|---|
| tcctaggctg tcccacagtc tttgctgccc ttagatgaag ccacttgttt caagatgact | 2940 |
| actttggggt tgggttttca tctaaacaca ttttttccagt cttattagat aaattagtcc | 3000 |
| atatggttgg ttaatcaaga gccttctggg tttggtttgg tggcattaaa tgg | 3053 |

<210> SEQ ID NO 46
<211> LENGTH: 3830
<212> TYPE: DNA
<213> ORGANISM: Homo sapiens

<400> SEQUENCE: 46

| | |
|---|---|
| gtcaccacca gcctagctcg dacggcaagc ggcgggagat tttcaaaatg ggagcccaga | 60 |
| ggcaccgccc aggcctcgga aggtgtcagg gagaactttc cgtggtttca gcgtcgtcgc | 120 |
| ctggagcggc ggtttagaga gccgagcctg atgggcgcca aggccggctg gctgcttgga | 180 |
| gcgctgcctc gaagggactg cgtgaaggaa gctaatccgg agaacccagg ccagagcctg | 240 |
| gaaatatggc gacctgcatc ggggagaaga tcgaggattt taaagttgga aatctgcttg | 300 |
| gtaaaggatc atttgctggt gtctacagag ctgagtccat tcacactggt ttggaagttg | 360 |
| caatcaaaat gatagataag aaagccatgt acaaagcagg aatggtacag agagtccaaa | 420 |
| atgaggtgaa aatacattgc caattgaaac atccttctat cttggagctt tataactatt | 480 |
| ttgaagatag caattatgtg tatctggtat tagaaatgtg ccataatgga gaatgaaca | 540 |
| ggtatctaaa gaatagagtg aaaaccttct cagaaaatga agctcgacac ttcatgcacc | 600 |
| agatcatcac agggatgttg tatcttcatt ctcatggtat actacaccgg gacctcacac | 660 |
| tttctaacct cctactgact cgtaatatga acatcaagat tgctgatttt gggctggcaa | 720 |
| ctcaactgaa aatgccacat gaaaagcact atacattatg tggaactcct aactacattt | 780 |
| caccagaaat tgccactcga agtgcacatg gccttgaatc tgatgtttgg tccctgggct | 840 |
| gtatgttta tacattactt atcgggagac cacccttcga cactgacaca gtcaagaaca | 900 |
| cattaaataa agtagtattg gcagattatg aaatgccatc tttttttgtca atagaggcca | 960 |
| aggaccttat tcaccagtta cttcgtagaa atccagcaga tcgtttaagt ctgtcttcag | 1020 |
| tattggacca tccttttatg tcccgaaatt cttcaacaaa aagtaaagat ttaggaactg | 1080 |
| tggaagactc aattgatagt gggcatgcca caatttctac tgcaattaca gcttcttcca | 1140 |
| gtaccagtat aagtggtagt ttatttgaca aagaagact tttgattggt cagccactcc | 1200 |
| caaataaaat gactgtattt ccaaagaata aagttcaac tgattttctc tcttcaggag | 1260 |
| atggaaacag tttttatact cagtggggaa atcaagaaac cagtaatagt ggaagggaa | 1320 |
| gagtaattca agatgcagaa gaaaggccac attctcgata ccttcgtaga gcttattcct | 1380 |
| ctgatagatc tggcacttct aatagtcagt ctcaagcaaa aacatataca atggaacgat | 1440 |
| gtcactcagc agaaatgctt tcagtgtcca aaagatcagg aggaggtgaa aatgaagaga | 1500 |
| ggtactcacc cacagacaac aatgccaaca tttttaactt cttttaaagaa aagcatccca | 1560 |
| gtagttctgg atcttttgaa agacctgata caatcaagc actctccaat catctttgtc | 1620 |
| caggaaaaac tccttttcca tttgcagacc cgacacctca gactgaaacc gtacaacagt | 1680 |
| ggtttgggaa tctgcaaata aatgctcatt taagaaaaac tactgaatat gacagcatca | 1740 |
| gcccaaaccg ggacttccag ggccatccag atttgcagaa ggacacatca aaaaatgcct | 1800 |
| ggactgatac aaaaagtcaaa aagaactctg atgcttctga taatgcacat tctgtaaaac | 1860 |
| agcaaaatac catgaaatat atgactgcac ttcacagtaa acctgagata atccaacaag | 1920 |

```
aatgtgtttt tggctcagat cctctttctg aacagagcaa gactagggt atggagccac    1980 catgggtta tcagaatcgt acattaagaa gcattacatc tccgttggtt gctcacaggt    2040
taaaaccaat cagacagaaa accaaaaagg ctgtggtgag catacttgat tcagaggagg    2100
tgtgtgtgga gcttgtaaag gagtatgcat ctcaagaata tgtgaaagaa gttcttcaga    2160
tatctagtga tggaaatacg atcactattt attatccaaa tggtggtaga ggttttcctc    2220
ttgctgatag accaccctca cctactgaca acatcagtag gtacagcttt gacaatttac    2280
cagaaaaata ctggcgaaaa tatcaatatg cttccaggtt tgtacagctt gtaagatcta    2340
aatctcccaa aatcacttat tttacaagat atgctaaatg cattttgatg gagaattctc    2400
ctggtgctga ttttgaggtt tggttttatg atggggtaaa aatacacaaa acagaagatt    2460
tcattcaggt gattgaaaag acagggaagt cttacactt aaaaagtgaa agtgaagtta    2520
atagcttgaa agaggagata aaaatgtata tggaccatgc taatgagggt catcgtatt     2580 gtttagcact ggaatccata atttcagaag aggaaaggaa aactaggagt gctccctttt    2640
tcccaataat cataggaaga aaacctggta gtactagttc acctaaggcc ttatcacctc    2700
ctccttctgt ggattcaaat tacccaacga gagagagagc atctttcaac agaatggtca    2760
tgcatagtgc tgcttctcca acacaggcac caatccttaa tccctctatg gttacaaatg    2820
aaggacttgg tcttacaact acagcttctg gaacagacat ctcttctaat agtctaaaag    2880
attgtcttcc taaatcagca caacttttga aatctgttt tgtgaaaaat gttggttggg    2940
ctacacagtt aactagtgga gctgtgtggg ttcagtttaa tgatgggtcc cagttggttg    3000
tgcaggcagg agtgtcttct atcagttata cctcaccaaa tggtcaaaca actaggtatg    3060
gagaaaatga aaaattacca gactacatca acagaaatt acagtgtctg tcttccatcc    3120
ttttgatgtt ttctaatccg actcctaatt ttcattgatt aaaactcctt tcagacatat    3180
aagtttaata aataactttt ttgttgactt tcaagtaaag tgatttttt taatttaaca    3240 taaagtcttc agaaagcctt tctatgaaag aatttttaacc tataatgtaa aggatgtatt    3300
ctgagagaac aaagcagaat gaaacttgag tcacttacta aatatagtgg atataaaata    3360
gaacacctga ctttgctctt agaccataac ccccgaactt actatgttca tatatttgta    3420
ttgaacaatc ttttaaaagc aaaaatgtaa atgatgtgta gtttatttgt gcttttattg    3480 ttttcccctgc gtctcagaca tgttgagaat catggacaaa acctgctgga attttggaat    3540
ttttgaagat gtaaataatg tgtatttatg ttataagtaa catatgtaaa catgtatatt    3600
tgttttatat ttattttgt aacaccagtg tctgatgaaa cattttttgca aatgcatttt    3660 ataaaaaaat aaatatagtg ataagttaca ttatctttg attcatttaa ttaaatactt    3720 attttttaaat aacttaccag taaactcact ttttaaattt tgttgcctgt tgaggagcca    3780
attaaatttt aaatattaat tttgcaaatg ttaaaaaaaa aaaaaaaaaa              3830
```

<210> SEQ ID NO 47
<211> LENGTH: 2130
<212> TYPE: DNA
<213> ORGANISM: Homo sapiens

<400> SEQUENCE: 47

```
ggttaaacgg ggcccaaggc aggggtggcg ggtcagtgct gctcggggc ttctccatcc       60 aggtccctgg agttcctggt ccctggagct ccgcacttgg cggcgcaacc tgcgtgaggc     120
agcgcgactc tggcgactgg ccggccatgc cttcccgggc tgaggactat gaagtgttgt     180
acaccattgg cacaggctcc tacggccgct gccagaagat ccggaggaag agtgatggca     240
```

```
agatattagt tggaaagaa cttgactatg gctccatgac agaagctgag aaacagatgc      300
ttgtttctga agtgaatttg cttcgtgaac tgaaacatcc aaacatcgtt cgttactatg      360
atcggattat tgaccggacc aatacaacac tgtacattgt aatggaatat tgtgaaggag      420
gggatctggc tagtgtaatt acaaagggaa ccaaggaaag gcaatactta gatgaagagt      480
ttgttcttcg agtgatgact cagttgactc tggccctgaa ggaatgccac agacgaagtg      540
atggtggtca taccgtattg catcgggatc tgaaaccagc caatgttttc ctggatggca      600
agcaaaacgt caagcttgga gactttgggc tagctagaat attaaaccat gacacgagtt      660
ttgcaaaaac atttgttggc acaccttatt acatgtctcc tgaacaaatg aatcgcatgt      720
cctacaatga gaaatcagat atctggtcat gggctgctt gctgtatgag ttatgtgcat      780
taatgcctcc atttacagct tttagccaga agaactcgc tgggaaaatc agagaaggca      840
aattcaggcg aattccatac cgttactctg atgaattgaa tgaaattatt acgaggatgt      900
taaacttaaa ggattaccat cgaccttctg ttgaagaaat tcttgagaac cctttaatag      960
cagatttggt tgcagacgag caaagaagaa atcttgagag aagagggcga caattaggag     1020
agccagaaaa atcgcaggat tccagccctg tattgagtga gctgaaactg aaggaaattc     1080
agttacagga gcgagagcga gctctcaaag caagagaaga aagattggag cagaaagaac     1140
aggagctttg tgttcgtgag agactagcag aggacaaact ggctagagca gaaaatctgt     1200
tgaagaacta cagcttgcta aaggaacgga agttcctgtc tctggcaagt aatccagaac     1260
ttcttaatct tccatcctca gtaattaaga agaaagttca tttcagtggg gaaagtaaag     1320
agaacatcat gaggagtgag aattctgaga gtcagctcac atctaagtcc aagtgcaagg     1380
acctgaagaa aaggcttcac gctgcccagc tgcgggctca agccctgtca gatattgaga     1440
aaaattacca actgaaaagc agacagatcc tgggcatgcg ctagccaggt agagagacac     1500
agagctgtgt acaggatgta atattaccaa cctttaaaga ctgatattca aatgctgtag     1560
tgttgaatac ttggttccat gagccatgcc tttctgtata gtacacatga tatttcggaa     1620
ttggttttac tgttcttcag caactattgt acaaaatgtt cacatttaat ttttctttct     1680
tcttttaaga acatattata aaaagaatac tttcttggtt gggcttttaa tcctgtgtgt     1740
gattactagt aggaacatga gatgtgacat tctaaatctt gggagaaaaa ataatgttag     1800
gaaaaaaata tttatgcagg aagagtagca ctcactgaat agttttaaat gactgagtgg     1860
tatgcttaca attgtcatgt ctagatttaa attttaagtc tgagatttta aatgttttg      1920 agcttagaaa acccagttag atgcaatttg gtcattaata ccatgacatc ttgcttataa     1980
atattccatt gctctgtagt tcaaatctgt tagctttgtg aaaattcatc actgtgatgt     2040
ttgtattctt tttttttttc tgtttaacag aatatgagct gtctgtcatt tacctacttc     2100
tttcccacta aataaaagaa ttcttcagtt                                      2130
```

<210> SEQ ID NO 48
<211> LENGTH: 3685
<212> TYPE: DNA
<213> ORGANISM: Homo sapiens

<400> SEQUENCE: 48

```
agtggactca cgcaggcgca ggagactaca cttcccagga actccgggcc gcgttgttcg       60
ctggtacctc cttctgactt ccggtattgc tgcggtctgt agggccaatc gggagcctgg      120
aattgctttc ccggcgctct gattggtgca ttcgactagg ctgcctgggt tcaaaatttc      180
```

```
aacgatactg aatgagtccc gcggcgggtt ggctcgcgct tcgttgtcag atctgaggcg    240
aggctaggtg agccgtggga agaaaagagg gagcagctag ggcgcgggtc tccctcctcc    300
cggagtttgg aacggctgaa gttcaccttc cagcccctag cgccgttcgc gccgctaggc    360
ctggcttctg aggcggttgc ggtgctcggt cgccgcctag gcggggcagg gtgcgagcag    420
gggcttcggg ccacgcttct cttggcgaca ggattttgct gtgaagtccg tccgggaaac    480
ggaggaaaaa aagagttgcg ggaggctgtc ggctaataac ggttcttgat acatatttgc    540
cagacttcaa gatttcagaa aagggtgaaa agagaagatt gcaactttga gtcagacctg    600
taggcctgat agactgatta aaccacagaa ggtgacctgc tgagaaaagt ggtacaaata    660
ctgggaaaaa cctgctcttc tgcgttaagt gggagacaat gtcacaagtt aaaagctctt    720
attcctatga tgcccctcg gatttcatca attttttcatc cttggatgat gaaggagata    780
ctcaaaacat agattcatgg tttgaggaga aggccaattt ggagaataag ttactgggga    840
agaatggaac tggagggctt tttcagggca aaactccttt gagaaaggct aatcttcagc    900
aagctattgt cacacctttg aaaccagttg acaacactta ctacaaagag gcagaaaaag    960
aaaatcttgt ggaacaatcc attccgtcaa atgcttgttc ttccctggaa gttgaggcag   1020
ccatatcaag aaaaactcca gcccagcctc agagaagatc tcttaggctt tctgctcaga   1080
aggatttgga acagaaagaa aagcatcatg taaaaatgaa agccaagaga tgtgccactc   1140
ctgtaatcat cgatgaaatt ctaccctcta agaaaatgaa agtttctaac aacaaaaaga   1200
agccagagga agaaggcagt gctcatcaag atactgctga aaagaatgca tcttccccag   1260
agaaagccaa gggtagacat actgtgcctt gtatgccacc tgcaaagcag aagtttctaa   1320
aaagtactga ggagcaagag ctggagaaga gtatgaaaat gcagcaagag gtggtggaga   1380
tgcggaaaaa gaatgaagaa ttcaagaaac ttgctctggc tggaataggg caacctgtga   1440
agaaatcagt gagccaggtc accaaatcag ttgacttcca cttccgcaca gatgagcgaa   1500
tcaaacaaca tcctaagaac caggaggaat ataaggaagt gaactttaca tctgaactac   1560
gaaagcatcc ttcatctcct gcccgagtga ctaagggatg taccattgtt aagcctttca   1620
acctgtccca aggaaagaaa agaacatttg atgaaacagt ttctacatat gtgccccttg   1680
cacagcaagt tgaagacttc cataaacgaa cccctaacag atatcatttg aggagcaaga   1740
aggatgatat taacctgtta ccctccaaat cttctgtgac caagatttgc agagacccac   1800
agactcctgt actgcaaacc aaacaccgtg cacgggctgt gacctgcaaa agtacagcag   1860
agctggaggc tgaggagctc gagaaattgc aacaatacaa attcaaagca cgtgaacttg   1920
atcccagaat acttgaaggt gggcccatct tgcccaagaa accacctgtg aaaccaccca   1980
ccgagcctat tggctttgat ttggaaattg agaaaagaat ccaggagcga gaatcaaaga   2040
agaaaacaga ggatgaacac tttgaatttc attccagacc ttgccctact aagattttgg   2100
aagatgttgt gggtgttcct gaaaagaagg tacttccaat caccgtcccc aagtcaccag   2160
cctttgcatt gaagaacaga attcgaatgc ccaccaaaga gatgaggaa gaggacgaac   2220
cggtagtgat aaaagctcaa cctgtgccac attatggggt gccttttaag ccccaaatcc   2280
cagaggcaag aactgtggaa atatgccctt tctcgtttga ttctcgagac aaagaacgtc   2340
agttacagaa ggagaagaaa ataaaagaac tgcagaaagg ggaggtgccc aagttcaagg   2400
cacttccctt gcctcatttt gacaccatta acctgccaga agaaggta agaatgtga   2460
cccagattga acctttctgc ttggagactg acagaagagg tgctctgaag gcacagactt   2520
ggaagcacca gctggaagaa gaactgagac agcagaaaga agcagcttgt ttcaaggctc   2580
```

```
gtccaaacac cgtcatctct caggagccct tgttcccaa gaaagagaag aaatcagttg      2640
ctgagggcct ttctggttct ctagttcagg aaccttttca gctggctact gagaagagag      2700
ccaaagagcg gcaggagctg gagaagagaa tggctgaggt agaagcccag aaagcccagc      2760
agttggagga ggccagacta caggaggaag agcagaaaaa agaggagctg gccaggctac      2820
ggagagaact ggtgcataag gcaaatccaa tacgcaagta ccagggtctg gagataaagt      2880
caagtgacca gcctctgact gtgcctgtat ctcccaaatt ctccactcga ttccactgct      2940
aaactcagct gtgagctgcg gataccgccc ggcaatggga cctgctctta acctcaaacc      3000
taggaccgtc ttgctttgtc attgggcatg gagagaaccc atttctccag acttttacct      3060
acccgtgcct gagaaagcat acttgacaac tgtggactcc agttttgttg agaattgttt      3120
tcttacatta ctaaggctaa taatgagatg taactcatga atgtctcgat tagactccat      3180
gtagttactt cctttaaacc atcagccggc cttttatatg ggtcttcact ctgactagaa      3240
tttagtctct gtgtcagcac agtgtaatct ctattgctat tgccccttac gactctcacc      3300
ctctccccac tttttttaaa aattttaacc agaaaataaa gatagttaaa tcctaagata      3360
gagattaagt catggtttaa atgaggaaca atcagtaaat cagattctgt cctcttctct      3420
gcataccgtg aatttatagt taaggatccc tttgctgtga gggtagaaaa cctcaccaac      3480
tgcaccagtg aggaagaaga ctgcgtggat tcatggggag cctcacagca gccacgcagc      3540
aggctctggg tggggctgcc gttaaggcac gttctttcct tactggtgct gataacaaca      3600
gggaaccgtg cagtgtgcat tttaagacct ggcctggaat aaatacgttt tgtctttccc      3660
tcaaaaaaaa aaaaaaaaa aaaaa                                             3685

<210> SEQ ID NO 49
<211> LENGTH: 2656
<212> TYPE: DNA
<213> ORGANISM: Homo sapiens

<400> SEQUENCE: 49
cacacctgat ggtgtgactc ggccgacgcg agcgccgcgc ttcgcttcag ctgctagctg       60
gcccaaggga ggcgaccgcg gagggtggcg aggggcggcc aggacccgca gccccggggc      120
cgggccggtc cggaccgcca gggagggcag gtcagtgggc agatcgcgtc cgcgggattc      180
aatctctgcc cgctctgata acagtccttt tccctggcgc tcacttcgtg cctggcaccc      240
ggctgggcgc ctcaagaccg ttgtctcttc gatcgcttct ttggacttgg cgaccatttc      300
agagatgtct tccagaagta ccaaagattt aattaaaagt aagtggggat cgaagcctag      360
taactccaaa tccgaaacta cattagaaaa attaaaggga gaaattgcac acttaaagac      420
atcagtggat gaaatcacaa gtgggaaagg aaagctgact gataaagaga gacacagact      480
tttggagaaa attcgagtcc ttgaggctga gaaggagaag aatgcttatc aactcacaga      540
gaaggacaaa gaaatacagc gactgagaga ccaactgaag gccagatata gtactaccgc      600
attgcttgaa cagctggaag agacaacgag agaaggagaa aggagggagc aggtgttgaa      660
agccttatct gaagagaaag acgtattgaa acaacagttg tctgctgcaa cctcacgaat      720
tgctgaactt gaaagcaaaa ccaatacact ccgtttatca cagactgtgg ctccaaactg      780
cttcaactca tcaataaata atattcatga aatggaaata cagctgaaag atgctctgga      840
gaaaaatcag cagtgctcg tgtatgatca gcagcgggaa gtctatgtaa aaggactttt      900
agcaaagatc tttgagttgg aaaagaaaac ggaaacagct gctcattcac tcccacagca      960
```

-continued

| | |
|---|---|
| gacaaaaaag cctgaatcag aaggttatct tcaagaagag aagcagaaat gttacaacga | 1020 |
| tctcttggca agtgcaaaaa aagatcttga ggttgaacga caaaccataa ctcagctgag | 1080 |
| ttttgaactg agtgaatttc gaagaaaata tgaagaaacc caaaagaag ttcacaattt | 1140 |
| aaatcagctt ttgtattcac aaagaagggc agatgtgcaa catctggaag atgataggca | 1200 |
| taaaacagag aagatacaaa aactcaggga agagaatgat attgctaggg gaaaacttga | 1260 |
| agaagagaag aagagatccg aagagctctt atctcaggtc cagtttcttt acacatctct | 1320 |
| gctaaagcag caagaagaac aaacaagggt agctctgttg gaacaacaga tgcaggcatg | 1380 |
| tactttagac tttgaaaatg aaaaactcga ccgtcaacat gtgcagcatc aattgcatgt | 1440 |
| aattcttaag gagctccgaa aagcaagaaa tcaaataaca cagttggaat ccttgaaaca | 1500 |
| gcttcatgag tttgccatca cagagccatt agtcactttc caaggagaga ctgaaaacag | 1560 |
| agaaaaagtt gccgcctcac caaaaagtcc cactgctgca ctcaatgaaa gcctggtgga | 1620 |
| atgtcccaag tgcaatatac agtatccagc cactgagcat cgcgatctgc ttgtccatgt | 1680 |
| ggaatactgt tcaaagtagc aaaataagta tttgttttga tattaaaaga ttcaatactg | 1740 |
| tattttctgt tagcttgtgg gcattttgaa ttatatattt cacattttgc ataaaactgc | 1800 |
| ctatctacct ttgacactcc agcatgctag tgaatcatgt atcttttagg ctgctgtgca | 1860 |
| tttctcttgg cagtgatacc tccctgacat ggttcatcat caggctgcaa tgacagaatg | 1920 |
| tggtgagcag cgtctactga gactactaac attttgcact gtcaaaatac ttggtgagga | 1980 |
| aaagatagct caggttattg ctaatgggtt aatgcaccag caagcaaaat attttatgtt | 2040 |
| ttgggggttt tgaaaaatca aagataatta accaaggatc ttaactgtgt tcgcattttt | 2100 |
| tatccaagca cttagaaaac ctacaatcct aattttgatg tccattgtta agaggtggtg | 2160 |
| atagatacta tttttttttt catattgtat agcggttatt agaaaagttg gggattttct | 2220 |
| tgatctttat tgctgcttac cattgaaact taacccagct gtgttcccca actctgttct | 2280 |
| gcgcacgaaa cagtatctgt ttgaggcata atcttaagtg gccacacaca atgttttctc | 2340 |
| ttatgttatc tggcagtaac tgtaacttga attacattag cacattctgc ttagctaaaa | 2400 |
| ttgttaaaat aaactttaat aaacccatgt agccctctca tttgattgac agtatttag | 2460 |
| ttattttgg cattcttaaa gctgggcaat gtaatgatca gatctttgtt tgtctgaaca | 2520 |
| ggtattttta tacatgcttt ttgtaaacca aaaactttta aatttcttca ggttttctaa | 2580 |
| catgcttacc actgggctac tgtaaatgag aaaagaataa aattatttaa tgttttaaaa | 2640 |
| aaaaaaaaaa aaaaaa | 2656 |

<210> SEQ ID NO 50
<211> LENGTH: 6714
<212> TYPE: DNA
<213> ORGANISM: Homo sapiens

<400> SEQUENCE: 50

| | |
|---|---|
| actgcggggt gtgcggcggc ccaagcggtt tcaaacggct tagagcaggc cgcttggttc | 60 |
| tgacccagct gaggaaatac tcttaattct aaggaaaacc tggaagcaca atgggagatg | 120 |
| acagtgagtg gttgaaactg ccagttgatc agaaatgtga acacaagctg tggaaagcaa | 180 |
| ggttaagtgg gtatgaagag gccctgaaga tcttccagaa aataaaggat gaaaagagcc | 240 |
| cagagtggtc caaattttta ggattgatca aaaaatttgt cactgattcc aatgcagtgg | 300 |
| ttcaattgaa aggattagaa gctgcacttg tttatgttga aaatgcccat gtagcaggaa | 360 |
| aaaccacagg agaagttgtg tcaggtgttg taagtaaggt gttcaatcaa cctaaagcta | 420 |

| | |
|---|---|
| aagccaagga gctgggcata gagatctgtc ttatgtacat agagattgag aaaggagagg | 480 |
| ctgttcaaga agagctcctg aaaggcttgg acaataagaa tcccaagatc atagtggcct | 540 |
| gtatagagac actgaggaaa gccttaagtg aatttggttc caaaatcatc ttgcttaagc | 600 |
| caattatcaa agtgttgcca aaactctttg agtctcgaga aaggctgtt cgagatgaag | 660 |
| ccaaactaat tgctgtggag atttacagat ggattcggga tgctctgaga cccccattac | 720 |
| aaaatataaa ctctgttcag ttgaaagaac tagaagaaga atgggtcaaa ctgccaacaa | 780 |
| gtgctcctag acctactcga tttcttcgtt cccaacaaga actagaagct aaattggaac | 840 |
| aacaacagtc tgctggtgga gatgctgaag gaggtggtga tgatggtgat gaggtgccac | 900 |
| aaatagatgc ttatgagctt ttagaagctg tagaaatcct ttccaaactt cccaaagact | 960 |
| tttatgacaa aattgaggca aaaaaatggc aagagagaaa agaggccctg gagtctgtag | 1020 |
| aagtactaat aaaaaacccc aaactggaag ctggcgatta tgcagattta gtaaaagcat | 1080 |
| taaagaaggt tgttggaaag gacaccaatg tcatgttggt ggctttggca gcaaaatgtc | 1140 |
| ttactggcct ggctgttggg ctaaggaaga aatttggaca atatgcagga catgttgtgc | 1200 |
| caaccatctt ggagaaattc aaagagaaga aacctcaagt ggtacaagcc tgcaggagg | 1260 |
| caattgatgc aatcttcctt actaccacac tacagaacat cagtgaggat gttttagcag | 1320 |
| taatggataa taaaaatcca accatcaagc agcagacatc tcttttatt gcaagaagtt | 1380 |
| tccgccactg cactgcttct accctgccaa agagcttgct aaagcccttt tgtgctgcac | 1440 |
| tacttaagca catcaatgat tctgctcctg aagtcagaga tgccgcattt gaagcattgg | 1500 |
| gtactgcttt gaaggtggtt ggcgagaaag cagtaaaccc attcctagct gatgtggaca | 1560 |
| aactcaagct tgataagatc aaagaatgtt cagaaaaggt agaactgata catggtaaga | 1620 |
| aagctggact agctgctgat aagaaggaat tcaaacctct gcctggaagg actgctgctt | 1680 |
| caggggctgc aggagataag gacacaaagg acatttctgc acccaaacca ggacctctaa | 1740 |
| aaaaggcacc tgctgctaag gctggtgggc caccaaaaaa ggggaaacca gctgcaccag | 1800 |
| gaggcgcagg gaatactgga accaagaaca agaaaggact ggagactaaa gaaatagtgg | 1860 |
| agcctgagct ctcgatagaa gtatgtgaag aaaaagcttc agctgttctt cccctacct | 1920 |
| gtatacagct tcttgacagc agtaactgga agaaaggct ggcttgtatg aagagttcc | 1980 |
| agaaggctgt tgagctaatg gaccgaactg aaatgccatg ccaggcatta gtgaggatgc | 2040 |
| tagccaagaa acctggatgg aaagaaacta attttcaggt gatgcaaatg aagcttcata | 2100 |
| tagttgcttt gattgcccag aagggaaatt tttccaaaac gtcagctcag gttgtattag | 2160 |
| atggccttgt ggacaagatt ggagatgtga atgtgggaa caatgcaaaa gaagctatga | 2220 |
| cagcaatagc cgaagcctgt atgttaccat ggactgctga acaggttgtg tcaatggctt | 2280 |
| tctcacaaaa gaatcccaaa aatcagtcag aaactctgaa ttggctatca aatgccataa | 2340 |
| aagaatttgg ttttttctggg ttgaatgtca agctttcat tagcaatgtg aagacagctc | 2400 |
| ttgctgcaac aaacccagct gtgaggactg ctgccataac cctgcttggc gtgatgtatc | 2460 |
| tgtatgttgg tccctctttg cgaatgttct ttgaggatga aagcctgcc ctcctatccc | 2520 |
| agatagatgc agaatttgag aagatgcagg acaaagtcc acctgctcca accagaggaa | 2580 |
| tttccaagca tagcacaagt ggtacagatg aaggagaaga tggagatgaa ccagatgacg | 2640 |
| ggagcaatga tgtcgttgat cttttgccga ggacggagat cagtgataaa atcacttcag | 2700 |
| agttggtatc taagattggt gataagaatt ggaagattag gaaagaaggc ctagatgaag | 2760 |

```
tggcaggtat tattaatgac gcaaaattta tccaaccgaa tataggtgaa cttccaactg    2820
ccttgaaggg tcgactcaat gattcaaata aaatcttggt acagcaaacg ctgaatatcc    2880
tgcaacaact ggcagtagcc atgggcccaa atattaagca acatgtaaaa aatttaggca    2940
tccctatcat cacagtcctt ggagacagca agaacaatgt tcgagctgct gccctagcga    3000
ctgtgaatgc ttgggcagaa cagactggca tgaaggaatg gctggaagga gaagatcttt    3060
ctgaagagct caaaaaggaa aatcctttct tgaggcaaga gcttctgggc tggctggctg    3120
agaaactacc tactcttcgt tccaccccta cagacttat cctttgtgtt cctcatctct     3180
actcctgcct agaagatcga aatggagatg tgcgaaagaa ggcccaagat gccttgccat    3240
tcttcatgat gcatttagga tatgaaaaaa tggccaaggc tactgggaaa ctaaagccaa    3300
cttctaaaga tcaggtattg gccatgctag agaaagccaa agttaacatg ccagccaagc    3360
ctgctccacc cactaaagca acttctaaac caatgggagg gtccgctcca gccaaattcc    3420
agcctgcatc agcacctgct gaagattgta tttccagcag tacagaaccc aaacctgatc    3480
caaaaaaggc caaagctcca ggattatcct ctaaagcaaa gagtgcacaa gggaagaaga    3540
tgccaagcaa aaccagctta aaggaggatg aagacaaatc cgggcctatt tttattgttg    3600
ttccaaatgg aaaagagcaa aggatgaaag atgaaaaagg attgaaggtg ctaaagtgga    3660
attttactac cccacgggat gaatacattg agcaactaaa gactcaaatg tctagctgtg    3720
tggctaaatg gttacaagat gagatgtttc actcagactt tcagcatcat aacaaagccc    3780
ttgctgttat ggttgatcac ttggagagtg aaaagaagg agttattggt tgcctggatc     3840
ttatcttaaa gtggcttacc ctgaggtttt ttgacaccaa tacaagcgtc ctgatgaaag    3900
cactagaata tttaaaattg ctcttcacct tgctaagtga agaagaatat catcttactg    3960
agaatgaagc atcttccttc atcccctatc ttgtcgtcaa ggttggagaa ccaaaggatg    4020
tcattcgtaa agatgttcgt gccatcctga accggatgtg ccttgtctac ccagctagca    4080
agatgtttcc ctttatcatg gaaggaacca atccaaaaa ctctaagcag agagcagagt      4140
gcctggaaga gctgggatgt ctggttgagt cctatggcat gaatgtttgc caaccaaccc    4200
caggaaaagc cttaaaggaa atagctgttc acataggaga ccgtgacaat gctgtacgca    4260
atgctgcact caacaccatt gtaacggtgt acaatgtaca tgggggatcag gtgttcaaac    4320 tgattggaaa tcttttctgaa aaggatatga gcatgctcga ggagaggatt aagcggtcag    4380
caaagagacc ctctgctgca ccaataaaac aggtggaaga gaaacctcag cgtgcacaga    4440
acataagctc caatgccaac atgttacgca agggaccagc tgaggacatg tcttccaaac    4500
tcaaccaagc ccgaagcatg agtgggcatc ctgaggcagc ccagatggtc cgccgagaat    4560
tccagctgga tctagatgag attgagaatg acaatggtac agtccgatgt gaaatgccag    4620
aacttgttca gcacaaactg gatgacattt ttgagccagt ccttattcct gaacccaaga    4680
tccgggctgt ttctccacac ttcgatgaca tgcacagtaa tacagcatcc acaatcaatt    4740
tcattatctc ccaagtagcc agtggtgaca tcaacacaag tatccaagct ctgacacaga    4800
tcgatgaggt cctgagacag gaagacaaag ctgaagccat gtccggccat attgatcagt    4860
ttctgatagc cacttttatg cagctaagac tcatctacaa cacacacatg gcagatgaga    4920
aattggagaa ggacgagatc atcaagttgt atagctgtat cattggcaac atgatttcgc    4980
tgtttcagat agagagcctt gcccgggagg cctccactgg agtactaaaa gacctaatgc    5040
atggcctcat caccttaatg ctggattctc ggattgaaga tcttgaggaa ggacaacagg    5100
tcatccgctc tgtgaacctc ttggtggtga aggttctgga gaagtcagac cagaccaaca    5160
```

```
tcctgagtgc cctacttgtt ttgctccaag acagcctgct agcaacagcc agttctccca    5220
aattctcaga gcttgttatg aagtgtctct ggagaatggt tcgactgttg cctgatacca    5280
tcaatagcat taacctagac agaattcttc tggatatcca cattttcatg aaggtcttcc    5340
ccaaagagaa actgaagcaa tgcaaaagtg aatttcccat aaggacccta agaccctgc     5400 tacacacctt atgcaaatta aagggccca agatcctgga ccacctaacg atgatcgaca     5460
acaaaaacga gtctgagctg gaggcccatc tctgccggat gatgaagcac agtatggacc    5520
agactgggag caagtctgat aaggaaacag aaaagggagc atctcgaata gatgaaaaat    5580
catcaaaggc caaagtgaat gatttcttag ctgagatttt taagaagatt ggctctaaag    5640
aaaacactaa gagggacta gcagagttat atgaatataa aagaaatac tcagatgctg       5700 acattgaacc atttctgaaa aattcctcac agttcttcca gagctatgtc gaaagaggcc    5760
ttcgggtgat tgagatggag agggagggca aaggtcgtat ttccacttca acaggcatct    5820
cccctcagat ggaagtcaca tgtgtgccca cgcccacaag cacagtgtcc tccataggta    5880
acacaaatgg ggaagaagtg gggccatctg tctacttgga aaggctaaag atcctccgac    5940
agcgatgtgg tctggacaac acaaagcaag atgaccgacc tcctttgacc tctttgctct    6000
ccaaaccagc agttcctact gtcgcctctt ccacagacat gctccacagc aaactctctc    6060
agctccggga gtcacgggag cagcaccagc attcagacct ggattctaac cagactcact    6120
cttcaggaac tgtgacctcc tcctcctcca cagctaacat agacgacttg aaaaaaagac    6180
tggagagaat aaagagcagt cgcaaatgaa gctgccccac tcccccggca ccctgcagct    6240 ttagttttact aaactagaag tcctcatagt ttaaaatggc ctcagcaggc ctagtgtata    6300
caaactggtt gtatgtatca tgccgtggag ctaggggag gagtcattgt ggcacaagta     6360
tttgtacata ctctgcttct ctctgtcagc gtcctgctgc tctagaagac tgtccgtgga    6420
tgagtttagt gtacagactt gtaaacagct gcccctctc tgctcagtct agttcccaga    6480 tcctttttctt ttcttttaa ttgctcattt gtaaaattgt cctaatcttt cctagctttt     6540
taatagttaa tattgaaaac tctttaatag ttttcctttc agtttgtgag ctcttctctg    6600
tcgccctgaa gggtcactgt attctgtatg aatgcatggc atgatacaac taatttaaga    6660 gtctttata aataaagttt gcattaacta tacctgacaa aaaaaaaaa aaaa            6714
```

<210> SEQ ID NO 51
<211> LENGTH: 5101
<212> TYPE: DNA
<213> ORGANISM: Homo sapiens

<400> SEQUENCE: 51

```
agcgcagcca ttggtccggc tactctgtct cttttcaaa ttgaggcgcc gagtcgttgc       60
ttagtttctg gggattcggg cggagacgag attagtgatt tggcggctcc gactggcgcg    120
ggacaaacgc cacggccaga gtaccgggta gagagcgggg acgccgacct gcgtgcgtcg    180
gtcctccagg ccacgccagc gcccgagagg gaccagggag actccggccc ctgtcggccg    240
ccaagcccct ccgcccctca cagcgcccag gtccgcggcc gggccttgat ttttggcgg     300 ggaccgtcat ggcgtcgcag ccaaattcgt ctgcgaagaa gaaagaggag aaggggaaga    360
acatccaggt ggtggtgaga tgcagaccat ttaatttggc agagcggaaa gctagcgccc    420
attcaatagt agaatgtgat cctgtacgaa aagaagttag tgtacgaact ggaggattgg    480
ctgacaagag ctcaaggaaa acatacactt ttgatatggt gtttggagca tctactaaac    540
```

```
agattgatgt ttaccgaagt gttgtttgtc caattctgga tgaagttatt atgggctata    600
attgcactat ctttgcgtat ggccaaactg gcactggaaa aacttttaca atggaaggtg    660
aaaggtcacc taatgaagag tatacctggg aagaggatcc cttggctggt ataattccac    720
gtacccttca tcaaattttt gagaaactta ctgataatgg tactgaattt tcagtcaaag    780
tgtctctgtt ggagatctat aatgaagagc ttttttgatct tcttaatcca tcatctgatg    840
tttctgagag actacagatg tttgatgatc cccgtaacaa gagaggagtg ataattaaag    900
gtttagaaga aattacagta cacaacaagg atgaagtcta tcaaatttta gaaaaggggg    960
cagcaaaaag gacaactgca gctactctga tgaatgcata ctctagtcgt tcccactcag   1020
ttttctctgt tacaatacat atgaaagaaa ctacgattga tggagaagag cttgttaaaa   1080
tcggaaagtt gaacttggtt gatcttgcag gaagtgaaaa cattggccgt tctggagctg   1140
ttgataagag agctcgggaa gctggaaata taaatcaatc cctgttgact ttgggaaggg   1200
tcattactgc ccttgtagaa agaacacctc atgttcctta tcgagaatct aaactaacta   1260
gaatcctcca ggattctctt ggagggcgta caagaacatc tataattgca acaatttctc   1320
ctgcatctct caatcttgag gaaactctga gtacattgga atatgctcat agagcaaaga   1380
acatattgaa taagcctgaa gtgaatcaga aactcaccaa aaaagctctt attaaggagt   1440
atacggagga gatagaacgt ttaaaacgag atcttgctgc agcccgtgag aaaaatggag   1500
tgtatatttc tgaagaaaat tttagagtca tgagtgaaaa attaactgtt caagaagagc   1560
agattgtaga attgattgaa aaaattggtg ctgttgagga ggagctgaat agggttacag   1620
agttgtttat ggataataaa aatgaacttg accagtgtaa atctgacctg caaaataaaa   1680
cacaagaact tgaaaccact caaaaacatt tgcaagaaac taaattacaa cttgttaaag   1740
aagaatatat cacatcagct ttggaaagta ctgaggagaa acttcatgat gctgccagca   1800
agctgcttaa cacagttgaa gaaactacaa aagatgtatc tggtctccat tccaaactgg   1860
atcgtaagaa ggcagttgac caacacaatg cagaagctca ggatattttt ggcaaaaacc   1920
tgaatagtct gtttaataat atggaagaat taattaagga tggcagctca aagcaaaagg   1980
ccatgctaga agtacataag accttatttg gtaatctgct gtcttccagt gtctctgcat   2040
tagataccat tactacagta gcacttggat ctctcacatc tattccagaa aatgtgtcta   2100
ctcatgtttc tcagattttt aatatgatac taaaagaaca atcattagca gcagaaagta   2160
aaactgtact acaggaattg attaatgtac tcaagactga tcttctaagt tcactggaaa   2220
tgattttatc cccaactgtg gtgtctatac tgaaaatcaa tagtcaacta agcatatttt   2280
tcaagacttc attgacagtg gccgataaga tagaagatca aaaaaaggaa ctagatggct   2340
ttctcagtat actgtgtaac aatctacatg aactacaaga aaataccatt tgttccttgg   2400
ttgagtcaca aaagcaatgt ggaaacctaa ctgaagacct gaagacaata aagcagaccc   2460
attcccagga acttttgcaag ttaatgaatc tttggacaga gagattctgt gctttggagg   2520
aaaagtgtga aaatatacag aaaccactta gtagtgtcca ggaaaatata cagcagaaat   2580
ctaaggatat agtcaacaaa atgacttttc acagtcaaaa attttgtgct gattctgatg   2640
gcttctcaca ggaactcaga aattttaacc aagaaggtac aaaattggtt gaagaatctg   2700
tgaaacactc tgataaactc aatggcaacc tggaaaaaat atctcaagag actgaacaga   2760
gatgtgaatc tctgaacaca agaacagttt attttttctga acagtgggta tcttccttaa   2820
atgaaaggga acaggaactt cacaacttat tggaggttgt aagccaatgt tgtgaggctt   2880
caagttcaga catcactgag aaatcagatg gacgtaaggc agctcatgag aaacagcata   2940
```

-continued

```
acatttttct tgatcagatg actattgatg aagataaatt gatagcacaa aatctagaac    3000
ttaatgaaac cataaaaatt ggtttgacta agcttaattg ctttctggaa caggatctga    3060
aactggatat cccaacaggt acgacaccac agaggaaaag ttatttatac ccatcaacac    3120
tggtaagaac tgaaccacgt gaacatctcc ttgatcagct gaaaaggaaa cagcctgagc    3180
tgttaatgat gctaaactgt tcagaaaaca acaagaaga gacaattccg gatgtggatg     3240
tagaagaggc agttctgggg cagtatactg aagaacctct aagtcaagag ccatctgtag    3300
atgctggtgt ggattgttca tcaattggcg gggttccatt tttccagcat aaaaaatcac    3360
atggaaaaga caagaaaac agaggcatta acacactgga gaggtctaaa gtggaagaaa     3420
ctacagagca cttggttaca aagagcagat tacctctgcg agcccagatc aacctttaat    3480
tcacttgggg gttggcaatt ttatttttaa agaaaactta aaaataaaac ctgaaacccc    3540
agaacttgag ccttgtgtat agattttaaa agaatatata tatcagccgg gcgcggtggc    3600
tcatgcctgt aatcccagca ctttgggagg ctgaggcggg tggattgctt gagcccagga    3660
gtttgagacc agcctggcca acgtggcaaa acctcgtctc tgttaaaaat tagccgggcg    3720
tggtggcaca ctcctgtaat cccagctact ggggaggctg aggcacgaga atcacttgaa    3780
cccaggaagc ggggttgcag tgagccaaag gtacaccact acactccagc ctgggcaaca    3840
gagcaagact cggtctcaaa aacaaaattt aaaaaagata taaggcagta ctgtaaattc    3900
agttgaattt tgatatctac ccattttttct gtcatcccta tagttcactt tgtattaaat    3960
tgggtttcat ttgggatttg caatgtaaat acgtatttct agttttcata taaagtagtt    4020
cttttataac aaatgaaaag tattttttctt gtatattatt aagtaatgaa tatataagaa    4080
ctgtactctt ctcagcttga gcttacatag gtaaatatca ccaacatctg tccttagaaa    4140
ggaccatctc atgttttttt tcttgctatg acttgtgtat tttcttgcat cctccctaga    4200
cttccctatt tcgctttctc ctcggctcac tttctcccctt tttattttttc accaaaccat    4260
ttgtagagct acaaaaggta tccttttctta tttttcagtag tcagaatttt atctagaaat    4320
cttttaacac ctttttagtg gttatttcta aaatcactgt caacaataaa tctaacccta    4380
gttgtatccc tccttttcagt attttttcact tgttgcccca aatgtgaaag catttcattc    4440
ctttaagagg cctaactcat tcaccctgac agagttcaca aaaagcccac ttaagagtat    4500
acattgctat tatgggagac cacccagaca tctgactaat ggctctgtgc ccacactcca    4560
agacctgtgc cttttagaga agctcacaat gatttaagga ctgtttgaaa cttccaatta    4620
tgtctataat ttatattctt ttgtttacat gatgaaactt tttgttgttg cttgtttgta    4680
tataatacaa tgtgtacatg tatctttttc tcgattcaaa tcttaaccct taggactctg    4740
gtatttttga tctggcaacc atatttctgg aagttgagat gtttcagctt gaagaaccaa    4800
aacagaagga atatgtacaa agaataaatt ttctgctcac gatgagttta gtgtgtaaag    4860
tttagagaca tctgactttg atagctaaat taaaccaaac cctattgaag aattgaatat    4920
atgctacttc aagaaactaa attgatctcg tagaattatc ttaataaaat aatggctata    4980
atttctctgc aaaatcagat gtcagcataa gcgatggata atacctaata aactgccctc    5040
agtaaatcca tggttaataa atgtggtttc tacattaaaa aaaaaaaaaa aaaaaaaaaa    5100
a                                                                   5101
```

<210> SEQ ID NO 52
<211> LENGTH: 4857
<212> TYPE: DNA

<213> ORGANISM: Homo sapiens

<400> SEQUENCE: 52

```
gcggcctcca tgcgggcgtc aacgtccgat ccaagcgcca aattcaaatt tgcggccatc      60
ttgagcgggc ggaattcagt cgcgcgcggt gcagtcggga ggtggaggca ccggctgcat     120
tgttttcggg atcgagggt gagggcgcta tggcacccgg ctgcaaaact gagttacgca     180
gcgtgacaaa tggtcagtct aaccaaccaa gtaatgaagg tgatgccatc aaagttttg      240
tgcgaattcg tcctcctgca gaaagatctg ggtcagctga tggagagcag aacttatgct     300
tatctgtgct gtcctccacg agtctccggc tgcactccaa ccctgagccc aagaccttca     360
cgtttgatca tgttgcagat gtggatacca ctcaggaatc tgtattcgca actgtggcta     420
aaagcattgt ggagtcttgc atgagcggtt ataatggtac catctttgca tatggacaga     480
ctggctcagg aagacatttt actatgatgg accatctga atctgataat ttttctcata      540
acctgagagg agtaatccca cgaagttttg aatatttgtt ttccttaatt gatcgtgaaa     600
aagaaaaggc tggagctgga aagagtttcc tttgtaagtg ttcctttatt gaatctaca      660
acgagcagat atatgatcta ctggactctg catcggctgg actgtactta agggagcata     720
tcaagaaggg agtctttgtt gttggtgcgg tggagcaggg ggtaacctca gctgctgaag     780
cctatcaggt gttgtctgga ggatggagga atagacgtgt ggcatcaaca tcaatgaaca     840
gagaatcgtc taggtctcat gccgtcttta caattacaat agagtcaatg agaaaagta     900
atgagattgt gaatatacgg acctccctac tcaacctggt ggatttagca ggatctgaaa     960
ggcaaaaaga tacccatgca gaagggatga gattgaagga agcaggtaac ataaatcgat    1020
cattgagctg cctgggccaa gtgattacag cacttgtcga cgtgggtaat ggaaaacaga    1080
gacatgtttg ctacagagac tccaaactta ccttcttact acgggattcc cttggaggta    1140
atgccaaaac agccataatt gcaaatgttc atcctggatc caggtgtttt ggggaacccc    1200
tatcaacact taactttgct caagagccaa gctgattaa aaacaaggca gtagtaaatg     1260
aagacaccca aggaaatgtg agccagctcc aagctgaagt gaagaggctc aaagaacaac    1320
tggcggagct tgcttcagga cagacaccac cagaaagctt cctgaccaga gacaaaaaga    1380
agactaacta tatggagtat ttccaggaag caatgttatt ctttaagaaa tctgaacagg    1440
aaaagaagtc tctgatagaa aaagttaccc aattagaaga cctcaccctc aaaaaggaaa    1500
aatttattca atctaataaa atgattgtga aattccgaga ggatcaaata tacgcttgg     1560
aaaagctcca caaggaatcc cggggaggtt ttctgcctga ggagcaggat cgtttgctct    1620
cagaattaag gaatgagatt caaactctgc gagaacaaat agagcaccac cccagagttg    1680
caaagtatgc tatggaaaat cattccctca gggaggagaa tagaagactg agattattag    1740
agcctgtgaa aagagctcaa gaaatggatg cccagaccat tgcaaaacta gaaaaagctt    1800
tctctgaaat aagtggcatg gagaaaagtg acaaaaatca gcaaggattt tcacctaaag    1860
ctcagaaaga gccatgtttg tttgcaaaca ctgagaagtt aaaagcacaa ctcctgcaaa    1920
ttcagacaga gctgaataat tcaaagcaag aatatgaaga attcaaagaa cttactagga    1980
aaaggcagct agaattggaa tcagagcttc agtctttgca aaaagcgaac cttaatcttg    2040
aaaaccttttt ggaagcaaca aaagcctgca agcggcaaga agtttctcag ctgaataaaa    2100
ttcatgctga acacttaag attataacta caccaaccaa ggcctaccaa cttcattccc     2160
gaccagtacc aaaattaagc cctgaaatgg gaagctttgg ctctctatac actcagaatt    2220
ctagcatatt agataatgat atattaaatg agccagttcc tcctgagatg aatgaacaag    2280
```

```
cttttgaggc catttctgaa gagcttagaa cagtgcagga acaaatgagt gctcttcaag    2340
ccaaactgga tgaagaagag cataaaaacc taaagcttca gcagcatgtt gacaaactgg    2400
aacatcattc tacccaaatg caggagcttt tctcatcaga agaattgat tggaccaaac     2460 agcaggaaga gcttctctca cagttgaatg tccttgaaaa gcagcttcaa gagactcaaa    2520
ctaaaaatga cttttgaaa agtgaggtac atgacctgcg agtagtcctt cattctgctg     2580
acaaggagct ttcttcagtg aaattggaat atagttcatt caaaacgaat caggagaaag    2640
aattcaacaa actttccgaa agacacatgc atgtacagct tcaattagat aatctcaggt    2700
tagaaaacga aaagctgctt gagagcaaag cctgcctaca ggattcctat gacaacttac    2760
aagaaataat gaaatttgag attgaccaac tttcaagaaa cctccaaaac ttcaaaaaag    2820
aaaatgaaac tctgaaatct gatctgaata atttgatgga gcttcttgag gcagaaaaag    2880
aacgcaataa caaattatca ttacagtttg aagaagataa agaaacagt tctaaagaaa     2940 tcttaaaagt tcttgaggct gtacgtcagg agaaacagaa agagacggcc aagtgtgagc    3000
agcagatggc aaaagtacag aaactagaag agagcttgct tgctactgaa aaagtgatca    3060
gttccctgga aaagtctaga gattctgata agaaagttgt agctgacctc atgaaccaga    3120
tccaggagct aagaacatcg gtctgtgaga aaacagaaac tatagacacc ctgaaacaag    3180
aactgaagga cataaattgc aaatacaact ctgctttggt tgacagagaa gagagcagag    3240
tgttgatcaa gaagcaggaa gtggatattc tggatctgaa agaaacccctt aggctgagaa    3300 tactttctga ggacatagag agggatatgc tctgtgagga cctggctcat gccactgagc    3360
agctgaacat gctcacagag gcctcaaaaa aacactcggg gctgctgcag tctgcccagg    3420
aagaactgac caagaaggaa gccctgattc aggaacttca gcacaagcta aaccaaaaga    3480
aagaggaagt agaacagaag aagaatgaat ataacttcaa aatgaggcaa ctagaacatg    3540
tgatggattc tgctgctgag gatccccaga gtcctaagac accacctcac tttcaaacac    3600
atttggcaaa actcctggaa acacaagaac aagagataga agatggaaga gcctctaaga    3660
cttctttgga acaccttgta acaaagctaa atgaagacag agaagtcaaa atgctgaaaa    3720
tcctcagaat gaaggagcag ttgcgtgaaa tggaaaacct acgcctggaa agtcagcagt    3780
taatagagaa aaactggctc ctgcaaggtc agctggatga tattaaaaga caaaaggaaa    3840
acagtgatca gaatcatcca gataatcaac agctgaagaa tgaacaagaa gaaagtatca    3900 agaaagact tgcaaaaagt aaaatagttg aagaatgct gaaaatgaaa gcagacctag     3960
aagaagtcca aagtgcccctt tacaacaaag agatggaatg ccttagaatg actgatgaag    4020
tcgaacgaac ccaaactttg gagtctaaag cattccagga aaagaacaa ctgagatcaa     4080 agctggaaga aatgtatgaa gaagagaga gaacatccca ggagatggaa atgttaagga    4140
agcaggtgga gtgtcttgct gaggaaatg gaaagttggt aggtcaccaa aatttgcatc     4200
agaagattca gtacgtagtg cgactaaaga aggaaaatgt caggcttgct gaggagcag    4260 aaaagttgcg tgccgaaaat gtatttttaa aagaaaagaa aagaagtgaa tcttgaggat    4320
tccggtcagc tacctaggca tcaccttgtt tgaagatgtt tcttctcttt tacaagtaag    4380
acctactcct ggccacttag gagagctgaa tttatggacc ttaattatta aatgtttata    4440
aggtggtggt aaccacctca agtttctgat gaacattctg catccatata caccctgtga    4500
cagtcagcag tctgctatta agtggcctac ttcaaggctt tgaatcaact taagggaaaa    4560 cctttgtct ttgtaaaaat aaaagcctgt agctaaggtt tacagtggac attagccaga    4620
```

-continued

| | |
|---|---|
| tcattttctt cttagattat gccataatct cctttgattc ttatggaagt tctaacaata | 4680 |
| tatggtggtt ccaacacctg cagtgagttt aatgactgac ttagtagcag gtacaagaag | 4740 |
| caaacttgtt aatatagatt attttttgtat tcttacttta ggtattttct tgagcattt | 4800 |
| ccatgactgt aaataaagcc attttttaag ataataaaaa aaaaaaaaaa aaaaaaa | 4857 |

<210> SEQ ID NO 53
<211> LENGTH: 3324
<212> TYPE: DNA
<213> ORGANISM: Homo sapiens

<400> SEQUENCE: 53

| | |
|---|---|
| gcagagcacc gcgccttagc cgcgaagttc tagttcttgc tgccggtcct aacgtcccgc | 60 |
| agtcttcgcc agccagccgt cccgcatgcg cgtttgggcg gcgtggagcc tgctgccatg | 120 |
| aagtcagcga gagctaagac accccggaaa cctaccgtga aaaagggtc ccaaacgaac | 180 |
| cttaaagacc cagttggggt atactgtagg gtgcgcccac tgggctttcc tgatcaagag | 240 |
| tgttgcatag aagtgatcaa taatacaact gttcagcttc atactcctga gggctacaga | 300 |
| ctcaaccgaa atggagacta aaggagact cagtattcat ttaaacaagt atttggcact | 360 |
| cacaccaccc agaaggaact cttttgatgtt gtggctaatc ccttggtcaa tgacctcatt | 420 |
| catggcaaaa atggtcttct ttttacatat ggtgtgacgg gaagtggaaa aactcacaca | 480 |
| atgactggtt ctccagggga aggagggctg cttcctcgtt gtttgacat gatctttaac | 540 |
| agtatagggt catttcaagc taacgatat gttttcaaat ctaatgatag gaatagtatg | 600 |
| gatatacagt gtgaggttga tgccttatta gaacgtcaga aaagagaagc tatgcccaat | 660 |
| ccaaagactt cttctagcaa acgacaagta gatccagagt ttgcagatat gataactgta | 720 |
| caagaattct gcaaagcaga agaggttgat gaagatagtg tctatggtgt atttgtctct | 780 |
| tatattgaaa tatataataa ttacatatat gatctattgg aagaggtgcc gtttgatccc | 840 |
| ataaaaccca aacctccaca atctaaattg cttcgtgaag ataagaacca taacatgtat | 900 |
| gttgcaggat gtacagaagt tgaagtgaaa tctactgagg aggcttttga agttttctgg | 960 |
| agaggccaga aaaagagacg tattgctaat acccatttga atcgtgagtc cagccgttcc | 1020 |
| catagcgtgt tcaacattaa attagttcag gctcccttgg atgcagatgg agacaatgtc | 1080 |
| ttacaggaaa aagaacaaat cactataagt cagttgtcct tggtagatct tgctggaagt | 1140 |
| gaaagaacta accggaccag agcagaaggg aacagattac gtgaagctgg taatattaat | 1200 |
| cagtcactaa tgacgctaag aacatgtatg gatgtcctaa gagagaacca aatgtatgga | 1260 |
| actaacaaga tggttccata tcgagattca aagttaaccc atctgttcaa gaactacttt | 1320 |
| gatggggaag aaaagtgcg gatgatcgtg tgtgtgaacc ccaaggctga agattatgaa | 1380 |
| gaaaacttgc aagtcatgag atttgcggaa gtgactcaag aagttgaagt agcaagacct | 1440 |
| gtagacaagg caatatgtgg tttaacgcct gggaggagat acagaaacca gcctcgaggt | 1500 |
| ccagttggaa atgaaccatt ggttactgac gtggttttgc agagttttcc acctttgccg | 1560 |
| tcatgcgaaa ttttggatat caacgatgag cagacacttc caaggctgat tgaagcctta | 1620 |
| gagaaacgac ataacttacg acaaatgatg attgatgagt ttaacaaaca atctaatgct | 1680 |
| tttaaagctt tgttacaaga atttgacaat gctgttttaa gtaaagaaaa ccacatgcaa | 1740 |
| gggaaactaa atgaaaagga gaagatgatc tcaggacaga aattggaaat agaacgactg | 1800 |
| gaaaagaaaa acaaaacttt agaatataag attgagattt tagagaaaac aactactatc | 1860 |
| tatgaggaag ataaacgcaa tttgcaacag gaacttgaaa ctcagaacca gaaacttcag | 1920 |

| | |
|---|---:|
| cgacagtttt ctgacaaacg cagattagaa gccaggttgc aaggcatggt gacagaaacg | 1980 |
| acaatgaagt gggagaaaga atgtgagcgt agagtggcag ccaaacagct ggagatgcag | 2040 |
| aataaactct gggttaaaga tgaaaagctg aaacaactga aggctattgt tactgaacct | 2100 |
| aaaactgaga agccagagag accctctcgg gagcgagatc gagaaaaagt tactcaaaga | 2160 |
| tctgtttctc catcacctgt gcctttactc tttcaacctg atcagaacgc accaccaatt | 2220 |
| cgtctccgac acagacgatc acgctctgca ggagacagat gggtagatca taagcccgcc | 2280 |
| tctaacatgc aaactgaaac agtcatgcag ccacatgtcc ctcatgccat cacagtatct | 2340 |
| gttgcaaatg aaaaggcact agctaagtgt gagaagtaca tgctgaccca ccaggaacta | 2400 |
| gcctccgatg gggagattga aactaaacta attaagggtg atatttataa aacaaggggt | 2460 |
| ggtggacaat ctgttcagtt tactgatatt gagactttaa agcaagaatc accaaatggt | 2520 |
| agtcgaaaac gaagatcttc cacagtagca cctgcccaac agatggtgc agagtctgaa | 2580 |
| tggaccgatg tagaaacaag gtgttctgtg gctgtggaga tgagagcagg atcccagctg | 2640 |
| ggacctggat atcagcatca cgcacaaccc aagcgcaaaa agccatgaac tgacagtccc | 2700 |
| agtactgaaa gaacattttc atttgtgtgg atgatttctc gaaagccatg ccagaagcag | 2760 |
| tcttccaggt catcttgtag aactccagct tgttgaaaaa tcacggacct cagctacatc | 2820 |
| atacactgac ccagagcaaa gctttcccta tggttccaaa gacaactagt attcaacaaa | 2880 |
| ccttgtatag tatatgtttt gccatattta atattaatag cagaggaaga ctccttttt | 2940 |
| catcactgta tgaattttt ataatgtttt tttaaaatat atttcatgta tacttataaa | 3000 |
| ctaattcaca caagtgtttg tcttagatga ttaaggaaga ctatatctag atcatgtctg | 3060 |
| attttttatt gtgacttctc cagccctggt ctgaatttct taaggtttta taaacaaatg | 3120 |
| ctgctatta ttagctgcaa gaatgcactt tagaactatt tgacaattca gactttcaaa | 3180 |
| ataaagatgt aaatgactgg ccaataataa ccattttagg aaggtgtttt gaattctgta | 3240 |
| tgtatatatt cactttctga catttagata tgccaaaaga attaaaatca aaagcactaa | 3300 |
| gaaataaaaa aaaaaaaaaa aaaa | 3324 |

<210> SEQ ID NO 54
<211> LENGTH: 4447
<212> TYPE: DNA
<213> ORGANISM: Homo sapiens

<400> SEQUENCE: 54

| | |
|---|---:|
| aattggttgg cgtctccggg acggatttga aacttggcgg ttaaagctcc ggctgggaca | 60 |
| gggcggcggg aggcccaggg agaacgggga agggacattt agtttgagac ggtgctgaga | 120 |
| taggatcatg aaggaagagg tgaagggaat tcctgtaaga gtggcgctgc gttgtcgccc | 180 |
| tctggtcccc aaagagatta gcgagggctg ccagatgtgc ctttccttcg tgcccggaga | 240 |
| gcctcaggtg gtggttggta cagataaatc cttcacctac gattttgtat ttgatccctc | 300 |
| tactgaacag gaagaagtct tcaatacagc agtagcgcca ctcataaaag gtgtatttaa | 360 |
| aggatataat gcaacggtcc tggcctatgg gcagactggc tctggaaaaa cctattcaat | 420 |
| gggaggtgca tatactgcag agcaagagaa tgaaccaaca gttgggggtta ttcctagggt | 480 |
| aatacaactg ctcttcaaag aaattgataa aaagagtgac tttgaattta ctctgaaagt | 540 |
| gtcttactta gagatttaca atgaagaaat tttggatctt ctatgcccat ctcgtgagaa | 600 |
| agctcaaata aatatacgag aggatcctaa ggaaggcata aagattgtgg gactcactga | 660 |

```
gaagactgtt ttggttgcct tggatactgt ttcctgtttg aacagggca acaactctag   720
gactgtggcc tccacggcta tgaactccca gtcgtcccga tctcatgcca tctttacaat   780
ctccttagag caaagaaaga aaagtgacaa gaatagcagc tttcgctcca agctgcatct   840
tgtagacctc gctggatcag aaagacagaa gaaaaccaag gctgaagggg atcgtctaaa   900
agagggtatt aatattaacc gaggcctcct atgcttggga aatgtaatca gtgctcttgg   960
agatgacaaa aagggtggct tgtgccctca cagagattcc aagttgactc gactgcttca  1020
agattctcta ggaggtaata gccatactct tatgatagcc tgtgtgagtc ctgctgactc  1080
caatctagag gaaacattaa ataccccttcg ctatgctgac agagcaagaa aaatcaagaa  1140
caaacctatt gttaatattg atccccagac agctgaactt aatcatctaa agcaacaggt  1200
acaacagcta caagtcttgt tgctacaggc ccatggaggt accctgcctg gatctataac  1260
tgtggaacca tcagagaatc tacaatccct gatggagaag aatcagtccc tggtagagga  1320
gaatgaaaaa ttaagtcgtg gtctgagcga ggcagctggt cagacagccc agatgttgga  1380
gaggatcatt ttgacagagc aagcgaatga aaaaatgaac gccaagctag aagagctcag  1440
gcagcatgcg gcctgcaaac tggatcttca aaagctagtg gagactttgg aagaccagga  1500
attgaaagaa aatgtagaga taatttgtaa cctgcagcaa ttgattaccc agttatcgga  1560
tgaaactgtt gcttgcatgg ctgcagccat tgatactgcg gtggagcaag aagcccaagt  1620
agaaaccagt ccagagacga gcaggtcttc tgacgctttt accactcagc atgctctccg  1680
tcaagcgcag atgtctaagg agctggttga gttgaataaa gcgcttgcac tgaaagaggc  1740
cctggctagg aagatgactc agaatgacag ccaactgcag cccattcagt accaatacca  1800
ggataacata aaagagctag aattagaagt catcaatctg caaaaggaaa aggaagaatt  1860
ggttcttgaa cttcagacag caaagaagga tgccaaccaa gccaagttga gtgagcgccg  1920
ccgcaaacgt ctccaggagc tggagggtca aattgctgat ctgaagaaga aactgaatga  1980
gcagtccaaa cttctgaaac taaaggaatc cacagagcgt actgtctcca aactgaacca  2040
ggagatacgg atgatgaaaa accagcgggt acagttaatg cgtcaaatga agaagatgc   2100
tgagaagttt agacagtgga agcagaaaaa agacaaagaa gtaatacagt taaaagaacg  2160
agaccgtaag aggcaatatg agctgctgaa acttgaaaga aacttccaga acaatccaa   2220
tgtgctcaga cgtaaaacgg aggaggcagc agctgccaac aagcgtctca aggatgctct  2280
ccagaaacaa cgggaggttg cagataagcg gaaagagact cagagccgtg aatggaagg   2340
cactgcagct cgagtgaaga attggcttgg aaacgaaatt gaggttatgg tcagtactga  2400
ggaagccaaa cgccatctga atgacctcct tgaagataga aagatcctgg ctcaagatgt  2460
ggctcaactc aaagaaaaaa aggaatctgg ggagaatcca cctcctaaac tccggaggcg  2520
tacattctcc cttactgaag tgcgtggtca agtttcggag tcagaagatt ctattacaaa  2580
gcagattgaa agcctagaga ctgaaatgga attcaggagt gctcagattg ctgacctaca  2640
gcagaagctg ctggatgcag aaagtgaaga cagaccaaaa caacgctggg agaatattgc  2700
caccattctg gaagccaagt gtgccctgaa atatttgatt ggagagctgg tctcctccaa  2760
aatacaggtc agcaaacttg aaagcagcct gaaacagagc aagaccagct gtgctgacat  2820
gcagaagatg ctgtttgagg aacgaaatca ttttgccgag atagagacag agttacaagc  2880
tgagctggtc agaatggagc aacagcacca agagaaggtg ctgtaccttc tcagccagct  2940
gcagcaaagc caaatggcag agaagcagtt agaggaatca gtcagtgaaa aggaacagca  3000
gctgctgagc acactgaagt gtcaggatga agaacttgag aaaatgcgag aagtgtgtga  3060
```

| | |
|---|---|
| gcaaaatcag cagcttctcc gagagaatga aatcatcaag cagaaactga ccctcctcca | 3120 |
| ggtagccagc agacagaaac atcttcctaa ggataccctt ctatctccag actcttcttt | 3180 |
| tgaatatgtc ccacctaagc caaaaccttc tcgtgttaaa gaaaagttcc tggagcaaag | 3240 |
| catggacatc gaggatctaa atattgttc agagcattct gtgaatgagc atgaggatgg | 3300 |
| tgatggtgat gatgatgagg gggatgacga ggaatggaag ccaacaaaat tagttaaggt | 3360 |
| gtccaggaag aacatccaag ggtgttcctg caagggctgg tgtggaaaca agcagtgtgg | 3420 |
| gtgcaggaag caaaagtcag actgtggtgt ggactgttgc tgtgacccca caaagtgtcg | 3480 |
| gaaccgccag caaggcaagg atagcttggg cactgttgaa cggacccagg attccgaagg | 3540 |
| ctccttcaaa ctggaggatc ctaccgaggt gaccccagga ttgagcttct ttaatcccgt | 3600 |
| ctgtgccacc cccaatagca agatcctgaa agagatgtgc gatgtggagc aggtgctgtc | 3660 |
| aaagaagact ccccagctc cctccccttt tgacctccca gagttgaaac atgtagcaac | 3720 |
| agaataccaa gaaaacaagg ctccaggaa gaaaagaaa cgggctctgg ccagcaacac | 3780 |
| cagcttcttc tctggctgct cccctatcga agaagaggcc cactgaagtt ggagtcatca | 3840 |
| tctctaccc cagtctggct tgggagatgc tttcaggttg cagccagaag gggttttta | 3900 |
| aatgacttct ctggatttca ggtttcttgc tgttgaaaaa aggaacaaag cgttactgaa | 3960 |
| aagaaggtaa cctttgttgg atgtgggcct tagcctccag gtccagacta ctactctatg | 4020 |
| ttctccagaa gggtgctaag tcacctactg aagagagaac caactgactt tcctattgac | 4080 |
| tcatcaggaa ccagtcctca gtctggtcaa gttgtttctt atttgtgagc agttcaggct | 4140 |
| atctcctgat ggggatgagg ccaaggcttt cttatctttt ggttgtctct gcttaatgga | 4200 |
| ggagcctggc ctaggatgga ggcctggctt agatctttca ttccacctca ggaatgaggt | 4260 |
| tgtgatcttt cctgtcctga ccctctctga attatgtttc aatagtactc ttgattgtct | 4320 |
| gccatgttgt tgaagcaaat gaattatttt taaatgttaa gtaagtaaat aaaccttagc | 4380 |
| ccgtctactg tttgggaaga tccttctgtg ctagagggag aaataaaatt tcaacctgtg | 4440 |
| ttcctca | 4447 |

<210> SEQ ID NO 55
<211> LENGTH: 7293
<212> TYPE: DNA
<213> ORGANISM: Homo sapiens

<400> SEQUENCE: 55

| | |
|---|---|
| ctggggagcc ggcgctggag gtggtgagtg gcgtggggac tgtgtcgagg gggtccccaa | 60 |
| ggtgccggac cctgcggagg ggcgaagttt cggcactggg gagggcgtgc ggacgctttc | 120 |
| cctacaggcg accactgctc tgcgggcggg tggtcttagc tccagtcccc cattcagttc | 180 |
| ctcagcattc caggtcggcg gcgaagggt ccccgaacga agggcgcaag gcagcgtctc | 240 |
| tgctgggacc gggaagccgg acttcagggc ctctcggccc gtgggcttct ccccgagtct | 300 |
| ccccgagtcg gttggcatta agagtttagc agatactttc agaaatggat acataagaaa | 360 |
| tggctggaaa tcaaatgaat gtccaaagaa gagcttaggg tcttagtaac attctttttt | 420 |
| aaaataactg tctgccaaaa tgtcattaca cagtactcat aatagaaata acagcggtga | 480 |
| tattcttgat attccttctt cccaaaatag ttcatcactg aatgccctca cccacagtag | 540 |
| ccgacttaag ctgcatttga agtcggatat gtcagaatgt gaaatgatg atccattatt | 600 |
| gagatctgca ggtaaagtca gagacataaa tagaacttat gttatttctg ccagtagaaa | 660 |

```
aacagcagac atgccccttc ccctaatcc tgtaggtaga ttggcacttc agaggagaac    720
tacaaggaac aaagaatcat ctttgcttgt tagtgagttg gaagacacaa ctgaaaaaac    780
agcagaaaca cgtcttacat tacaacgtcg tgctaaaaca gattctgcag aaaagtggaa    840
aacagctgaa atagattctg tcaaaatgac actgaatgtg ggaggtgaaa cagaaaataa    900
tggtgtttct aaggaaagta gaacaaatgt aaggattgta ataatgctaa aaactctttt    960
tgttgcctct tctgtacctt tagatgaaga tccacaggtc attgaaatga tggctgataa    1020
gaaatacaaa gaaacatttt ctgcccccag tagagcaaat gaaaatgttg cacttaagta    1080
ctcaagtaat agaccaccca ttgcttccct gagtcagact gaagttgtta gatcaggaca    1140
cttgacaacg aaacctactc agagcaagtt ggatatcaaa gtgttgggaa caggaaactt    1200
gtatcataga agtattggga aggaaattgc aaaaacttca aataaatttg ggagcttaga    1260
aaaaagaaca cctacaaaat gtacaacaga acacaaactg acaacaaagt gcagcctgcc    1320
tcagcttaag agcccagctc catcaatact gaagaataga atgtctaacc ttcaagttaa    1380
acaaagacca aaaagttcct ttcttgcaaa taaacaggaa agatccgcag aaaatacaat    1440
tcttcccgaa gaagaaactg tagttcagaa cacctctgca ggaaaagacc ccttaaaagt    1500
agagaatagt caagtgacag tggcagtacg cgtaagacct ttcaccaaga gagagaagat    1560
tgaaaaagca tcccaggtag tcttcatgag tgggaaagaa ataactgtgg aacaccctga    1620
cacgaaacaa gtttataatt ttatttatga tgtttcattc tggtcttttg atgaatgtca    1680
tcctcactac gctagccaga caactgtcta tgagaagcta gcagcaccac tcctagaaag    1740
agccttcgaa ggcttcaata cctgtctttt tgcttatggt cagactggct ctggaaaatc    1800
atatacgatg atgggattta gtgaagaacc aggaataatt ccaagatttt gtgaagatct    1860
tttttctcaa gtagccagaa acaaaccca agaggtcagc tatcacattg aaatgagctt    1920
ctttgaagta tataatgaaa aaattcacga ccttctggtt tgtaaagatg aaaatgggca    1980
gagaaagcaa ccactgagag tgagggaaca tcctgtttat ggaccatatg ttgaagcact    2040
gtcaatgaac attgtcagtt cttacgctga tatccagagt tggctagaat gggaaataa    2100
acaaagagct actgctgcta ctggtatgaa tgataaaagt tcccgatctc attcagtttt    2160
caccctggtg atgacccaga ccaagacaga atttgtggaa ggggaagaac acgatcacag    2220
aataacaagt cgaattaacc taatagatct ggcaggcagt gagcgctgct ctacggctca    2280
cactaatgga gatcgactaa aggaaggtgt gagtattaat aagtccttgc taactttggg    2340
aaaagttata tctgcacttt cggaacaagc aaaccaaagg agtgttttta ttccttatcg    2400
tgaatctgtt cttacatggc tgttaaaaga agtctgggt ggaaattcaa aaactgcaat    2460
gattgctacg attagtcccg ctgccagcaa catagaagaa acattaagca cacttagata    2520
tgctaaccaa gcccgtttaa tagtcaacat tgctaaagta aatgaagata tgaacgctaa    2580
gttaattaga gaattgaagg cagaaattgc aaagctaaaa gctgctcaga gaacagtcg    2640
gaatattgac cctgaacgat acaggctctg tcggcaagaa ataacatcct taagaatgaa    2700
actgcatcaa caggagagag acatggcaga atgcaaaga gtgtggaaag aaaagtttga    2760
acaagctgaa aaaagaaaac ttcaagaaac aaaagagtta cagaaagcag gaattatgtt    2820
tcaaatggac aatcatttac caaaccttgt taatctgaat gaagatccac aactatctga    2880
gatgctgcta tatatgataa agaaggaac aactacagtt ggaaagtata aaccaaactc    2940
aagccatgat attcagttat ctggggtgct gattgctgat gatcattgta ctatcaaaaa    3000
ttttggtggg acagtgagta ttatcccagt tggggaagca aagacatatg taaatggaaa    3060
```

```
acatattttg gaaatcacag tattacgtca tggtgatcga gtgattcttg gtggagatca    3120
ttattttaga tttaatcatc cagtagaagt ccagaaagga aaaaggccat ctggaagaga    3180
tactcctata agtgagggtc caaaagactt tgaatttgca aaaaatgagt tgctcatggc    3240
acagagatca caacttgaag cagaaataaa agaggctcag ttgaaggcaa aggaagaaat    3300
gatgcaagga atccagattg caaagaaat ggctcagcaa gagctttctt ctcaaaaagc    3360
tgcatatgaa agcaaaataa aagcactgga agcagaactg agagaagagt ctcaaaggaa    3420
aaaaatgcag gaaataaata accagaaggc taatcacaaa attgaggaat tagaaaaggc    3480
aaagcagcat cttgaacagg aaatatatgt caacaaaaag cgattagaaa tggaaacatt    3540
ggctacaaaa caggctttag aagaccatag catccgccat gcaagaattc tggaagcttt    3600
agaaactgaa aagcaaaaaa ttgctaaaga agtacaaatt ctacagcaga atcggaataa    3660
tagggataaa acttttacag tgcagacaac ttggagctct atgaaactct caatgatgat    3720
tcaggaagcc aatgctatca gcagcaaatt gaaaacatac tatgtttttg cagacatga    3780 tatatcagat aaaagtagtt ctgacacttc tattcgggtt cgtaacctga aactaggaat    3840
ctcaacattc tggagtctgg aaaagtttga atctaaactt gcagcaatga agaacttta    3900 tgagagtaat ggtagtaaca ggggtgaaga tgccttttgt gatcctgaag atgaatggga    3960
acccgacatt acagatgcac cagtttcttc actttctaga aggaggagta ggagtttgat    4020
gaagaacaga agaatttctg gttgtttaca tgacatacaa gtccatccaa ttaagaattt    4080
gcattcttca cattcatcag gtttaatgga caaatcaagc actatttact caaattcagc    4140
agagtccttt cttcctggaa tttgcaaaga attgattggt tcttcgttag attttttggg    4200
acagagttat gatgaagaaa gaactatagc agacagccta attaatagtt ttcttaaaat    4260
ttataatggg ctatttgcca tttccaaggc tcatgaagaa caagatgaag aaagtcaaga    4320
taacttgttt tcttctgatc gagcaatcca gtcacttact attcagactg catgtgcttt    4380
tgagcagcta gtagtgctaa tgaaacactg gctgagtgat ttactgcctt gtaccaacat    4440
agcaagactt gaggatgagt tgagacaaga agttaaaaaa ctgggaggct acttacagtt    4500
atttttgcag ggatgctgtt tggatatttc atcaatgata aaagaggctc aaaagaatgc    4560
aatccaaatt gtacaacaag ctgtaaagta tgtgggcag ttagcagttc tgaaagggag    4620
caagctacat tttctagaaa acggtaacaa taaagctgcc agtgtccagg aggaattcat    4680
ggatgctgtt tgtgatggtg taggcttagg aatgaagatt ttattagatt ctggactgga    4740
aaaagcaaaa gaacttcagc atgaactctt taggcagtgt acaaaaatg aggttaccaa    4800 agaaatgaaa actaatgcca tgggattgat tagatctctt gaaaacatct ttgctgaatc    4860
gaaaattaaa agtttcagaa ggcaagtaca agaagaaaac tttgaatacc aagatttcaa    4920
gaggatggtt aatcgtgctc cagaattctt aaagttaaaa cattgcttag agaaagctat    4980
tgaaattatt atttctgcac tgaaaggatg ccatagtgat ataaatcttc tccagacttg    5040
tgttgaaagt attcgcaact tggccagtga ttttttacagt gacttcagtg tgccttctac    5100
ttctgttggc agctatgaga gtagagtaac tcacattgtc caccaggaac tagaatctct    5160
agctaagtct ctcctctttt gttttgaatc tgaagaaagc cctgatttgt tgaaaccctg    5220
ggaaacttat aatcaaaata ccaaagaaga acaccaacaa tctaaatcaa gcgggattga    5280
cggcagtaag aataaaggtg taccaaagcg tgtctatgag ctccatggct catcccagc    5340 agtgagctca gaggaatgca cacccagtag gattcagtgg gtgtgaatac tgatgtgtag    5400
```

-continued

```
gcactttat gaccacccat gaaagaaaaa gaacacttgc tcggtaattt tctttatgca      5460
ggagagttta agagaaatca gcacagatat ttcaaaaaag tccatgtctt tttatcttta      5520
aaatatctat ttatcaaagg ccagacacag tggctcacgc ctgtaatccc agcactttgg     5580
gaggcgggca gatcacaagg tcaggagttt gagaccggcc tggccaacat ggcgaaaccc     5640
cgtctctact aaaaatacaa aaatttgctg ggcatggtgg cgcgtgcctg taatcccagc     5700
tactagggg gctgaggcag gaggatcgct tgaacctgag aggcagaggt tgcagtgagc     5760
caagatcatg ccactttact ccagtctgag caacagaacg agacttagtc aaaataaata     5820
aataaataaa taaataaata aataaataaa taaataaaat atattttat ctttaaagtg     5880
tttaacattg gtatactgtc tgtagttggt tcattagtcg tttataaagg gttatttct     5940
catgagtgga aacctgaaca atcagttacc tttgtgccta tgccttctct ctcctcagac    6000
agctgggatg tttatggtga aatggcctgt acaagtttaa ctaagacaac ttaacttgca    6060
ttgttaatca aaaattcttt tctcaaaggg ttaactggtt gccatttga atagtatgtt    6120
caagggtgta gcttcctgtt tctttccaaa ttataagtag ctacctaaat atagtataat    6180
tatatattaa taatatggct tgctggcaca gtagtttacc ctgttatctg tgtttcataa    6240
tgggggctgt atgaatatta tttaaaacta ataaaatgtt gccagaatta tactaaactg    6300
ttggatgaga ttaggagatc agaggctgga ccttctcttg ataatgcttg ttttgttaaa    6360
ggtataatga aataatttgt atatgatttg atgaagatta aagacccta ttttccacag    6420
cttaaaaaa aaacctttat ttatgatcaa gtaataaga taatattcta cttgtgggat     6480
cttacattac ggaaatagtt tgacgttttt gacctcaaga gtatgtataa tttgaagaga    6540
tactttgtaa ctatgcttgg gtgatattga gcagttccta agaataatt catttaaaaa    6600
aaagaagaa aaaaaagaa gaattcattt aaataacctg atcctttcat ttgcccttt      6660
cgaatttaca gatactactt gtacatttgg cataactagt tgaaattggc cattcgtacc   6720
atgaataaat ctgatagttt ccttgttagg aagagattgt aagtaaatac agtcattgca    6780
gtcagaacag tattagtgaa ccttgtgtgg tgttttcaag ctcttaaaaa tggtacaatg    6840
tagcacattt gctttcattt cttttttat ttttggcatt tgaccttgta ttctttctga    6900
agctctatat gtgttttat tagtcaataa tctggcaagt agcactttgc ctgtgcagtt    6960
tgctggagtg tagatgtaca tatgaggatt tcccgggagg tgcacttctt tgaagaactt    7020
cctaaagtac ctgtatagta gttttcatct taatattcag tatttaatct tcagtttgtg   7080
ctttgtaaac tcatgactta attggtcaga aacttttag tgtctttata aaatttgta    7140
tacatattta tactaaacac attgtgatac tgtatttgaa tgaatggtga aaaaatattt   7200
gctattggaa ttatgtgcac tgacaagaaa tgttataaag agaatgcctt taataaatct   7260
tttcagcatt agaattgaaa aaaaaaaaa aaa                                   7293
```

<210> SEQ ID NO 56
<211> LENGTH: 3463
<212> TYPE: DNA
<213> ORGANISM: Homo sapiens

<400> SEQUENCE: 56

```
aatgaaacga agcgctgagg aaagtggctt gggtttgaat attgtggttg agtctgaagc       60
gctgggaggc ggacattaaa gtgaagtggt tgcggtaacc tggcctgggc ctgaagtgag      120
tgagaggcac atgaagagaa gtattcaagt atttatacag ataggaatca agataatcaa      180
caatgtctgt cactgaggaa gacctgtgcc accatatgaa agtagtagtt cgtgtacgtc      240
```

```
cggaaaacac taaagaaaaa gcagctggat ttcataaagt ggttcatgtt gtggataaac    300
atatcctagt ttttgatccc aaacaagaag aagtcagttt tttccatgga aagaaaacta    360
caaatcaaaa tgttataaag aaacaaaata aggatcttaa atttgtattt gatgctgttt    420
ttgatgaaac gtcaactcag tcagaagttt ttgaacacac tactaagcca attcttcgta    480 gtttttttgaa tggatataat tgcacagtac ttgcctatgg tgccactggt gctgggaaga    540
cccacactat gctaggatca gctgatgaac ctggagtgat gtatctaaca atgttacacc    600
tttacaaatg catggatgag attaaagaag agaaaatatg tagtactgca gtttcatatc    660
tggaggtata taatgaacag attcgtgatc tcttagtaaa ttcagggcca cttgctgtcc    720
gggaagatac ccaaaaaggg gtggtcgttc atggacttac tttacaccag cccaaatcct    780
cagaagaaat tttacattta ttggataatg aaacaaaaa caggacacaa catcccactg    840
atatgaatgc cacatcttct cgttctcatg ctgttttcca aatttacttg cgacaacaag    900
acaaaacagc aagtatcaat caaaatgtcc gtattgccaa gatgtcactc attgacctgg    960
caggatctga gcgagcaagt acttccggtg ctaagggac ccgatttgta gaaggcacaa   1020
atattaatag atcactttta gctcttggga atgtcatcaa tgcttagca gattcaaaga   1080 gaaagaatca gcatatccct tacagaaata gtaagcttac tcgcttgtta aaggattctc   1140
ttggaggaaa ctgtcaaact ataatgatag ctgctgttag tccttcctct gtattctacg   1200
atgacacata taacactctt aagtatgcta accgggcaaa ggacattaaa tcttctttga   1260
agagcaatgt tcttaatgtc aataatcata taactcaata tgtaaagatc tgtaatgagc   1320
agaaggcaga gattttattg ttaaaagaaa aactaaaagc ctatgaagaa cagaaagcct   1380
tcactaatga aaatgaccaa gcaaagttaa tgatttcaaa ccctcaggaa aaagaaatcg   1440
aaaggtttca agaaatcctg aactgcttgt tccagaatcg agaagaaatt agacaagaat   1500
atctgaagtt ggaaatgtta cttaaagaaa atgaacttaa atcattctac caacaacagt   1560
gccataaaca aatagaaatg atgtgttctg aagacaaagt agaaaaggcc actggaaaac   1620
gagatcatag acttgcaatg ttgaaaactc gtcgctccta cctggagaaa aggagggagg   1680
aggaattgaa gcaatttgat gagaatacta attggctcca tcgtgtcgaa aaagaaatgg   1740
gactcttaag tcaaaacggt catattccaa aggaactcaa gaaagatctt cattgtcacc   1800
atttgcacct ccagaacaaa gatttgaaag cacaaattag acatatgatg gatctagctt   1860
gtcttcagga acagcaacac aggcagactg aagcagtatt gaatgcttta cttccaaccc   1920
taagaaaaca atattgcaca ttaaaagaag ccggcctgtc aaatgctgct tttgaatctg   1980
acttcaaaga gatcgaacat ttggtagaga ggaaaaaagt ggtagtttgg gctgaccaaa   2040
ctgccgaaca accaaagcaa aacgatctac cagggatttc tgttcttatg acctttccac   2100
aacttggacc agttcagcct attccttgtt gctcatcttc aggtggaact aatctggtta   2160
agattcctac agaaaaaaga actcggagaa aactaatgcc atctcccttg aaaggacagc   2220
atactctaaa gtctccacca tctcaaagtg tgcagctcaa tgattctctt agcaaagaac   2280
ttcagcctat tgtatataca ccagaagact gtagaaaagc ttttcaaaat ccgtctacag   2340
taaccttaat gaaaccatca tcatttacta caagttttca ggctatcagc tcaaacataa   2400
acagtgataa ttgtctgaaa atgttgtgtg aagtagctat ccctcataat agaagaaaag   2460
aatgtggaca ggaggacttg gactctacat ttactatatg tgaagacatc aagagctcga   2520
agtgtaaatt acccgaacaa gaatcactac caaatgataa caaagacatt ttacaacggc   2580
```

-continued

| | | |
|---|---|---|
| ttgatccttc ttcattctca actaagcatt ctatgcctgt accaagcatg gtgccatcct | 2640 | |
| acatggcaat gactactgct gccaaaagga aacggaaatt aacaagttct acatcaaaca | 2700 | |
| gttcgttaac tgcagacgta aattctggat ttgccaaacg tgttcgacaa gataattcaa | 2760 | |
| gtgagaagca cttacaagaa aacaaaccaa caatggaaca taaagaaac atctgtaaaa | 2820 | |
| taaatccaag catggttaga aaatttggaa gaaatatttc aaaggaaat ctaagataaa | 2880 | |
| tcacttcaaa accaagcaaa atgaagttga tcaaatctgc ttttcaaagt ttatcaatac | 2940 | |
| cctttcaaaa atatatttaa aatctttgaa agaagaccca tcttaaagct aagtttaccc | 3000 | |
| aagtactttc agcaagcaga aaaatgaaac tctttgtttt cttcttttgt gttctaaaaa | 3060 | |
| aataaaattt caaaagaaaa ggttgtcttt taagttttt aaatatttgt tgccttttaa | 3120 | |
| aatccctgag tgtaagttac catggtggca gcttagtttt actatgccac aacaagttga | 3180 | |
| ctaggacatt ttagtaaatg gtagtgagtt aaattatctt tattattttt taaaaataag | 3240 | |
| aatttagaag tggtaaaatt atggcccaag atgtatttgg ttctctatta tgttttgata | 3300 | |
| cattatttta atcatatata tgactttcct tttcaaaaat actttaatgt acaagtgtaa | 3360 | |
| atatatgtgc ccataaaatc attgtaaata ttatttagtc atcacaaata aaatattgtc | 3420 | |
| ccttgctact tgatatatta aagatgtaga ttttaaagtg ttt | 3463 | |

<210> SEQ ID NO 57
<211> LENGTH: 3471
<212> TYPE: DNA
<213> ORGANISM: Homo sapiens

<400> SEQUENCE: 57

| | | |
|---|---|---|
| tttttcccct taagacaaag caagcaccct aaaccagtta ccctgtgcac tcctgttaag | 60 | |
| attgttgcta aggaaggaca gggagttggct gctgaagcct caagatttcc tttaggctct | 120 | |
| taggtaagaa atgtctaagg ttcaaggaaa aaggttaagt tggaagaatc ccaggcaaaa | 180 | |
| taagtgcgaa tccacgacag ttggtaaccc ggacccacat tagaactcag aggtcaagca | 240 | |
| gaagcgaacg actggaattc cagtcaggcc cgcccctttt ccttacgcgg attggtagct | 300 | |
| gcaggcttcc ctatctgatt ggccgaacga acgcagcgcg taatttaaaa tattgtatct | 360 | |
| gtaacaaagc tgcacctcgt gggcggagtt gtgctctgcg gctgcgaaag tccagcttcg | 420 | |
| gcgactaggt gtgagtaagc cagtatccca ggaggagcaa gtggcacgtc ttcggaccta | 480 | |
| ggctgcccct gccgtcatgt cgcaagggat cctttctccg ccagcgggct tgctgtccga | 540 | |
| tgacgatgtc gtagtttctc ccatgtttga gtccacagct gcagatttgg ggtctgtggt | 600 | |
| acgcaagaac ctgctatcag actgctctgt cgtctctacc tccctagagg acaagcagca | 660 | |
| ggttccatct gaggacagta tggagaaggt gaaagtatac ttgagggtta ggcccttgtt | 720 | |
| accttcagag ttggaacgac aggaagatca gggttgtgtc cgtattgaga atgtggagac | 780 | |
| ccttgttcta caagcaccca aggactcttt tgccctgaag agcaatgaac ggggaattgg | 840 | |
| ccaagccaca cacaggttca cctttcccca gatctttggg ccagaagtgg gacaggcatc | 900 | |
| cttcttcaac ctaactgtga aggagatggt aaaggatgta tcaaagggc agaactggct | 960 | |
| catctataca tatggagtca ctaactcagg gaaaacccac acgattcaag gtaccatcaa | 1020 | |
| ggatggaggg attctccccc ggtccctggc gctgatcttc aatagcctcc aaggccaact | 1080 | |
| tcatccaaca cctgatctga agcccttgct ctccaatgag gtaatctggc tagacagcaa | 1140 | |
| gcagatccga caggaggaaa tgaagaagct gtccctgcta aatggaggcc tccaagagga | 1200 | |
| ggagctgtcc acttccttga gaggagtgt ctacatcgaa agtcggatag gtaccagcac | 1260 | |

-continued

```
cagcttcgac agtggcattg ctgggctctc ttctatcagt cagtgtacca gcagtagcca      1320
gctggatgaa acaagtcatc gatgggcaca gccagacact gccccactac ctgtcccggc      1380
aaacattcgc ttctccatct ggatctcatt ctttgagatc tacaacgaac tgctttatga      1440
cctattagaa ccgcctagcc aacagcgcaa gaggcagact ttgcggctat gcgaggatca      1500
aaatggcaat ccctatgtga aagatctcaa ctggattcat gtgcaagatg ctgaggaggc      1560
ctggaagctc ctaaaagtgg gtcgtaagaa ccagagcttt gccagcaccc acctcaacca      1620
gaactccagc cgcagtcaca gcatcttctc aatcaggatc ctacaccttc aggggaagg      1680 agatatagtc cccaagatca gcgagctgtc actctgtgat ctggctggct cagagcgctg      1740
caaagatcag aagagtggtg aacggttgaa ggaagcagga acattaaca cctctctaca      1800 caccctgggc cgctgtattg ctgcccttcg tcaaaaccag cagaaccggt caaagcagaa      1860
cctggttccc ttccgtgaca gcaagttgac tcgagtgttc caaggtttct tcacaggccg      1920
aggccgttcc tgcatgattg tcaatgtgaa tccctgtgca tctacctatg atgaaactct      1980
tcatgtggcc aagttctcag ccattgctag ccagcttgtg catgccccac ctatgcaact      2040
gggattccca tccctgcact cgttcatcaa ggaacatagt cttcaggtat cccccagctt      2100
agagaaaggg gctaaggcag acacaggcct tgatgatgat attgaaaatg aagctgacat      2160
ctccatgtat ggcaaagagg agctcctaca agttgtggaa gccatgaaga cactgctttt      2220
gaaggaacga caggaaaagc tacagctgga gatgcatctc cgagatgaaa tttgcaatga      2280
gatggtagaa cagatgcaac agcgggaaca gtggtgcagt gaacatttgg acacccaaaa      2340
ggaactattg gaggaaatgt atgaagaaaa actaaatatc ctcaaggagt cactgacaag      2400
tttttaccaa gaagagattc aggagcggga tgaaaagatt gaagagctag aagctctctt      2460
gcaggaagcc agacaacagt cagtggccca tcagcaatca gggtctgaat tggccctacg      2520
gcggtcacaa aggttggcag cttctgcctc cacccagcag cttcaggagg ttaaagctaa      2580
attacagcag tgcaaagcag agctaaactc taccactgaa gagttgcata agtatcagaa      2640
aatgttagaa ccaccaccct cagccaagcc cttcaccatt gatgtggaca agaagttaga      2700
agagggccag aagaatataa ggctgttgcg gacagagctt cagaaacttg gtgagtctct      2760
ccaatcagca gagagagctt gttgccacag cactggggca ggaaaacttc gtcaagcctt      2820
gaccacttgt gatgacatct taatcaaaca ggaccagact ctggctgaac tgcagaacaa      2880
catggtgcta gtgaaactgg accttcggaa gaaggcagca tgtattgctg agcagtatca      2940
tactgtgttg aaactccaag gccaggtttc tgccaaaaag cgccttggta ccaaccagga      3000
aaatcagcaa ccaaaccaac aaccaccagg gaagaaacca ttccttcgaa atttacttcc      3060
ccgaacacca acctgccaaa gctcaacaga ctgcagccct tatgcccgga tcctacgctc      3120
acggcgttcc cctttactca aatctgggcc ttttggcaaa aagtactaag gctgtgggga      3180
aagagaagag cagtcatggc cctgaggtgg gtcagctact ctcctgaaga ataggtctc      3240 ttttatgctt taccatatat caggaattat atccaggatg caatactcag acactagctt      3300
ttttctcact tttgtattat aaccacctat gtaatctcat gttgttgttt ttttttattt      3360
acttatatga tttctatgca cacaaaaaca gttatattaa agatattatt gttcacattt      3420
tttattgaat tccaaatgta gcaaaatcat taaaacaaat tataaaaggg a             3471
```

<210> SEQ ID NO 58
<211> LENGTH: 2896
<212> TYPE: DNA

<213> ORGANISM: Homo sapiens

<400> SEQUENCE: 58

| | |
|---|---|
| acgcttgcgc gcgggattta aactgcggcg gtttacgcgg cgttaagact tcgtagggtt | 60 |
| agcgaaattg aggtttcttg gtattgcgcg tttctcttcc ttgctgactc tccgaatggc | 120 |
| catggactcg tcgcttcagg cccgcctgtt tcccggtctc gctatcaaga tccaacgcag | 180 |
| taatggttta attcacagtg ccaatgtaag gactgtgaac ttggagaaat cctgtgtttc | 240 |
| agtggaatgg gcagaaggag gtgccacaaa gggcaaagag attgattttg atgatgtggc | 300 |
| tgcaataaac ccagaactct tacagcttct tcccttacat ccgaaggaca atctgccctt | 360 |
| gcaggaaaat gtaacaatcc agaaacaaaa acggagatcc gtcaactcca aaattcctgc | 420 |
| tccaaaagaa agtcttcgaa gccgctccac tcgcatgtcc actgtctcag agcttcgcat | 480 |
| cacggctcag gagaatgaca tggaggtgga gctgcctgca gctgcaaact cccgcaagca | 540 |
| gttttcagtt cctcctgccc ccactaggcc ttcctgccct gcagtggctg aaataccatt | 600 |
| gaggatggtc agcgaggaga tggaagagca agtccattcc atccgaggca gctcttctgc | 660 |
| aaaccctgtg aactcagttc ggaggaaatc atgtcttgtg aaggaagtgg aaaaaatgaa | 720 |
| gaacaagcga aagagaagaa aggcccgaaa ctctgaaatg agaatgaaga gagctcagga | 780 |
| gtatgacagt agttttccaa actgggaatt tgcccgaatg attaaagaat tcgggctac | 840 |
| tttggaatgt catccactta ctatgactga tcctatcgaa gagcacagaa tatgtgtctg | 900 |
| tgttaggaaa cgcccactga ataagcaaga attggccaag aaagaaattg atgtgatttc | 960 |
| cattcctagc aagtgtctcc tcttggtaca tgaacccaag ttgaaagtgg acttaacaaa | 1020 |
| gtatctggag aaccaagcat tctgctttga cttggcattt gatgaaacag cttcgaatga | 1080 |
| agttgtctac aggttcacag caaggccact ggtacagaca atctttgaag gtggaaaagc | 1140 |
| aacttgtttt gcatatggcc agacaggaag tgcaagaca catactatgg gcggagacct | 1200 |
| ctctgggaaa gcccagaatg catccaaagg gatctatgcc atggcctccc gggacgtctt | 1260 |
| cctcctgaag aatcaaccct gctaccggaa gttgggcctg gaagtctatg tgacattctt | 1320 |
| cgagatctac aatgggaagc tgtttgacct gctcaacaag aaggccaagc tgcgcgtgct | 1380 |
| ggaggacggc aagcaacagg tgcaagtggt ggggctgcag gagcatctgg ttaactctgc | 1440 |
| tgatgatgtc atcaagatga tcgacatggg cagcgcctgc agaacctctg gcagacatt | 1500 |
| tgccaactcc aattcctccc gctcccacgc gtgcttccaa attattcttc gagctaaagg | 1560 |
| gagaatgcat ggcaagttct ctttggtaga tctggcaggg aatgagcgag gcgcggacac | 1620 |
| ttccagtgct gaccggcaga cccgcatgga gggcgcagaa atcaacaaga gtctcttagc | 1680 |
| cctgaaggag tgcatcaggg ccctgggaca gaacaaggct cacacccgt tccgtgagag | 1740 |
| caagctgaca caggtgctga gggactcctt cattggggag aactctagga cttgcatgat | 1800 |
| tgccacgatc tcaccaggca taagctcctg tgaatatact ttaaacaccc tgagatatgc | 1860 |
| agacagggtc aaggagctga gcccccacag tgggcccagt ggagagcagt tgattcaaat | 1920 |
| ggaaacagaa gagatggaag cctgctctaa cggggcgctg attccaggca atttatccaa | 1980 |
| ggaagaggag gaactgtctt cccagatgtc cagctttaac gaagccatga ctcagatcag | 2040 |
| ggagctggag gagaaggcta tggaagagct caaggagatc atacagcaag gaccagactg | 2100 |
| gcttgagctc tctgagatga ccagcagcc agactatgac ctggagacct tgtgtaacaa | 2160 |
| agcggaatct gctctggccc agcaagccaa gcatttctca gccctgcgag atgtcatcaa | 2220 |
| ggccttgcgc ctggccatgc agctggaaga gcaggctagc agacaaataa gcagcaagaa | 2280 |

```
acggcccag tgacgactgc aaataaaaat ctgtttggtt tgacacccag cctcttccct    2340
ggccctcccc agagaacttt gggtacctgg tgggtctagg cagggtctga gctgggacag    2400
gttctggtaa atgccaagta tgggggcatc tgggcccagg gcagctgggg aggggtcag    2460 agtgacatgg gacactcctt ttctgttcct cagttgtcgc cctcacgaga ggaaggagct    2520
cttagttacc cttttgtgtt gcccttcttt ccatcaaggg gaatgttctc agcatagagc    2580
tttctccgca gcatcctgcc tgcgtggact ggctgctaat ggagagctcc ctggggttgt    2640
cctggctctg ggagagaga cggagccttt agtacagcta tctgctggct ctaaaccttc    2700
tacgcctttg ggccgagcac tgaatgtctt gtactttaaa aaaatgtttc tgagacctct    2760 ttctactta ctgtctccct agagatccta gaggatccct actgttttct gttttatgtg    2820
tttatacatt gtatgtaaca ataaagagaa aaataaatc agctgtttaa gtgtgtggaa    2880
aaaaaaaaaa aaaaaa                                                    2896
```

<210> SEQ ID NO 59
<211> LENGTH: 3916
<212> TYPE: DNA
<213> ORGANISM: Homo sapiens

<400> SEQUENCE: 59

```
agagtgctga tttagaagaa tacaaatcat ggctgaaaat agtgtattaa catccactac      60
tgggaggact agcttggcag actcttccat ttttgattct aaagttactg agatttccaa     120
ggaaaactta cttattggat ctacttcata tgtagaagaa gagatgcctc agattgaaac     180
aagagtgata ttggttcaag aagctggaaa acaagaagaa cttataaaag ccttaaagga     240
cattaaagtg ggctttgtaa agatggagtc agtggaagaa tttgaaggtt tggattctcc     300
ggaatttgaa aatgtatttg tagtcacgga cttcaggat tctgtcttta atgacctcta     360
caaggctgat tgtagagtta ttggaccacc agttgtatta aattgttcac aaaaaggaga     420
gcctttgcca ttttcatgtc gcccgttgta ttgtacaagt atgatgaatc tagtactatg     480
ctttactgga tttaggaaaa agaagaact agtcaggttg gtgacattgg tccatcacat     540
gggtggagtt attcgaaaag actttaattc aaaagttaca catttggtgg caaattgtac     600
acaaggagaa aaattcaggg ttgctgtgag tctaggtact ccaattatga agccagaatg     660
gatttataaa gcttgggaaa gcggaatgat acaggatttc tatgcagcag ttgatgactt     720
tagaaatgaa tttaaagttc ctccatttca agattgtatt ttaagtttcc tgggatttc     780 agatgaagag aaaaccaata tggaagaaat gactgaaatg caaggaggta atatttacc     840 gcttggagat gaaagatgca ctcaccttgt agttgaagag aatatagtaa aagatcttcc     900
ctttgaacct tcaagaaaac tttatgttgt caagcaagag tggttctggg gaagcattca     960
aatggatgcc cgagctggag aaactatgta tttatatgaa aaggcaaata tcctgagct    1020 caagaaatca gtgtcaatgc tttctctaaa taccctaac agcaatcgca aacgacgtcg    1080
tttaaaagaa acacttgctc agctttcaag agagacagac gtgtcaccat ttccacccg    1140 taagcgccca tcagctgagc attccctttc catagggtca ctcctagata tctccaacac    1200
accagagtct agcattaact atggagacac cccaaagtct tgtactaagt cttctaaaag    1260
ctccactcca gttccttcaa agcagtcagc aaggtggcaa gttgcaaaag gctttatca    1320 aactgaaagt aattatgtta atatattggc aacaattatt cagttatttc aagtaccatt    1380
ggaagaggaa ggacaacgtg gtggacctat ccttgcacca gaggagatta agactatttt    1440
```

```
tggtagcatc ccagatatct ttgatgtaca cactaagata aaggatgatc ttgaagacct   1500
tatagttaat tgggatgaga gcaaaagcat tggtgacatt tttctgaaat attcaaaaga   1560
tttggtaaaa acctaccctc cctttgtaaa cttctttgaa atgagcaagg aaacaattat   1620
taaatgtgaa aaacagaaac caagatttca tgcttttctc aagataaacc aagcaaaacc   1680
agaatgtgga cggcagagcc ttgttgaact tcttatccga ccagtacaga ggttacccag   1740
tgttgcatta cttttaaatg atcttaagaa gcatacagct gatgaaaatc cagacaaaag   1800
cactttagaa aaagctattg gatcactgaa ggaagtaatg acgcatatta atgaggataa   1860
gagaaaaaca gaagctcaaa agcaaatttt tgatgttgtt tatgaagtag atggatgccc   1920
agctaatctt ttatcttctc accgaagctt agtacagcgg gttgaaacaa tttctctagg   1980
tgagcacccc tgtgacagag gagaacaagt aactctcttc ctcttcaatg attgcctaga   2040
gatagcaaga aaacggcaca aggttattgg cacttttagg agtcctcatg gccaaacccg   2100 accccccagct tctcttaagc atattcacct aatgcctctt tctcagatta agaaggtatt   2160
ggacataaga gagacagaag attgccataa tgcttttgcc ttgcttgtga ggccaccaac   2220
agagcaggca aatgtgctac tcagtttcca gatgacatca gatgaacttc caaaagaaaa   2280
ctggctaaag atgctgtgtc gacatgtagc taacaccatt tgtaaagcag atgctgagaa   2340
tcttatttat actgctgatc cagaatcctt tgaagtaaat acaaaagata tggacagtac   2400
attgagtaga gcatcaagag caataaaaaa gacttcaaaa aaggttacaa gagcattctc   2460
tttctccaaa actccaaaaa gagctcttcg aagggctctt atgacatccc acggctcagt   2520
ggagggaaga agtccttcca gcaatgataa gcatgtaatg agtcgtcttt ctagcacatc   2580
atcattagca ggtatccctt ctccctccct tgtcagcctt ccttccttct ttgaaaggag   2640
aagtcatacg ttaagtagat ctacaactca tttgatatga agcgttacca aaatcttaaa   2700
ttatagaaat gtatagacac ctcatactca aataagaaac tgacttaaat ggtacttgta   2760
attagcactt ggtgaaagct ggaaggaaga taaataacac taaactatgc tatttgattt   2820
ttcttcttga aagagtaagg tttacctgtt acattttcaa gttaattcat gtaaaaaatg   2880
atagtgattt tgatgtaatt tatctcttgt ttgaatctgt cattcaaagg ccaataattt   2940
aagttgctat cagctgatat tagtagcttt gcaaccctga tagagtaaat aaattttatg   3000
ggcgggtgcc aaatactgct gtgaatctat ttgtatagta tccatgaatg aatttatgga   3060
aatagatatt tgtgcagctc aatttatgca gagattaaat gacatcataa tactggatga   3120
aaacttgcat agaattctga ttaaatagtg ggtctgtttc acatgtgcag tttgaagtat   3180
ttaaataacc actcctttca cagtttattt tcttctcaag cgttttcaag atctagcatg   3240 tggatttaa aagatttgcc ctcattaaca agaataacat ttaaaggaga ttgtttcaaa   3300
atatttttgc aaattgagat aaggacagaa agattgagaa acattgtata ttttgcaaaa   3360
acaagatgtt tgtagctgtt tcagagagag tacggtatat ttatggtaat tttatccact   3420
agcaaatctt gatttagttt gatagtgtgt ggaatttat tttgaaggat aagaccatgg   3480
gaaaattgtg gtaaagactg tttgtaccct tcatgaaata attctgaagt tgccatcagt   3540
tttactaatc ttctgtgaaa tgcatagata tgcgcatgtt caacttttta ttgtggtctt   3600
ataattaaat gtaaaattga aaattcattt gctgtttcaa agtgtgatat ctttcacaat   3660
agccttttta tagtcagtaa ttcagaataa tcaagttcat atggataaat gcatttttat   3720
ttcctatttc tttagggagt gctacaaatg tttgtcactt aaatttcaag tttctgtttt   3780
aatagttaac tgactataga ttgttttcta tgccatgtat gtgccacttc tgagagtagt   3840
```

-continued

| | |
|---|---|
| aaatgactct tgctacatt ttaaaagcaa ttgtattagt aagaactttg taaataaata | 3900 |
| cctaaaaccc aagtgt | 3916 |

<210> SEQ ID NO 60
<211> LENGTH: 4786
<212> TYPE: DNA
<213> ORGANISM: Homo sapiens

<400> SEQUENCE: 60

| | |
|---|---|
| ctcggcgctg aaattcaaat ttgaacggct gcagaggccg agtccgtcac tggaagccga | 60 |
| gaggagagga cagctggttg tgggagagtt cccccgcctc agactcctgg ttttttccag | 120 |
| gagacacact gagctgagac tcactttct cttcctgaat ttgaaccacc gtttccatcg | 180 |
| tctcgtagtc cgacgcctgg ggcgatggat ccgtttacgg agaaactgct ggagcgaacc | 240 |
| cgtgccaggc gagagaatct tcagagaaaa atggctgaga ggcccacagc agctccaagg | 300 |
| tctatgactc atgctaagcg agctagacag ccactttcag aagcaagtaa ccagcagccc | 360 |
| ctctctggtg gtgaagagaa atcttgtaca aaccatcgc catcaaaaaa acgctgttct | 420 |
| gacaacactg aagtagaagt ttctaacttg gaaaataaac aaccagttga gtcgacatct | 480 |
| gcaaaatctt gttctccaag tcctgtgtct cctcaggtgc agccacaagc agcagatacc | 540 |
| atcagtgatt ctgttgctgt cccggcatca ctgctgggca tgaggagagg gctgaactca | 600 |
| agattggaag caactgcagc ctcctcagtt aaaacacgta tgcaaaaact tgcagagcaa | 660 |
| cggcgccgtt gggataatga tgatatgaca gatgacattc ctgaaagctc actcttctca | 720 |
| ccaatgccat cagaggaaaa ggctgcttcc cctcccagac ctctgctttc aaatgcctcg | 780 |
| gcaactccag ttggcagaag gggccgtctg gccaatcttg ctgcaactat ttgctcctgg | 840 |
| gaagatgatg taaatcactc atttgcaaaa caaaacagtg tacaagaaca gcctggtacc | 900 |
| gcttgtttat ccaaatttc ctctgcaagt ggagcatctg ctaggatcaa tagcagcagt | 960 |
| gttaagcagg aagctacatt ctgttcccaa agggatggcg atgcctcttt gaataaagcc | 1020 |
| ctatcctcaa gtgctgatga tgcgtctttg gttaatgcct caatttccag ctctgtgaaa | 1080 |
| gctacttctc cagtgaaatc tactacatct atcactgatg ctaaaagttg tgaggacaa | 1140 |
| aatcctgagc tacttccaaa aactcctatt agtcctctga aaacgggggt atcgaaacca | 1200 |
| attgtgaagt caactttatc ccagacagtt ccatccaagg gagaattaag tagagaaatt | 1260 |
| tgtctgcaat ctcaatctaa agacaaatct acgacaccag gaggaacagg aattaagcct | 1320 |
| ttcctggaac gctttggaga gcgttgtcaa gaacatagca agaaagtcc agctcgtagc | 1380 |
| acaccccaca gaaccccat tattactcca aatacaaagg ccatccaaga aagattattc | 1440 |
| aagcaagaca catcttcatc tactacccat ttagcacaac agctcaagca ggaacgtcaa | 1500 |
| aaagaactag catgtcttcg tggccgattt gacaagggca atatatggag tgcagaaaaa | 1560 |
| ggcggaaact caaaagcaa acaactagaa accaaacagg aaactcactg tcagagcact | 1620 |
| cccctcaaaa aacaccaagg tgtttcaaaa actcagtcac ttccagtaac agaaaaggtg | 1680 |
| accgaaaacc agataccagc caaaaattct agtacagaac ctaaaggttt cactgaatgc | 1740 |
| gaaatgacga aatctagccc tttgaaaata acattgtttt tagaagagga caaatcctta | 1800 |
| aaagtaacat cagacccaaa ggttgagcag aaaattgaag tgatacgtga aattgagatg | 1860 |
| agtgtggatg atgatgatat caatagttcg aaagtaatta atgacctctt cagtgatgtc | 1920 |
| ctagaggaag gtgaactaga tatggagaag agccaagagg agatggatca agcattagca | 1980 |

```
gaaagcagcg aagaacagga agatgcactg aatatctcct caatgtcttt acttgcacca    2040
ttggcacaaa cagttggtgt ggtaagtcca gagagtttag tgtccacacc tagactggaa    2100
ttgaaagaca ccagcagaag tgatgaaagt ccaaaaccag gaaaattcca agaactcgt     2160 gtccctcgag ctgaatctgg tgatagcctt ggttctgaag atcgtgatct tctttacagc    2220
attgatgcat atagatctca aagattcaaa gaaacagaac gtccatcaat aaagcaggtg    2280
attgttcgga aggaagatgt tacttcaaaa ctggatgaaa aaataatgc ctttccttgt     2340 caagttaata tcaaacagaa aatgcaggaa ctcaataacg aaataaatat gcaacagaca    2400
gtgatctatc aagctagcca ggctcttaac tgctgtgttg atgaagaaca tggaaaaggg    2460
tccctagaag aagctgaagc agaaagactt cttctaattg caactgggaa gagaacactt    2520
ttgattgatg aattgaataa attgaagaac gaaggacctc agaggaagaa taaggctagt    2580
ccccaaagtg aatttatgcc atccaaagga tcagttactt tgtcagaaat ccgcttgcct    2640
ctaaaagcag attttgtctg cagtacggtt cagaaaccag atgcagcaaa ttactattac    2700
ttaattatac taaaagcagg agctgaaaat atggtagcca caccattagc aagtacttca    2760
aactctctta acggtgatgc tctgacattc actactacat ttactctgca agatgtatcc    2820
aatgactttg aaataaatat tgaagtttac agcttggtgc aaaagaaaga tccctcaggc    2880
cttgataaga agaaaaaaac atccaagtcc aaggctatta ctccaaagcg actcctcaca    2940
tctataacca caaaaagcaa cattcattct tcagtcatgg ccagtccagg aggtcttagt    3000
gctgtgcgaa ccagcaactt cgcccttgtt ggatcttaca cattatcatt gtcttcagta    3060
ggaaatacta agtttgttct ggacaaggtc ccctttttat cttctttgga aggtcatatt    3120
tatttaaaaa taaatgtca agtgaattcc agtgttgaag aaagaggttt tctaaccata    3180
tttgaagatg ttagtggttt tggtgcctgg catcgaagat ggtgtgttct ttctggaaac    3240
tgtatatctt attggactta tccagatgat gagaaacgca agaatcccat aggaaggata    3300
aatctggcta attgtaccag tcgtcagata gaaccagcca acagagaatt ttgtgcaaga    3360
cgcaacactt ttgaattaat tactgtccga ccacaaagag aagatgaccg agagactctt    3420
gtcagccaat gcagggacac actctgtgtt accaagaact ggctgtctgc agatactaaa    3480
gaagagcggg atctctggat gcaaaaactc aatcaagttc ttgttgatat tcgcctctgg    3540
caacctgatg cttgctacaa acctattgga aagccttaaa ccgggaaatt tccatgctat    3600
ctagaggttt ttgatgtcat cttaagaaac acacttaaga gcatcagatt tactgattgc    3660
attttatgct ttaagtacga aagggtttgt gccaatattc actacgtatt atgcagtatt    3720
tatatctttt gtatgtaaaa ctttaactga tttctgtcat tcatcaatga gtagaagtaa    3780
atacattata gttgattttg ctaaatctta atttaaaagc ctcattttcc tagaaatcta    3840
attattcagt tattcatgac aatatttttt taaaagtaag aaattctgag ttgtcttctt    3900
ggagctgtag gtcttgaagc agcaacgtct ttcaggggtt ggagacagaa acccattctc    3960
caatctcagt agttttttcg aaaggctgtg atcatttatt gatcgtgata tgacttgtta    4020
ctagggtact gaaaaaaatg tctaaggcct ttacagaaac atttttagta atgaggatga    4080 gaacttttc aaatagcaaa tatatattgg cttaaagcat gaggctgtct tcagaaaagt     4140
gatgtggaca taggaggcaa tgtgtgagac ttgggggttc aatattttat atagaagagt    4200
taataagcac atggtttaca tttactcagc tactatatat gcagtgtggt gcacattttc    4260
acagaattct ggcttcatta agatcattat ttttgctgcg tagcttacag acttagcata    4320
ttagtttttt ctactcctac aagtgtaaat tgaaaaatct ttatattaaa aaagtaaact    4380
```

```
gttatgaagc tgctatgtac taataatact ttgcttgcca aagtgtttgg gttttgttgt      4440
tgtttgtttg tttgtttgtt tttggttcat gaacaacagt gtctagaaac ccattttgaa      4500
agtggaaaat tattaagtca cctatcacct ttaaacgcct tttttttaaaa ttataaaata     4560 ttgtaaagca gggtctcaac ttttaaatac actttgaact tcttctctga attattaaag      4620
ttctttatga cctcatttat aaacactaaa ttctgtcacc tcctgtcatt ttatttttta     4680
ttcattcaaa tgtattttt cttgtgcata ttataaaaat atattttatg agctcttact       4740
caaataaata cctgtaaatg tctaaaggaa aaaaaaaaa aaaaaa                      4786
```

<210> SEQ ID NO 61
<211> LENGTH: 1899
<212> TYPE: DNA
<213> ORGANISM: Homo sapiens

<400> SEQUENCE: 61

```
agcgcgcgac tttttgaaag ccaggagggt tcgaattgca acggcagctg ccgggcgtat        60
gtgttggtgc tagaggcagc tgcagggtct cgctgggggc cgctcgggac caattttgaa      120
gaggtacttg gccacgactt attttcacct ccgacctttc cttccaggcg gtgagactct      180
ggactgagag tggctttcac aatggaaggg atcagtaatt tcaagacacc aagcaaatta      240
tcagaaaaaa agaaatctgt attatgttca actccaacta taaatatccc ggcctctccg      300
tttatgcaga agcttggctt tggtactggg gtaaatgtgt acctaatgaa aagatctcca      360
agaggtttgt ctcattctcc ttgggctgta aaaaagatta atcctatatg taatgatcat      420
tatcgaagtg tgtatcaaaa gagactaatg gatgaagcta agattttgaa aagccttcat      480
catccaaaca ttgttggtta tcgtgctttt actgaagcca atgatggcag tctgtgtctt      540
gctatggaat atggaggtga aaagtctcta aatgacttaa tagaagaacg atataaagcc      600
agccaagatc cttttccagc agccataatt taaaagttg ctttgaatat ggcaagaggg       660
ttaaagtatc tgcaccaaga aaagaaactg cttcatggag acataaagtc ttcaaatgtt      720
gtaattaaag gcgattttga aacaattaaa atcgtgatg taggagtctc tctaccactg       780
gatgaaaata tgactgtgac tgaccctgag gcttgttaca ttggcacaga gccatggaaa     840
cccaaagaag ctgtggagga aatggtgtt attactgaca aggcagacat atttgccttt       900
ggccttactt tgtgggaaat gatgacttta tcgattccac acattaatct ttcaaatgat     960
gatgatgatg aagataaaac ttttgatgaa agtgattttg atgatgaagc atactatgca     1020
gcgttgggaa ctaggccacc tattaatatg gaagaactgg atgaatcata ccagaaagta    1080
attgaactct tctctgtatg cactaatgaa gaccctaaag atcgtccttc tgctgcacac    1140
attgttgaag ctctggaaac agatgtctag tgatcatctc agctgaagtg tggcttgcgt    1200
aaataactgt ttattccaaa atatttacat agttactatc agtagttatt agactctaaa    1260
attggcatat ttgaggacca tagttttctt ttaacatatg gataactatt tctaatatga    1320
aatatgctta tattggctat aagcacttgg aattgtactg ggttttctgt aaagttttag    1380
aaactagcta cataagtact ttgatactgc tcatgctgac ttaaaacact agcagtaaaa     1440
cgctgtaaac tgtaacatta aattgaatga ccattacttt tattaatgat ctttcttaaa     1500
tattctatat tttaatggat ctactgacat tagcactttg tacagtacaa aataaagtct     1560
acatttgttt aaaacactga accttttgct gatgtgttta tcaaatgata actgaagct     1620 gaggagaata tgcctcaaaa agagtagctc cttggatact tcagactctg gttacagatt    1680
```

```
gtcttgatct cttggatctc ctcagatctt tggttttttgc tttaatttat taaatgtatt   1740
ttccatactg agtttaaaat ttattaattt gtaccttaag catttcccag ctgtgtaaaa   1800
acaataaaac tcaaatagga tgataaagaa taaaggacac tttgggtacc agaaaaaaaa   1860
aaaaaaaaaa aaaaaaaaaa aaaaaaaaaa aaaaaaaaa                          1899

<210> SEQ ID NO 62
<211> LENGTH: 3128
<212> TYPE: DNA
<213> ORGANISM: Homo sapiens

<400> SEQUENCE: 62
gcttcgcccc gtggcgcggt ttgaaatttt gcggggctca acggctcgcg gagcggctac     60
gcggagtgac atcgccggtg tttgcgggtg gttgttgctc tcggggccgt gtggagtagg    120
tctggacctg gactcacggc tgcttggagc gtccgccatg aggagaagtg aggtgctggc    180
ggaggagtcc atagtatgtc tgcagaaagc cctaaatcac cttcgggaaa tatgggagct    240
aattgggatt ccagaggacc agcggttaca agaactgagt gtggtaaaga agcatatcaa    300
ggaactcctg gatatgatga ttgctgaaga ggaaagcctg aaggaaagac tcatcaaaag    360
catatccgtc tgtcagaaag agctgaacac tctgtgcagc gagttacatg ttgagccatt    420
tcaggaagaa ggagagacga ccatcttgca actagaaaaa gatttgcgca cccaagtgga    480
attgatgcga aaacagaaaa aggagagaaa acaggaactg aagctacttc aagagcaaga    540
tcaagaactg tgcgaaattc tttgtatgcc ccactatgat attgacagtg cctcagtgcc    600
cagcttagaa gagctgaacc agttcaggca acatgtgaca actttgaggg aaacaaaggc    660
ttctaggcgt gaggagtttg tcagtataaa gagacagatc atactgtgta tggaagaatt    720
agaccacacc ccagacacaa gctttgaaag agatgtggtg tgtgaagacg aagatgcctt    780
ttgtttgtct ttggagaata ttgcaacact acaaaagttg ctacggcagc tggaaatgca    840
gaaatcacaa aatgaagcag tgtgtgaggg gctgcgtact caaatccgag agctctggga    900
caggttgcaa atacctgaag aagaaagaga agctgtggcc accattatgt ctgggtcaaa    960
ggccaaggtc cggaaagcgc tgcaattaga agtggatcgg ttggaagaac tgaaaatgca   1020
aaacatgaag aaagtgattg aggcaattcg agtggagctg gttcagtact gggaccagtg   1080
cttttatagc caggagcaga gacaagcttt tgcccctttc tgtgctgagg actacacaga   1140
aagtctgctc cagctccacg atgctgagat tgtgcggtta aaaaactact atgaagttca   1200
caaggaactc tttgaaggtg tccagaagtg ggaagaaacc tggaggcttt tcttagagtt   1260
tgagagaaaa gcttcagatc caaatcgatt tacaaaccga ggaggaaatc ttctaaaaga   1320
agaaaaacaa cgagccaagc tccagaaaat gctgcccaag ctggaagaag agttgaaggc   1380
acgaattgaa ttgtgggaac aggaacattc aaaggcattt atggtgaatg ggcagaaatt   1440
catggagtat gtgcagaac aatgggagat gcatcgattg gagaaagaga gagccaagca   1500
ggaaagacaa ctgaagaaca aaaaacagac agagacagag atgctgtatg cagcgctcc   1560 tcgaacacct agcaagcggc gaggactggc tcccaataca ccgggcaaag cacgtaagct   1620
gaacactacc accatgtcca atgctacggc aatagtagc attcggccta tctttggagg   1680
gacagtctac cactcccccg tgtctcgact tcctccttct ggcagcaagc cagtcgctgc   1740
ttccacctgt tcagggaaga aaacaccccg tactggcagg catggagcca acaaggagaa   1800
cctggagctc aacggcagca tcctgagtgg tgggtaccct ggctcggccc cctccagcg   1860 caacttcagc attaattctg ttgccagcac ctattctgag tttgcgaagg atccgtccct   1920
```

```
ctctgacagt tccactgttg ggcttcagcg agaactttca aaggcttcca aatctgatgc    1980
tacttctgga atcctcaatt caaccaacat ccagtcctga gaagccctga tcagtcaacc    2040
agctgtggct tcctgtgcct agactggacc taattatatg ggggtgactt tagttttttct   2100 tcagcttagg cgtgcttgaa accttggcca ggttccatga ccatgggcct aacttaaaga    2160
tgtgaatgag tgttacagtt gaaagcccat cataggttta gtggtcctag gagacttggt    2220
tttgacttat atacatgaaa agtttatggc aagaagtgca aattttagca tatgggccct    2280
gacttctcta ccacataatt ctacttgctg aagcatgatc aaagcttgtt ttatttcacc    2340
actgtaggaa aatgattgac tatgcccatc cctgggggta atttttggcat gtatacctgt   2400 aactagtaat taacatcttt tttgtttagg catgttcaat taatgctgta gctatcatag    2460
ctttgctctt acctgaagcc ttgtccccac cacacaggac agccttcctc ctgaagagaa    2520
tgtctttgtg tgtccgaagt tgagatggcc tgccctactg ccaagaggt gacaggaagg     2580 ctgggagcag ctttgttaaa ttgtgttcag ttctgttaca cagtgcattg ccctttgttg    2640
ggggtatgca tgtatgaaca cacatgcttg tcggaacgct ttctcggcgt ttgtcccttg    2700
gctctcatct cccccattcc tgtgcctact ttgcctgagt tcttctaccc ccgcagttgc    2760
cagccacatt gggagtctgt ttgttccaat gggttgagct gtctttgtcg tggagatctg    2820
gaactttgca catgtcacta ctggggaggt gttcctgctc tagcttccac gatgaggcgc    2880
cctctttacc tatcctctca atcactactc ttcttgaagc actattattt attcttccgc    2940
tgtctgcctg cagcagtact actgtcaaca tagtgtaaat ggttctcaaa agcttaccag    3000
tgtggacttg gtgttagcca cgctgtttac tcatacagta cgtgtcctgt ttttaaaata    3060
tacaattatt cttaaaaata aattaaaatc tgtatactta catttcaaaa agaaaaaaaa    3120
aaaaaaaa                                                              3128
```

<210> SEQ ID NO 63
<211> LENGTH: 2218
<212> TYPE: DNA
<213> ORGANISM: Homo sapiens

<400> SEQUENCE: 63

```
acagcgcgtg cgccgccgca agcatggctg gtgatgattg gacgactggt aacaggggc      60 ggagggctcc gaagtctggt tttgggcggg aattgaaacc gccgctgaag ccaacaagaa    120
tttgagaact gtaaatacca agccttgaaa gggaccatgg tgcggcctgt gagacataag    180
aaaccagtca attactcaca gtttgaccac tctgacagtg atgatgattt tgtttctgca    240
actgtaccct taaacaagaa atccagaaca gcaccaaagg agttaaaaca agataaaacca    300 aaacctaact tgaacaatct ccggaaagaa gaaatcccag tacaagagaa accccctaaa    360
aaaaggatgg ctttagatga caagctctac cagagagact tagaagttgc actagcttta    420
tcagtgaagg aacttccaac agtcaccact aatgtgcaga actctcaaga taaaagcatt    480
gaaaaacatg gcagtagtaa aatagaaaca atgaataagt ctcctcatat ctctaattgc    540
agtgtagcca gtgattattt agatttggat aagattactg tggaagatga tgttggtggt    600
gttcaaggga aaagaaaagc agcatctaaa gctgcagcac agcagaggaa gattcttctg    660
gaaggcagtg atggtgatag tgctaatgac actgaaccag actttgcacc tggtgaagat    720
tctgaggatg attctgattt ttgtgagagt gaggataatg acgaagactt ctctatgaga    780
aaaagtaaag ttaaagaaat taaaagaaa gaagtgaagg taaaatcccc agtagaaaag    840
```

```
aaagagaaga aatctaaatc caaatgtaat gctttggtga cttcggtgga ctctgctcca      900
gctgccgtca aatcagaatc tcagtccttg ccaaaaaagg tttctctgtc ttcagatacc      960
actaggaaac cattagaaat acgcagtcct tcagctgaaa gcaagaaacc taaatgggtc     1020
ccaccagcgg catctggagg tagcagaagt agcagcagcc cactggtggt agtgtctgtg     1080
aagtctccca atcagagtct ccgccttggc ttgtccagat tagcacgagt taaacctttg     1140
catccaaatg ccactagcac ctgagtgtgg tacaggagga atgtttggtt gggagaatca     1200 cagcttttaca agggtgttta tatttgattt gtgtttatat ttgaggcagg tattgtaata     1260
taaaggaatc cattaccatg tcctataaat gacctctagc cattttatga ttatgttctc     1320
tgtaaaactc ttcaagactt caatgagaag tttgtttata agaattatct tctcatacct     1380
ttccttgtga agagcgtatt ctgttttttct atcagttcga catgaagtcc acatcacatg    1440
ctgttctttt ctagttacat gatgtgcctt tctagctttg tctagtttat agcaccttaa     1500
ctttaactgt tcagttttat ctggcagagg aaaacattct tatttctttc agaagacatt     1560
tctgaaatct tataagctac ttaagctacg ttgtcagttt tatcgcaaag atgttttgta     1620
ttttagccaa atctttttat agtacaaact tagaattatt ttacacacta aaatggttgc     1680
agttttatgg catatgtctc cgatttagat ggttattctc tagaaaatag tatttaaaga     1740
cattttatga aatcttcatt gtcaaaacct ttaataaaag tggaaatatt ttgaaatgcc     1800 cttttttcttg ataccactca tccacgtgtt cctgattgtc cacatttcat gataaaatga    1860
gagctccgca gagaatgtta gccttttctgt tgtaaatgta atcttcaagt agtcactttt    1920
tgttaagttc tttagaaagt agttgtcaag tacttagtca tccctattat gatatgagat     1980
agtacagctt tcaggaagc ttagatctga atttactttg aaaaacaatt gtaatgaata      2040
ttttatattt acattgagaa tttcaactag cttctgatca atttttaata aaaaattttc     2100
aaatcatgtt agctgttaaa aaatgtataa taactcagtt tttcttggtt tatggaaata     2160
tctatattaa tgtgaaaata attaatttag aattgtgatt aaagtgagca tttgtcta      2218
```

<210> SEQ ID NO 64
<211> LENGTH: 1148
<212> TYPE: DNA
<213> ORGANISM: Homo sapiens

<400> SEQUENCE: 64

```
gcgccgagac ccgctcctgc agtattagtt cttgcagctg gtggtggcgg ctgaggcggc       60
atggatctca gcgagctgga gagagacaat acaggccgct gtcgcctgag ttcgcctgtg      120
cccgcggtgt gccgcaagga gccttgcgtc ctgggcgtcg atgaggcggg caggggcccc      180
gtgctgggcc ccatggtcta cgccatctgt tattgtcccc tgcctcgcct ggcagatctg      240
gaggcgctga agtggcaga ctcaaagacc ctattggaga gcgagcggga aaggctgttt       300
gcgaaaatgg aggacacgga cttgtcggc tgggcgctgg atgtgctgtc tccaaacctc       360
atctctacca gcatgcttgg gcgggtcaaa tacaacctga actccctgtc acatgataca      420
gccactgggc ttatacagta tgcattggac caggggcgtga acgtcaccca ggtattcgtg     480
gacaccgtag gatgccaga gcataccag gcgcggctgc agcaaagttt tcccgggatt       540
gaggtgacgg tcaaggccaa agcagatgcc ctctacccgg tggttagtgc tgccagcatc     600
tgtgccaagg tggccgggga ccaggccgtg aagaaatggc agttcgtgga gaaactgcag     660
gacttggata ctgattatgg ctcaggctac cccaatgatc ccaagacaaa agcgtggttg     720
aaggagcacg tggagcctgt gttcggcttc ccccagtttg tccggttcag ctggcgcacg     780
```

```
gcccagacca tcctggagaa agaggcggaa gatgttatat gggaggactc agcatccgag      840
aatcaggagg gactcaggaa gatcacatcc tacttcctca atgaagggtc ccaagcccgt      900
ccccgttctt cccaccgata tttcctggaa cgcggcctgg agtcagcaac cagcctctag      960
cagctgcctc tacgcgctct acctgcttcc ccaacccaga cattaaaatt gtttaaggag     1020
aaccacacgt aggggatgta cttttgggac agaagcaagg tgggagtgtg ctctgcagcc     1080
gggtccagct acttcctttt ggaaccttaa atagaatggg tgttggttga ttaattttat     1140
ttaaaaaa                                                              1148

<210> SEQ ID NO 65
<211> LENGTH: 2372
<212> TYPE: DNA
<213> ORGANISM: Homo sapiens

<400> SEQUENCE: 65
cgaagctagg gcggggcccg cgggctgagg cagcggctgt ggcggcgacg ctgggcgtga       60
ggtggcggcg gccgcgccct ggttgggtcc ccactgctct cggggcgcc atggacgagg      120 ccgtgggcga cctgaagcag gcgcttccct gtgtggccga gtcgccaacg gtccacgtgg      180
aggtgcatca gcgcggcagc agcactgcaa agaaagaaga cataaacctg agtgttagaa      240
agctactcaa cagacataat attgtgtttg gtgattacac atggactgag tttgatgaac      300
cttttttgac cagaaatgtg cagtctgtgt ctattattga cacagaatta aaggttaaag      360
actcacagcc catcgatttg agtgcatgca ctgttgcact tcacattttc cagctgaatg      420
aagatggccc cagcagtgaa aatctggagg aagagacaga aaacataatt gcagcaaatc      480
actgggttct acctgcagct gaattccatg ggctttggga cagcttggta tacgatgtgg      540
aagtcaaatc ccatctcctc gattatgtga tgacaacttt actgttttca gacaagaacg      600
tcaacagcaa cctcatcacc tggaaccggg tggtgctgct ccacggtcct cctggcactg      660
gaaaaacatc cctgtgtaaa gcgttagccc agaaattgac aattagactt tcaagcaggt      720
accgatatgg ccaattaatt gaaataaaca gccacagcct ctttctaag tggttttcgg      780 aaagtggcaa gctggtaacc aagatgtttc agaagattca ggatttgatt gatgataaag      840
acgccctggt gttcgtgctg attgatgagg tggagagtct cacagccgcc cgaaatgcct      900
gcagggcggg caccgagcca tcagatgcca tccgcgtggt caatgctgtc ttgacccaaa      960
ttgatcagat taaaggcat tccaatgttg tgattctgac cacttctaac atcaccgaga     1020
agatcgacgt ggccttcgtg gacagggctg acatcaagca gtacattggg ccaccctctg     1080
cagcagccat cttcaaaatc tacctctctt gtttggaaga actgatgaag tgtcagatca     1140 tatacctcg ccagcagctg ctgacccctcc gagagctaga gatgattggc ttcattgaaa     1200
acaacgtgtc aaaattgagc cttcttttga atgacatttc aaggaagagc gagggcctca     1260
gcggccgggt cctgagaaaa ctccccttc tggctcatgc gctgtatgtc caggccccca     1320
ccgtcaccat agagggtttc ctccaggccc tgtctctggc agtggacaag cagtttgaag     1380
agagaaagaa gcttgcagct acatctgat cctgggcttc cccatctggt gcttttccca     1440
tggagaacac acaaccagta agtgaggttg ccccacacag ccgtctccca gggaatccct     1500
tctgcaaacc aaacgttact tagactgcaa gctagaaagc caccaaggcc aggctttgtt     1560
aaaagaagtg tattctattt atgttgtttt aaaatgcata ctgagagaca acatcttgt     1620 cattttcact gtttgtaaaa gataattcag attgtttgtc tccttgtgaa gaaccatcga     1680
```

| | |
|---|---|
| aacctgtttg ttcccagccc acccccagtg gatgggatgc ataatgccag caagttttgt | 1740 |
| ttaacagcaa aaaaggaaga ttaatgcagg tgttatagaa gccagaagag aaactgtgtc | 1800 |
| accctaaaga agcatataat catagcatta aaaatgcaca cattactcca ggtggaaggt | 1860 |
| ggcaattgct ttctgatatc agctcgtttg atttagtgca aaaatgtttt caagactatt | 1920 |
| taatggatgt aaaaaagcct atttctacat tataccaact gagaaaaaaa tggtcggtaa | 1980 |
| agtgttcttt cataataaat aatcagacat ggtcccattt gcaggaaaag tgcagactct | 2040 |
| gagtgttcca gggaaacaca tgctggacat cccttgtaac ccggtatggg cgcccctgca | 2100 |
| ttgctgggat gtttctgccc acggttttgt ttgtgcaata cgttatcac atttctaatg | 2160 |
| aggattcaca ttaatataat ataaaataaa taggtcagtt actggtctct ttctccgaat | 2220 |
| gttatgtttt gcttttatct cacagtaaaa taaatataat taatggtttg catgtgaaat | 2280 |
| tcacttttga aagaacatgt taccttacct tttgttttag aagttttcaa gtattaaaat | 2340 |
| attttttaga aaaaaaaaa aaaaaaaaa aa | 2372 |

<210> SEQ ID NO 66
<211> LENGTH: 3735
<212> TYPE: DNA
<213> ORGANISM: Homo sapiens

<400> SEQUENCE: 66

| | |
|---|---|
| ggagtccccg aggtcacaag gcagtggcag gtgtctgtag tcctcgggtt gactgcagct | 60 |
| cgcggtggtc cctctccgag cccaggaagc cactccagtg ccgagggaga ggcctgggag | 120 |
| cgctcggagt gtgcgcggac tggagaaggg ggaggtggcg gagtgattcg tagagtaaat | 180 |
| tcggtaccga ggggcggggt cggggatttg aatcggtcgg cgggcggagg aggcgggtgg | 240 |
| aggaggctgc cgggcagagc gcaggccagg atcagcgcag gctgtgagtc caggtcagcc | 300 |
| gtcgggacct cgggctccgg gttcgaagag cggctcccgg ctgcgggtgc tttgccagga | 360 |
| gagcccttcc ggacagagga gccggggtct ggaaggagcg gccgacgcga cgctcgcctg | 420 |
| ccacggggct ctgggagtaa gcctgtctgc ctggcgggcc ttcaggtgcg gcgtgagaga | 480 |
| tggatgccaa ttcaaaagac aagcccctg aaaccaagga gtctgcaatg aataatgctg | 540 |
| gaaatgcctc tttcattttg ggaactggga agattgtgac tcctcagaag catgccgaat | 600 |
| tacctcctaa tccttgcaca ccagatactt ttaaatcacc tttgaacttt tccacagtaa | 660 |
| ccgtagagca attgggaatt acacctgaaa gctttgttag gaactctgca ggaaagtcat | 720 |
| catcctacct taaaaaatgt agacgacgtt ctgcagtcgg tgctcgggc tctcctgaaa | 780 |
| caaaccatct gattcgtttc attgctcggc agcaaaatat aaagaatgct aggaaatctc | 840 |
| ctttggcaca agattctcct tcccagggca gccctgcact gtatcgaaat gttaacactt | 900 |
| taagagaacg aatatcagcc ttccagtcag cttttcactc cataaaggaa aacgagaaaa | 960 |
| tgaccggctg tctggaattc tcagaggcag gaaaagagtc cgagatgaca gacttgacca | 1020 |
| gaaaggaagg tctcagcgct tgccagcagt ctgggttccc tgcagtgttg tcctccaaac | 1080 |
| gtcggagaat atcctatcag agagactctg atgaaaatct gacggatgct gaaggaaaag | 1140 |
| taattggtct ccagatattc aatattgata cagacagagc atgtgcagtt gaaacttctg | 1200 |
| tagatctttc tgagatatca tctaaacttg gttcaacaca gtctggattt ttagttgaag | 1260 |
| agtctcttcc cctttcagag ctcacagaga cttcaaatgc actaaaggtt gctgactgtg | 1320 |
| tagtgggcaa aggatcaagt gatgccgttt cgcctgacac gttcacagca gaagtgagct | 1380 |
| cagacgcagt ccctgatgtc aggtcaccag ctactccagc ctgcaggagg gaccttccca | 1440 |

-continued

```
cccccaagac ctttgtactt cgttctgtac tgaagaaacc ctctgttaag atgtgtctag    1500
agagcttaca ggaacactgt aacaacctct atgatgatga tgggactcat ccgagcttaa    1560
tctcaaatct cccaaactgt tgcaaagaga aagaagcaga agatgaagaa aattttgaag    1620
cacctgcctt tctaaatatg aggaagagga agagagttac ttttggagag acttaagcc     1680 cggaagtgtt tgatgaatct ttgccagcaa atactccatt gcgtaaagga ggaacacctg    1740
tttgtaaaaa agacttcagt ggtctcagtt ccctgctgct tgagcagtca cctgttcctg    1800
agccattacc tcaaccagat tttgatgaca agggggagaa tcttgaaaac atagaaccac    1860
ttcaagtatc atttgccgtt ctcagttctc ctaataaatc atcaatctct gagacccttt    1920
caggcactga tacctttagt tcttcaaata accatgagaa aatatcctct cctaaagttg    1980
gtagaataac aaggacttct aacagaagaa atcaattggt cagtgttgta gaagagagtg    2040
tttgcaactt attgaataca gaagttcagc cttgtaaaga aaagaaaatt aataggagga    2100
agtctcaaga aacaaagtgt acaaagagag cacttcctaa gaagagtcag gttttaaaaa    2160
gttgcagaaa gaagaaagga aagggaaaga aaagtgttca gaaatcttta tatggggaaa    2220
gagacattgc ttctaagaag cccctcctca gtcctattcc cgagctgcct gaagtccctg    2280
agatgacacc ttccattccg agcatccgaa gactgggttc aggttatttc agttcaaatg    2340
gcaaactgga agaagtgaag actcctaaaa atccagtgaa aagaaaggat cttttgcgtc    2400
atgacccaga tttgcatatg catcaaggct atgataaata tgatgtctct gaattctgct    2460
cttatataaa aagttcctca tcgcttggca atgctacttc tgatgaagat ccaaatacaa    2520
atataatgaa cattaatgaa aataaaaata ttccaaaagc aaaaaataag tcagaaagtg    2580
aaaatgaacc aaaagctgga actgacagtc ctgtttcttg tgcttctgta actgaagaac    2640
gtgtggcatc agatagtccc aaacctgctc tgaccctgca gcagggtcaa gaattttctg    2700
ctggtggtca aaatgcagaa aacctttgtc agttctttaa aatttcacca gatttaaaca    2760
taaagtgtga agaaaggat gacttcttag gagctgcaga aggaaaactg caatgcaatc     2820
gtttaatgcc taattcacaa aaagactgtc attgtttagg agatgtctta attgaaaata    2880
cgaaagaatc taaaagccag agtgaggatt tgggaagaaa acccatggaa gtagcagtg     2940 ttgtgagttg cagagacagg aaagatagaa gacgttccat gtgttattct gatggtcgaa    3000
gtttacattt ggaaaaaaat ggaaatcaca caccatcctc cagtgtgggc agctctgtag    3060
aaattagttt agaaaattct gaactgttta agatttgtc tgatgccatt gagcaaacct     3120
ttcagaggag aaatagtgaa accaaagtgc gacgtagcac gaggctacag aaggatttag    3180
aaaacgaagg tcttgtatgg atttcacttc cacttccttc cacttcccaa aaagccaaaa    3240
gaagaacaat atgtacattt gacagcagtg gatttgaaag tatgtctccc ataaaagaaa    3300
ctgtgtcctc cagacaaaaa ccgcagatgg cacctcccgt ctcagatcca gaaaacagcc    3360
agggccctgc tgctggttct tccgatgaac ctggtaagag gaggaagagc ttttgtatat    3420
ctacacttgc aaatactaaa gccacttccc agttcaaagg ctaccggaga agatcctctc    3480
ttaatgggaa gggagagagc tctctgactg ccttggaaag gattgaacat aatggagaaa    3540
gaaagcagta attgacattt cctgcagagt ctgtggcaag agggaaagta accatctatg    3600
ctgaaatgat ctgtctagtt cccattctct gttcaacctc agtgtttcaa aagttcctaa    3660
taaataaact catttgagtt gaacctactt ttatgtagaa ataaataagt ttcttcatca    3720
ttaaaaaaaa aaaaa                                                     3735
```

<210> SEQ ID NO 67
<211> LENGTH: 2803
<212> TYPE: DNA
<213> ORGANISM: Homo sapiens

<400> SEQUENCE: 67

| | | | | | |
|---|---|---|---|---|---|
| agcgcggaag | cggggagtta | aagagtctat | gcctgtcgtg | gaagctggcc | tggcccccgg | 60 |
| agctccctgg | agtcggtact | gggggcttcg | ttttgtacgc | accgttttct | ctctgtgcta | 120 |
| tgggagatgt | caaggaatca | aagatgcaaa | taacaccaga | aactccagga | aggatccctg | 180 |
| ttttaaatcc | ttttgaaagt | cctagtgatt | attctaatct | ccatgaacaa | actctcgcca | 240 |
| gtccttctgt | ttttaaatca | acaaaattac | caactccagg | gaaatttaga | tggtctattg | 300 |
| atcaactagc | tgtaataaat | cctgtagaaa | tagacccaga | agatattcat | cgtcaagctt | 360 |
| tatacttaag | tcattctcga | atagataaag | atgtggaaga | caaaagacaa | aaagccattg | 420 |
| aagagttttt | cactaaagat | gtcatcgtac | cctctccttg | gactgatcat | gaagggaaac | 480 |
| agctttcaca | atgtcattcc | agtaaatgca | ctaacataaa | tagtgactct | ccagttggaa | 540 |
| aaaagctgac | cattcattct | gagaaaagcg | atgctgcttg | tcagacattg | ctgtctcttc | 600 |
| ctgtggattt | taatttagaa | aatatattag | gtgactattt | tagagctgat | gaatttgcag | 660 |
| atcaatctcc | tggaaacctc | agttcttcat | ccctcagaag | aaagctgttt | ttagatggga | 720 |
| acggaagcat | ctccgactcc | ttaccttcgg | cttctcccgg | aagtcctcac | agtggtgttc | 780 |
| aaacatcact | agagatgttt | tattcaatag | atttgtctcc | tgtaaagtgt | aggagcccct | 840 |
| tgcagacacc | aagttcgggg | cagttttctt | ctagccctat | tcaggctagt | gcaaaaaat | 900 |
| acagcttggg | aagcataact | agtccttcgc | ctatttcttc | acccactttc | tcaccaattg | 960 |
| aatttcagat | aggagagact | ccactctcag | aacaaaggaa | gtttactgtt | cattctcctg | 1020 |
| atgcttcatc | tggaacaaat | tctaatggga | taactaatcc | gtgtatcaga | agtccttata | 1080 |
| tagatggctg | ctcgccaatt | aaaaattggt | ctcctatgag | acttcagatg | tatagtggtg | 1140 |
| gtactcagta | tcggacctca | gtgattcaga | tacctttttac | tcttgagact | caaggtgaag | 1200 |
| atgaggaaga | taaagagaat | attccttcca | cagatgtctc | atcacccgcc | atggatgctg | 1260 |
| ctggaataca | cctacggcag | tttagtaatg | aggcttctac | ccatggtaca | catttggttg | 1320 |
| tgactgccat | gtctgttaca | caaaatcagt | ccagtgcttc | tgagaaagaa | ttagcactgt | 1380 |
| tgcaggatgt | tgaaagggag | aaagacaata | acactgtgga | tatggttgat | cctatagaga | 1440 |
| tagcagatga | gaccacttgg | attaaggagc | cggttgataa | tggcagttta | cccatgactg | 1500 |
| attttgtaag | tggcattgcc | ttcagtattg | aaaactctca | tatgtgcatg | tcacctcttg | 1560 |
| ctgaaagcag | tgtcattcct | tgtgaaagca | gtaacattca | gatggatagt | ggctataata | 1620 |
| cgcagaattg | tggaagcaat | attatggata | cagttggggc | agaaagttac | tgcaaagaaa | 1680 |
| gtgatgcaca | acatgtgaa | gttgagagta | aatctcaagc | atttaatatg | aagcaagacc | 1740 |
| acacaacaca | gaggtgttgg | atgaaaacag | caagccctt | tcaatgcagc | agtccataga | 1800 |
| atgcctctgt | cagaatcaaa | gactaagctt | aagagttcct | cgcatatatc | gttgtgcaca | 1860 |
| ggatcaacat | gatggtgact | gggaaaaaat | tacttcaagt | aacatgctta | gctttccctc | 1920 |
| cttaatgtga | aaaatcaagg | gcttactgac | ataggaacaa | cagaaatgct | cctggaactt | 1980 |
| caagttgctg | aattataagt | ttattttta | tcaataaata | tttttatact | tacattgagt | 2040 |
| gatgtgttta | acaacaaatt | gtgacagagc | tgagtgctcc | tatcttacag | ggtcaatgaa | 2100 |
| ctacttatta | agccttactg | gtagcactga | atttagcagt | tctgagaaca | tgtgaaacta | 2160 |

```
tgttaaaact gaaggcacta tatattttta cataaaagct tgaacataca gatgaattat    2220
aacctatgtg aagaaatctt agatataaaa ctaactttc aaagatacaa aagaaattaa    2280
acaggtttcc tgaaatttta gttcttggtc tgttcacctc tgtggggaaa attcttagtt    2340
ccagtgataa ctgttctagt tactactttt aagtatgtaa atactagaaa ggtagtacta    2400
gtgacatcat cacgtgtatt gttatctatg gggcaaatgt gtggtgccca gaataaaata    2460
tacctcatgc ctagggtagg gacatccttt ccagctcaaa cgtgggtagg gatgtgggag    2520
aataagaatg tgggagaacc aagagaaaaa gtggggctgg gagagtggag ttcccgtagg    2580
gcataggcct gtgaagtaac actggggcag atatgtatgt tatatacaac tatttttta    2640 aaaaacttat atccatgttg ggagtagatg ggtatataac agtttggaaa tactatcttt    2700
ggagaatgta tttttgtatt tataaatcaa cttttaaaaa ctgtctcatt caaaagggaa    2760
taaagacctg tgtaaaaaaa aaaaaaaaaa aaaaaaaaa aaa                      2803
```

PROGNOSTIC MOLECULAR SIGNATURE OF SARCOMAS, AND USES THEREOF

CROSS-REFERENCE TO RELATED APPLICATIONS

This application is a National Stage entry of International Application No. PCT/FR2010/000323, filed Apr. 21, 2010, which claims priority to French Patent Application No. 09/01936 filed Apr. 22, 2009 and U.S. Patent Application No. 61/171,495 filed Apr. 22, 2009, the disclosure of the prior applications are incorporated in their entirety by reference.

FIELD OF THE INVENTION

The present invention relates to a prognostic molecular signature of sarcomas, in particular of genetically complex sarcomas, and to the use thereof for predicting the metastasis-free survival and the overall survival of sarcoma patients.

It finds many applications, in particular in the area of sarcoma prognosis or diagnosis or for monitoring the treatment of sarcoma patients.

PRIOR ART

Soft tissue sarcomas (STSs) in adults are rare and heterogeneous in terms of localization, histology, molecular abnormalities and prognosis. Poorly differentiated STSs are the commonest malignant tumors in adults, representing about 50% of pathological diagnoses, and mainly comprise sarcomas with a complex karyotype, namely leiomyosarcomas (LMS), undifferentiated sarcomas (US) or malignant fibrohistiocytomas (MFH), and dedifferentiated liposarcomas (DD-LPS) (FLETCHER et al., World Health Organization (WHO) classification of tumours. Pathology and genetics of tumours of soft tissue and bone. Lyons, IARC Press, 2002). At the genetic level, the poorly differentiated STSs can be divided into two main groups, a group with a complex genomic profile (80%) including essentially the USs, LMSs, pleomorphic rhabdomyosarcomas and pleomorphic liposarcomas, associated with very complex, but recurrent profiles of genomic imbalances (IDBAIH et al., Lab. Invest., 85 (2): 176-181, 2005; CHIBON et al., Cancer Genet. Cytogenet., 141 (1): 75-78, 2003; DERRE et al., Lab. Invest., 81 (2): 211-215, 2001), and a second group with a simple genetic profile (20%) based on a high level of limited amplifications and composed exclusively of the DD-LPSs (CHIBON et al., Cancer Genet. Cytogenet., 139 (1): 24-29, 2002; COINDRE et al., Mod. Pathol., 16 (3): 256-262, 2003). The STSs are aggressive tumors capable of local and metastatic relapse. Patients with such tumors usually have a poor prognosis, and 40 to 50% eventually develop distant metastases, principally in the lungs, generally within 5 years of diagnosis (WEITZ et al., J. Clin. Onc., 21 (14): 2719-2725, 2003; ZAGARS et al., Cancer, 97 (10): 2530-2543, 2003).

The clinical treatment of the STSs consists principally of surgical resection, with adjuvant therapies whose duration and nature depend on the surgical margins, the tumor histotype and the histologic grade. However, the benefits of adjuvant therapies such as chemotherapy are currently contested although recent studies tend to demonstrate an effect on local and distant relapses (SMAC, Lancet, 350 (9092): 1647-1654, 1997; FRUSTACI et al., J. Clin. Oncol., 19 (5): 1238-1247, 2001; PERVAIZ et al., Cancer, 113 (3): 573-581, 2008). Nevertheless, the efficacy of chemotherapy is marginal (from 3 to 10% according to the criterion for evaluation, PERVAIZ et al., 2008 op. cit.); this might result from selection of patients for whom tumor malignancy is evaluated by the histologic grade. Moreover, the management of patients depends essentially on the stage of the disease. Although it supplies valid information with respect to the clinical evolution of certain types of sarcomas, histologic typing has limited predictive value for other types of sarcomas, notably sarcomas that are unclassified, poorly differentiated and nontranslocation-associated. To increase the predictive value of histology in terms of prognosis, several grading systems have been elaborated (BRODERS et al., Surg. Gynecol, Obstet., 69: 267-280, 1939; RUSSELL et al., Cancer, 40 (4): 1562-1570, 1977; MARKHEDE et al., Cancer, 49 (8): 1721-1733, 1982; TROJANI et al., Int. J. Cancer, 33 (1): 37-42, 1984; COSTA et al., Cancer, (3): 530-541, 1984). Among the latter, the systems of the National Cancer Institute (NCI) (COSTA et al., 1984, op. cit.) and of the National Federation of Centers Combating Cancer (Fédération Nationale des Centres de Lutte Contre le Cancer, FNCLCC) (TROJANI et al., 1984, op. cit.) have been used widely although the second system slightly increases the capacity for predicting distant metastases and has been regarded as the "gold standard" for this (GUILLOU et al., J. Clin. Onc., 15 (1): 350-362, 1997).

To date, the histologic grade is the best criterion for predicting metastasis-free survival and overall survival. The FNCLCC grade, the most effective, was established more than 20 years ago and is still the system most commonly used. It is based on semi-quantitative evaluation of tumor differentiation, necrosis, and mitotic index. However, this system has several limitations: its reproducibility from one pathologist to another is not perfect, it does not apply to all types of sarcomas (COINDRE et al., Cancer, 91 (10): 1914-1926, 2001) and it is not informative for cases classified as grade 2 (which represent about 40% of cases). However, despite these limitations, for more than 20 years, no study has supplied prognostic criteria that can replace this histologic grading system.

The last ten years have seen the emergence of prognostic molecular signatures in an increasing number of pathologies. To date, the best example of molecular signature is certainly that of breast cancer in which an expression signature for predicting metastatic relapse was established in 2002 and then validated that same year by the same team on an independent group of 295 tumors (VAN'T VEER et al., Nature, 415 (6871): 530-536, 2002; VAN de VIJVER et al., N. Engl. J. Med., 347 (25): 1999-2009, 2002).

Until now, in the field of sarcomas, expression profiles have been established in particular for the purpose of identifying new diagnostic markers or for better understanding the oncogenesis of these tumors in relation to tumor differentiation (NIELSEN et al., Lancet, 359 (9314): 1301-1307, 2002; BAIRD et al., Cancer Res., 65 (20): 9226-9235, 2005; FRITZ et al., Cancer Res., 62 (11): 2993-2998, 2002; MATUSHANSKY et al., Am. J. Pathol., 172 (4): 1069-1080, 2008; SEGAL et al., Am. J. Pathol., 163 (2): 691-700, 2003; LEE et al., J. Cancer, 88 (4): 510-515, 2003; NAKAYAMA et al., Mod. Pathol., 20 (7): 749-759, 2007; SINGER et al., Cancer Res., 67 (14): 6626-6636, 2007). Only two studies, relating to 30 leiomyosarcomas (LEE et al., Cancer Res., 64 (20): 7201-7204, 2004) and to 89 pleomorphic sarcomas (FRANCIS et al., BMC Genomics, 8: 73, 2007) propose a prognostic molecular signature. However, these two signatures are composed of numerous genes (335 and 244, respectively) without a clear biological link between them.

Moreover, these two signatures were established on the basis of a relatively limited number of subtypes of specific sarcomas giving relatively low significance. Finally, to date, these two signatures have not been compared with the FNCLCC grading system and have not yet been validated on an independent group, thus limiting their clinical usefulness.

In the area of sarcomas, it should be noted that the number of studies seeking to correlate molecular changes to the prognosis is necessarily limited owing to the difficulty of obtaining a homogeneous study group of fully documented tumors. Also, so far no clear and proven correlation has been established between genetic profile and metastasis-free survival.

Accordingly, tumor progression is still difficult to predict within a group of sarcomas, and treatments are not as tailored as they could be. Consequently, there is a definite need for improving the prognosis and diagnosis of sarcomas and consequently ensuring better clinical after-care of patients.

One aim of the present invention is therefore to provide a grading system that is more effective, reliable and reproducible, to overcome the drawbacks of the prior art. Another aim of the present invention is to provide the means and kits for implementing said grading system.

DESCRIPTION OF THE INVENTION

Based on the assumption that the FNCLCC grading system could represent a phenotypic summary of genomic changes, the present inventors discovered completely unexpectedly that establishment of a molecular profile by means of emergent technologies, such as DNA chips, could enable changes/genes at the origin of tumor aggressiveness to be identified, thus offering the possibility of defining a more effective grading system based on molecular changes; this leads to a major advance in the area of analysis of sarcomas.

Whereas the number of studies seeking to correlate the molecular changes to the prognosis is limited owing to the difficulty of obtaining a homogeneous study group of fully documented tumors, the inventors initiated an original project with the aim of determining the genomic and expression profiles from 183 genetically complex primary tumors, untreated and completely documented, referenced in the database of the GSF (Groupe Sarcome Français/French Sarcoma Group), an integral part of the European Conticabase (www.conticabase.org). Group analysis was used for identifying the molecular changes associated with the patient's clinical outcome.

This approach, illustrated below in the experimental section, made it possible to identify a particular set of genes, called "pool" or "molecular signature", associated with genome complexity, tumor aggressiveness, and whose expression profile allowed establishment of a reliable prognosis of sarcoma patients, in particular for predicting the appearance of metastases, but also for distinguishing, within a group of sarcoma patients of the same histologic grade, subgroups having significantly different prognoses.

The present invention therefore relates, firstly, to a pool of polynucleotides comprising at least two polynucleotides selected from the polynucleotide sequences SEQ ID NO: 1 to SEQ ID NO: 67. In other words, the pool of polynucleotides of the invention can comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, or 67 polynucleotides selected from the polynucleotide sequences SEQ ID NO: 1 to SEQ ID NO: 67.

Analysis of the 67 genes identified (SEQ ID NO: 1 to SEQ ID NO: 67) by the Gene Ontology (GO) database showed, moreover, that they were all involved in the same biological process, i.e. control of chromosome integrity.

Furthermore, the inventors demonstrated that these genes can be distributed in 5 main groups according to their role in mitosis: point of control of mitosis and of the cell cycle (12 genes, SEQ ID NOs: 1-12); biogenesis of chromosomes, condensation, alignment and segregation (26 genes, SEQ ID NOs: 13-38); mitotic spindle and centrosome (12 genes, SEQ ID NOs: 39-50); microtubular motor, kinesin complex (8 genes, SEQ ID NOs: 51-58), and cytokinesis (4 genes, SEQ ID NOs: 59-62); among the last 5 genes, grouped together on the basis of experimental results (SEQ ID NOs: 63-67), 3 are known to be involved in chromosomal instability (SEQ ID NOs: 63-65) and 2 are associated with the histologic grade according to the study (SEQ ID NOs: 66 and 67).

Table 1 below gives the name of each of the genes, their distribution in five main groups, and their respective sequences (GenBank references and SEQ ID NO:).

TABLE 1

| SET | Name of the gene | ProbeSet Affymétrix ™ reference | GenBank reference | SEQ ID NO: |
|---|---|---|---|---|
| Set 1: mitosis and cell cycle | ASPM | 219918_a_at | NM_018136 | 1 |
| | FOXM1 | 202580_x_at | NM_021953 | 2 |
| | PAK3/UBE2C | 202954_at | NM_002578 | 3 |
| | CDC7 | 204510_at | NM_003503 | 4 |
| | CDC20 | 202870_s_at | NM_001255 | 5 |
| | CDC45L | 204126_s_at | NM_003504 | 6 |
| | CCNA2 | 203418_at | NM_001237 | 7 |
| | CCNB1 | 214710_s_at | NM_031966 | 8 |
| | CCNB2 | 202705_at | NM_004701 | 9 |
| | CKS2 | 204170_s_at | NM_001827 | 10 |
| | MELK | 204825_at | NM_014791 | 11 |
| | CDCA3 | 223307_at | NM_031299 | 12 |
| Set 2: biogenesis of the chromosomes, alignment, segregation | NCAPH | 212949_at | NM_015341 | 13 |
| | HP1BP3 | 1554251_at | NM_016287 | 14 |
| | CENPA | 204962_s_at | NM_001042426 | 15 |
| | KIAA1794 | 213007_at | NM_018193 | 16 |
| | SMC2 | 204240_s_at | NM_001042550 | 17 |
| | CHEK1 | 205394_at | NM_001274 | 18 |
| | H2AFX | 205436_s_at | NM_002105 | 19 |
| | OIP5 | 213599_at | NM_007280 | 20 |
| | MCM2 | 202107_s_at | NM_004526 | 21 |
| | MCM7 | 210983_s_at | NM_005916 | 22 |
| | BIRC5 | 202095_s_at | NM_001012270 | 23 |
| | AURKA | 204092_s_at | NM_003600 | 24 |
| | MAD2L1 | 1554768_a_at | NM_002358 | 25 |
| | BUB1 | 215509_s_at | NM_004336 | 26 |
| | AURKB | 239219_at | NM_004217 | 27 |
| | BUB1B | 203755_at | NM_001211 | 28 |
| | SGOL2 | 230165_at | NM 152524 | 29 |
| | PTTG1 | 203554_x_at | NM_004219 | 30 |
| | CENPE | 205046_at | NM_001813 | 31 |
| | NUF2 | 223381_at | NM_031423 | 32 |
| | CDCA8 | 221520_s_at | NM_018101 | 33 |
| | CENPL | 1554271_a_at | NM_033319 | 34 |
| | ZWINT | 204026_s_at | NM_001005413 | 35 |
| | SPBC25 | 209891_at | NM_020675 | 36 |
| | TOP2A | 201291_s_at | NM_001067 | 37 |
| | ESPL1 | 38158_at | NM_012291 | 38 |
| Set 3: mitotic spindle and centrosome | CDC2 | 203213_at | NM_001786 | 39 |
| | TTK | 204822_at | NM_003318 | 40 |
| | RRM2 | 201890_at | NM_001034 | 41 |
| | SPAG5 | 203145_at | NM_006461 | 42 |
| | FBX05 | 234863_x_at | NM_012177 | 43 |
| | NDE1 | 222625_s_at | NM_017668 | 44 |
| | CDC6 | 203967_at | NM_001254 | 45 |

TABLE 1-continued

| SET | Name of the gene | ProbeSet Affymétrix ™ reference | GenBank reference | SEQ ID NO: |
|---|---|---|---|---|
| | PLK4 | 204886_at | NM_014264 | 46 |
| | NEK2 | 204641_at | NM_002497 | 47 |
| | TPX2 | 210052_s_at | NM_012112 | 48 |
| | CEP55 | 218542_at | NM_018131 | 49 |
| | CKAP5 | 1555278_a_at | NM_001008938 | 50 |
| Set 4: Microtubules | KIF11 | 204444_at | NM_004523 | 51 |
| | KIF15 | 219306_at | NM_020242 | 52 |
| | KIF23 | 244427_at | NM_004856 | 53 |
| | KIF4A | 218355_at | NM_012310 | 54 |
| | KIF14 | 236641_at | NM_014875 | 55 |
| | KIF18A | 221258_s_at | NM_031217 | 56 |
| | KIF20A | 218755_at | NM_005733 | 57 |
| | KIF2C | 209408_at | NM_006845 | 58 |
| Cytokinesis | ECT2 | 219787_s_at | NM_018098 | 59 |
| | ANLN | 1552619_a_at | NM_018685 | 60 |
| | PBK | 219148_at | NM_018492 | 61 |
| | PRC1 | 218009_s_at | NM_003981 | 62 |
| Set 5: Carter instability Grade in the study | RAD51AP1 | 204146_at | NM_006479 | 63 |
| | RNASEH2A | 203022_at | NM_006397 | 64 |
| | TRIP13 | 204033_at | NM_004237 | 65 |
| | CDCA2 | 236957_at | NM_152562 | 66 |
| | C13orf34 | 219544_at | NM_024808 | 67 |

Advantageously, the pool of polynucleotides can comprise the polynucleotides of sequences SEQ ID NO: 10, SEQ ID NO: 3, SEQ ID NO: 47, SEQ ID NO: 58, SEQ ID NO: 24.

Advantageously, the pool of polynucleotides can comprise the polynucleotides of sequences SEQ ID NO: 10, SEQ ID NO: 3, SEQ ID NO: 47, SEQ ID NO: 58, SEQ ID NO: 24 and at least one gene whose sequence is selected from the other 62 gene sequences identified in the context of the invention. In other words, the pool of polynucleotides can comprise the polynucleotides of sequences SEQ ID NO: 10, SEQ ID NO: 3, SEQ ID NO: 47, SEQ ID NO: 58, SEQ ID NO: 24 and at least one polynucleotide whose sequence is selected from the sequences SEQ ID NO: 1, SEQ ID NO: 2, SEQ ID NO: 4 to SEQ ID NO: 9, SEQ ID NO: 11 to SEQ ID NO: 23, SEQ ID NO: 25 to SEQ ID NO: 46, SEQ ID NO: 48 to SEQ ID NO: 57, SEQ ID NO: 59 to SEQ ID NO: 67.

Alternatively, the pool of polynucleotides can be constituted of the polynucleotides of sequences SEQ ID NO: 10, SEQ ID NO: 3, SEQ ID NO: 47, SEQ ID NO: 58 and SEQ ID NO: 24. In other words, the pool of polynucleotides can comprise only the polynucleotides of sequences SEQ ID NO: 10, SEQ ID NO: 3, SEQ ID NO: 47, SEQ ID NO: 58 and SEQ ID NO: 24.

Alternatively, the pool of polynucleotides of the invention can be constituted of the polynucleotides of sequences SEQ ID NO: 10, SEQ ID NO: 3, SEQ ID NO: 47, SEQ ID NO: 58, SEQ ID NO: 24 and of at least one gene whose sequence is selected from the other 62 gene sequences identified in the context of the invention. In other words, the pool of polynucleotides can be constituted only of the polynucleotides of sequences SEQ ID NO: 10, SEQ ID NO: 3, SEQ ID NO: 47, SEQ ID NO: 58 and SEQ ID NO: 24 and of at least one polynucleotide whose sequence is selected from the sequences SEQ ID NO: 1, SEQ ID NO: 2, SEQ ID NO: 4 to SEQ ID NO: 9, SEQ ID NO: 11 to SEQ ID NO: 23, SEQ ID NO: 25 to SEQ ID NO: 46, SEQ ID NO: 48 to SEQ ID NO: 57, SEQ ID NO: 59 to SEQ ID NO: 67.

According to another embodiment of the present invention, the pool of polynucleotides of the invention can comprise at least one polynucleotide selected from each of the following sets of polynucleotides:

Set 1: SEQ ID NO: 1 to SEQ ID NO: 12;
Set 2: SEQ ID NO: 13 to SEQ ID NO: 38;
Set 3: SEQ ID NO: 39 to SEQ ID NO: 50;
Set 4: SEQ ID NO: 51 to SEQ ID NO: 58, and SEQ ID NO: 59 to SEQ ID NO: 62;
Set 5: SEQ ID NO: 63 to SEQ ID NO: 65, and SEQ ID NO: 66 to SEQ ID NO: 67.

According to another embodiment of the present invention, the pool of polynucleotides of the present invention can be selected from Sets 1 to 5. In other words, the pool of at least two polynucleotides can be constituted wholly or partly of Set 1, Set 2, Set 3, Set 4 or Set 5. In other words, the pool of the present invention can be constituted wholly or partly of Set 1, or wholly or partly of set 2, or wholly or partly of set 3, or wholly or partly of set 4, or wholly or partly of set 5.

According to another embodiment of the present invention, the pool of polynucleotides can comprise the polynucleotides of sequences SEQ ID NO: 10, SEQ ID NO: 3, SEQ ID NO: 47, SEQ ID NO: 58 and SEQ ID NO: 24 and at least one polynucleotide selected from set 5. This pool of polynucleotides can further comprise at least one of the other genes identified in the context of the invention.

According to another embodiment of the present invention, the pool of polynucleotides can be constituted of the polynucleotides of sequences SEQ ID NO: 10, SEQ ID NO: 3, SEQ ID NO: 47, SEQ ID NO: 58 and SEQ ID NO: 24 and of at least one polynucleotide selected from set 5.

According to another embodiment of the present invention, the pool of polynucleotides of the invention comprises the polynucleotides of sequences SEQ ID NO: 1 to SEQ ID NO: 67. It can for example be a pool consisting of the sequences SEQ ID NO: 1 to SEQ ID NO: 67.

Regardless of the embodiment of the invention, advantageously, the pool of polynucleotides can comprise advantageously at most 10 polynucleotides. It can for example be a pool comprising at most 10 polynucleotides, comprising the polynucleotides of sequences SEQ ID NO: 10, SEQ ID NO: 3, SEQ ID NO: 47, SEQ ID NO: 58 and SEQ ID NO: 24 and at least one polynucleotide of sequence selected from SEQ ID NO: 1, SEQ ID NO: 2, SEQ ID NO: 4 to SEQ ID NO: 9, SEQ ID NO: 11 to SEQ ID NO: 23, SEQ ID NO: 25 to SEQ ID NO: 46, SEQ ID NO: 48 to SEQ ID NO: 57, SEQ ID NO: 59 to SEQ ID NO: 67.

Regardless of the embodiment of the present invention, advantageously the pool of polynucleotides of the invention is immobilized on a support, for example a solid support or a liquid support. In the case when the support is a liquid support, it can comprise beads on which the nucleic acids are fixed. The liquid medium can be a cell culture supernatant, serum, plasma, this list not being exhaustive. It can for example be the support employed in the Luminex® technology. In the case when the support is a solid support, it is preferably selected from the group comprising a nylon membrane, a nitrocellulose membrane, a glass plate, glass beads, a membrane on a glass support or a silicon chip, a plastic support. Especially preferably, the solid support can be a nucleic acid chip, for example a DNA chip (also called gene chip, biochip, expression chip). Said chips allow quantitative measurement of a change in expression (differential expression) of two or more polynucleotides of the pool of polynucleotides of the invention between (i) 2 experimental conditions: generally a reference condition and a pathological condition or (ii) several tumors in order to determine a mean value of expression, as a function of which the tumors can be classified relative to one other. As a nonlimiting example, it can be an Affimétrix® DNA chip, or a DNA chip from the company Agilent Technologies.

The genes identified by the present inventors, all of which are involved in the same biological process, can moreover be potential targets of novel therapeutic approaches targeting the early step of acquisition of metastatic potential. Moreover, a vital prognosis of patients on the basis of the expression profile of these genes can be made very early, or even during the initial diagnosis.

Thus, according to a particular embodiment of the present invention, the pool of polynucleotides of the invention can be used for the detection, prognosis, diagnosis of a soft tissue sarcoma (STS) or of a gastrointestinal stromal tumor (GIST), or for monitoring the treatment of a patient with a soft tissue sarcoma (STS) or a gastrointestinal stromal tumor (GIST).

According to another particular embodiment of the present invention, the pool of polynucleotides of the invention can be used for obtaining a compound intended for treating a soft tissue sarcoma (STS) or a gastrointestinal stromal tumor (GIST).

In order to identify, generally from the data of DNA expression chips, the expression profile associated with a prognosis group, two main approaches can be used, the supervised descending or "top-down" approach intended for selecting the genes directly correlated with a poor prognosis (VAN'T VEER et al., 2002, op. cit.; SOTIRIOU et al., J. Natl. Cancer Inst, 98 (4): 262-272, 2006) and the supervised "bottom-up" approach by which the expression profiles associated with a particular biological phenotype are firstly identified and then subsequently correlated to a clinical outcome (SOTIRIOU et al., N. Engl. J. Med., 360 (8): 790-800, 2009). In the context of the present invention, the second "bottom-up" approach was applied in the sense that the tumor expression profiles were compared as a function of the biological phenotypes (chromosomal instability, genomic complexity and histologic grades) but instead of direct selection of the genes, the biological pathways particularly relevant to the phenotypes tested were first identified and then the genes significantly involved in these pathways were identified. This selection of biological pathway (and not of genes) is the important step that led to the fortunate results of the present invention in a heterogeneous group such as that of nontranslocation-associated sarcomas, and moreover in different types of tumors such as GISTs (gastrointestinal stromal tumors) and breast cancers.

The present invention therefore also relates to an in-vitro method of selection of a pool of polynucleotides, for example those of the invention, comprising the following steps:

a) supplying tumor biological samples obtained from patients with a soft tissue sarcoma (STS) or a gastrointestinal stromal tumor (GIST);

b) detecting and/or quantifying each of the polynucleotides, separately in each of the tumor biological samples;

c) comparing the expression profile of the pools of polynucleotides obtained in step c) relative to a biological phenotype, preferably of chromosomal instability, genomic complexity or histologic grade, for each of the tumor biological samples;

d) selecting the statistically significant (p<$10^{-5}$) biological pathway for the phenotype tested;

e) selecting the polynucleotides significantly involved in this biological pathway, and whose expression is indicative of the probability of appearance of metastases.

"Expression profile" means the totality of the results obtained when the expression of a set of polynucleotides is determined. Said profile facilitates the use of quantitative statistical analysis techniques and permits rapid visual comparison of the results. Preferably, said profile is obtained from a solid support, such as a DNA chip.

"Biological phenotype" means, in the sense of the present invention, the manifestation of a genetic status, or the set of observable characteristics characterizing a sample obtained from a patient with an STS or a GIST, which reflect the expression of the information carried by the chromosomes (the genotype).

"Chromosomal instability" means, in the sense of the present invention, clonal or nonclonal rearrangements. This instability leads to losses and gains of chromosome arms and to unbalanced chromosome rearrangements. The instability of the chromosomes within the nucleus of an individual's cells makes the latter more vulnerable in terms of neoplasia (appearance of cancer). It is in the tumor cells that this instability is found.

"Genomic complexity" means, in the sense of the present invention, determination of the number of imbalances and of the nature of the chromosome fragments involved.

"Histologic grade" means, in the sense of the present invention, a consensual indicator of tumor proliferation, risk of metastases and response to adjuvant therapy (chemotherapy). The histologic or tumor grade is a decision factor for treatment of a tumor. It is determined by histologic examination of the tumor and the grading system used is for example that of the FNCLCC. This system adopted by the Fédération Nationale des Centres de Lutte Contre le Cancer (FNCLCC) is based on the following 3 characteristics:

| Tumor differentiation | Mitotic index | Tumor necrosis |
|---|---|---|
| Score 1 | Score 1 | Score 0 |
| Sarcoma resembling normal adult tissue | 0-9 mitoses for 10 fields | no necrosis |
| Example: well differentiated liposarcoma | Score 2 10-19 mitoses for 10 fields | Score 1 <50% of tumor necrosis |
| Score 2 Sarcoma for which the diagnosis of histologic type is certain Example: myxoid liposarcoma | Score 3 >19 mitoses for 10 fields one field measures 0.1734 mm$^2$ | Score 2 >50% of tumor necrosis |
| Score 3 Embryonic sarcoma, epithelioid sarcoma, synovial sarcoma, clear cell sarcoma, alveolar soft part sarcoma, undifferentiated sarcoma and sarcoma for which the histologic type is uncertain. | | |

The histologic grade of soft tissue tumors of the FNCLCC is the sum of the 3 scores "Differentiation", "Mitotic index" and "Tumor necrosis": Grade 1 (total score of 2 or 3), Grade 2 (total score of 4 or 5), and Grade 3 (total score from 6 to 8).

The present invention also relates to an in-vitro method of analysis of a soft tissue sarcoma (STS) or of a gastrointestinal stromal tumor (GIST), said method comprising determination of the expression level of a pool of polynucleotides according to the invention in a tumor biological sample.

"Tumor biological sample" means, in the sense of the present invention, a tissue sample obtained optionally (i) from a primary tumor (ii) from the center of a tumor (iii) from a site in the tumor other than the center and (iv) from any tumor localized outside of the tumor tissue per se of a patient with an STS. Said tumor biological sample can originate for example from surgery or from a tumor resection performed on a patient's STS, from a biopsy where a portion of the tumor tissue is collected from a patient's STS for subsequent analysis; from a blood sample, for example of whole blood, plasma or serum, containing tumor cells from the primary tumor or tumor proteins produced by the tumor cells from the primary tumor.

The expression level of a pool of polynucleotides of the present invention can be determined by any method known from the prior art. For example, the expression level of at least two polynucleotides implicated in the molecular signature of the invention in the samples obtained from patients with an STS can be determined by measuring the level of mRNA corresponding to the polynucleotide and/or the protein encoded by the polynucleotide. The RNA can be isolated from the samples by methods that are well known by a person skilled in the art, for example by that described in AUSUBEL et al. (Curr. Protocols Mol. Biol., 1: 4.1.1-4.2.9 and 4.5.1-4.5.3, John Wiley & Sons, Inc., 1996). The methods for detecting the expression level of mRNA that can be used for implementing the present invention are well known in the prior art and comprise, but are not limited to, expression chips, Northern blotting, real-time quantitative PCR, RT-PCR, RT-PCT with Taqman probes or microfluidic cards, and generally, hybridization techniques (namely association, by noncovalent bonds, of two single-stranded polynucleotides that are fully complementary or sufficiently complementary for hybridizing to one another, to form a double-stranded structure).

Advantageously, when the pool of polynucleotides comprises at most 10 polynucleotides, the expression level of a pool of polynucleotides of the present invention can be determined routinely by quantitative PCR. It may moreover be possible to use RNAs obtained from paraffin blocks containing samples of tissues or organs, or biological samples.

According to the invention, a particularly effective method for detecting the level of mRNA transcripts expressed from a plurality of polynucleotides described involves the hybridization of labeled mRNA to an oligonucleotide chip (also called DNA chip, gene chip, expression chips). Said method provides simultaneous determination of the transcription level of a plurality of polynucleotides to generate expression profiles of the polynucleotides.

The oligonucleotides used in this method of hybridization are generally fixed on a support, for example a solid support or a liquid support. In the case when the support is a liquid support, it can comprise beads on which the nucleic acids are fixed. The liquid medium can be a cell culture supernatant, serum, plasma, this list not being exhaustive. It can for example be the support employed in Luminex® technology. Examples of solid supports comprise, but are not limited to, membranes, filters, slides, paper, nylon, fibers, beads whether or not magnetic, gels, polymers and any solid support known by a person skilled in the art. Any solid support on which oligonucleotides can be immobilized, either directly or indirectly, either covalently or noncovalently, can be used. A particularly advantageous solid support consists of a nucleic acid chip, in particular a DNA chip. These chips contain a particular oligonucleotide probe in a predefined localization of the chip. Each predefined localization can contain more than one molecule of the particular probe. Because the oligonucleotides are located at specific positions of the support, the hybridization profiles and the intensities (which together form a unique expression profile) can be interpreted in terms of expression level of particular polynucleotides.

The oligonucleotide probes are preferably of sufficient length to hybridize specifically, only to the complementary transcripts of the polynucleotides of the invention. "Oligonucleotides" means, in the sense of the present invention, a single-stranded nucleic acid. Generally the oligonucleotide probes consist of 16-20 nucleotides, and in certain cases up to 25 nucleotides, or even up to 500 nucleotides or more.

Once the probes are brought into contact with the mRNA or a copy of the cDNA, the presence of the mRNA or of the hybridized cDNA is detected by methods known from the prior art. For example, the oligonucleotide probes are labeled with one or more markers to permit detection of the hybridized probe/target polynucleotide complexes. The markers can comprise compositions that can be detected by spectroscopic, biochemical, photochemical, bioelectronic, immunochemical, electrical, optical or chemical means. Examples of markers comprise, but are not limited to, radioisotopes, chemiluminescent compounds, labeled binding proteins, heavy metal atoms, spectroscopic markers, such as fluorescent markers and dyes, bound enzymes, mass spectrometry labels and magnetic markers. For example, it may be $Cy^3/Cy^5$ or Alexa labeling for biochips, FAM (6-carboxyfluorescein) or TAMRA (tetra-methyl-6-carboxyrhodamine) labeling for Taqman probes.

The oligonucleotide probe chips for monitoring expression can be prepared and used according to methods that are well known in the prior art, as described for example in LOCKHART et al. (Nature Biotechnol., 14: 1675-1680, 1996; McGALL et al., Proc. Natl. Acad. Sci. USA., 93: 13555-13460, 1996; U.S. Pat. No. 6,040,138. Said biochips are commercially available, for example from Affimétrix (Santa Clara, Calif.).

It is also possible to detect the expression of a protein encoded by two or more of the polynucleotides implicated in the molecular signature of the invention. This can be performed by methods that are well known from the prior art, such as, for example, the use of a probe that is labeled detectably, or that can be labeled subsequently. Generally, the probe is an antibody that recognizes the protein expressed. The expression level of the protein in the sample is then determined by an immunoassay technique using antibodies, for example dot blotting, Western blotting, ELISA, immunohistochemistry, FACS, etc.

According to a particular embodiment, the method of the invention makes it possible to establish the prognosis of a patient with an STS or a GIST, and in particular makes it possible to determine the risk of/predict the appearance of metastases.

"Predict the appearance of metastases" means, in the sense of the present invention, determine a relative value making it possible to quantify the probability of appearance of metastases of one or more tissues or organs, in a patient with an STS or a GIST. Preferably, the prediction of the appearance of metastases is expressed by a statistical value, including a p value, calculated from the values of expression obtained for each of the polynucleotides tested.

According to another particular embodiment, the method of the invention makes it possible to establish the prognosis of a patient with an STS or a GIST, in particular to distinguish subgroups of good or poor prognosis in a group of soft tissue sarcomas (STS) or of a gastrointestinal stromal tumor (GIST) initially regarded as belonging to the same histologic grade.

"Good prognosis" means, in the sense of the present invention, the indication of patients who are not likely to present a relapse, i.e. appearance of metastases, during their treatment or within 5 to 6 years following their treatment, i.e. a significantly different long-term metastasis-free survival. Thus, in the context of the present invention, it can be considered that patients with an STS or a GIST belong to a "good prognosis" subgroup when they under-express the genes of the molecular signature of the invention and are likely to develop metastases in less than 20% of cases of sarcomas of any type, and in particular in none of the cases of GIST. Conversely, "poor prognosis" means the indication of patients likely to present a relapse (appearance of metastases) during their treatment or within 5 to 6 years following their treatment. Thus, in the context of the present invention, it can be considered that patients with an STS or a GIST belong to a poor prognosis subgroup when they overexpress the genes of the molecular signature and are likely to develop metastases in at least 50% of cases.

Advantageously, determination of the expression level of the pool of polynucleotides in the method of the invention is performed on a nucleic acid chip, also called biochip, DNA chips, gene chip, expression chip. Said chips allow quantitative measurement and rapid visualization of a change in expression level, or differential expression, of two or more polynucleotides between (i) 2 experimental conditions, for example a reference and a pathological experimental condition, from a biological sample from a patient or (ii) several tumors in order to determine a mean value of expression, as a function of which the tumors can be classified relative to one other. As a nonlimiting example, it is possible to use Affimétrix™ DNA chips, or DNA chips of the company Agilent Technologies.

According to a particular embodiment, the method of the invention can be used for the detection, prognosis, diagnosis of a soft tissue sarcoma (STS) or of a gastrointestinal stromal tumor (GIST), or for monitoring the treatment of a patient with a soft tissue sarcoma (STS) or a gastrointestinal stromal tumor (GIST), comprising application of a method of the invention on the nucleic acids of a biological sample from said patient.

The present invention also relates to an in-vitro method of predicting the appearance of metastases in a patient with a soft tissue sarcoma (STS) or a gastrointestinal stromal tumor (GIST) comprising the following steps:

a) supplying a tumor biological sample previously collected from said patient to be tested;

b) determining, in said tumor biological sample, the expression level of a pool of polynucleotides of the invention;

c) comparing the expression level obtained in step b) with the expression level of the same pool of polynucleotides measured in a control biological sample; a deregulation of the expression level of the pool of oligonucleotides relative to its corresponding expression level measured in a control biological sample being predictive of the appearance of metastasis.

"Deregulation of the expression level" means the overexpression or the underexpression of two or more polynucleotides of a pool of polynucleotides according to the invention measured in a tumor biological sample of a patient with an STS or a GIST to be tested, relative to the corresponding expression measured in a control biological sample as defined below. In particular, a higher expression level in the tumor biological sample of a patient with an STS or a GIST to be tested relative to that of a control biological sample is an indication of a patient who is likely to develop metastases, which is comparable to indication of a poor prognosis. Conversely, a lower expression level in the tumor biological sample from a patient with an STS or a GIST to be tested relative to that of a control biological sample is an indication of a patient who is unlikely to develop metastases, i.e. comparable to indication of a good prognosis.

"Control biological sample" means, in the sense of the present invention, (i) a tissue sample obtained from a tumor of a patient with an STS or a GIST other than the one to be tested or (ii) a tissue sample from a healthy subject, namely an individual not presenting any pathology or pathological symptoms diagnosed by a physician. Thus, the tumors can be classified relative to one other, as a function of the expression level of the genes of the molecular signature of the invention in each case.

The present invention also relates to an in-vitro method of evaluation of the prognosis of a patient with a soft tissue sarcoma (STS) or a gastrointestinal stromal tumor (GIST), comprising the following steps:

a) supplying a tumor biological sample previously collected from the patient with an STS or a gastrointestinal stromal tumor (GIST) to be tested;

b) determining, in said tumor biological sample, the expression level of a pool of polynucleotides of the invention;

c) comparing the expression level obtained in step b) with the expression level of the same pool of polynucleotides measured in a control biological sample, where a deregulation of the expression level of the pool of oligonucleotides relative to its corresponding expression level measured in a control biological sample makes it possible to identify a subgroup of good prognosis or a subgroup of poor prognosis.

The present invention also relates to an in-vitro method of screening of candidate compounds for treating a soft tissue sarcoma (STS) or a gastrointestinal stromal tumor (GIST) comprising the following steps:

a) bringing a tumor biological sample previously collected into contact with a test compound;

b) determining, in said tumor biological sample, the expression level of a pool of polynucleotides of the invention;

c) comparing said expression level obtained in step b) with that of the same tumor biological sample that has not been brought into contact with the test compound, where a decrease in the expression level in the tumor biological sample in the presence of the test compound relative to that of the tumor biological sample in the absence of the test compound is an indication of a candidate compound for treating an STS or a GIST.

The present invention also relates to an in-vitro method of monitoring the antimetastatic efficacy of a treatment of a patient with a soft tissue sarcoma (STS) or a gastrointestinal stromal tumor (GIST), comprising the following steps:

a) supplying a tumor biological sample previously collected from said treated patient to be tested;

b) determining, in said tumor biological sample, the expression level of a pool of polynucleotides of the invention;

c) comparing said expression level obtained in step b) with that of a control biological sample or of a tumor biological sample from said patient before treatment, where a decrease in the expression level of the tumor biological sample after treatment relative to that of the control biological sample or of the tumor biological sample before treatment is an indication of antimetastatic efficacy of the therapeutic treatment.

The present invention relates, fourthly, to a kit comprising a pool of polynucleotides of the invention.

According to the invention, this kit can be used for example for the in-vitro prediction of the appearance of metastases and/or for evaluation of the prognosis of a patient with a soft tissue sarcoma (STS) or a gastrointestinal stromal tumor (GIST) and/or for monitoring the antimetastatic efficacy of a therapeutic treatment of a patient with a soft tissue sarcoma (STS) or a gastrointestinal stromal tumor (GIST).

According to the invention, this kit can further comprise means for detecting and/or quantifying the expression of a pool of nucleotides of the invention. These means can be for example one of those defined above or given in the following examples.

The present invention relates, fifthly, to a nucleic acid chip, in particular to a DNA chip, comprising or consisting of a pool of polynucleotides of the invention. This DNA chip can be for example as defined above, notably concerning the support.

Advantageously, a nucleic acid chip of the invention can comprise "probes", for example cDNA fragments or oligonucleotides (for example with 60 to 80 bases, or more), etc., fixed on a solid support. These "probes" fix specifically, by hybridization, the "targets", for example the complementary genes, present in the biological samples to be tested. This hybridization requires the association, by noncovalent bonds, of the single-stranded nucleic acid sequences, fully complementary or sufficiently complementary to hybridize to one another, and form a double-stranded structure.

EXAMPLES

Figure 1:
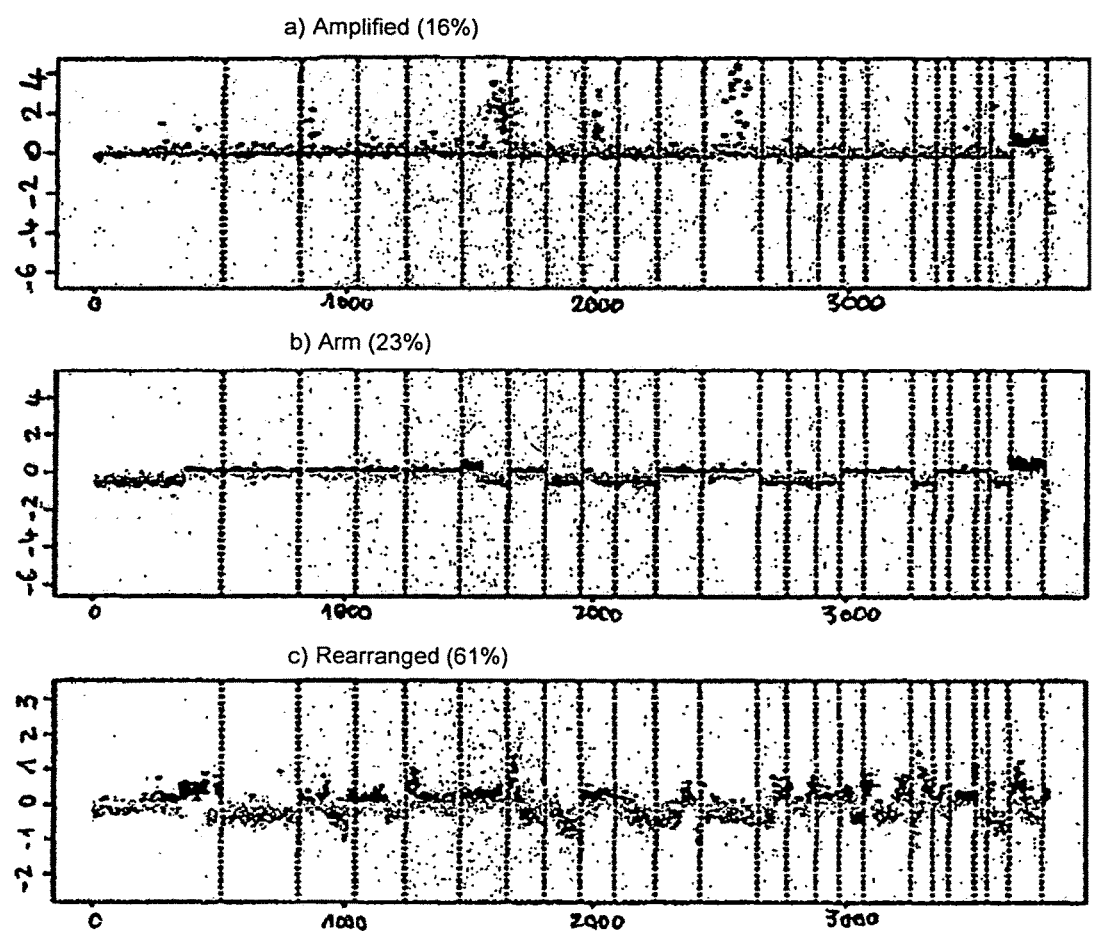
FIG. 1 shows 3 types of genomic profile (a) amplified (16%) (a) arms (23%) and (d) rearranged (61%).

Example 1: Pool of the Present Invention

Patients and Samples

The database of the French sarcoma group (groupe sarcome Français, GSF) as an entity of Conticabase (www.conticabase.org) contains the data of soft tissue sarcomas in adults treated in 11 centers with the description of the patients, of the primary tumors, of the treatments, of the follow-up and of the tumor samples. This database contained about 3800 cases at the time of the study. All the cases were reviewed by the subgroup of pathologists and were classified according to the WHO 2002 classification using histology, immunohistochemistry and cytogenetics and molecular genetics when this was necessary. For this study, soft tissue sarcomas without recurrent chromosomal translocations were selected, for which a frozen tissue sample of the untreated primary tumor was available. Finally, the biological samples obtained from 183 patients described in Table 2 below were investigated.

TABLE 2

| Characteristic | Tumor group (n = 183) | p value |
|---|---|---|
| Average follow-up (months) | 64 | |
| Average age (years) | 63 | 0.07 |
| Standard deviation | 15 | |
| Male sex (%) | 98 (53) | 0.75 |
| FNCLCC grade (%) | | 0.43 |
| 1 | 7 (4) | |
| 2 | 62 (34) | |
| 3 | 102 (56) | |
| n.d. | 12 (6) | |
| Histotype (%) | | 0.01 |
| Undifferentiated sarcomas | 71 (39) | |
| Leiomyosarcomas | 52 (28) | |
| Dedifferentiated liposarcomas | 44 (24) | |
| Others | 16 (9) | |
| Localization (%) | | 0.23 |
| Wall of the trunk | 28 (16) | |
| Limbs | 113 (62) | |
| Head and neck | 2 (1) | |
| Trunk, internal | 39 (21) | |
| Average size (cm) | 10 | 0.33 |
| Deep tumor (%) | | n.d. |
| Yes | 173 (95) | |
| No | 10 (5) | |
| Invasion of vessels, nerves or bones (%) | | <0.001 |
| Yes | 27 (15) | |
| No | 156 (85) | |
| Relapse events (%) | | |
| Metastases | 78 (43) | |
| Local relapses | 72 (39) | |
| Type of treatment (%) | | |
| Surgery | 50 (27) | |
| Surgery + radiotherapy | 80 (44) | |
| Surgery + chemotherapy | 10 (5) | |
| Surgery + radiotherapy + chemotherapy | 40 (22) | |
| Data missing | 3 (2) | |

DNA Extraction and Analysis by CGH (Comparative Genomic Hybridization) on DNA Chip The genomic DNA of frozen tumor tissues was isolated using a standard protocol for extraction with phenol-chloroform and was analyzed on a spectrophotometer (Nanodrop). Thus, after digestion with DpnII (Ozyme, Saint-Quentin en Yvelines, France) and column purification (Qiagen PCR Purification Kit, Qiagen), 1.5 μg of tumor DNA and 1.5 μg of normal DNA were labeled using the BioPrime DNA labeling System Kit (Invitrogen, Cergy Pontoise, France) with Cy5-dCTP or Cy3-dCTP (Perkin Elmer), respectively. The labeled normal and tumor DNAs were mixed and precipitated together with 100 µg of human Cot-1 DNA (Invitrogen), resuspended in 72 µl of hybridization buffer (50% formamide, 40 mM $NaH_2PO_4$, 0.1% SDS, 10% dextran sulfate, 2×SSC). Prehybridized probes were deposited on slides and put in humid chambers (Corning) and hybridization took place at 37° C. for 48 h.

In order to establish the genomic profiles, BAC (Bacterial Artificial Chromosome) chips composed of 3803 BAC clones were made with an average of 1 Mb between the clones. The BAC clones were deposited in triplicate.

The washings after hybridization were performed as follows: washing at 65° C. in 0.5×SSC, 0.03% SDS, followed by washing at 45° C. in the same solution.

The slides were scanned (Scanarray 4000XL, Packard Bioscience) and analyzed with the image analysis software GenePix Pro 5.1. Normalization, subdivided filtration, group analysis and graphical representation were performed using the CGH on DNA chip analysis platform (CAPWeb). Clones with more than 50% of values missing were discarded. Cy5-Cy3 ratios above 2 were regarded as amplifications, ratios above 1.2 and below 0.8 were regarded as gains and losses, respectively.

The analysis by CGH on DNA chip (calculation of genomic changes) was performed by VAMP interface (LA ROSA et al., Bioinformatics, 22 (17): 2066-2073, 2006).

RNA Extraction and Analysis of Expression

The total RNA was extracted from frozen tumor samples with TRIzol reagent (Life technologies, Inc.). The RNA was then purified using the RNeasy® Min Elute™ Cleanup Kit (Qiagen), according to the manufacturer's instructions. The quality of the RNA was verified on the Agilent 2100 bioanalyzer (Agilent Technologies).

The samples were then analyzed on the Human genome U133 Plus 2.0 chip (Affimétrix®), according to the manufacturer's instructions. All the data from the DNA chips were normalized simultaneously using the GCRMA algorithm (WU et al., J. Am. Stat. Assoc., 99: 909-917, 2004). Hierarchical group analyses were performed using the dChip software (http://biosunl.harvard.edu/complab/dchip/). For the Welch, Willcoxon and SAM tests, the p values were adjusted using the Benjamini-Hochberg procedure (R-multitest package).

Analysis in the Gene Ontology database (GO; http://www.geneontology.org/) was performed for statistical enhancement to the limits of GO.

Statistical Analysis

Chi-squared ($X^2$) tests were performed for evaluating the link between the various tumor characteristics, genomic changes, expression profiles and clinical outcome. The mutual influence of the various predictive factors was determined by a multivariate analysis using a test of ascending logistic regression. All the factors were included in the analyses of logistic regression, without taking into account their P values obtained by univariate analysis, but only those with a value P≤5% were used in the final models. The metastasis-free survivals were obtained by the Kaplan-Meier method and were compared with the logarithmic rank test. All the statistical tests were two-faced and the significance threshold was p=0.05. All the statistical analyses (logistic regression model) were performed using version 8 of the SAS software.

Results

Genomic Profile of the 183 Poorly Differentiated Sarcomas

The genomic profile of the 183 poorly differentiated sarcomas was established by CGH analysis on a BAC chip containing 3803 clones. Three main recurrent profiles were identified, according to both the number and the type of changes identified, among 174 genomic profiles that could be interpreted in fine (FIG. 1). A first group of 28 tumors (16%) with simple genetics, designated "amplified" profile, based on the co-amplifications and corresponding almost exclusively to dedifferentiated liposarcomas; a second group of 40 tumors (23%), designated "arm" profile, with some changes (less than 30), mainly involving a change of the whole chromosome or of a complete arm of the chromosome; a third group of 106 tumors (61%), designated "rearranged" profile, characterized by a high level of chromosomal complexity with more than 30 to 85 changes.

It still has to be demonstrated whether the genomic profile is associated with the clinical outcome.

Group analysis supervised according to the genomic profile ("arm" profile vs "rearranged" profile) did not permit significant prediction of the appearance of metastases (p=0.17). Interestingly, a positive correlation was found between the "rearranged" profile and histologic grade 3, in the 183 sarcomas of the study (p=0.001), and in the sub-group of the 117 sarcomas of the limbs with complex genetics with the "arm" and "rearranged" profiles (p=2.2× $10^{-4}$). As the histologic grade is an indirect evaluation of tumor aggressiveness, it was shown that, even if no correlation with a poor clinical outcome was obtained, the genomic complexity is associated with tumor aggressiveness.

It has still to be demonstrated whether gene expression associated with genomic complexity and/or the tumor grade could be predictive of the appearance of metastases.

Expression Profiles and Establishment of the Prognostic Molecular Signature

The gene expression profiles of the 183 sarcomas of the study were reconsidered in order to test the hypothesis of a correlation between the specific expression of the genes in the tumors with complex genome and the appearance of metastases.

To do this, the 183 samples were first grouped as a function of a previously established signature composed of 70 genes selected as being linked to chromosomal instability (CARTER et al., Nat. Genet., 38 (9): 1043-1048, 2006). But this led to a prediction of trend but was not significant of metastasis-free survival.

Also, secondly, the aim was to establish a set of genes specific to the sarcomas, associated with the level of imbalances and capable of predicting the future outcome for a patient. In three supervised analyses, the expression profiles were analyzed of tumors classified in two groups according to i) the number of CGH imbalances, fewer than 20 imbalances vs more than 35 imbalances, ii) the histologic grade FNCLCC 3 vs tumor grade 2, and iii) the Carter signature. From the first two comparisons, 118 clones corresponding to 86 genes and 92 clones corresponding to 73 genes were significantly expressed in a differential manner between the tumors stratified either by CGH imbalances (differential expression factor (=number of times where the gene is more expressed)>3; or not, p<0.01) or by grade (differential expression factor >2; p<0.01), respectively. These genes were then analyzed by the Gene Ontology database with the aim of determining the pathways associated with the CGH imbalances and with the histologic grade. Interestingly, these pathways are extremely similar in the groups determined according to CGH imbalances and those determined by comparisons of histologic grade, and are mainly involved in chromosome integrity and control of mitosis (Table 3). Among the genes of the Carter signature, 22 genes, which have not yet been identified in the first two comparisons, were significantly expressed ($p<10^{-5}$) in a differential manner between the two groups of sarcomas.

Based on these results, all the significant genes belonging to the pathways significantly over-represented from the first two comparisons ($p<10^{-5}$; Table 3) and the 22 genes of the Carter signature defined above were selected.

TABLE 3

| GO Identification | Observed in the selection | Observed on chip | Fisher's exact p value | GO Limit |
| --- | --- | --- | --- | --- |
| a) according to the Welch test Number of input probes/clones: 92 Number of identifications found: 73 | | | | |
| GO:0007067 | 19 | 122 | 1.46E−24 | Mitosis |
| GO:0051301 | 19 | 174 | 7.10E−22 | Cell division |
| GO:0007049 | 21 | 422 | 1.36E−17 | Cell cycle |
| GO:0000775 | 6 | 37 | 1.78E−08 | Chromosome, pericentric region |
| GO:0000074 | 8 | 181 | 1.02E−06 | Regulation of progression through cell cycle |
| GO:0005694 | 6 | 118 | 1.02E−05 | Chromosome |
| GO:0004674 | 8 | 338 | 7.96E−05 | Serine/threonine kinase activity |
| GO:0008283 | 7 | 248 | 8.41E−05 | Cellular proliferation |
| GO:0006270 | 3 | 19 | 1.00E−04 | Initiation of DNA replication |
| GO:0000776 | 3 | 21 | 1.20E−04 | Centromere |
| GO:0003777 | 4 | 62 | 1.54E−04 | Motor activity of the microtubules |
| GO:0007018 | 4 | 75 | 3.22E−04 | Movement based on microtubules |
| GO:0000079 | 3 | 35 | 5.23E−04 | Regulation of kinase cycline-dependent activity |
| GO:0005813 | 3 | 48 | 1.14E−03 | Centrosome |
| GO:0005875 | 3 | 54 | 1.58E−03 | Complex associated with the microtubules |
| GO:0006468 | 7 | 475 | 3.67E−03 | Phosphorylation of protein amino acids |
| GO:0046982 | 3 | 80 | 4.83E−03 | Activity of protein heterodimerization |
| GO:0005874 | 4 | 178 | 6.25E−03 | Microtubules |
| GO:0006260 | 3 | 96 | 8.13E−03 | DNA Replication |
| GO:0016301 | 3 | 184 | 4.18E−02 | Kinase activity |
| b) according to the Welch test Number of input probes/clones: 118 Number of identifications found: 86 | | | | |
| GO:0007067 | 23 | 122 | 4.50E−28 | Mitosis |
| GO:0051301 | 23 | 174 | 7.15E−25 | Cell division |
| GO:0007049 | 27 | 422 | 1.48E−21 | Cell cycle |
| GO:0000775 | 8 | 37 | 9.04E−11 | Chromosome, pericentric region |
| GO:0005819 | 6 | 14 | 7.45E−10 | Spindle |
| GO:0007018 | 9 | 75 | 8.12E−10 | Movement based on microtubules |
| GO:0003777 | 8 | 62 | 1.51E−09 | Motor activity of the microtubules |
| GO:0005876 | 5 | 12 | 2.39E−08 | Microtubule of the spindle |
| GO:0000074 | 10 | 181 | 9.46E−08 | Regulation of progression through the cell cycle |
| GO:0008283 | 11 | 248 | 1.72E−07 | Cellular proliferation |
| GO:0005874 | 8 | 178 | 7.01E−06 | Microtubules |

TABLE 3-continued

| GO Identification | Observed in the selection | Observed on chip | Fisher's exact p value | GO Limit |
| --- | --- | --- | --- | --- |
| GO:0007089 | 3 | 5 | 9.18E−06 | Passage through control point, start of mitotic cell cycle |
| GO:0005875 | 5 | 54 | 1.62E−05 | Complex associated with the microtubules |
| GO:0005694 | 6 | 118 | 5.52E−05 | Chromosome |
| GO:0005871 | 3 | 16 | 1.39E−04 | Kinesin complex |
| GO:0000079 | 3 | 35 | 1.23E−03 | Regulation kinase cycline-dependent activity |
| GO:0004674 | 7 | 338 | 1.40E−03 | Serine/threonine kinase activity |
| GO:0006468 | 8 | 475 | 5.32E−03 | Phosphorylation of protein amino acid |
| GO:0006260 | 3 | 96 | 1.79E−02 | DNA replication |
| GO:0008284 | 3 | 145 | 4.99E−02 | Positive regulation of cellular proliferation |

This final set of genes, designated by the inventors CINSARC (Complexity INdex SARComas), consists of 67 genes, all involved in control of the genome.

Figure 2:
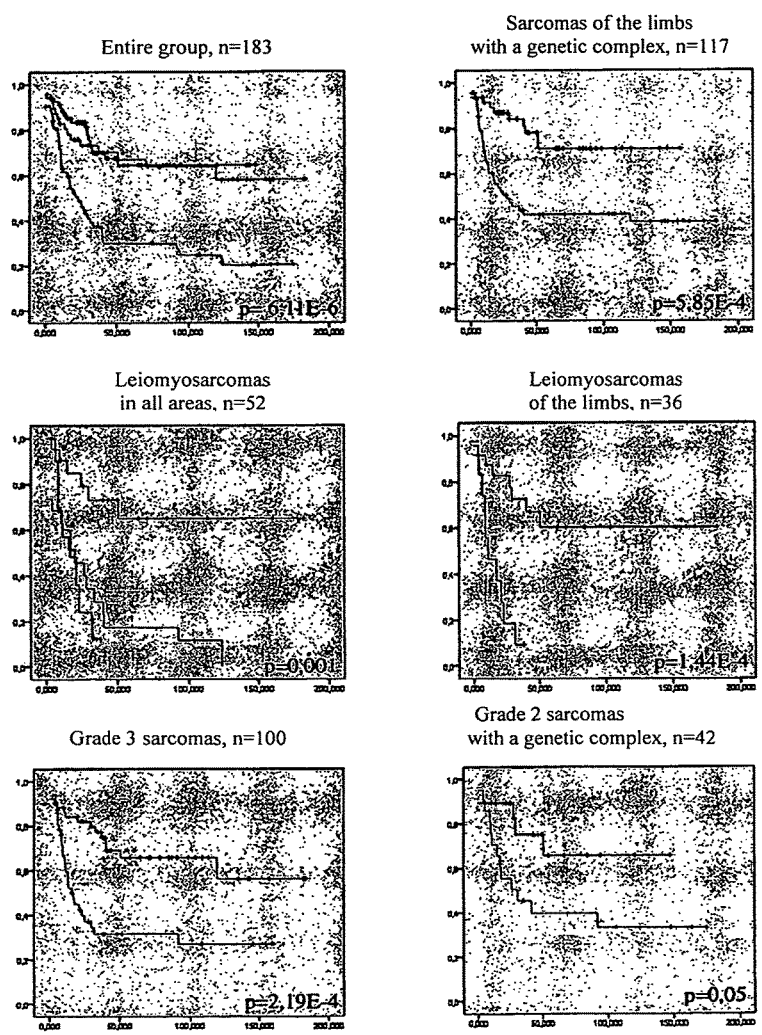
FIG. 2 shows the Kaplan-Meier curves of metastasis-free survival of different groups of sarcomas according to the CINSARC signature.

Example 2: Prediction of the Appearance of Metastases in Sarcomas by Means of CINSARC The correlation of the CINSARC expression signature with the appearance of metastases was evaluated in the entire group of the study (183 sarcomas). Group analysis made it possible to classify the tumors in three subgroups (subgroups 1, 2, 3), with a significant difference in appearance of metastases (FIG. 2). Multivariate analysis showed that the tumors of subgroup 3 have triple the risk of metastases in comparison with the tumors of subgroup 1 (Kaplan-Meier analysis; HR=3.01; 95% CI [1.8-5.2]; $p<10^{-3}$). A multivariate analysis taking into account other standard prognostic factors, such as the histologic type, FNCLCC tumor grade, size of the tumors, localization, invasion of vessels, nerves or bones, sex and age, also showed a three times greater risk of metastases for subgroup 3 compared with subgroup 1 (Cox model; HR=3.1; 95% CI [1.8-5.4], $p<10^{-3}$). These results showed that the CINSARC signature is an independent prognostic factor strongly associated with the development of metastases.

After this validation of the CINSARC signature as an independent prognostic factor, 6 specific subgroups of sarcomas were also tested by an unsupervised group analysis (FIG. 2). Among the 117 genetically complex sarcomas of the limbs, univariate analysis distributed the tumors in two subgroups and demonstrated a three times greater risk of metastases for subgroup 2 vs subgroup 1 (Kaplan-Meier analysis; HR=3.1; 95% CI [1.6-6.0]; $p<10^{-3}$). Similarly, among the 52 leiomyosarcomas, three subgroups of different significant clinical outcome (p=0.001) were found (it is interesting to note that subgroup 2 consists almost exclusively of LMSs developed in the internal trunk instead of the external trunk for the other two subgroups). Also when only the LMSs of the external trunk are taken into consideration in an unsupervised group analysis, the 36 patients are distributed in two subgroups with a six-fold difference of metastatic risk (Kaplan-Meier analysis; HR=6; 95% CI [2.1-16.9]; $p<10^{-3}$).

The performance of the CINSARC signature was also analyzed for patients of the same histologic grade (FIG. 2). Within the tumors of grade 3 (100 cases), a three times greater metastatic risk was observed in the tumors of subgroup 2 vs the tumors of subgroup 1 (Kaplan-Meier analysis; HR=3; 95% CI [1.6-5.6]; $p<10^{-3}$) and within the tumors of grade 2 (40 cases) with arm or rearranged profiles (namely all except the DD-LPSs), the patients were also distributed in two groups of different clinical outcome (Kaplan-Meier analysis; HR=2.6; 95% CI [1-7.5]; p=0.05). The metastasis-free survival is not significantly different in the two groups of dedifferentiated liposarcomas grouped according to the CINSARC signature.

Thus, the CINSARC signature of the present invention made it possible to separate tumors considered to have the same metastatic potential according to the FNCLLC grading system (FIG. 2) into two groups having a different probability of appearance of metastases. This result is perhaps the most important, as it clearly demonstrates that the CINSARC signature can be a more effective system than that currently used for determining therapeutic strategies.

Moreover, for the first time in the area of sarcomas, a gene expression profile attributes a clinical prognosis better than that obtained with the FNCLLC grading system. Thus, in the entire group combining different histotypes, the CINSARC signature made it possible to identify a subgroup of tumors with a poor prognosis whereas the FNCLLC grading system was unable to separate these tumors with separate prognoses (data not shown).

Figure 3:
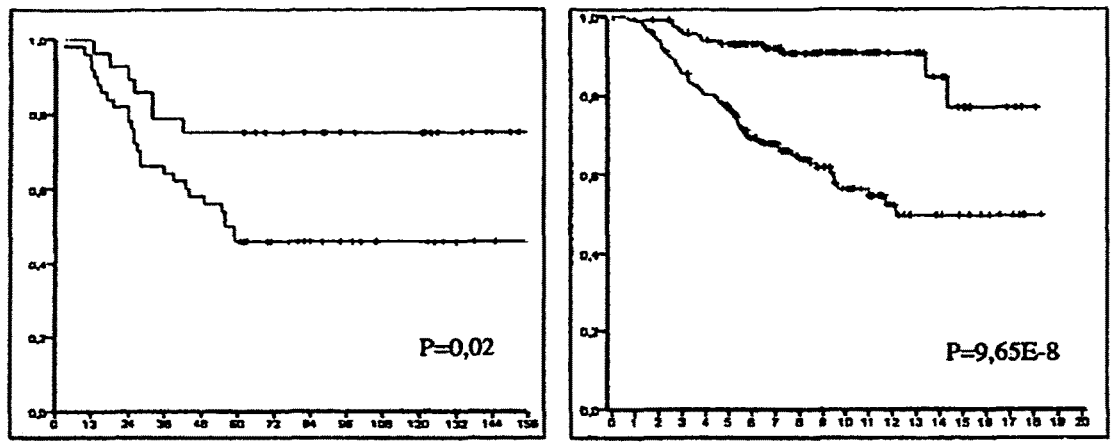
FIG. 3 shows the Kaplan-Meier curves of survival without progression/metastases of three groups of tumors according to the CINSARC signature.
Figure 3:
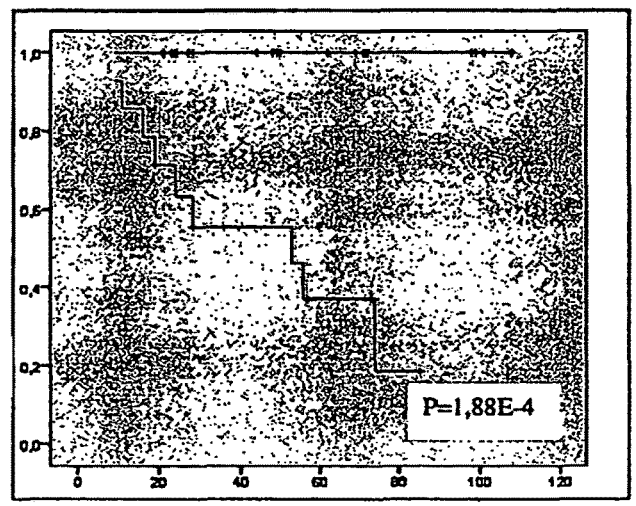

Example 3: Prediction of the Appearance of Metastases in Other Cancers by Means of CINSARC The predictive value of CINSARC in other sarcomas was tested and a series of 32 GISTs was analyzed (YAMAGUCHI et al., J; Olin. Oncol., 26 (25): 4100-4108, 2008). As shown in FIG. 3, the CINSARC signature permitted an unsupervised hierarchical group analysis leading to two groups of GISTs with a different prognosis (p<10-3). Interestingly, this classification is independent of localization even if the GISTs of the small intestine and those of the stomach form two separate groups in each different prognosis group.

As the CINSARC signature is composed exclusively of genes involved in chromosome integrity and expression is associated with chromosomal imbalances, the CINSARC signature could also have a prognostic value for greatly rearranged tumors, such as breast carcinomas. Consequently, two series of breast cancer (78 and 295 cases) of the Cancer Institute of the Netherlands (VAN'T VEER et al., 2002, op. cit.; VAN de VIJVER et al., 2002, op. cit.) were assembled according to the CINSARC signature, and once again two groups of patients with a very significant different clinical outcome ($p<10^{-3}$) were obtained (FIG. 3).

As demonstrated in the study, the CINSARC signature is a powerful independent predictive tool providing better evaluation of the appearance of metastases as well as attribution of a better clinical prognosis to the patients relative to the FNCLCC grading system. This new molecular grading system should thus make it possible to improve clinical after-care of the patients. Moreover, this biological significance of the genes of the CINSARC signature defines them as potential targets of novel therapeutic approaches targeting the early stage of acquisition of metastatic potential.

The fact that the CINSARC signature is associated with the appearance of metastases across such heterogeneous groups of tumors (from sarcomas to carcinomas) is sufficiently encouraging for envisaging, in place of the existing histologic grading system, the use of this expression profile for identifying patients at high risk of metastases and targeting additional chemotherapy strategies.

The current therapeutic strategies combine surgical resection and chemotherapy/radiotherapy in adjuvant or neoadjuvant situations. However, only sarcomas having a high metastatic potential ought to benefit from such treatment. This is currently the case for GISTs for which adjuvant treatment with imatinib is undergoing validation for tumors at high risk of recurrence. However, the systems used at present are imperfect. The use of the CINSARC signature could improve the selection of these patients and thus increase the benefits of adjuvant therapies.

There is therefore considerable interest in using the CINSARC signature as a major decision criterion for the admissibility of an adjuvant therapy, in particular with respect to GISTs (gastrointestinal stromal tumors) for which a targeted therapy already exists (Glivec®).

Figure 4:
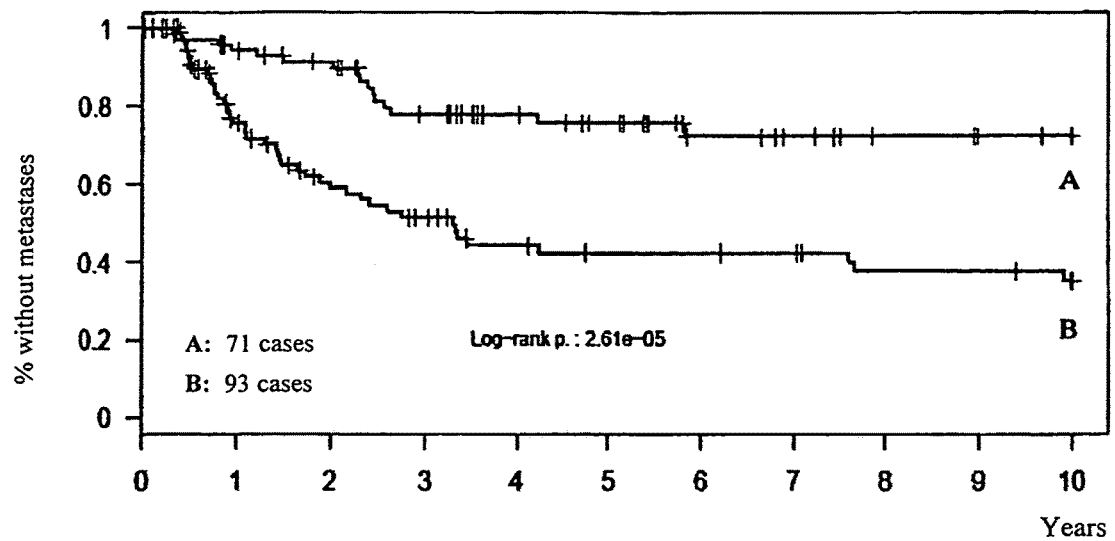
FIG. 4 shows the Kaplan-Meier curves of survival without progression/metastases (% of cases without metastases as a function of years after treatment) of a group of sarcomas (group of tumors in which the signature was defined) according to the signature by means of the pool of nucleotides consisting of the polynucleotides of sequences SEQ ID NO: 10, SEQ ID NO: 3, SEQ ID NO: 47, SEQ ID NO: 58 and SEQ ID NO: 24. Curve A shows a curve of survival of patients with good prognosis, presenting about 80% of cases without metastases at 5 years. Curve B shows a curve of survival of patients with a poor prognosis, presenting about 50% of cases without metastases at 5 years.
Figure 5:
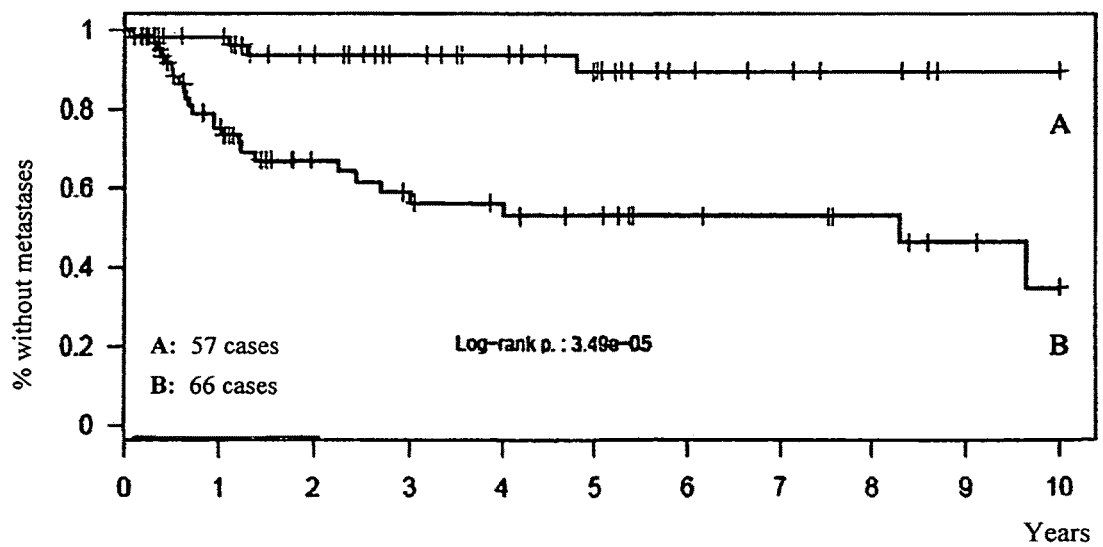
FIG. 5 shows the Kaplan-Meier curves of survival without progression/metastases (% of cases without metastases as a function of years after treatment) of a group of sarcomas (group of tumors independent of identification of the signature) according to the signature by means of the pool of nucleotides consisting of the polynucleotides of sequences SEQ ID NO: 10, SEQ ID NO: 3, SEQ ID NO: 47, SEQ ID NO: 58 and SEQ ID NO: 24. Curve A shows a curve of survival of patients with good prognosis, presenting about 90% of cases without metastases at 5 years. Curve B shows a curve of survival of patients with a poor prognosis, presenting about 50% of cases without metastases at 5 years.

Example 4: Prediction of the Appearance of Metastases in Sarcomas with the Aid of a Pool of 5 Polynucleotides of CINSARC Correlation of the expression signature of the 5 polynucleotides of sequences SEQ ID NO: 10, SEQ ID NO: 3, SEQ ID NO: 47, SEQ ID NO: 58 and SEQ ID NO: 24 of CINSARC with the appearance of metastases was evaluated on two series of sarcomas (FIGS. 4 and 5). Group analysis made it possible to classify the tumors in two subgroups (subgroups A and B), with a significant difference in appearance of metastases. Analysis by the method of nearest centers showed that the tumors in subgroup B have a greater risk of metastases compared with the tumors in subgroup A. These results showed that the CINSARC signature with 5 genes is an independent prognostic factor strongly associated with the development of metastases.

This is an important result, insofar as it clearly demonstrates that the five-gene CINSARC signature can be a more effective system than that currently used for determining therapeutic strategies.

Moreover, for the first time in the area of sarcomas, a gene expression profile attributes a better clinical prognosis than that obtained with the FNCLLC grading system. Thus, in the whole group combining different histotypes, the CINSARC signature made it possible to identify a subgroup of tumors with a poor prognosis whereas the FNCLLC grading system was not able to separate these tumors with different prognoses (data not shown).

The invention claimed is:

1. A set of polynucleotides consisting of the polynucleotides of SEQ ID NO: 1 to SEQ. ID NO: 67.

2. A set of polynucleotides consisting of the polynucleotides of SEQ ID NO: 10, SEQ ID NO: 3, SEQ ID NO: 47, SEQ ID NO: 58 and SEQ ID NO: 24.

3. The set of polynucleotides as claimed in claim 1, wherein said set of polynucleotides consists of at most ten polynucleotides.

4. The set of polynucleotides as claimed in claim 1, wherein said set of polynucleotides is immobilized on a solid support.

5. The set of polynucleotides as claimed in claim 4, wherein said solid support is a nucleic acid chip.

6. The set of polynucleotides as claimed in claim 2, wherein said set of polynucleotides is immobilized on a solid support.

7. The set of polynucleotides as claimed in claim 6, wherein said solid support is a nucleic acid chip.

* * * * *